United States Patent [19]
Loosmore et al.

[11] Patent Number: 5,977,337
[45] Date of Patent: Nov. 2, 1999

[54] LACTOFERRIN RECEPTOR GENES OF MORAXELLA

[75] Inventors: Sheena M. Loosmore, Aurora; Run-Pan Du; Quijun Wang, both of Thornhill; Yan-Ping Yang; Michel H. Klein, both of Willowdale, all of Canada

[73] Assignee: Connaught Laboratories Limited, North York, Canada

[21] Appl. No.: 08/867,941

[22] Filed: Jun. 3, 1997

[51] Int. Cl.$^6$ .................................................. C07H 21/04
[52] U.S. Cl. .................... 536/23.7; 536/23.1; 536/24.32; 536/24.3; 530/350; 435/69.1; 435/69.3; 435/69.4; 424/256.1
[58] Field of Search .................................. 536/23.1, 23.7, 536/24.32, 24.3; 530/350; 435/69.1, 69.3, 69.4; 424/256.1

[56] References Cited

U.S. PATENT DOCUMENTS

| | | |
|---|---|---|
| 4,258,029 | 3/1981 | Moloney et al. . |
| 4,855,283 | 8/1989 | Lockhoff et al. . |
| 4,952,496 | 8/1990 | Studier et al. . |
| 5,194,254 | 3/1993 | Barber et al. . |

FOREIGN PATENT DOCUMENTS

| | | |
|---|---|---|
| 2162193 | 5/1997 | Canada . |
| WO 90/12591 | 11/1990 | WIPO . |
| WO 92/17167 | 10/1992 | WIPO . |
| WO 94/12641 | 6/1994 | WIPO . |
| WO 95/34308 | of 0000 | WIPO . |
| WO 96/12733 | of 0000 | WIPO . |

OTHER PUBLICATIONS

Du, R–P et al; vol. 66, No. 8, Aug. 1998; pp. 3656–3665.
Brorson, J–E., A. Axelsson, and S.E. Holm. 1976. Studies on *Branhamella catarrhalis* (*Neisseria catarrhalis*) with special reference to maxillary sinusitis. Scan. J. Infect. Dis. 8:151–155.
Catlin, B.W., 1990. *Branhamella catarrhalis:*an organism gaining respect as a pathogen. Clin. Microbiol. Rev. 3: 293–320.
Hager, H., A. Verghese, S. Alvarez, and S.L. Berk. 1987. *Branhamella catarrhalis* respiratory infections. Rev. Infect. Dis. 9:1140–1149.
McLeod, D.T., F. Ahmad, M.J. Croughan, and M.A. Calder. 1986. Bronchopulmonary infection due to *M. catarrhalis*. Clinical features and therapeutic respsonse. Drugs 31(Suppl.3):109–112.
Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.
Ninane, G., J. Joly, and M. Kraytman. 1978. Bronchopulmonary infection due to *Branhamella catarrhalis* 11 cases assessed by transtracheal puncture. Br.Med.Jr. 1:276–278.
Srinivasan, G., M.J. Raff, W.C. Templeton, S.J. Givens, R.C. Graves, and J.C. Mel. 1981. *Branhamella catarrhalis* pneumonia. Report of two cases and review of the literature. Am. Rev. Respir. Dis. 123:553–555.
West, M., S.L. Berk, and J.K. Smith. 1982. *Branhamella catarrhalis* pneumonia., South Med. J. 75:1021–1023.
Christensen, J.J., and B. Bruun. 1985. Bacteremia caused by a beta–lactamase producing strain of *Branhamella catarrhalis*. Acta. Pathol. Microbiol. Immunol. Scand. Sect. B 93:273–275.
Craig, D.B., and P.A. Wehrle. 1983. *Branhamella catarrhalis* septic arthritis. J. Rheumatol. 10:985–986.
Guthrie, R., K. Bakenhaster, R. Nelson, and R. Woskobnick. 1988. *Branhamella catarrhalis* sepsis: a case report and review of the literature. J. Infect. Dis. 158:907–908.
Hiroshi, S., E.J. Anaissie, N. Khardori, and G.P. Bodey. 1988. *Branhamella catarrhalis* septicemia in patients with leukemia. Cancer 61:2315–2317.
O'Neill, J.H., and P.W. Mathieson. 1987. Meningitis due to *Branhamella catarrhalis*. Aust. N.Z. J. Med. 17:241–242.
Murphy, T.F. 1989. The surface of *Branhamella catarrhalis:* a systematic approach to the surface antigens of an emerging pathogen. Pediatr. Infect. Dis. J. 8:S75–S77.
Van Hare, G.F., P.A. Shurin, C.D. Marchant, N.A. Cartelli, C.E.Johnson, D. Fulton, S. Carlin, and C.H. Kim. Acute otitis media caused by *Branhamella catarrhalis:* biology and therapy. Rev. Infect. Dis. 9:16–27.
Jorgensen, J.H., Doern, G.V., Maher, L.A., Howell, A.W., and Redding, J.S., 1990 Antimicrobial resistance among respiratory isolates of *Haemophilus influenza, Moraxella catarrhalis*, and *Streptococcus pneumoniae* in the United States. Antibicrob. Agents Chemother. 34: 2075–2080.
Schryvers, A.B. and Lee, B.C. (1988) Comparative analysis of the transferrin and lactoferrin binding proteins in the family Neisseriaceae. Can. J. Microbiol. 35, 409–415.
O'Hagan, DT. 1992. Oral deleivery of vaccines. Formulation and clinical pharmaco kinetic considerations. Clin. Pharmacokinet 22(t): 1–10.
Ulmer et al. 1993. Curr. Opinion Invest. Drugs 2:983–989.
Lockhoff, O., Glycolipids as immunomodulators: Synthesis and properties, 1991, pp. 1611–1630.
Nixon–George A., et al., 1990. The adjuvant effect of stearyl tyrosine on a recombinant subunit hepatitis B surface antigen. J Immunol 144 (12): 4798–4802.

(List continued on next page.)

*Primary Examiner*—James C. Housel
*Assistant Examiner*—Jennifer Graser
*Attorney, Agent, or Firm*—Sim & McBurney

[57] ABSTRACT

Purified and isolated nucleic acid molecules are provided which encode lactoferrin receptor proteins of Moraxella, such as *M. catarrhalis*, or a fragment or an analog of the lactoferrin receptor protein. The nucleic acid sequence may be used to produce recombinant lactoferrin receptor proteins Lbp1, Lbp2 and Lbp3 of the strain of Moraxella free of other proteins of the Moraxella strain for purposes of diagnostics and medical treatment. Furthermore, the nucleic acid molecule may be used in the diagnosis of infection.

7 Claims, 111 Drawing Sheets

OTHER PUBLICATIONS

Wallace, R.J. et al., 1990. Antibiotic susceptibilities and drug resistance in *Moraxella* (*Branhaemella*) *catarrhalis*. Am. J. Med. 88(5A):465–505.

Nissinen A, et al., 1995. Development of beta–lactamase–mediated resistance to penicillin in middle–ear isolates of *Moraxella catarrhalis* in Finnish children, 1978–1993. Clin. Infect Dis 21 (5): 1193–1196.

Pettersson, A., et al., 1994. Identification of iroa Gene Product of *Neisseria meningitides* as a Lactoferrin Receptor. J. Bacteriol. 176(6): 1764–1766.

Biswas GD, Sparring PF. 1995. Characterization of 1bpa, the structural gene for a lactoferrin receptor in *Neisseria gonorrhoeae*. Infect Inimun 63 (8): 2958–2967.

Legrain M, et al. 1993. Cloning and characterization of *Neisseria meningitides* genes encoding the transferrin–binding proteins Tbp1 and Tbp2. Gene 130 (1): 73–80.

Cornelissen CN, Biswas GD, Sparling PF. 1993. Expression of gonococcal transferrin–binding protein 1 causes *Escherichia coli* to bind human transferrin. J Bacteriol 175 (8): 2448–2450.

Anderson JE, Sparling PF, Cornelissen CN. 1994. Gonococcal transferrin–binding protein 2 facilitates but is not essential for transferrin utilization. J Bacteriol 176 (11):3162–3170.

Ogunnariwo JA, Schryvers AB. 1996. Rapid identification and cloning of bacterial transferrin ad lactoferrin receptor protein genes. J Bacteriol 178 (24): 7326–7328.

Loosmore SM, et al. 1996. Cloning and expression of the *Haemophilus influenzae* transferrin receptor genes. Mol Microbiol 19 (3): 575–586.

Pettersson, A. et al. 1993. Molecular Characterization of the 98–Kilodalton Iron–Regulated Outer membrane Protein of *Neisseria meningitides*. Infect. Immun. 61 (ti): 4724–4733.

FIG. 1A

Alignment of translated 2.2kb lbpA PCR fragments

```
MNQSKQNNKSKKSKQVLKLSALSLGLLNITQVALANTTADK                                       Tbp1
MSKSITKTQTPSVHTMTTHRLNLAIKAALFGVAVLPLSVWAQENTQTDAN                              Lbp1

AEATDKTNLVVLDETVVTAKKNAPVSRKANEVTGLGKVVKTAETINKEQ                               Tbp1
SDAKDTKTPVVYLDAITVTAAPSA---RFDTDVTGLGKTVKTADTLAKEQ                              Lbp1

VLNIRDLTRYDPGIAVVEQGRGASSGYSIRGMDKNRVAVLVDGINQAQHY                              Tbp1
VQGIRDLVRYETGVSVVEQGRGGSSGFAIHGVDKNRVGITVDGIAQIQSY                              Lbp1

--QGPVAGKNYAAGGAINEIEYENVRSVEISKGANSSEYGSGALSGSVAFVT                            Tbp1
ALKDESTKRAGAGSGAMNEIEIENIAAVAINKGGNALEAGSGALGGSVAFHT                            Lbp1

KTADDIIKDGKDWGVQTKTAYASKNNAWVNSVAAAGKAGSFSGLIIYTDR                              Tbp1
KDVSDVLKSGKNLGAQSKTTYNSKNDHFSQTLAAAGKTERVEAMVQYTYR                              Lbp1
                                            QYT-R                               PCR4
                                            QYT-R                               PCR5

RGQEYKAHDDAYQGSQSFDRAVATTDPNNRTFLIANECANGNYEACAAGG                              Tbp1
KGKENKAHSDLNGINQSLYRLGAWQQKYDLRKPNELFAGTSYITESCLAS                              Lbp1
KG-ENKAHSDLNGINQSLYRLGAMQQKYDLRKPNELFAGTSYITESCLAS                              PCR4
KG-ENKAHSDLNGINQSLYRLGAWQQKYDLRKPNELFAGTSYITESCLAS                              PCR5

QTKLQAKPTNVRDKVNVKDYTGPNRLIPNPLTQDSKSLLLRPGYQLNDKH                              Tbp1
DDPKSCVQYPYVYTKARPDGIGNRNFSELSDAEKAQYLASTHPHEVVSAK                              Lbp1
DDPKSCVQYPYVYTKARPDGIGNRNFSELSDAEKAQYLASTHPHEVVSAK                              PCR4
DDPKSCVQYPYVYTKARPDGIGNRNFSELSDAEKAQYLASTHPHEVVSAK                              PCR5
```

FIG. 1B

```
YVGGVYEITKQNYAMQDKTVPAYLAVHDIEKSRLSNHAQANGYYQGNNLGERIRDT  Tbp1
DYTGIYRLLPDPMDYRSDSYLARLNIKITPNLVSKLLLEDTKQTYNIRDM        Lbp1
DYTGIYRLLPDPMDYRSDSYLARLNIKITPNLVXKLLLEDTKQTYNIRDM        PCR4
DYTGTYRLLPDPMDYRSDSYLARLNIKITPNLVSKLLLEDTKQTYNIRDM        PCR5

IGPDSGYGINYAHGVFYDEKHQKDRLGLEYVYDSKGENKWFDDVRVSYDKQDIT    Tbp1
RHCSYHGARLGNDGKPANGGSIVLCDDYQEYLNANDASQALFRPGANDAP        Lbp1
RHCSYHGARLGNDGKPANGGSIVLCDDYQEYLNANDASQALFRPGANDAP        PCR4
RHCSYHGARLGNDGKPANGGSIVLCDDYQEYLNANDASQASFRPGANDAP        PCR5

LRSQLTNTHCSTYPHIDKNCTPDVNKPFSVKEVDNNAYKEQHNLIKAVFN        Tbp1
IPKLAYARSSVFNQEHGKTRYGLSFEFKPDTPWFKQAKLNLHQQNIQIIN        Lbp1
IPKLAYARSSVFNQEHGKTRYGLSFEEKPDTPWFKQAKLNLHQQNIQIIN        PCR4
IPKLAYARSSVFNQEHGKTRYGLGFEFKPDTPWFKQAKLNLHQQNIQIIN        PCR5

KKMALGSTHHHINLQVGYDKFNSSLSRVEYRLATHQSYQKLDYTPPSNPL        Tbp1
HDIKKSCSQYPKVDLNCGISEIGHYEYQNNYRYKEGRASLTGKLDFNFDL        Lbp1
HDIKKSCSQYPKVDSNCGISEIGHYEYQXNYRYKEGRASLTGKLDFNFDL        PCR4

PDKFKPILGSNNKPICLDAYGYGHDHPQACNAKNSTYQNFAIKKGIEQYN        Tbp1
LGQHDLTVLAGADKVKSQFRANNPRRTIIDTTQGDAIIDESTLTAQEQAK        Lbp1
LGQHDLTVLAGTDKVKSQFRANNPRRTIIDTTQGDAIIDESTLTAQEQAK        PCR4
```

FIG.1C

```
                                                                    Tbp1
QKTNTDKIDYQAIIDQYDKQNPNSTLKPFEKIKQSLGQEKYNKIDELGFK                  Tbp1
FKQSGAAWIVKNRLGRLEEKDACGNANECERAPIHGSNQYVGINNLYTPN                  Lbp1
FKQSGAAWIVKNRLGRLEEKDACGNANECERAPIHGSNQYVGINNLYTPN                  PCR4

AYKDLRNEWAGWTNDNSQQNANKGTDNIYQPNQATVVKDDKCKYSETNSY                  Tbp1
DYVDLSFGGRLDKQRIHSTDSNIISKTYTNKSYNFGAAVHLTPDFSLLYK                  Lbp1
DYVDXSFGGRLDKQRIHSTDSNIISKTYTNKSYNFGAAVHLTPDFSLLYK                  PCR4
             TDSNIISKTYTNKSYNFGAAVHXTPDFSLLYK                       PCR5

ADCSTTRHISGDNYFIALKDNMTINKYVDLGLGARYDRIKHKSDVPLVDNSASNQLSWNFGVV     Tbp1
TAKGFRTPSFYELYNYNSTAAQHKNDPDVSFPKRAVDVKPETSNTNEYGF                  Lbp1
TAKGFRTPSFYELYNYNSTAAQHKNDPDVSFPKRAVDVKPETSNTNEYGF                  PCR4
TAKGFRTPSFYELYNYNSTAAQHKNDPDVSFPKRAVDVKPETSNTNEYGF                  PCR5

VKPTNWLDIAYRSSQGFRMPSFSEMYGERFGVTIGKGTQHGCKGLYYICQQTV               Tbp1
RYQHPWGDVEMSMFKSRYKDMLDKAIPNLTKAQQEYCKAHLDSNECVGNP                  Lbp1
RYQHPWGDVEMSMFKSRYKDMLDKAIPNLTKAQQEYCRAHLDSNECVGNP                  PCR4
RYQHPWGDIEMSMFKSRYKDMLDKAIPNLTKAQQEYCKAHLDSNECVGNP                  PCR5

HQTKLKPEKSFNQEIGATLHNHLGSLEVSYFKNRYTDLIVGKSEEIRTLT                  Tbp1
PTPKTSDEVFANLYNATIKGVSVKGKLDLHAMTSKLPDGLEMTLGYGHTK                  Lbp1
PTPKTSDEVFANLYNATIKGVSVKGKLDLHAMTSKLPDGLEMTLGYGHTK                  PCR4
PTPKTSDEVFANLYNATIKGVSVKGKLDLHAMTSKLPDGLEMTLGYGHTK                  PCR5

QGDNAGKQRGKGDLGFHNGQDADLTGINILGRLDLNAANSRLPYGLYSTL                  Tbp1
```

FIG.1D

```
AYNKVDVKGKTLNPTLAGTNILFDAIQPSRYVVGLGYDAPSQKWGANAIF         Tbp1
LGKFDYIAPKDADGWYQARPAFWDAITPARYVVGLNYDHPSQVWGIGTTL         Lbp1
LGKFXYIAPKDADGWYQARPAFWDAITPARYVVGLNYDHPSQVWGIGATL         PCR4
LGKFXYIAPKDADGWYQARPAFWDAITPARYVVGLNYDHPSQVWGIGTTL         PCR5

HSDAKNPSELLADKNLGNGNIQTKQATKAKSTPWQTL-DLSGYVNIKDNFT         Tbp1
THSKQKDENELSALRIR-NGKRETQTLTHTIPKAYTLLDMTGYYSPTESIT         Lbp1
THSKQKDENELSALRIR-NGKRETQTLTHTIPKAYTLLDMTGYYSPTESIT         PCR4
THSKQKDENELSALRIR-NGKREIQTLTHTIPKAYTLLDMTGYYSPTESIT         PCR5

LRAGVYNVFNTYYTTWEALRQTAKGAVNQHTGLSQDKHYGRYAAPGRNYQLALEMKF*  Tbp1
ARLGINNVLNTRYTTWEAARQ------LPSEAASSTQSTRYIAPGRSYFASLEMKF*  Lbp1
ARLGINNVLNTRYTTWEAARQ------LPSEAASSTQSTRYIAPGRSYFASLEMKF*  PCR4
ARLGINNVLNTRYTTWEAARQ------LPSEAASSTQSTRYIAPGRSYFASLEMKF*  PCR5
```

FIG.2A

M. catarrhalis 4223 lfr sequence

```
A A G C T T A G C A T G A T G G C A T C G G C T G A T T G T
                    10                  20                  30
C T T T T T G C C T T G T T G T G T G T T T G T G G G A G T
            40                  50                  60
T G A T T G T A C T T A C C T T A G T G G T G G A T G C T T
                    70                  80                  90
         -35                                      -10
G G G C T G A T T T A A T A A A G C G G T C T T C A C A A C
            100                 110                 120
                    RBS          Lbp2
                                 MET SER THR
A C A C C A A A C G A G A T A T C A C C A T G A G T A C T G
                    130                 140                 150
VAL LYS THR PRO HIS ILE PHE TYR GLN LYS A
T C A A A A C C C C A C A T T T C T A C C A A A A A C
            160                 170                 180
RG THR LEU SER LEU ALA ILE ALA SER ILE
G C A C C C T T A G C C C T T G C C A T C G C C A G T A T T T
                    190                 200                 210
PHE ALA ALA LEU VAL MET THR GLY CYS ARG S
T T G C T G C C T T G G T G A T G A C A G G C T G C C G C T
            220                 230                 240
```

FIG.2B

ER  ASP  ASP  ILE  SER  VAL  ASN  ALA  PRO  ASN
C T G A T G A C A T C A G C C G T C A A T G C A C C C A A T G
            250                 260                 270
                    VAL  THR  GLN  LEU  PRO  GLN  GLY  THR  VAL  SER  P
                    T T A C C C A A C T G C C C C A A G G C A C G G T T T C A C
                                280                 290                 300

RO  ILE  PRO  ASN  THR  GLY  HIS  ASP  ASN  THR
C A A T A C C G A A C A C A G G T C A T G A C A A C A C C A
            310                 320                 330
                    ASN  ASN  THR  ASN  GLN  GLY  ASN  ASN  THR  A
                    A T A A C C A A C A A T C A G G G C A A C A A C A C G G
                                340                 350                 360

SP  ASN  SER  THR  SER  THR  THR  ASP  PRO  ASN
A T A A C A G C A C C A G C A C A A C T G A C C C A A A T G
            370                 380                 390
                    GLY  ASP  ASN  ASN  GLN  LEU  THR  GLN  ALA  GLN  L
                    G C G A T A A C A A C C A A C T G A C A C A A G C A C A A A
                                400                 410                 420

FIG.2C

```
YS  THR ALA ALA ALA ALA GLY PHE PHE VAL
AGA CCG GCC GCT GCC GCA GGG TTT TTT GTG A
        430               440         450

MET GLY LYS ILE ARG ASP THR SER PRO LYS A
TGG GTA AAA TTC GTG ATA CCA GCC CAA AAA A
        460               470         480

SN  ASP PRO ASP TYR SER ASN ASP LEU VAL
ATG ACC CAG ATT ATA GCA ATG ATT TAG TAC
        490               500         510

GLN GLN TRP GLN GLY LYS LEU TYR VAL GLY I
AGC AGT GGC AAG GCA AAA TTA TAT GTT GGT A
        520               530         540

LE  ASP ALA HIS ARG PRO ASP GLY ILE GLY
TTG ATG CCC ATC GCC CAG ATG GCA TCG GCA
        550               560         570

THR GLY LYS ASN LEU ARG GLN PRO ILE THR A
CAG GTA AAA ACT TGC GTC AGC CCA TCA CCG
        580               590         600
```

FIG.2D

```
LA  ASN ASP ILE LYS PRO LEU TYR PHE ASN
C C A A T G A C A T C A A A C C C T T G T A T T T T A A C A
                        610                       630

LYS PHE PRO ALA LEU SER ASP LEU HIS LEU A
                                  A T T C C C T G C A T T G T C T G A T T T G C A T T T A G
                                        640                       660

SP  SER GLU ARG HIS ARG PHE ASP PRO LYS
A C A G T G A A C G C C A C C G T T T G A C C C C A A A A
                        670                       690

LYS LEU ASN THR ILE LYS VAL TYR GLY TYR G
                                  A G C T A A A C A C C A T T A A A G T G T A T G G T T A T G
                                        700                       720

LY  ASN LEU THR THR PRO SER LYS ASN ASN
G C A A C T T A A C A A C A C C C T C T A A A A A C A A C A
                        730                       750

THR TYR ILE ASN HIS GLN GLN ALA ASP ASN L
                                  C T T A C A T C A A T C A T C A G C A A G C T G A T A A A T A
                                        760                       780
```

FIG.2E

```
YS  LYS ASN ASN LYS PRO VAL ASP PRO TYR
A G A A A A T A A C A A G C C C T G T G A C C C T T A T
            790                   800                810
                GLU ASN ILE ARG PHE GLY TYR LEU GLU LEU G
                G A A A A T A T C C G T T T T G G G T A T C T T G A A C T A C
                        820                  830                  840

LN  GLY SER SER LEU THR GLN LYS ASN ALA
A A G G A A G C A G T C T G A C C C A A A A A A A T G C C G
            850                   860                870
                ASP THR PRO ASN ASP LYS ASP ARG ILE PRO L
                A T A C T C C A A A T G A C A A A G A C C G C A T T C C C A
                        880                  890                  900

YS  PRO MET PRO ILE LEU PHE TYR HIS GLY
A A C C C A T G C C C A T T T T G T T T T A T C A C G G A G
            910                   920                930
                GLU ASN ALA SER SER GLN LEU PRO SER ALA G
                A A A C G C C A G C A G C C A G C C A G T G C T G
                        940                  950                960
```

FIG.2F

```
LY  LYS PHE ASN TYR THR GLY ASN TRP LEU
GTAAAATTTAACTACACAGGCAACTGGCTGT
                     980            990
            TYR LEU SER ASP VAL LYS LYS ARG PRO ALA L
            ACCTAAGTGATGTCAAAAAACGCCCTGCAC
                    1000           1010           1020

EU  SER ALA SER ASP ASP ARG VAL GLY VAL
TTTCAGCATCAGATGATCGAGTGGGGGTCT
                    1030           1040           1050
            TYR LEU ASN ALA SER GLY LYS SER ASN GLU G
            ATCTCAATGCCAGTGGCAAATCCAATGAGG
                    1060           1070           1080

LY  ASP VAL VAL SER ALA ALA HIS ILE TYR
GCGATGTCGTCAGTGCCGCCCACATTTATC
                    1090           1100           1110
            LEU ASN GLY PHE GLN TYR LYS HIS THR PRO A
            TAAACGGCTTTCAATATAAGCACACGCCCTG
                    1120           1130           1140
```

FIG.2G

```
LA  THR TYR GLN VAL ASP PHE ASP THR ASN
C C A C T T A T C A G G T G G A T T T T G A C A C A A A C T
        1150                1160                1170
                                        SER LEU THR GLY LYS LEU SER TYR TYR ASP A
                                        C A T T A A C A G G C A A G C T G T C T T A T T A T G A C A
                                                1180                1190                1200

SN  PRO ASN GLN GLN THR ALA GLN GLY LYS
A T C C C A A C C A G C A A A A C T G C C C A A G G C A A A T
        1210                1220                1230
                                        TYR ILE LYS SER GLN PHE ASP THR THR LYS L
                                        A C A T C A A A A A G C C A A T T T G A C A C T A C C A A A A
                                                1240                1250                1260

YS  VAL ASN GLU THR ASP VAL TYR GLN ILE
A A G T C A A T G A A A C C G A T G T G T A T C A A A T T G
        1270                1280                1290
                                        ASP ALA LYS ILE ASN GLY ASN ARG PHE VAL G
                                        A T G C C A A A A T C A A C G G C A A C C G C T T C G T C G
                                                1300                1310                1320
```

FIG.2H

LY THR ALA LYS SER LEU VAL ASN GLU ASN
G T A C G G G C C A A A T C T T T G G T T A A T G A G A A C A
  1330            1340            1350

THR GLU THR ALA PRO PHE ILE LYS GLU LEU P
C A G A A A C C G C A C C T T T T A T C A A A G A G C T G T
      1360            1370            1380

HE SER LYS LYS ALA ASN PRO ASN ASN PRO
T C T C C A A A A A A G C C A A T C C C A A T A A C C C A A
      1390            1400            1410

ASN PRO ASN SER ASP THR LEU GLU GLY P
A C C C T A A T T C A G A C A C G C T A G A A G G C G G G T
      1420            1430            1440

HE TYR GLY GLU SER GLY ASP GLU LEU ALA
T T T A T G G T G A G T C G G G C G A T G A G C T G G C G G
      1450            1460            1470

GLY LYS PHE LEU SER ASN ASP ASN ALA SER T
G T A A A T T T T T A T C C A A T G A C A A C G C A T C T T
      1480            1490            1500

FIG. 2I.

```
YR  VAL VAL PHE GLY GLY LYS ARG ASP LYS
    ATG TGG TCT TTG GTG GTA AAC GAG ACA AAA
        1510            1520            1530
                    THR ASP LYS PRO VAL ALA THR LYS THR VAL  T
                    CAG ACA AAA CCT GTC GCC ACA AAA CGG TGT
                        1540            1550            1560

YR  PHE SER ALA GLY PHE GLU LYS PRO SER
    ATT TTA GTG CAG GCT TTG AAA AAC CTA GCA
        1570            1580            1590
                    THR SER PHE VAL ASP ASN GLU THR ILE GLY  A
                    CCA GTT TTG TGG ATA AAC GAT TGG CA
                        1600            1610            1620

RG  ILE ILE ASN SER LYS LYS LEU ASN ASP
    GAA TTA TTA ACA GCA AAA AAG TTA AAT GAT G
        1630            1640            1650
                    ALA VAL ASN GLU LYS ILE ASP ASN GLY ASP  I
                    CGG TGA ATG AGA AAA TTG ATA ATG GTG ATA
                        1660            1670            1680
```

FIG.2J

```
LE  PRO THR SER ASP GLU ARG TYR ASP GLU
TTCCTACCAGTGATGAAACGCTATGATGAAT
    1690                    1700              1710
            PHE PRO TRP GLY GLU LYS LYS ALA GLU PHE T
            TTCCTTGGGGCGAAAAAAGCAGAATTCA
               1720              1730              1740

HR  LYS LYS VAL SER SER SER THR GLN ALA
CCAAAAAAGTCAGCAGCAGCACCCAAGCCG
    1750              1760              1770
            VAL PRO ALA TYR PHE GLY GLN HIS ASP LYS P
            TGCCAGCTTATTTTGGGCAACATGATAAAT
               1780              1790              1800

HE  TYR PHE ASN GLY ASN TYR TYR ASP LEU
TTTATTTTAATGGCAACTATTATGACCTAT
    1810              1820              1830
            SER ALA SER SER VAL ASP LYS LEU ALA PRO A
            CAGCCAGCAGTGTTGATAAATTGGCCCCTG
               1840              1850              1860
```

FIG.2K

```
LA  ASP ALA VAL LYS ALA ASN GLN SER ILE                 LYS GLU LYS TYR PRO ASN ALA THR LEU ASN L
CCGATGCTGTCAAAGCCAACCAATCCATTA                          AAGAAAAATACCCTAATGCCACACTAAATA
         1870               1880           1890                  1900            1910           1920

YS  ASP ASN GLN VAL THR ALA ILE VAL LEU                 GLN GLU ALA LYS ASP ASN LYS PRO TYR THR A
AGGACAACCAAGTTACCGCCATCGTGCTAC                          AAGAAGCCAAAGATAATAAGCCTTATACCG
         1930               1940           1950                  1960            1970           1980

LA  ILE ARG ALA LYS SER TYR GLN HIS ILE                 SER PHE GLY GLU THR LEU TYR ASN ASP ALA A
CCATTCGTGCCAAAAGCTATCAGCACATCA                          GTTTTGGCGAGACGCTGTATACGATGCCAA
         1990               2000           2010                  2020            2030           2040
```

FIG.2L

```
SN  GLN THR PRO THR ARG SER TYR PHE VAL           ARG SER TYR PHE VAL THR L
    ACCAAACCCCAACACGCAGTTATTTTGTGC                                    2100
    2050                          2070
              GLN GLY GLY ARG ALA ASP THR SER THR THR
              AAGGCGGTAGGGCAGATACCAGCACCACGC
              2080                          2090

EU  PRO LYS ALA GLY LYS PHE THR TYR ASN                GLY TYR LEU ILE GLN LYS L
    TGCCCAAGGCAGGTAAATTCACTTACAACG                                      2160
    2110                          2130
              GLY LEU TRP ALA GLY TYR LEU ILE GLN LYS
              GTCTTTGGGCAGGCTATCTTATCCAAAAA
              2140                          2150

YS  ASP LYS GLY TYR SER ASN ASN GLU GLU              HIS GLN ASP TYR L
    AGGACAAAGGTTATAGCAATAATGAAGAAA                                  2220
    2170                          2190
              THR ILE LYS LYS LYS GLY HIS GLN ASP TYR
              CCATCAAGAAAAAAGGCCATCAAGATTATC
              2200                          2210
```

FIG.2M

```
LEU  LEU  THR  GLU  ASP  PHE  THR  PRO  GLU  ASP
TGTTAACCGAAGACTTCACCCCAGAAGATG
              2230                    2240                    2250

ASP  ASP  ASP  LEU  THR  ALA  SER  ASP  ASP  S
ATGACGATGATTTGACCGCATCTGATGATT
              2260                    2270                    2280

ER  GLN  ASP  ALA  HIS  GLY  ASP  ASP
CACAAGATGATGCACATGGCGATGATG
              2290                    2300                    2310

ASP  LEU  ILE  ALA  SER  ASP  ASP  SER  GLN  ASP  A
ATTTGATTGCATCTGATGATTCACAAGATG
              2320                    2330                    2340

SP  ASP  ALA  ASP  GLY  ASP  ASP  ASP  SER  ASP
ATGACGCAGATGGCGATGACGATTCAGATG
              2350                    2360                    2370

ASP  LEU  GLY  ASP  GLY  ALA  ASP  ASP  ALA  ALA  A
ATTTGGGTGATGGTGCAGATGACGCCGCCG
              2380                    2390                    2400
```

FIG.2N

```
LA  GLY LYS VAL TYR HIS ALA GLY ASN ILE
CAGGCAAAGTGTATCATGCAGGTAATATTC
         2410              2420              2430

ARG PRO GLU PHE GLU ASN LYS TYR LEU PRO  I
              GCCCTGAATTTGAAACAAATACTTGCCCA
                        2440              2450              2460

LE  ASN GLU PRO THR HIS GLU LYS THR PHE
TTAATGAGCCTACTCATGAAAAACCTTTG
         2470              2480              2490

ALA LEU ASP GLY LYS ASN LYS ALA LYS PHE  A
              CCCTAGATGGTAAAAATAAAGCTAAGTTTG
                        2500              2510              2520

SP  VAL ASP PHE ASP THR ASN SER LEU THR
ATGTGGATTTTGACACCAACAGCCTAACTG
         2530              2540              2550

GLY LYS LEU ASN ASP GLU ARG GLY ASP ILE  V
              GTAAATTAAACGATGAGAGAGGTGATATCG
                        2560              2570              2580
```

FIG.20

```
AL  PHE ASP ILE LYS ASN GLY LYS ILE ASP
    TCTTTGATATCAAAAATGGCAAAATTGATG
                                 2610
                2600
               2590

GLY THR GLY PHE THR ALA LYS ALA ASP VAL P
     GCACAGGCTTTACCGCCAAAGCCGATGTGC
              2620         2630         2640

RO  ASN TYR ARG GLU GLU VAL GLY ASN ASN
    CAAACTATCGTGAAGAAGTGGGTAACAACC
                2650              2670
                         2660

GLN GLY GLY PHE LEU TYR ASN ILE LYS A
     AAGGTGGCGGTTTCTTATACAACATCAAAG
              2680         2690         2700

SP  ILE ASP VAL LYS GLY GLN PHE PHE GLY
    ATATTGATGTCAAGGGGCAATTTTTTGGCA
              2710              2730
                        2720

THR ASN GLY GLU GLU LEU ALA GLY GLN LEU G
     CAAATGGCGAAGAGTTGGCAGGGCAGTTAC
              2740         2750         2760
```

FIG.2P

```
  N  TYR ASP LYS GLY ASP GLY ILE ASN ASP
AGTACGACAAAGGCGATGGCATCAATGACA
        2770              2780            2790
                    THR ALA GLU LYS ALA GLY ALA VAL PHE GLY A
                    CCGCCGAAAAGCAGGGGCTGTCTTTGGGG
                          2800            2810            2820

LA VAL LYS ASP LYS ***
CTGTTAAAGATAAATAAAGCCCCCTTCATC
        2830              2840            2850
                    ATCGTTTAGTCGCTTGACCGACAGTTGATG
                          2860            2870            2880

ACGCCCTTGGCAATGTCTTAAAACAGCACT
        2890              2900            2910
                    TTGAAACAGTGCCTTGGGCGAATTCTTGGA
                          2920            2930            2940

TAAATGCACCAGATTTGCCCTTGGGCTAATA
        2950              2960            2970
              -35
                    TCTTGATAAAACATCGCCATAAAATAGAAA
                          2980            2990            3000
                                -10
```

FIG.2Q

```
                                    Lbp1
            RBS·                    MET SER LYS
ATAAAGTTTAGGATTTTTTTATGTCAAAAT
         3010              3020             3030
                   SER ILE THR LYS THR GLN THR PRO SER VAL H
                   CTATCACAAAAACACAAACCACCATCAGTCC
                             3040             3050            3060

2nd possible start
IS  THR MET THR THR HIS ARG LEU ASN LEU
ATACCATGACCACCGCCTTAAACCTTG
         3070             3080             3090
                   ALA ILE LYS ALA ALA LEU PHE GLY VAL ALA V
                   CCATCAAAGCGGCGTTATTGGTGTGGCAG
                             3100             3110            3120

AL  LEU PRO LEU SER VAL TRP ALA GLN GLU
TTTACCCCTATCCGTCTGGGCGCAAGAGA
         3130             3140             3150
                   ASN THR GLN THR ASP ALA ASN SER ASP ALA L
                   ACACTCAGACAGATGCCAACTCTGATGCCA
                             3160             3170            3180
```

FIG.2R

```
YS  ASP THR LYS THR PRO VAL VAL TYR LEU
    AAGACACAAAACCCCTGTCTATTTAG
              3190                3210

ASP ALA ILE THR VAL THR ALA ALA PRO SER A
                  ATGCCATCACGGTAACCGCGCCCATCTG
                      3220              3230          3240

LA  PRO VAL SER ARG PHE ASP THR ASP VAL
    CCCCTGTTTCTCGGTTTGACACCGATGTAA
              3250              3270

THR GLY LEU GLY LYS THR VAL LYS THR ALA A
                  CAGGGCTTGGCAAAACGGTCAAAACCGCTG
                      3280              3290          3300

SP  THR LEU ALA LYS GLU GLN VAL GLN GLY
    ACACGCTGGCAAAAGAACAAGTGCAGGGC
              3310              3330

ILE ARG ASP LEU VAL ARG TYR GLU THR GLY V
                  ATTCGTGATTTGGTGCGTTATGAAACTGGGG
                      3340              3350          3360
```

FIG.2S

```
AL  SER  VAL  VAL  GLU  GLN  GLY  ARG  GLY  GLY
T G A G T G T G G T T G A G C A G G G G C G T G G C A
               3370                        3380                       3390
                                   SER  SER  GLY  PHE  ALA  ILE  HIS  GLY  VAL  ASP  L
                                   G C A G C G G A T T T G C C A T T C A T G G C G T G G A T A
                                            3400                       3410                      3420

YS  ASN  ARG  VAL  GLY  ILE  THR  VAL  ASP  GLY
A A A C C G A G T G G G C A T T A C C G T A G A T G G C A
               3430                        3440                       3450
                                   ILE  ALA  GLN  ILE  GLN  SER  TYR  LYS  ASP  GLU  S
                                   T T G C C C A A A T T C A A T C C T A C A A A G A T G A A T
                                            3460                       3470                      3480

ER  THR  LYS  ARG  ALA  GLY  ALA  GLY  SER  GLY
C C A C C A A A C G A G C T G G T G C A G G C T C T G G G G
               3490                        3500                       3510
                                   ALA  MET  ASN  GLU  ILE  GLU  ILE  GLU  ASN  ILE  A
                                   C G A T G A A T G A G A T A G A G A T T G A A A A C A T T G
                                            3520                       3530                      3540
```

FIG.2T

```
 LA  ALA VAL ALA ILE ASN LYS GLY GLY ASN
 CCGCCGTTGCCATCAATAAAGGTGGTAATG
              3550              3560         3570

ALA LEU GLU ALA GLY SER GLY ALA LEU GLY G
                CCCTAGAAGCAGGCTCTGGTGCGTTGGGCG
                     3580              3590              3600

LY SER VAL ALA PHE HIS THR LYS ASP VAL
 GTTCGGTGGCGTTTCATACCAAAGATGTGA
              3610              3620         3630

SER ASP VAL LEU LYS SER GLY LYS ASN LEU G
                GCGATGTCTTAAAATCTGGTAAAATCTTG
                     3640              3650              3660

LY ALA GLN SER LYS THR THR TYR ASN SER
 GCGCTCAAAGCAAAACCACTTATAACAGCA
              3670              3680         3690

LYS ASN ASP HIS PHE SER GLN THR LEU ALA A
                AAAATGACCATTTTAGTCAGACGCTGGCAG
                     3700              3710              3720
```

FIG. 2U

```
ALA ALA GLY LYS THR GLU ARG VAL GLU ALA              VAL GLN TYR THR TYR ARG LYS GLY LYS G
CGGCAGGTAAAACCGAGCGTGTGGAAGCGA                       TGGTGCAATATACCTACCGTAAAGGCAAAG
        3730              3740             3750             3760             3770        3780
                                            MET

LEU ASN LYS ALA HIS SER ASP LEU ASN GLY              ILE ASN GLN SER LEU TYR ARG LEU GLY ALA T
AAAACAAAGCACACAGCGACCTAAATGGCA                       TCAACCAAAGCCTATATCGCTTGGGTGCAT
        3790             3800             3810             3820             3830        3840

ARG GLN GLN LYS TYR ASP LEU ARG LYS PRO              ASN GLU LEU PHE ALA GLY THR SER TYR ILE T
GGCAACAAAAATATGATTTAAGAAAGCCCA                       ATGAACTGTTTGCAGGCACAAGCTACATCA
        3850             3860             3870             3880             3890        3900
```

FIG.2V

```
HR  GLU SER CYS LEU ALA SER ASP ASP PRO
    CCGAAAGCTGTTTGGCAAGTGATGACCCAA
         3910                  3920              3930
                    LYS SER CYS VAL GLN TYR PRO TYR VAL TYR T
                    AAAGCTGCGTACAATACCCTTATGTCTACA
                         3940              3950              3960

HR  LYS ALA ARG PRO ASP GLY ILE GLY ASN
    CCAAAGCCCGACCAGATGGCATCGGCAATC
         3970                  3980              3990
                    ARG ASN PHE SER GLU LEU SER ASP ALA GLU L
                    GCAATTTTCTGAGTTAAGCGATGCTGAAA
                         4000              4010              4020

YS  ALA GLN TYR LEU ALA SER THR HIS PRO
    AAGCACAATATTTGGCATCCACGCACCCCC
         4030                  4040              4050
                    HIS GLU VAL VAL SER ALA LYS ASP TYR THR G
                    ATGAGGTTGTCTCTGCCAAAGATTATACAG
                         4060              4070              4080
```

FIG.2W

```
LY  ILE TYR ARG LEU LEU PRO ASP PRO MET
GCATTTATCGGTTGTTACCTGACCCCATGG
        4090                4100            4110
                ASP TYR ARG SER ASP SER TYR LEU ALA ARG  L
                ACTATCGTTCAGACTCGTATTTGGCACGCC
                    4120            4130            4140

EU  ASN ILE LYS ILE THR PRO ASN LEU VAL
TTAACATCAAAATCACCCCAAATCTGGTCA
        4150            4160            4170
                SER LYS LEU LEU LEU GLU ASP THR LYS GLN  T
                GTAAACTGTTATTAGAAGACACCAAGCAAA
                    4180            4190            4200

HR  TYR ASN ILE ARG ASP MET ARG HIS CYS
CATACAACATTCGTGATATGCGTCATTGTA
        4210            4220            4230
                SER TYR HIS GLY ALA ARG LEU GLY ASN ASP  G
                GTTACCATGGGGCAAGATTGGGCAATGATG
                    4240            4250            4260
```

FIG.2X

```
LY  LYS PRO ALA ASN GLY GLY SER ILE VAL
GTAAGCCTGCCAATGGTGGCTCCATTGTTC
              4270              4280              4290
              LEU CYS ASP ASP TYR GLN GLU TYR LEU ASN A
              TTTGCGATGATTATCAAGAGTATCTAAACG
                        4300              4310              4320

LA  ASN ASP ALA SER GLN ALA LEU PHE ARG
CCAATGACGCATCACAAGCATTATTTAGAC
              4330              4340              4350
              PRO GLY ALA ASN ASP ALA PRO ILE PRO LYS L
              CAGGTGCTAATGATGCCCCATTCCAAAAC
                        4360              4370              4380

EU  ALA TYR ALA ARG SER SER VAL PHE ASN
TGGCTTTATGCCAGAAGCAGTGTGTTTAACC
              4390              4400              4410
              GLN GLU HIS GLY LYS THR ARG TYR GLY LEU S
              AAGAGCATGGCAAAACTCGCTATGGGTTAA
                        4420              4430              4440
```

FIG.2Y

```
ER  PHE GLU PHE LYS PRO ASP THR PRO TRP
GTTTGAGTTTAAGCCTGACACGCCATGGT
         4450              4460              4470
        PHE LYS GLN ALA LYS LEU ASN LEU HIS GLN G
        TTAAGCAAGCAAAATTAAACCTACACCAAC
                 4480              4490              4500

LN  ASN ILE GLN ILE ILE ASN HIS ASP ILE
AAATATCCAAATCATTAACCATGACATTA
         4510              4520              4530
        LYS LYS SER CYS SER GLN TYR PRO LYS VAL A
        AAAAATCGTGCAGCCAATATCCTAAGGTGG
                 4540              4550              4560

SP  LEU ASN CYS GLY ILE SER GLU ILE GLY
ATTTAAATTGTGGCATCAGTGAAATTGGGC
         4570              4580              4590
        HIS TYR GLU TYR GLN ASN ASN TYR ARG TYR L
        ATTATGAATATCAAAATAATTACCGTTATA
                 4600              4610              4620
```

FIG.2Z

```
YS  GLU GLY ARG ALA SER LEU THR GLY LYS
AAG AAG GGC GTG CCA GCT TGA CAG GCA AAC
         4630              4640         4650

LEU ASP PHE ASN PHE ASP LEU LEU GLY GLN  H
        TTG ATT TTA ATT TTG ACC TGC TGG GTC AGC
                 4660              4670         4680

IS  ASP LEU THR VAL LEU ALA GLY ALA ASP
ACG ATT TGA CGG GTG TTG GCT GGT GCA GAT A
         4690              4700         4710

LYS VAL LYS SER GLN PHE ARG ALA ASN ASN  P
        AAG TTA AAA GCC AAT TTC GTG CCA ACA ACC
                 4720              4730         4740

RO  ARG ARG THR ILE ILE ASP THR THR GLN
CCA GAC GCA CAA TCA TTG ACC ACC CCA AG
         4750              4760         4770

GLY ASP ALA ILE ILE ASP GLU SER THR LEU  T
        GCG ATG CCA TCA TTG ATG AAA GCA CGC TGA
                 4780              4790         4800
```

FIG.2A'

```
HR  ALA GLN GLU GLN ALA LYS PHE LYS GLN
    CAGCACAGGAGCAAGCCAAATTTAAGCAAT
            4810            4820            4830
                SER GLY ALA ALA TRP ILE VAL LYS ASN ARG L
                CGGGGGCGGCATGGATTGTCAAAATCGCC
                    4840            4850            4860

EU  GLY ARG LEU GLU GLU LYS ASP ALA CYS
    TTGGACGCTTAGAAGAAAAAGACGCCTGTG
            4870            4880            4890
                GLY ASN ALA ASN GLU CYS GLU ARG ALA PRO I
                GCAATGCCAATGAATGTGAACGCGCCCCA
                    4900            4910            4920

LE  HIS GLY SER ASN GLN TYR VAL GLY ILE
    TTCATGGCAGTAACCAATATGTGGGCATTA
            4930            4940            4950
                ASN ASN LEU TYR THR PRO ASN ASP TYR VAL A
                ACAACCTTTATACACCAAATGATTATGTGG
                    4960            4970            4980
```

FIG.2B'

```
SP  LEU SER PHE GLY GLY ARG LEU ASP LYS
    ATTAAGTTTTGGTGGACGCTTGGATAAAC
              4990                5000              5010
    GLN ARG ILE HIS SER THR ASP SER ASN ILE  I
    AACGCATTCACAGCACCGATTCAAACATCA
              5020              5030              5040

LE  SER LYS THR TYR THR ASN LYS SER TYR
    TCAGCAAAAACTTACACCAACAAAAGCTATA
              5050              5060              5070
    ASN PHE GLY ALA ALA VAL HIS LEU THR PRO  A
    ATTTTGGAGCGGCGGTTCATCTGACACCTG
              5080              5090              5100

SP  PHE SER LEU LEU TYR LYS THR ALA LYS
    ATTTTAGCCCTGTTGTATAAAACTGCCAAAG
              5110              5120              5130
    GLY PHE ARG THR PRO SER PHE TYR GLU LEU  T
    GCTTTCGTACGCCAAGTTTTATGAACTGT
              5140              5150              5160
```

FIG.2C'

```
YR  ASN TYR ASN SER THR ALA ALA GLN HIS
    A C A A C T A T A A C A G C A C C C G C C C C A G C A T A
                        5170                            5180                            5190
                                    LYS ASN ASP PRO ASP VAL SER PHE PRO LYS A
                                    A A A A T G A C C C T G A T G T G T T T C C C A A A C
                                            5200                    5210                    5220

RG  ALA VAL ASP VAL LYS PRO GLU THR SER
    G A G C G G G T T G A T G T C A A A C C T G A A A C T T C C A
                        5230                            5240                            5250
                                    ASN THR ASN GLU TYR GLY PHE ARG TYR GLN H
                                    A T A C C A A T G A A T A C G G C T T T C G C T A T C A G C
                                            5260                    5270                    5280

IS  PRO TRP GLY ASP VAL GLU MET SER MET
    A C C C T T G G G G G A T G T T G A G A T G A G C A T G T
                        5290                            5300                            5310
                                    PHE LYS SER ARG TYR LYS ASP MET LEU ASP L
                                    T C A A A G C C G T T A C A A G G A C A T G T T A G A T A
                                            5320                    5330                    5340
```

FIG.2D'

```
YS  ALA ILE PRO ASN LEU THR LYS ALA GLN
AAGCCATACCGAACCTAACCAAAGCCCAAC
    5350                    5370
                                      GLN GLU TYR CYS LYS ALA HIS LEU ASP SER A
                                      AAGAGTATTGTAAGGCTCATTTGGATTCCA
                                          5380              5390           5400

SN  GLU CYS VAL GLY ASN PRO PRO THR PRO
ATGAATGTGTTGGCAATCCGCCCACGCCCA
    5410                    5430
                                      LYS THR SER ASP GLU VAL PHE ALA ASN LEU T
                                      AAACCAGTGATGAGGTATTTGCCAACTTAT
                                          5440              5450           5460

YR  ASN ALA THR ILE LYS GLY VAL SER VAL
ATAATGCCACCATCAAAGGGGTGAGTGTCA
    5470                    5490
                                      LYS GLY LYS LEU ASP LEU HIS ALA MET THR S
                                      AAGGCAAAACTGGATTTGCATGCCATGACAT
                                          5500              5510           5520
```

FIG.2E'

```
ER  LYS LEU PRO ASP GLY LEU GLU MET THR
CAAAACTGCCAGATGGTCTTGAAATGACCT
                5530              5540              5550
                              LEU GLY TYR GLY HIS THR LYS LEU GLY LYS P
                              TGGGTTATGGTCATACCAAATTGGGGAAAT
                                      5560              5570              5580

HE  ASP TYR ILE ALA PRO LYS ASP ALA ASP
TTGATTACATTGCACCCAAAGATGCCGATG
                5590              5600              5610
                              GLY TRP TYR GLN ALA ARG PRO ALA PHE TRP A
                              GTTGGTATCAGGCTCGCCCTGCTTTTTGGG
                                      5620              5630              5640

SP  ALA ILE THR PRO ALA ARG TYR VAL VAL
ATGCCATCACCCCAGCGCTATGTGTGGTCG
                5650              5660              5670
                              GLY LEU ASN TYR ASP HIS PRO SER GLN VAL T
                              GTCTAAACTATGACCACCCCAGTCAAGTAT
                                      5680              5690              5700
```

FIG.2F'

```
RP  GLY  ILE  GLY  THR  THR  LEU  THR  HIS  SER
G G G G C A T T G G C A C A A C T T T A A C G C A C A G C A
         5710                5720                5730
                    LYS  GLN  LYS  ASP  GLU  ASN  GLU  LEU  SER  ALA  L
                    A A C A A A A A G A T G A A A A T G A G C T A A G T G C C C
                             5740                5750                5760

EU  ARG  ILE  ARG  ASN  GLY  LYS  ARG  GLU  THR
T T A G A A T C C G A A A T G G C A A A A G A G A A A C A C
         5770                5780                5790
                    GLN  THR  LEU  THR  HIS  THR  ILE  PRO  LYS  ALA  T
                    A A A C C T T A A C G C A C A C A A T A C C C A A A G C C T
                             5800                5810                5820

YR  THR  LEU  LEU  ASP  MET  THR  GLY  TYR  TYR
A T A C C T T A C T G G A C A T G A C A G G C T A T T A T A
         5830                5840                5850
                    SER  PRO  THR  GLU  SER  ILE  THR  ALA  ARG  LEU  G
                    G C C C A A C T G A G A G C A T C A C C G C T C G T C T T G
                             5860                5870                5880
```

FIG.2G'

```
LY  ILE ASN ASN VAL LEU ASN THR ARG TYR
GTATCAACAATGTATTAAACACCCGCTACA
              5890              5900              5910
                    THR THR TRP GLU ALA ALA ARG GLN LEU PRO S
                    CCACATGGGAAGCGGCACGCCAACTGCCCA
                              5920              5930              5940

ER  GLU ALA ALA SER SER THR GLN SER THR
GCGAAGCTGCAAGCAGTACCCAATCAACCC
              5950              5960              5970
                    ARG TYR ILE ALA PRO GLY ARG SER TYR PHE A
                    GTTACATTGCACCAGGTCGCAGTTACTTTG
                              5980              5990              6000
                                                ORF3
                                                MET THR
LA  SER LEU GLU MET LYS PHE ***
CCAGTCTTGAAATGAAGTTTTAATATGACC
              6010              6020              6030
                    CYS LEU PRO LYS THR ASN PRO ALA LEU . LYS
                    TGTTTACCAAAGACCAACCCTGCTTTAAAA
                              6040              6050              6060
```

FIG.2H'

```
VAL LYS HIS ARG PHE LEU LYS GLN VAL LEU
GTCAAGCACAGATTTTTAAAGCAGGTGCTG
                6070              6080        6090
                    LEU LEU CYS VAL ASP THR LEU THR ALA
                    TTATTGCTTTGTGTTGATACATTAACAGCA
                          6100         6110          6120

GLN ALA TYR ALA HIS SER HIS HIS THR PRO
CAGGCGTACGCCCACAGCCATCATACGCCC
                6130          6140         6150
                    ILE HIS THR PRO THR HIS GLU LEU PRO SER
                    ATTCATACACCCACGCATGAGCTGCCATCT
                          6160         6170          6180

ALA ASP ALA LEU SER ASP GLU GLY LEU GLY
GCTGATGCTTTATCAGATGAAGGCTTGGGT
                6190          6200         6210
                    LYS ASP LEU GLY SER LEU ASP SER LEU ASP
                    AAGGATTTGGGCAGTTTGGACAGTTTGGAT
                          6220         6230          6240
```

FIG.2I'

```
SER PRO ASP GLY LEU GLY ASP GLY LEU GLY
AGCCCAGATGGTTTGGGTGATGGTTTAGGC
         6250                6260              6270
                    ASP GLY LEU GLY ASP GLY LEU LYS SER ASP
                    GATGGTTTGGGTGATGGCTTAAAAAGTGAT
                             6280              6290              6300

LYS ALA PRO LEU PRO ILE ASN ALA LEU THR
AAAGCCCCTTTACCCATCAACGCCCTTGACC
         6310              6320              6330
                    ALA HIS GLN THR ASN GLU SER GLN PRO ALA
                    GCCCATCAGACCAATGAGAGCCAGCCTGCC
                             6340              6350              6360

PRO PRO SER VAL ASP VAL ASN PHE LEU LEU
CCACCGAGCGTAGATGTCAATTTTTTACTT
         6370              6380              6390
                    ALA GLN PRO GLU ALA PHE TYR HIS VAL PHE
                    GCCCAGCCAGAGGCATTTTATCATGTCTTT
                             6400              6410              6420
```

FIG.2J'

```
HIS GLN ALA ILE VAL GLN ASP ASP VAL ALA
CATCAAGCGATTGTGCAAGATGATGTGGCA
           6430              6440              6450
                THR LEU ARG LEU LEU LEU PRO PHE TYR ASP
                ACATTACGCTTGTTATTGCCATTTTATGAC
                       6460              6470              6480

ARG LEU PRO ASP ASP TYR GLN ASP ASP VAL
CGCCTGCCTGATGATTATCAAGATGATGTT
           6490              6500              6510
                LEU LEU PHE ALA GLN SER LYS LEU ALA
                TTGTTGTTATTTGCCCAAAGTAAACTTGCC
                       6520              6530              6540

LEU SER ASP GLY ASN THR LYS LEU ALA LEU
CTAAGTGATGGCAATACCAAATTGGCATTG
           6550              6560              6570
                ASN LEU LEU THR ASP LEU SER ASN LYS GLU
                AATCTGCTGACCGATTTGAGTAACAAAGAG
                       6580              6590              6600
```

FIG.2K'

```
PRO THR LEU THR ALA VAL LYS LEU GLN LEU
C C A A C A C T T A C G G C G G T A A A A T T A C A A C T T
        6610                6620                6630
                    ALA SER LEU LEU LEU THR ASN LYS HIS ASP
                    G C T T C C T T G T T G C T G A C C A A C A A G C A C G A T
                            6640                6650                6660

LYS HIS ALA GLN MET VAL LEU ASP GLU LEU
A A A C A C G C C C A A A T G G T G C T A G A T G A A C T C
        6670                6680                6690
                    LYS ASP ASP ALA HIS PHE LEU LYS LEU SER
                    A A A G A T G A T G C C C A C T T T T T A A A A T T A A G C
                            6700                6710                6720

LYS LYS GLU GLN ARG TRP VAL LEU SER GLN
A A A A A A G A G C A A A G A T G G G T G C T A T C G C A A
        6730                6740                6750
                    SER ARG TYR LEU HIS LYS LYS TYR LYS MET
                    A G T C G C T A T T T A C A T A A A A A A T A T A A A A T G
                            6760                6770                6780
```

FIG.2L'

```
GLY LEU ASP LEU GLY ILE ASN TYR LEU HIS
GGCTTGGATTTGGGCATCAACTATCTGCAT
         6790                    6800                    6810
                         LEU ASP ASN ILE ASN ALA ALA SER THR ILE
                         TTGGATAATATCAACGCCGCCTCCACCATC
                                  6820                    6830                    6840

THR GLN PRO ASN ILE LYS LYS ASP ALA PRO
ACCCAGCCCAATATTAAAAAAGATGCCCCA
         6850                    6860                    6870
                         LYS PRO ALA HIS GLY LEU ALA LEU SER LEU
                         AAACCTGCTCATGGGCTTGCCTTATCGCTT
                                  6880                    6890                    6900

GLY VAL ASN LYS TYR THR PRO LEU SER HIS
GGTGTGAATAAATACACGCCGCTTAGTCAT
         6910                    6920                    6930
                         GLY MET SER ILE TYR THR ALA LEU ASP VAL
                         GGCATGAGTATTTATACAGCCCTAGATGTT
                                  6940                    6950                    6960
```

FIG.2M'

```
ASP GLY LYS PHE TYR ASP ASP LYS SER HIS
GATGGTAAATTTTATGATGACAAAAGCCAC
    6970                    6990
                ASN GLU LEU ALA VAL PHE ALA HIS ALA GLY
                AATGAACTGGCGGTTTTTGCTCATGCTGGA
                    6980        7000        7020
                                    7010

LEU ARG LYS ASP HIS GLN LYS GLY TYR VAL
CTAAGAAAAGATCACCAAAAAGGTTATGTT
    7030                    7050
                ASP VAL VAL PRO PHE VAL GLY ARG ILE PHE
                GATGTCGTACCTTTTGTTGGGCGTATTTTT
                    7040        7060        7080
                                    7070

ALA THR ASN GLN GLN HIS GLY ARG LEU SER
GCCACCAATCAGCAGCATGGCAGATTATCC
    7090                    7110
                PRO ARG LYS ASP SER GLN GLY VAL ALA PHE
                CCCAGAAAAGACAGTCAGGGGCGTGGCGTTT
                    7100        7120        7140
                                    7130
```

FIG.2N'

```
GLY SER HIS HIS ARG ILE ASN ASP LYS TRP
GGCAGCCATCATCGGATCAATGATAAATGG
         7150              7160              7170
                                    GLN ASN ALA PHE PHE ALA ARG MET GLU LYS
                                    CAAAATGCGTTTTTTGCACGCATGGAAAAA
                                              7180              7190              7200

GLY ASN TYR THR GLU ARG TYR GLN GLY TYR
GGCAATTATACCGAGCGTTATCAAGGTTAT
         7210              7220              7230
                                    ASP GLY LYS ARG TYR HIS VAL ASN ASP THR
                                    GATGGCAAGCGTTATCATGTGAATGACACC
                                              7240              7250              7260

ILE LEU LEU GLN ASP GLY PRO ASN ARG ARG
ATTTGTTGCAAGATGGCCCAAATCGTCGT
         7270              7280              7290
                                    TYR SER LEU GLY VAL GLY TYR GLN LEU SER
                                    TACTCTTTGGGCGTGGGGTATCAGCTTAGC
                                              7300              7310              7320
```

FIG.2O'

HIS LEU GLN ASP ALA THR LYS SER SER HIS
CATCTGCAAGATGCAACAAAAAGCAGTCAT
           7330                    7340              7350

ALA THR LYS ILE HIS PHE GLY VAL LEU GLN
              GCCACAAAGATACATTTTGGGGTGTTGCAA
                       7360              7370              7380

ARG LEU PRO ASN GLY LEU THR VAL GLN GLY
AGATTGCCAAATGGTCTGACCGTGCAAGGT
           7390                    7400              7410

ARG VAL SER ALA GLU ARG GLU ARG TYR HIS
              AGAGTGAGTGCTGAGCGTGAGCGTTATCAT
                       7420              7430              7440

GLY LYS LEU LEU ARG LEU VAL ASN PRO ASP
GGTAAATTATTGCGTCTGGTTAATCCTGAT
           7450                    7460              7470

ASP VAL TYR ARG THR ASP LYS THR LEU THR
              GATGTGTATCGCACAGATAAAACCCTAACC
                       7480              7490              7500

FIG.2P'

| LEU | GLN | THR | SER | ILE | TRP | HIS | LYS | ASP | ILE |
|---|---|---|---|---|---|---|---|---|---|

C T A C A A A C C T C C A T T T G G C A C A A A G A C A T T
       7510                7520                7530

| HIS | TRP | LEU | GLY | LEU | THR | PRO | LYS | LEU | THR |
|---|---|---|---|---|---|---|---|---|---|

C A C T G G C T T G G A T T A A C G C C A A A G C T G A C T
       7540                7550                7560

| TYR | ARG | TYR | SER | LYS | ASN | ASN | SER | ASN | LEU |
|---|---|---|---|---|---|---|---|---|---|

T A T C G T T A C A G T A A A A A T A A C A G T A A C T T A
       7570                7580                7590

| PRO | ALA | LEU | TYR | SER | HIS | ASN | LYS | GLN | ASN |
|---|---|---|---|---|---|---|---|---|---|

C C A G C A C T T T A T A G C C A T A A C A A A C A A A A T
       7600                7610                7620

| PHE | TYR | LEU | GLU | LEU | GLY | ARG | SER | PHE | *** |
|---|---|---|---|---|---|---|---|---|---|

FIG.4A  *M. catarrhalis* Q8 lfr sequence

```
A A G C T T A G C A T G A T G G C A T C G G C T G A T T G T
        10              20              30
                                C T T T T T G C C T T G T T G T G T T T G T G G G A G T
                                        40              50              60

T G A T T G T A C T T A C C T T A G T G T G G A T G C T T
        70              80              90
                                        -35                   -10
                                G G G C T G A T T T A A T T A A A T T T A A T C A A A G C G
                                        100             110             120

G T C T T C A C A A C A C A C C A A A A C G A G A T A T C A C
        130             140             150
                        RBS
                        Lbp2
                        MET SER THR VAL LYS THR PRO HIS ILE PHE
                                C A T G A G T A C T G T C A A A A C C C C C A T A T T T
                                        160             170             180

TYR GLN LYS ARG THR LEU SER LEU ALA ILE    ALA SER ILE PHE ALA ALA LEU VAL MET THR
C T A C C A A A A A C G C A C C C T T A G C C C T T G C C A T
        190             200             210
                                C G C C A G T A T T T T T G C T G C C T T G G T G A T G A C
                                        220             230             240
```

FIG.4B

```
GLY CYS ARG SER ASP ASP ILE SER VAL ASN
AGGCTGCCGCTCTGATGACATCAGCGTCAA
         250                    260                    270
                                                         ALA PRO ASN VAL THR GLN LEU PRO GLN GLY
                                                         TGCACCCCAATGTTACCCCAGCTGCCCCAAGG
                                                                  280                    290                    300

THR VAL SER PRO THR PRO ASN THR GLY HIS
CACGGTTTCACCAACGCCGAACACAGGTCA
         310                    320                    330
                                                         ASP ASN ALA ASN THR ASN ASN GLN GLY
                                                         TGACAACGCCAATAACACCAACAATCAGGG
                                                                  340                    350                    360

ASN ASN THR ASP ASN SER THR THR
CAACAACACGGATAACAGCACCACCAAC
         370                    380                    390
                                                         ASP PRO ASN GLY ASP ASN ASN GLN LEU THR
                                                         TGACCCCAAATGGCGATAACAACCAACTGAC
                                                                  400                    410                    420
```

FIG.4C

```
GLN ALA GLN LYS THR ALA ALA ALA ALA GLY
ACAAGCGCAAAAACTGCCGCCGCCGCAGG
            430                  440        450

PHE PHE VAL MET GLY LYS ILE ARG ASP THR
          GTTTTTTGTGATGGGTAAAATTCGTGATAC
                        460            470            480

SER GLU LYS ASN ASP PRO ASP TYR SER ASP
CAGCGAAAAAATGACCCAGATTATAGTGAT
            490                  500        510

ASP LEU LYS GLN TRP LEU GLY LYS LEU
          TGATTTAAAACAGCAGTGGCTGGGCAAATT
                        520            530            540

TYR VAL GLY ILE ASP ALA HIS ARG PRO ASP
ATATGTTGGTATTGATGCCCATCGCCCAGA
            550                  560        570

GLY ILE GLY LYS GLY LYS ASN LEU ARG GLN
          TGGCATCGGAAAAGGTAAAAACTTGCGTCA
                        580            590            600
```

FIG.4D

```
PRO ILE THR ALA ASN ASP ILE LYS PRO LEU
GCCCATCACCGCCAATGACATCAAACCCTT
   610             620           630

TYR PHE ASN LYS PHE PRO ALA LEU SER ASP
       GTATTTTAACAAATTCCCTGCATTGTCTGA
            640           650           660

LEU HIS LEU ASP SER GLU ARG HIS ARG PHE
TTTGCACTTAGACAGTGAACGCCATCGTTT
   670             680           690

ASP PRO GLN LYS ILE ASN THR ILE LYS VAL
       TGACCCCCAAAAGATAAACACCATTAAAGT
            700           710           720

TYR GLY TYR GLY ASN LEU THR THR PRO SER
GTATGGTTATGGTAACTTAAACAACACCATC
   730             740           750

ASN ASN ASN THR HIS ILE ASN HIS GLN GLN
       CAACAACAACACTCACATCAATCATCAGCA
            760           770           780
```

FIG.4E

```
ALA ASP ASN LYS LYS ASN ASN LYS PRO VAL
AGCTGATAATAAGAAAAATAACAAGCCTGT
            790              800         810
                ASP PRO TYR GLU ASN ILE ARG PHE GLY TYR
                TGACCCTTATGAAAATATCCGTTTTGGGTA
                          820              830              840

LEU GLU LEU GLN GLY SER SER LEU THR GLN
TCTTGAACTACAAGGAAGCAGCCTGACCCA
            850              860         870
                LYS ASN ALA ASP ASN GLN ASN GLU GLN ASP
                AAAAAATGCCGATAATCAAAATGAGCAAGA
                          880              890              900

ARG ILE PRO LYS PRO MET PRO ILE LEU PHE
CCGCATTCCCAAACCCATGCCCATTTTGTT
            910              920         930
                TYR HIS GLY GLU ASN ALA SER SER GLN LEU
                TTATCATGGAGAAAACGCCAGCAGCCAGCT
                          940              950              960
```

FIG. 4F

```
PRO SER ALA GLY LYS PHE ASN TYR THR GLY
GCC CAG CGC TGG TAA AAT TTA ACT ACA CAG G
            970         980         990

ASN TRP LEU TYR LEU SER ASP VAL LYS LYS
            CAA CTG GCT GTA CCT AAG TGA TGT CAA AAA
                1000        1010        1020

ARG PRO ALA LEU SER ALA SER ALA SER ASP GLU ARG
ACG CCC CTG CCC TTT CAG CAT CAG CAT CAG ATG AGC G
            1030        1040        1050

VAL GLY VAL TYR LEU ASN ALA SER GLY LYS
            AGT GGG GGT CTA TCT CAA TGC CAG TGG CAA
                1060        1070        1080

ALA ASN GLU GLY ASP VAL VAL SER ALA ALA
AGC CAA CGA GGG CGA TGT CGT CAG TGC CGC
            1090        1100        1110

HIS ILE TYR LEU ASN GLY PHE GLN TYR LYS
            CCA CAT TTA TCT AAA CGG CTT TCA ATA TAA
                1120        1130        1140
```

FIG. 4G

```
HIS THR PRO ALA THR TYR GLN VAL ASP PHE
GCACACGCCCTGCCACTTATCAGGTGGATTT
              1150              1160              1170

ASP THR ASN SER LEU THR GLY LYS LEU SER
                              TGACACAAACTCATTAACAGGCAAGCTGTC
                                  1180              1190              1200

TYR TYR ASP ASN PRO ASN GLN GLN ASN ASN
CTATTATGACAATCCCAATCAGCAAAATAA
              1210              1220              1230

LYS GLY GLU TYR LEU LYS SER GLN PHE ASP
                              TAAAGGCGAATATCTCAAAAGCCAATTTGA
                                  1240              1250              1260

THR THR LYS LYS VAL ASN GLU THR ASP VAL
CACTACCAAAAAAGTCAATGAAACCGATGT
              1270              1280              1290

TYR GLN ILE ASP ALA LYS ILE ASN GLY ASN
                              GTATCAAATTGATGCCAAAATCAACGGTAA
                                  1300              1310              1320
```

FIG.4H

```
ARG PHE VAL GLY THR ALA LYS SER LEU VAL
CCG CTT TGT CGG TAC GGG CCA AAT CTT TGG T
            1330                    1340                    1350
                                                    ASN GLU LYS THR GLN THR ALA PRO PHE ILE
                                                    T AAT GAG AAA ACA CAA ACC GCA CCT TTT AT
                                                              1360                    1370                    1380

LYS GLU LEU PHE SER LYS LYS ALA ASN PRO
CAA AGA GCT GTT CTC CAA AAA GCC AAC CC
            1390                    1400                    1410
                                                    ASN ASN PRO ASN PRO ASN SER ASP THR LEU
                                                    C AAT AAC CCA AAC CCT AAT TCA GAC ACG CT
                                                              1420                    1430                    1440

GLU GLY GLY PHE TYR GLY GLU SER GLY ASP
AGA AGG CGG ATT TTA TGG TGA GTC GGG CGA
            1450                    1460                    1470
                                                    GLU LEU ALA GLY LYS PHE LEU SER ASN ASP
                                                    T GAG CTG GCG GGT AAA TTT TTA TCC AAT GA
                                                              1480                    1490                    1500
```

FIG. 4I

```
ASN ALA SER TYR VAL VAL PHE GLY GLY LYS
CAACGCATCTTATGTGTGGTCTTTGGTGGCAA
            1510              1520          1530
                    ARG ASP LYS THR THR LYS PRO VAL ALA THR
                    ACGAGACAAAACGACTAAACCTGTCGCCAC
                         1540           1550           1560

LYS THR VAL TYR PHE SER ALA GLY PHE GLU
AAAAACGGTGTATTTTAGTGCAGGCTTTGA
            1570              1580          1590
                    LYS PRO SER THR SER PHE VAL ASP ASN GLU
                    AAAACCCAGCACCAGTTTTGTGGATAATGA
                         1600           1610           1620

THR ILE GLY GLY ILE ILE ASP ARG LYS GLY
AACGATTGGTGGAATTATTGACCGTAAAGG
            1630              1640          1650
                    LEU ASN ASN HIS ILE ASN GLU ASP GLU ILE
                    GTTAAATAATCACATTAATGAAGATGAAAT
                         1660           1670           1680
```

FIG.4J

```
ILE PRO SER ASP ASP SER TYR TYR GLY TYR
TATTCCCAGTGATGATAGTTATTATGGATA
         1690              1700            1710
                    THR TRP GLY LYS PRO GLU LYS GLN PHE THR
                    TACTTGGGGCAAGCCAGAGAAGCAGTTCAC
                         1720            1730            1740

LYS LYS VAL SER SER SER THR GLN VAL VAL
CAAAAAAGTCAGCAGCACCCAAGTCGT
         1750            1760            1770
                    PRO ALA TYR PHE GLY GLN HIS ASP LYS PHE
                    GCCAGCTTATTTTGGGCAACATGATAAATT
                         1780            1790            1800

TYR PHE ASN GLY ASN TYR TYR ASP LEU SER
TTATTTTAATGGCAACTATTATGACCTATC
         1810            1820            1830
                    ALA SER ARG VAL ASP LYS LEU ALA PRO ALA
                    AGCCAGTCGTGTTGATAAATTAGCCCCTGC
                         1840            1850            1860
```

FIG.4K

```
ASP ALA VAL LYS ALA ASN GLN SER ILE LYS
CGATGCTGTCAAAGCCAACCAATCCATTAAA
            1870              1880            1890

GLU LYS TYR PRO ASN ALA THR LEU ASN LYS
              AGAAAAATACCCTAATGCCACACTAAATAA
                    1900            1910            1920

ASP ASN GLN VAL THR ALA ILE VAL LEU GLN
GGACAACCAAGTTACCGCCATCGTGCTACA
            1930            1940            1950

GLU ALA LYS ASP ASN LYS PRO TYR THR ALA
              AGAAGCCAAAGATAATAAGCCTTATACCGC
                    1960            1970            1980

ILE ARG ALA LYS SER TYR GLN HIS ILE SER
CATTCGTGCCAAAAGCTATCAGCACATCAG
            1990            2000            2010

PHE GLY GLU THR LEU TYR ASN ASP ALA ASN
              TTTTGGCGAGACGCTGTATAACGATGCCAA
                    2020            2030            2040
```

FIG.4L

```
GLN THR PRO THR ARG SER TYR PHE VAL GLN
C C A A C C C C A A C A C G C A G T T A T T T T G T G C A
              2050                          2060                    2070
                          GLY GLY ARG ALA ASP THR SER THR LEU
                          A G G C G G T A G G G C A G A T A C C A G C A C A A C T T T
                                    2080                    2090                    2100

PRO GLN ALA GLY LYS PHE THR TYR ASN GLY
G C C C C A G G C A G G T A A A T T C A C T T A C A A C G G
              2110                          2120                    2130
                          LEU TRP ALA GLY TYR LEU THR GLN LYS LYS
                          T C T T T T G G G C A G G C T A C C C T G A C C C A A A A A A A
                                    2140                    2150                    2160

ASP LYS GLY TYR SER ASP ASN ALA GLU THR
G G A C A A A G G T T A T A G C G A T A A T G C A G A A A C
              2170                          2180                    2190
                          ILE LYS GLU GLY LYS GLY HIS PRO GLY TYR LEU
                          C A T C A A G G A A A A A G G T C A T C C A G G T T A T C T
                                    2200                    2210                    2220
```

FIG.4M

```
LEU THR GLU ASN PHE THR PRO GLU ASP ASP
GTTAACCGAAAACTTCACCCCAGAAGATGA
            2230                2240            2250
                                ASP ASP LEU THR ALA SER ASP ASP SER
                                TGACGATGATTTGACCGCATCTGATGATTC
                                        2260            2270            2280

GLN ASP ASN THR HIS GLY ASP ASP
ACAAGATGATAATACACATGGCGATGATGA
            2290            2300            2310
                                LEU ILE ALA SER ASP SER GLN ASP ASP
                                TTTGATTGCATCTGATGATTCACAAGATGA
                                        2320            2330            2340

ASP ALA ASP GLY ASP ASP SER ASP ASP
TGACGCAGATGGAGATGACGATTCAGATGA
            2350            2360            2370
                                LEU GLY ASP GLY ALA ASP ASP ALA ALA
                                TTTGGGTGATGGTGCAGATGATGACGCCGC
                                        2380            2390            2400
```

FIG.4N

```
GLY LYS VAL TYR HIS ALA GLY ASN ILE ARG
AGGCAAAGTGTATCATGCAGGTAATATTCG
         2410              2420              2430
                    PRO GLU PHE GLU ASN LYS TYR LEU PRO ILE
                    CCCTGAATTTGAAAACAAATACTTGCCCAT
                              2440              2450              2460

ASN GLU PRO THR HIS GLU LYS THR PHE ALA
TAATGAGCCTACTCATGAAAAAACCTTTGC
         2470              2480              2490
                    LEU ASP GLY LYS ASN LYS ALA LYS PHE GLU
                    CCTAGATGGTAAAAATAAAGCTAAGTTTGA
                              2500              2510              2520

VAL ASP PHE ASN THR ASN SER LEU THR GLY
AGTGGATTTTAACACCAACAGCCTAACTGG
         2530              2540              2550
                    LYS LEU ASN ASP GLU ARG GLY ASP ILE VAL
                    TAAATTAAACGATGAGAGAGGTGATATCGT
                              2560              2570              2580
```

FIG.4O

```
PHE ASP ILE LYS ASN GLY LYS ILE ASP GLY
CTTTGATATCAAAAATGGCAAAATTGATGG
          2590                    2600                   2610
                        THR GLY PHE THR ALA LYS ALA ASP VAL PRO
                        CACAGGATTTACCGCCAAAGCCGATGTGCC
                                 2620                    2630                    2640

ASN TYR ARG GLU GLU VAL GLY ASN ASN GLN
AAACTATCGTGAAGAAGTGGGTAACAACCA
          2650                    2660                   2670
                        GLY GLY GLY PHE LEU TYR ASN ILE LYS ASP
                        AGGTGGCGGTTTCTTATACAACATCAAAGA
                                 2680                    2690                    2700

ILE ASP VAL LYS GLY GLN PHE PHE GLY THR
TATTGATGTTAAGGGGCAATTTTTTGGCAC
          2710                    2720                   2730
                        ASN GLY GLU GLU LEU ALA GLY GLN LEU HIS
                        AAATGGCGAAGAGTTGGCAGGACAGTTACA
                                 2740                    2750                    2760
```

FIG. 4P

```
HIS ASP LYS GLY ASP GLY ILE ASN ASP THR
TCATGACAAAGGCGATGGCATCAATGACAC
        2770                    2780                    2790
                            ALA GLU LYS ALA GLY ALA VAL PHE GLY ALA
                            CGCCGAAAAGCAGGGGCTGTCTTTGGGGC
                            2800        2810        2820

VAL LYS ASP LYS ***
TGTTAAAGATAAATAAAGCCCCCCCTTCATC          ATCGTTTAGTCGCTTGACCGACAGTTGATG
        2830        2840        2850              2860        2870        2880

ACGCCCTTGGCAATGTCTTAAAAACAGCACT          TTGAAACAGTGCCCTTGGGCGAATTCTTGGA
        2890        2900        2910              2920        2930        2940

TAAATGCACCAGATTTGCCTTGGGCTAATA
        2950        2960        2970
                        -10                         -35
                TCTTGATAAAACATCGCCATAAAATAGAAA
                        2980        2990        3000
```

FIG. 4Q

```
                              Lbp1
                              MET SER LYS
        RBS
ATAAAGTTTAGGATTTTTTATGTCAAAA
        3010                  3020           3030

SER ILE THR LYS THR GLN THR PRO SER VAL H
    TCTATCACAAAAACACAAACACCATCAGTCC
                3040              3050           3060

IS  THR MET THR HIS ARG LEU ASN LEU
ATACCATGACCACGCACCGCTTAAACCTTG
        3070              3080           3090
    ALA ILE LYS ALA ALA LEU PHE GLY VAL ALA V
    CCATCAAAGCGGCGTTATTTGGTGTGGCAG
                3100              3110           3120

AL  LEU PRO LEU SER VAL TRP ALA GLN GLU
TTTACCCCTATCCGTCTGGGCGCAAGAGA
        3130              3140           3150
    ASN THR GLN THR ASP ALA ASN SER ASP ALA L
    ACACTCAGACAGATGCCAACTCTGATGCCA
                3160              3170           3180
```

FIG.4R

```
YS  ASP THR LYS THR PRO VAL VAL TYR LEU
  A A G A C A C A A A A C C C C T G T C G T C T A T T T A G
                        3190                    3200                    3210
                                        ASP ALA ILE THR VAL THR ALA ALA PRO SER  A
                                      A T G C C A T C A C G G T A A C C G C C C C A T C T G
                                                      3220                    3230                    3240

LA  PRO VAL SER ARG PHE ASP THR ASP VAL
  C C C C T G T T T C T C G G T T T G A C A C C G A T G T A A
                        3250                    3260                    3270
                                        THR GLY LEU GLY LYS THR VAL LYS THR ALA  A
                                      C A G G G C T T G G C A A A A C C G T C A A A A C C G C T G
                                                      3280                    3290                    3300

SP  THR LEU ALA LYS GLU GLN VAL GLN GLY
  A C A C G C T G G C A A A A G A A C A A G T A C A G G G C A
                        3310                    3320                    3330
                                        ILE ARG ASP LEU VAL ARG TYR GLU THR GLY  V
                                      T T C G T G A T T T G G T G C G T T A T G A A A C T G G G G
                                                      3340                    3350                    3360
```

FIG.4S

```
AL  SER  VAL  VAL  GLU  GLN  GLY  ARG  GLY  GLY
T G A G T G T G G T T G A G C A G G G C G T G G T G G C A
                         3370                    3380                    3390
         SER  SER  GLY  PHE  ALA  ILE  HIS  GLY  VAL  ASP  L
         G C A G C G G A T T T G C C A T T C A T G G C G T G G A T A
                         3400                    3410                    3420

YS  ASN  ARG  VAL  GLY  ILE  THR  VAL  ASP  GLY
A A A A C C G A G T G G G C A T T A C C G T A G A T G G C A
                         3430                    3440                    3450
         ILE  ALA  GLN  ILE  GLN  SER  TYR  LYS  ASP  GLU  S
         T T G C C C A A A T T C A A T C C T A C A A A G A C G A A T
                         3460                    3470                    3480

ER  THR  LYS  ARG  ALA  GLY  ALA  GLY  SER  GLY
C C A C T A A G C G A G A G C T G G G G G C A G G C T C T G G G G G
                         3490                    3500                    3510
         ALA  MET  ASN  GLU  ILE  GLU  ILE  GLU  ASN  ILE  A
         C G A T G A A C G A G A T A G A G A T T G A A A A C A T T G
                         3520                    3530                    3540
```

FIG.4T

```
LA  ALA  VAL  ALA  ILE  ASN  LYS  GLY  GLY  ASN
CCGCCGTTGCCATCAATAAAGGCGGTAATG
       3550              3560              3570
                              ALA  LEU  GLU  ALA  GLY  SER  GLY  ALA  LEU  GLY  G
                              CCTTAGAAGCAGGCTCTGGTGCCGTTGGGTG
                                   3580              3590              3600

LY  SER  VAL  ALA  PHE  HIS  THR  LYS  ASP  VAL
GTTCGGTGGCGTTTCATACCAAAGATGTGA
       3610              3620              3630
                              SER  ASP  VAL  LEU  LYS  SER  GLY  ASN  ASN  LEU  G
                              GCGATGTCTTAAAATCTGGTAACAATCTTG
                                   3640              3650              3660

LY  ALA  GLN  SER  LYS  THR  THR  TYR  ASN  SER
GTGCTCAAAGCAAAACCACTTATAACAGCA
       3670              3680              3690
                              LYS  ASN  ASP  HIS  PHE  SER  GLN  THR  LEU  ALA  A
                              AAAATGACCATTTTAGTCAGACGCTGGCAG
                                   3700              3710              3720
```

FIG.4U

```
LA  ALA GLY LYS THR GLU ARG VAL GLU ALA
    CGGCAGGTAAAACCGAGCGTGTGGAAGCGA
             3730              3740      3750
    MET VAL GLN TYR THR TYR ARG LYS GLY LYS G
    TGGTGCAATATACCTACCGTAAAGGCAAAG
         3760              3770              3780

LU  ASN LYS ALA HIS SER ASP LEU ASN GLY
    AAACAAAGCACACAGCGACCTAAATGGCA
             3790              3800      3810
    ILE ASN GLN SER LEU TYR ARG LEU GLY ALA T
    TCAACCAAAGCCTATATCGCTTGGGTGCAT
         3820              3830              3840

RP  GLN GLN LYS TYR ASP LEU ARG LYS PRO
    GGCAACAAAAATATGATTTAAGAAAGCCTA
             3850              3860      3870
    ASN GLU LEU PHE ALA GLY THR SER TYR ILE T
    ACGAACTGTTTGCAGGCACAAGCTATATCA
         3880              3890              3900
```

FIG. 4V

```
HR  GLU  SER  CYS  LEU  ALA  SER  ASP  ASP  PRO
C C G A A A G C T G T T T G G C A A G T G A T G A C C C A A
         3910                3920              3930
                    LYS  SER  CYS  VAL  GLN  TYR  PRO  TYR  VAL  TYR  T
                    A A A G C T G C G T A C A A T A C C C T T A T G T C T A C A
                             3940              3950              3960

HR  LYS  ALA  ARG  PRO  ASP  GLY  ILE  GLY  ASN
C C A A A G C C C G A C C A G A T G G T A T C G G C A A T C
         3970                3980              3990
                    ARG  ASN  PHE  SER  GLU  LEU  SER  ASP  ALA  GLU  L
                    G C A A T T T T T C T G A G T T A A G C G A T G C T G A A A
                             4000              4010              4020

YS  ALA  GLN  TYR  LEU  ALA  SER  THR  HIS  PRO
A A G C A C A A T A T T T G G C G T C C A C G C A C C C C C
         4030                4040              4050
                    HIS  GLU  VAL  VAL  SER  ALA  LYS  ASP  TYR  THR  G
                    A T G A G G T T G T C T C T G C C A A A G A T T A T A C A G
                             4060              4070              4080
```

FIG.4W

```
LY  THR TYR ARG LEU LEU PRO ASP PRO MET
G C A C T T A T C G G T T G T T A C C T G A C C C C A T G G
                    4090                    4100         4110
                                        ASP TYR ARG SER ASP SER TYR LEU ALA ARG  L
                                        A C T A T C G T T C A G A C T C G T A T T T G G C A C G C C
                                                    4120                    4130                    4140

EU  ASN ILE LYS ILE THR PRO ASN LEU VAL
T T A A C A T C A A A A T C A C C C C A A A T T T G G T C A
                    4150                    4160         4170
                                        SER LYS LEU LEU LEU GLU ASP THR LYS GLN  T
                                        G T A A A C T G T T A T T A G A A G A C A C C A A G C A A A
                                                    4180                    4190                    4200

HR  TYR ASN ILE ARG ASP MET ARG HIS CYS  S
C A T A C A A C A T T C G T G A T A T G C G T C A T T G T A
                    4210                    4220         4230
                                        ER  TYR HIS GLY ALA ARG LEU GLY ASN ASP  G
                                        G T T A T C A T G G G G C A A G A T T G G G C A A T G A C G
                                                    4240                    4250                    4260
```

FIG.4X

```
LY  LYS PRO ALA ASN GLY GLY SER ILE VAL
GTAAGCCTGCCAATGGCGGCTCCATTGTCC
             4270            4280            4290
                LEU CYS ASP TYR ASP TYR GLN GLU TYR LEU ASN A
                TTTGCGATGATTATCAAGAGTATCTAAATG
                    4300            4310            4320

LA  ASN ASP ALA SER GLN ALA SER PHE ARG
CCAATGACGGCATCACAAGCATCATTTAGAC
             4330            4340            4350
                PRO GLY ALA ASN ASP ALA PRO ILE PRO LYS L
                CAGGGGCTAATGACGCCCCATTCCAAAAC
                    4360            4370            4380

EU  ALA TYR ALA ARG SER SER VAL PHE ASN
TGGCTTATGCCAGAAGCAGTGTGTTTAACC
             4390            4400            4410
                GLN GLU HIS GLY LYS THR ARG TYR GLY LEU G
                AAGAGCATGGCAAAACTCGCTATGGGTTAG
                    4420            4430            4440
```

FIG.4Y

```
LY  PHE GLU PHE LYS PRO ASP THR PRO TRP
GTTTGAGTTTAAGCCTGACACGCCATGGT
        4450              4460              4470
                    PHE LYS GLN ALA LYS LEU ASN LEU HIS GLN G
                    TTAAACAAGCAAAATTAAACCTACATCAAC
                          4480              4490              4500

LN  ASN ILE GLN ILE ILE ASN HIS ASP ILE
AAAATATCCAAATCATTAACCATGACATTA
        4510              4520              4530
                    LYS SER CYS SER GLN TYR PRO LYS VAL A
                    AAAAATCGTGCAGCCAATATCCCAAGGTGG
                          4540              4550              4560

SP  LEU ASN CYS GLY ILE SER GLU ILE GLY
ATTTAAATTGTGGCATCAGTGAAATTGGGC
        4570              4580              4590
                    HIS TYR GLU TYR GLN ASN ASN TYR ARG TYR L
                    ATTATGAATATCAAAACAATTACCGTTATA
                          4600              4610              4620
```

FIG. 4Z

```
YS  GLU GLY ARG THR SER LEU THR GLY LYS
AAG AAG GGC GTA CCA GTT TGA CAG GCA AAC
        4630                    4640               4650
                    LEU ASP PHE ASN PHE ASP LEU LEU GLY GLN H
                    TTG ATT TTA ATT TTT GAC CTG CTG GGC CAG C
                            4660              4670              4680

IS  ASP LEU THR VAL LEU ALA GLY ALA ASP
ACG ATT TGA CGG TGT TGG CTG GTG CAG ATA
        4690                    4700               4710
                    LYS VAL LYS SER GLN PHE ARG ALA ASN ASN P
                    AAG TTA AAA GCC AAT TTC GTT GCC AAC AAC C
                            4720              4730              4740

RO  ARG ARG THR ILE ILE ASP THR THR GLN
CCA GAC GCA CAA TCA TTG ACA CCA CCC AAG
        4750                    4760               4770
                    GLY ASP ALA ILE ILE ASP GLU SER THR LEU T
                    GCG ATG CCA TCA TTG ATG AAA GCA CGC TGA
                            4780              4790              4800
```

FIG.4A'

```
HR  ALA GLN GLU GLN ALA LYS PHE LYS GLN
    CAGCACAGGAGCAAGCCAAATTTAAGCAAT
           4810          4820      4830
    SER GLY ALA ALA TRP ILE VAL LYS ASN ARG  L
    CAGGGGCAGCATGGATTGTCAAAAATCGCT
         4840          4850          4860

EU  GLY ARG LEU GLU GLU LYS ASP ALA CYS
    TAGGACGCTTAGAAGAAAAGACGCCCTGTG
           4870          4880      4890
    GLY ASN ALA ASN GLU CYS GLU ARG ALA PRO  I
    GCAATGCCAATGAATGTGAACGCGCGCCCA
         4900          4910          4920

LE  HIS GLY SER ASN GLN TYR VAL GLY ILE
    TTCATGGCAGTAACCAATATGTGGGCATTA
           4930          4940      4950
    ASN ASN LEU TYR THR PRO ASN ASP TYR VAL  A
    ACAACCTTTATACACCAAATGATTATGTGG
         4960          4970          4980
```

FIG.4B'

```
SP  LEU SER PHE GLY GLY ARG LEU ASP LYS
    ATTTAAGTTTTGGTGGACGCTTGGATAAAC
                4990                    5010
                        GLN ARG ILE HIS SER THR ASP SER ASN ILE I
                        AACGCATTCACAGCACCGATTCAAACATCA
                                5020            5030            5040

LE  SER LYS THR TYR ASN LYS SER TYR
    TCAGCAAAACTTACACCAACAAAAGCTATA
                5050                    5070
                        ASN PHE GLY ALA ALA VAL HIS LEU THR PRO A
                        ATTTTGGAGCGGCGGTTCATCTGACACCTG
                                5080            5090            5100

SP  PHE SER LEU LEU TYR LYS THR ALA LYS
    ATTTAGCCTGTGTTGTATAAAACTGCCAAAG
                5110                    5130
                        GLY PHE ARG THR PRO SER PHE TYR GLU LEU T
                        GCTTTCGTACGCCAAGTTTTATGAACTGT
                                5140            5150            5160
```

FIG.4C'

```
YR  ASN TYR ASN SER THR ALA ALA GLN HIS
    ACAACTATAACAGCACCGCCGCCCAGCATA
                 5170              5180              5190
    LYS ASN ASP PRO GLU ASP VAL SER PHE PRO LYS A
    AAAATGACCCCTGATGTGTCTTTTCCCAAAC
                 5200              5210              5220

RG  ALA VAL ASP VAL LYS PRO GLU THR SER
    GAGCGGGTTGATGTCAAACCTGAAACTTCCA
                 5230              5240              5250
    ASN THR ASN GLU TYR GLY PHE ARG TYR GLN H
    ATACCAATGAATACGGCTTTCGCTATCAGC
                 5260              5270              5280

IS  PRO TRP GLY ASP ILE GLU MET SER MET
    ACCCTTGGGGGGATATTGAGATGAGCATGT
                 5290              5300              5310
    PHE LYS SER ARG TYR LYS ASP MET LEU ASP L
    TCAAAAGCCGTTACAAGGACATGTTAGATA
                 5320              5330              5340
```

FIG.4D'

```
YS  ALA  ILE  PRO  ASN  LEU  THR  LYS  ALA  GLN
    AAGCCATACCGAACCTAACCAAAGCCCAGC
              5350              5360              5370
              GLN  GLU  TYR  CYS  LYS  ALA  HIS  LEU  ASP  SER  A
              AAGAGTATTGTAAGGCTCATTTGGATTCCA
                        5380              5390              5400

SN  GLU  CYS  VAL  GLY  ASN  PRO  PRO  THR  PRO
    ATGAATGTGTTGGTAATCCACCACGCCCA
              5410              5420              5430
              LYS  THR  SER  ASP  GLU  VAL  PHE  ALA  ASN  LEU  T
              AAACCAGTGATGAGGTATTTGCCAACTTAT
                        5440              5450              5460

YR  ASN  ALA  THR  ILE  LYS  GLY  VAL  SER  VAL
    ATAATGCCACCATCAAAGGGGTGAGTGTCA
              5470              5480              5490
              LYS  GLY  LYS  LEU  ASP  LEU  HIS  ALA  MET  THR  S
              AAGGCAAACTGGATTTGCATGCCATGACAT
                        5500              5510              5520
```

FIG.4E'

```
ER  LYS  LEU  PRO  ASP  GLY  LEU  GLU  MET  THR
C A A A A C T G C C A G A T G G T C T T G A A A T G A C C T
                  5530                        5540                        5550
                                    LEU  GLY  TYR  GLY  HIS  THR  LYS  LEU  GLY  LYS  P
                                    T G G G T T A T G G T C A T A C C A A A T T G G G G A A A T
                                                      5560                        5570                        5580

HE  ASP  TYR  ILE  ALA  PRO  LYS  ASP  ALA  ASP
T T G A T T A C A T T G C A C C C A A A G A T G C C G A T G
                  5590                        5600                        5610
                                    GLY  TRP  TYR  GLN  ALA  ARG  PRO  ALA  PHE  TRP  A
                                    G T T G G T A T C A G G C T C G C C C T G C T T T T G G G
                                                      5620                        5630                        5640

SP  ALA  ILE  THR  PRO  ALA  ARG  TYR  VAL  VAL
A T G C C A T C A C C C C A G C G C G C T A T G T G G T C G
                  5650                        5660                        5670
                                    GLY  LEU  ASN  TYR  ASP  HIS  PRO  SER  GLN  VAL  T
                                    G T C T A A A C T A T G A C C A C C C C A G T C A A G T A T
                                                      5680                        5690                        5700
```

FIG.4F'

```
RP  GLY ILE GLY THR THR LEU THR HIS SER
G G G G C A T T G G C A C A A C T T T A A C G C A C A G C A
    5710                  5720                  5730
                LYS GLN LYS ASP GLU ASN GLU LEU SER ALA  L
                A A C A A A A A G A T G A A A A T G A G C T A A G T G C C C
                            5740                  5750                  5760

EU  ARG ILE ARG ASN GLY LYS ARG GLU ILE
T T A G A A T C C G A A A T G G C A A A A G A G A A A T A C
    5770                  5780                  5790
                GLN THR LEU THR HIS THR ILE PRO LYS ALA  T
                A A A C C T T A A C G C A C A C A A T A C C C A A A G C C T
                            5800                  5810                  5820

YR  THR LEU LEU ASP MET THR GLY TYR TYR
A T A C C T T A C T G G A C A T G A C A G G C T A T T A T A
    5830                  5840                  5850
                SER PRO THR GLU SER ILE THR ALA ARG LEU  G
                G C C C A A C T G A G A G C A T C A C C G C T C G T C T T G
                            5860                  5870                  5880
```

FIG.4G'

```
LY  ILE ASN ASN VAL LEU ASN THR ARG TYR
GTATCAACAATGTATTAAACACCCGCTA
        5890            5900
                              THR THR TRP GLU ALA ALA ARG GLN LEU PRO S
                              CACCACATGGGAAGCGGCACGCCAACTGCCCCA
                                      5910        5920        5930       5940

ER  GLU ALA ALA SER SER THR GLN SER THR
GCGAAGCTGCAAGCAGTACCCAATCAACCC
        5950            5960            5970
                              ARG TYR ILE ALA PRO GLY ARG SER TYR PHE A
                              GTTACATTGCACCAGGTCGCAGTTACTTTG
                                      5980        5990        6000

ORF 3
                MET THR
LA  SER LEU GLU MET LYS PHE ***
CCAGTCTTGAAATGAAGTTTTAATATGACC
        6010            6020            6030
                              CYS LEU PRO LYS THR ASN PRO ALA LEU LYS
                              TGTTTACCAAAGACCAACCCTGCTTTAAAA
                                      6040        6050        6060
```

FIG.4H'

```
VAL LYS HIS ARG PHE LEU LYS GLN VAL LEU
GTCAAGCACAGATTTTAAAGCAGGTGCTG
        6070            6080          6090
                    LEU LEU CYS VAL ASP THR LEU THR ALA
                    TTATTGCTTTGTGTTGATACATTAACAGCA
                        6100          6110          6120

GLN ALA TYR ALA HIS SER HIS HIS THR PRO
CAGGGCGTACGCCCACAGCCATCATACGCCC
        6130          6140          6150
                    ILE HIS THR PRO THR HIS GLU LEU SER SER
                    ATTCATACACCCACGCATGAGCTGTCATCT
                        6160          6170          6180

ALA ASP ALA LEU SER ASP GLU GLY LEU GLY
GCTGATGCTTTATCAGATGAAGGCTTGGGT
        6190          6200          6210
                    LYS ASP LEU GLY SER LEU ASP SER PRO ASP
                    AAGGATTTGGGCAGTTTGGACAGCCCAGAT
                        6220          6230          6240
```

FIG. 4I'

```
GLY LEU GLY ASP GLY LEU GLY ASP GLY LEU
GGTTTGGGTGATGGTTTAGGCGATGGTTTG
         6250                    6260                    6270
              GLY ASP GLY LEU LYS SER ASP LYS THR PRO
              GGTGATGGCTTAAAAAGTGATAAACCCCT
                       6280                    6290                    6300

LEU PRO ILE ASN ALA LEU THR VAL ASN GLN
TTACCCATCAACGCCCTTGACCGTTAATCAG
         6310                    6320                    6330
              SER ASN GLU SER GLN PRO ALA PRO PRO SER
              AGCAATGAGAGCCAGCCCTGCCCCACCGAGC
                       6340                    6350                    6360

VAL ASP VAL ASN PHE LEU LEU ALA GLN PRO
GTAGATGTCAATTTTTTACTTGCCCAGCCA
         6370                    6380                    6390
              GLU ALA PHE TYR HIS VAL PHE HIS GLN ALA
              GAGGCATTTTATCATGTCTTTCATCAAGCG
                       6400                    6410                    6420
```

FIG.4J'

```
ILE VAL GLN ASP ASP VAL ALA THR LEU ARG
ATTGTGCAAGATGATGTGGCAACATTACGC
              6430                6440                6450

LEU LEU LEU PRO PHE TYR ASP ARG LEU PRO
                    TTGTTATTGCCATTTTATGACCGCCTGCCT
                          6460                6470                6480

ASP ASP TYR GLN ASP ASP VAL LEU LEU LEU
GATGATTATCAAGATGATGTTTTGTTA
              6490                6500                6510

PHE ALA GLN SER LYS LEU ALA LEU SER ASP
                    TTTGCCCAAAGTAAACTTGCCCTAAGTGAT
                          6520                6530                6540

GLY ASN THR LYS LEU ALA LEU ASN LEU LEU
GGCAATACCAAATTGGCATTGAATCTGCTG
              6550                6560                6570

THR ASP LEU SER ASN LYS GLU PRO THR LEU
                    ACCGATTTGAGTAACAAAGAGCCAACACTT
                          6580                6590                6600
```

FIG.4K'

```
THR ALA VAL LYS LEU LEU GLN LEU ALA SER LEU
ACGGCGGGTAAAATTACAACTTGCTTCCTTG
              6610                    6620                   6630
                                    LEU LEU THR ASN LYS HIS ASP LYS HIS ALA
                                    TTGCTGACCAACAAGCACGATAAACACGCC
                                         6640                 6650                  6660

GLN MET VAL LEU ASP GLU LEU LYS ASP ASP
CAAATGGTGCTAGATGAACTCAAAGATGAT
              6670                    6680                   6690
                                    ALA HIS PHE LEU LYS LEU SER LYS LYS GLU
                                    GCCCACTTTTTAAAATTAAGCAAAAAGAG
                                         6700                 6710                  6720

GLN ARG TRP VAL LEU SER GLN SER ARG TYR
CAAAGATGGGTGCTATCGCAAAGTCGCTAT
              6730                    6740                   6750
                                    LEU HIS LYS LYS TYR LYS MET GLY LEU ASP
                                    TTACATAAAAAATATAAAATGGGCTTGGAT
                                         6760                 6770                  6780
```

FIG.4L'

```
LEU GLY ILE ASN TYR LEU HIS LEU ASP ASN
TTGGGCATCAACTATCTGCATTTGGATAAT
              6790                    6800                    6810
                              ILE ASN ALA ALA SER THR ILE THR GLN PRO
                              ATCAACGCCGCCTCCACCATCACCCAGCCC
                                      6820                    6830                    6840

ASN ILE LYS LYS ASP ALA PRO LYS PRO ALA
AACATTAAAAAAGATGCCCCAAAACCTGCT
              6850                    6860                    6870
                              HIS GLY LEU ALA LEU SER LEU GLY VAL ASN
                              CATGGGCTTGCCTTATCGCTTGGTGTGAAT
                                      6880                    6890                    6900

LYS TYR THR PRO LEU SER HIS GLY MET SER
AAATACACGCCGCTTAGTCATGGCATGAGT
              6910                    6920                    6930
                              ILE TYR THR ALA LEU ASP VAL ASP GLY LYS
                              ATTTATACAGCCCTAGATGTTGATGGTAAA
                                      6940                    6950                    6960
```

FIG.4M'

```
PHE TYR ASP ASP LYS SER HIS ASN GLU LEU
TTTTATGATGACAAAAGCCACAATGAACTG
    6970              6980          6990
                ALA VAL PHE ALA HIS ALA GLY LEU ARG LYS
                GCGGTTTTTGCTCATGCTGGACTAAGAAAA
                    7000           7010         7020

ASP HIS GLN LYS GLY TYR VAL ASP VAL VAL
GATCACCAAAAAGGTTATGTTGATGTCGTA
    7030          7040           7050
                PRO PHE VAL GLY ARG ILE PHE ALA THR ASN
                CCTTTTGTTGGGCGTATTTTTGCCACCAAT
                    7060         7070           7080

GLN GLN HIS GLY ARG LEU SER PRO ARG LYS
CAGCAGCATGGCAGATTATCCCCAGAAAA
    7090         7100            7110
                ASP SER GLN GLY VAL ALA PHE GLY SER HIS
                GACAGTCAGGGCGTTGGCGTTTGGCAGCCAT
                    7120          7130           7140
```

FIG.4N'

```
HIS ARG ILE ASN ASP LYS TRP GLN ASN ALA PHE PHE ALA ARG MET GLU LYS GLY ASN TYR
CATCGGATCAATGATAAATGGCAAAATGCG TTTTTGCACGCATGGAAAAAGGCAATTAT
          7150              7170              7180              7190        7200
                                  7160

THR GLU HIS TYR GLN GLY TYR ASP GLY LYS ARG TYR HIS VAL ASN ASP THR ILE LEU LEU
ACCGAGCATTATCAAGGTTATGATGGCAAG CGTTATCATGTGAATGACACCATTTTGTTG
          7210              7230              7240              7250        7260
                                  7220

GLN ASP GLY PRO ASN ARG ARG TYR SER LEU GLY VAL GLY TYR GLN LEU SER HIS LEU GLN
CAAGATGGCCCAAATCGTCGTTACTCTTTG GGCGTGGGGTATCAGCTTAGCCATCTGCAA
          7270              7290              7300              7310        7320
                                  7280
```

FIG.4.0'

| ASP | ALA | THR | LYS | SER | SER | HIS | ALA | THR | LYS |
|---|---|---|---|---|---|---|---|---|---|
GATGCAACAAAAGCAGTCATGCCACAAAG
7330                7340              7350

| ILE | HIS | PHE | GLY | VAL | LEU | GLN | ARG | LEU | PRO |
|---|---|---|---|---|---|---|---|---|---|
ATACATTTTGGGGTGTTGCAAAGATTGCCA
        7360              7370              7380

| ASN | GLY | LEU | THR | VAL | GLN | GLY | ARG | VAL | SER |
|---|---|---|---|---|---|---|---|---|---|
AATGGTCTGACCGTGCAAGGTAGAGTGAGT
7390                7400              7410

| ALA | GLU | GLU | ARG | TYR | HIS | GLY | LYS | LEU |
|---|---|---|---|---|---|---|---|---|
GCTGAGGCGTGAGCGTTATCATGGTAAATTA
        7420              7430              7440

| LEU | ARG | LEU | VAL | ASN | PRO | ASP | ASP | VAL | TYR |
|---|---|---|---|---|---|---|---|---|---|
TTGCGTCTGGTTAATCCCTGATGATGTGTAT
7450                7460              7470

| ARG | THR | ASP | LYS | THR | LEU | THR | LEU | GLN | THR |
|---|---|---|---|---|---|---|---|---|---|
CGCACAGATAAAACCCTAACCCTACAAACC
        7480              7490              7500

FIG.4P'

```
SER ILE TRP HIS LYS ASP ILE HIS TRP LEU
TCCATTTGGCACAAAGACATTCACTGGCTT
      7510              7520          7530
GLY LEU THR PRO LYS LEU THR TYR ARG TYR
GGATTAACGCCAAAGCTGACTTATCGTTAC
      7540              7550          7560

SER LYS ASN ASN SER ASN LEU PRO ALA LEU
AGTAAAAATAACAGTAACTTACCAGCACTT
      7570              7580          7590
TYR SER HIS ASN LYS GLN ASN PHE TYR LEU
TATAGCCCATAACAAACAAAATTTTTATTTG
      7600              7610          7620

GLU LEU GLY ARG SER PHE ***
GAGCTTGGTCGGTCGTTTTAA
      7630              7640
```

FIG.6A
Alignment of Lbp2 proteins

```
         10        20        30        40        50        60
MSKSITKTQTPSVHTMTTHRLNLAIKAALF-GVAVLPLSWAQENTQTDANSDAKDTKTPV
.................................................................
.N.KHGFQL.LTA------......VA...-.PSY.AN.------......E.A..-.P..AQ.QS--    4223
.N.KHSFPL.LTA------......AT.-.PSY.ANS------......E.A.....-Q.QS--      Q8
.N.KHGFPL.LTA------......AT.-.PAY.AQA------......GAA.-.L..AQSQS--    BNCV
                                                                        H44/76
                                                                        FA19

70        80        90       100
VYLDAITVTAAPSAPVSRFDTDVTGLGKTVKTADTLAKEQ
---.KEV..R..K---..G.RSKEA.......IA..SE..N...
---.KEV..R..K---..G.RSKE........I...SE..N...
---.KEV..R..K---..G.RSKEA.......I....SE..N...

110       120       130       140       150       160
VQGIRDLVRYETGVSVEQGRGGSSGFAIHGVDKNRVGITVDGIAQIQSYKDESTKRAGA-
.L....T..DP.A......N.A.G.YS.R......AVS....V.....AFTVQGSLSGYGG
.L....T..DP.A......N.A.G.YS.R......AVS....V.....AFTVQGSLSGYGG
.L....T..DP.A......N.A.G.YS.R......AVS....V.....AFTVQGSLSGYGG 170       180       190       200
--GSGAMNEIEIENIAAVAINKGGNALEAGSGALGGSVAFHT
--
RG.....I...Y...ST.E.D..AGSSDH.......A...R.       4223
RG.....I...Y...ST.E.D..AGSSDH.......A...R.       Q8
RG.....I...Y...ST.E.D..AGSSDH.......A...R.       BNCV
                                                  H44/76
                                                  FA19
```

FIG.6B

```
        210       220       230       240       250       260
KDVSDVLKSGKNLGAQSKTTYNSKNDHFSQTLAAAGKTERVEAMVQYTYRKGKENKAHSDL
........N...................................................                    4223
.EAA.LISD..SW.I.A..A.G....RQ.MKS.G.GFSKDGW.GLLIR.E.Q.R.THP.G.I                   Q8
.EAA.LISD..SW.I.A..A.G....RQ.MKS.G.GFSKDGW.GLLIR.E.Q.R.TRP.G.I                   ENCV
.EAA.LISD..SW.I.A..A.G....RQ.MKS.G.GFSKDGW.GLLIR.E.Q.R.TRP.G.I                   H44/76
.EAA.LISD..SW.I.A..A.G....RQ.MKS.G.GFSKDGW.GLLIR.E.Q.R.TRP.G.I                   FA19

270       280       290       300
-NGINQSLYRLGAWQQKYDL-RKPNELFAGTSYITESCLAS
-...........................
AD.VAYGIN..D.FR.T.GI-K..S.GGEYFLAEG..E.KP
AD.VAYGID..D.FR.T..I-Q.QNKKAEYFLAEG..E.KP
AD.VAYGID..D.FR.T..IK..TT.P.--FLAEG.NT.KP 310       320       330       340       350       360
DDPKSCVQYPYVYTKARPDGIGNRNFSELSDAEKAQYLASTHPHEVVSAKDYTGIYRLLPD
............................................T...............
VAKVAGNGNYLNNQIN.WKERIEQNQP..AE.E.MVREAQAR..NL..QA...GG.I....
AAKLAGNGNYLNNQIN.WKERKNNQS..AE.E.MVREAQAR..NL..QA...GG.I....
VAKLAGYGIYINRQLN.WKERIEQNQP..AE.E..VREAQAR..NL..QA...GG.I....

370       380       390       400
PMDYRSDSYLARLNIKITPNLVSKLLEDIKQTYNIRDM                                           4223
.....................................                                           Q8
......G.W..K.GYRFGGRHYVGGVF......R.D....                                         ENCV
......G.W..K.GYRFGGRHYVGGVF......R.D....                                         H44/76
......G.W..K.GYRFGGRHYVGGVF......R.D....                                         FA19
```

FIG. 6C

```
          410       420       430       440       450       460
RHCSYHGARLGNDGKPANGGSIVLCDDYQEYLNANDASQALFRPGANDAPIPKLAYARSSV              4223
............................S...............................              Q8
TEKQ.Y.TDEAKFRDKS.--VYDG..FRDG.YFVPNIEE-WKGDQKLIRGIG.K.S.TK-              BNCV
TEKQ.Y.TDEATKFSDKS.--VYDG..FRDG.YFVPNIEE-WKGDK.LVKGIG.K.S.TK-             H44/76
TEKQ.Y.TDEAEKFRDKS.--VYDG..FRDG.YFVPNIEE-WKGDK.LVKGIG.K.S.TK-             FA19

470       480       490       500
FNQEHGKITRY-GLSFEF---KPDTPWFKQAKLNLHQQNIQIIN                              4223
.............-...G....-...................                                Q8
.ID..HRR.RM..LYRYENE.YSDN.ADK.V.SFDK.GVAID.                               BNCV
.ID..HRR.RM..LYRYENEAYSDN.ADK.V.SFDK.GVAID.                               H44/76
.ID..HRR.RM..LYRYENE.YSDN.ADK.V.SFDK.GVAID.                               FA19

510       520       530       540       550       560
HDIKKSCSQYPKVDLNCGISEIGHYEYQ---NNYRYKEGRASLIGKLDFNFDL-LGQHDLIVLAG         4223
.........................-.......-........T............-...........      Q8
NTL.IN.AV..A..A.KS.RA.ADKP.S.DSSDRFH.R.QHNV.NASFEKSLKNKWTK.H..LGF.         BNCV
NTL.IN.AV..A..A.KA.RA.ADKP.S.DSSDRFH.R.QHNV.NALFEKSLKNKWTK.H..LGF.         H44/76
NTL.IN.AV..A..A.KA.RA.ADKP.S.DSSDRFH.R.QHNV.NASFEKSLKNKWTK.H..LGF.         FA19

570       580       590       600
ADKVKSQFRANNPRRTIDTIQGDAIIDESTLTAQEQAK                                    4223
.....................................                                    Q8
Y.ASNAIS.PEQLSHNAARISEYSDYT.KGD---                                        BNCV
Y.AS.AIS.PEQLSHNAARISEFSDYA.DGKY---                                       H44/76
Y.AS.AIS.PEQLSHNAARISE-STGF..KNQD---                                      FA19
```

FIG. 6D

```
           610        620        630        640        650
           FKQSGAAWIVKNRLGRLEEKDA--CGNANECERAP-----IHGSNQYVGINNLYTPNDYVD    4223
           ..........................................................    Q8
           -------YL..KP.VVEGSV..YIETLRSRKCVPRK.N...IHISL.DRFSIGK.F.....    BNCV
           -------YL..KP.VVEGSV..YIETLRSRKCVPRK.N...IHISL.DRFSIGK.F.....    H44/76
           -------Y...KP.VVEGSV..YIETLRSRKCVPRK.N...IHISL.DRFSIGK.F.....    FA19

660        670        680        690        700
           LSFGGRLDKQRIHSTDSNIISKTYTNKSYNFGAAVHLTPDFSLLYK                   4223
           ..............................................                  Q8
           F.L...Y.RKNFTTSEEHLVR.GR.VDR.W.S.IVFKPNRH...S.R.                 BNCV
           F.L...Y.RQNFTTSEEHLVR.GR..DR.W.S.IVFKPSRHL..S.R.                 H44/76
           F.L...Y.RKNFTTSEEHLVR.GR.ADR.W.S.IVFKPNRH.VS.R.                  FA19

710        720        730        740        750        760
           TAKGFRTPSFYELYNYNSTAAQHKNDPDVSFPKRAVDVKPETSNIINEYGFRYQHPMGDVEM    4223
           ..........................................I..................  Q8
           ASS.......Q..FGIDIYH-------YPKGMQRPAL.S.KAANR.I.LQWKGDF.FL.I     BNCV
           ASS.......Q..FGIDIYH-------YPKGMQRPAL.S.KAANR.I.LQWKGDF.FL.I     H44/76
           ASS.......Q..FGIDIYH-------YPKGMQRPAL.S.KAANR.I.LQWKGDF.FL.I     FA19

770        780        790        800
           SMFKSRYKDMLDKAIPNLTKAQ-QEYCKAHLDSNECVGNP                         4223
           .......................................                         Q8
           .S.RN..T..IAV.DHK-..LPN.AQGLTEI.IRDYY----                        BNCV
           .S.RN..T..IAV.DHK-..LPN.AGRLTEI.IRDYY----                        H44/76
           .S.RN..T..IAV.DQK-..LPDSAGRLTEI.IRDYY----                        FA19
```

FIG.6E

```
          810       820       830       840       850       860
PTPKTSDEVFANLYNATIKGVSVKGKLDLHAMTSKLPDGLEMTLGYGHTKLGKFDYIAPKD
..........--------.AQ.MSLQ..NIL...I.WNGVYG...E..YT..A.NRI.------.S
..........--------.AQ.MSLQ..NIL...I.WNGVYG...E..YT..A.NRI.------.S
..........--------.AQ.MSLQ..INIL...I.WNGVYG...E..YT..A.NRI.------.S 870       880       890       900
ADGMYQA--RPAFWDAITPARYVVGLNYDHPSQWMGIGTTL                    BNCV
.........--..................................
V

FIG.7A
Alignment of M. catarrhalis Lbp2 proteins

```
            10        20        30        40        50        60
    MSTVKTPHIFYQKRTLSLAIASIFAALVMIGCRSDDISVNAPNVTQLPQGTVSPTPNIGH           Q8
    .........P..................................................           4223
    ....V...................V...................................           VH19

70        80        90       100
    DVANNINNQGNINIDNSTSTTDPNGDNNQLTQAQKTAAAAG                               Q8
    ...T....................................                               4223
    ...T.I..................................                               VH19

110       120       130       140       150
    FFVMGKIRDTSEKNDPDYSDDLKQQW----LGKLYVGIDAHRPDGIGKRNLRQPITAND            Q8
    .......P........N.V..--Q..................T...................        4223
    TK..QGSVHTAGQ.LQ.L.TKEP...T.T.............                             VH19

160       170       180       190       200
    IKPLYFNKFPALSDLHLDSERHRFDPQKINTIKVYGYGNLTTPS                            Q8
    .........................D.................                            4223
    T....D..KI.....ENSE.V..AK.A.N..I...A.SS.A                              VH19
                               K.L.

210       220       230       240       250       260
    NNNTHINHQQADNKKNNKPVDPYENIRFGYLEHQGSSLTQKNADNQNEQDR-IPKMPILF           Q8
    K..Y........................................P.DK.-.....              4223
    K.P.YM.Y..EQ.I.K.G.D.Q.....M.RELD.NK.G...SDKN.A.IFTT.T..              VH19

270       280       290       300
    YHGENASSQLPSAGKFNYTGWMLYLSDVKKRPALSASDER                               Q8
    .......................................D.                             4223
    .....TH..K....D.E.....T.......F.DKT.DK                                 VH19
```

FIG. 7B

```
       310       320       330       340       350       360
VGVYLNASGKANEGDVVSAAHIYLNGFQYKHTPATYQVDFDTNSLTGKLSYYDNPNQQN          Q8
.......S....................................................TA     4223
...T.F.STR.S....L.........S.K.......S....Q.T.K........K.TA         VH19
                      370       380       390       400
                 KGEYLKSQFDTTKKVNEIDVYQIDAKINGRFVGTAKSLV              Q8
                 .Q.K.I..............................               4223
                 D.R.IR....D...A..E........T......I                 VH19

410       420       430       440       450       460
NEKTQTAPFIKELFSKKANPNNPNSDTLEGGFYGESDELAGKFLSNDNASYVVFGGK            Q8
..N.E.....................................TF......                 4223
DDN.N...V.........D.........................G..E..S....G..         VH19
                      470       480       490       500
                 RDKTITKPVAIKTVYFSAGFEKPSTSFVDNETIGGIIDRKG             Q8
                 .........D..............................R..NS.K     4223
                 .........E........T............G..E..S....G..      VH19

510       520       530       540       550
LN----NHINEDEIIP-SDDSYYGYIMGKPEKQFTKKVSSTQVVPAYFGQHDKFYFNGN          Q8
..DAVNEK.DNGD.PT-...ER.DEFP..EKKAE......A..........                 4223
..DEVN.Q.-....TV.V.NKE..E.NY.R.N......INA.V.KN....                  VH19
                      560       570       580       590       600
                 YDLSASRVDKLAPADAVKANQSIKEKYPNATLNKDNQVTAIVLQ          Q8
                 ..............S.............................       4223
                 .......KEAN..GVSQDTST.K..LA...D.KVST..K..K....      VH19
```

FIG.7C

```
         610        620        630        640        650        660
EAKDNKPYTAIRAKSYQHISFGETLYNDANQTPTRSYFVQGGRADTSTTLPQAGKFTYNG
Q.. -......H...D......V....NKGN.........Q.V.Q.S.........K..
                                        LK.I.TAEAD-I.T..AR.T.
         670        680        690        700
LWAGYLTQKDKGYSDNAETIKEKGHPGYLLTENFTPEDD                          Q8
.......I........N.E...K...QD....D......                          4223
...........KDED..Q..LKD.I..KD.I.Q...                             VH19
-----------------------------------                              H44/76

710        720        730        740        750
DDD---LTIASDDSQDDNTHGDDDLIASDDSQDDDADGDDSDDLGDGADDDAAGKVYHA
.........................DA........................A.....
...DDS...................................T...............
T.EARISKPIQMDNHADKKAA---------------------------------

760        770        780        790        800
GNIRPEFENKYLPINEPTHEKTFALDGKNKAKFEVDENINSLTG                     Q8
.........................................D..D...........       4223
.........................................D.N.D..........       VH19
.....................................E.D...GEK.IS.             H44/76
```

FIG.7D

```
         810       820       830       840       850
         KLNDERGDIV-FDIKNGKIDGTGFTAKADVPNYREEV-GNNQGGGFLYNIKDIDVKG
         ..............................................
         ..............................................
         T.TEKN.VQPA.H.E..V.E.N..H.T.RTRDNGINLS..DSTNPPSFKANNLL.T.
                                 RDNGINLS..GSTNPPSFKADNLL.T.
                              860       870       880
                              QFFGTNGEELAGQLHHDKGD--GINDTAEKA---------       Q8
                              ..........QY................             4223
                              R.........................             VH19
                              G.Y.PKA...G.IIFNND.KSL..TEGT.NKVE-ADVDVDVDVD     BNCV
                              G.Y.PQA...G.IIFNND.KSL..TEDT.NEAE-AEVENEAGVG---  H44/76
                              G.Y.PQAA..G.IIFNND.KSL..TEDI.NEVENEADVG------    FA19

890
         ---------GAVEGAVKD-----K*                        Q8
         ------------..............*                     4223
         ----------------...........*                    VH19
         ADADVEQLKPEVKPQF.V....K..NKEVE.*                 BNCV
         ----EQLKPEAKPQF.V....K..NKEVE.*                  H44/76
         ----EQLEPEVKPQF.V....K..NKEVE.*                  FA19
```

FIG.8A  M. catarrhalis strain 4223 Tbp2/Lbp2 comparison

```
         MKHIPLT--TLCVAISA----VLLTACGGSGGS-NPPAPT------PIPNASGSGNTG      Tbp2
MSTVKTP..FYQKR..SL..ASIFAALVM.G.RSDDI.V.A.NV.QLPQGTVS...TGHD-..N       Lbp2
  **      ******                *  *   *  *        *         **

NTGNAGG-TDNTANAGNTGGTNSGTGSANTPEPKYQDVPTEKNEKDKVSSIQEPAMG----YGM       Tbp2
..N.Q.NN...STSTTDPN.D.NQLTQ..QKTAAAAGFFVMG.I-R.TSPKNDPYSNDLVQQWQG     Lbp2
 ** *     ******                 *     ** **                *

ALSKINLHNRQDTPLDEKNIITLDGKKQVAEGKKSPLPFSLDVENKLLDGYIAKMNVADKNAIGD     Tbp2
K.YVGIDAH.P.GIGTG..LRQPITANDIKPLYFNKF.ALS.L-------HL.SERHRF           Lbp2
 *   ***        ***                     **          *

RIKKGNKEISDEELAKQIKEAVRKSHEFQQVLSSLENKIFHSNDGTTKATTRDLKYVDYGYYLAN     Tbp2
DP..L.TIKVYGYGNLTTPSKNNTYINH..ADNKKN..PVDPYENIRFGYLELQGSSLTQKNADT     Lbp2
 *  *                *    ***                  ***

DGNYLTVKTDKLWNLGPVGGVFYNGTTTAKELPTQDAVKYKGHWDFMTDVANRRNRFSEVKENSQ    Tbp2
PNDKDRIPK------.MPIL..H.ENASSQ..SAGKFN.T.N.LYLS..KK.PALSASDDRV--     Lbp2
                   *            *     ******        *

AGWYYGASSKDEYNRLLTKEDSAPDGHSGEYGHSSEFTVNFKEKKLTGKL-------F           Tbp2
-.V.LN..G.SNEGDVVSAAHIYLN.FQYKHTPAT-YQ.D.DTNS.....SYYDNPQQTAQGKY    Lbp2
   *  *                                 ******              *

SNLQDRHKGNVTKTERYDIDANIHGNRFRGSATA-----SNKNDTSKHPFTSDAN------NR     Tbp2
IKS.FDTTKK.NE.DV.Q...K.N....V.T.KSLVNENTETAPFI.EL.SKK..PNNPNPNSDT   Lbp2
   *                                         **
```

FIG. 8B

```
LEGGFYGPKGEELAGKFLTNDNKLFGVFGAKRESKAEEKTEAILDAYALGTFNTSNATTFTPFTE      Tbp2
........ES.D......S.....ASYV...G..DKTDKPVATKTVYFS.AFEKP-----          Lbp2
********    *************     *  *  *******           *

KQLDNFGNAKKLVLGSTVIDLVPTDATKNEFTKDKPESATNEAGETLMVNDEVSVKTYGKNFEYL     Tbp2
                                                                     Lbp2

KFGELSIGGSHSVFLQGERTATTGEKAVPTTGTAKYLGNWGYITGKDTGTGTGKSFTDAQDVAD      Tbp2
                                                                     Lbp2

FDIDFGNKSVSGKLITKGRQDPVFSITGQIAGNGWTGTASTTKADAGGYKIDSSTGKSIAIKDA      Tbp2
------------------------------------.IKNG...GTGFTAKADVPNY            Lbp2
                                     *        *   *  ****   *

-----NVTGGFYGPNAN-EMGGSFTHN-----ADDS----------KASVVFGTKRQQEVK*        Tbp2
REEVGN.QG...LYNIKDIDVK.Q.FGTNGEEL.GQLQYDKGDGINDTAE..GA...AVKD---.*    Lbp2
     *            *    *    *      *           *  *  *  ****   *
```

FIG.9A  Alignment of *M. catarrhalis* Lbp3 sequences

```
         10         20         30         40         50
MTCLPKTNPALKVKHRFLKQVLLLLCVDTLTAQAYAHSHHTPIHTPTHEL          4223
..................................................         Q8

60         70         80         90        100
PSADALSDEGLGKDLGSLDSLDSPDGLGDGLGDGLKSDKAPLPINA              4223
........................................T....              Q8

110        120        130        140        150
LTAHQTNESQPAPPSVDVNFLLAQPEAFYHVFHQAIVQDDVATLRLLLPF          4223
..VN.S...........................................          Q8

160        170        180        190        200
YDRLPDDYQDDVLLLFAQSKLALSDGNTKLALNLLTDLSNKEPTLTAVKL          4223
.................................................          Q8

210        220        230        240        250
QLASLLLTNKHDKHAQMVLDELKDDAHFLKLSKKEQRWVLSQSRYLHKKY          4223
.................................................          Q8

260        270        280        290        300
KMGLDLGINYLHLDNINAASTITQPNIKKDAPKPAHGLALSLGVNKYTPL          4223
.................................................          Q8

310        320        330        340        350
SHGMSIYTALDVDGKFYDDKSHNELAVFAHAGLRKDHQKGYVDVVPFVGR          4223
.................................................          Q8
```

FIG.9B

```
        360       370       380       390       400
         |         |         |         |         |
IFATNQQHGRLSPRKDSQGVAFGSHHRINDKWQNAFFARMEKGNYTERYQ    4223
................................................H..  Q8

410       420       430       440       450
         |         |         |         |         |
GYDGKRYHVNDTILLQDGPNRRYSLGVGYQLSHLQDATKSSHATKIHFGV    4223
.................................................   Q8

460       470       480       490       500
         |         |         |         |         |
LQRLPNGLTVQGRVSAERERYHGKLLRLVNPDDVYRTDKTLTLQTSIWHK    4223
.................................................   Q8

510       520       530       540
         |         |         |         |
DIHWLGLTPKLTYRYSKNNSNLPALYSHNKQNFYLELGRSF*           4223
........................................*           Q8
```

Figure 11. Expression of Q8 and 4223 rLbp 1 proteins
A. Q8 rLbp1
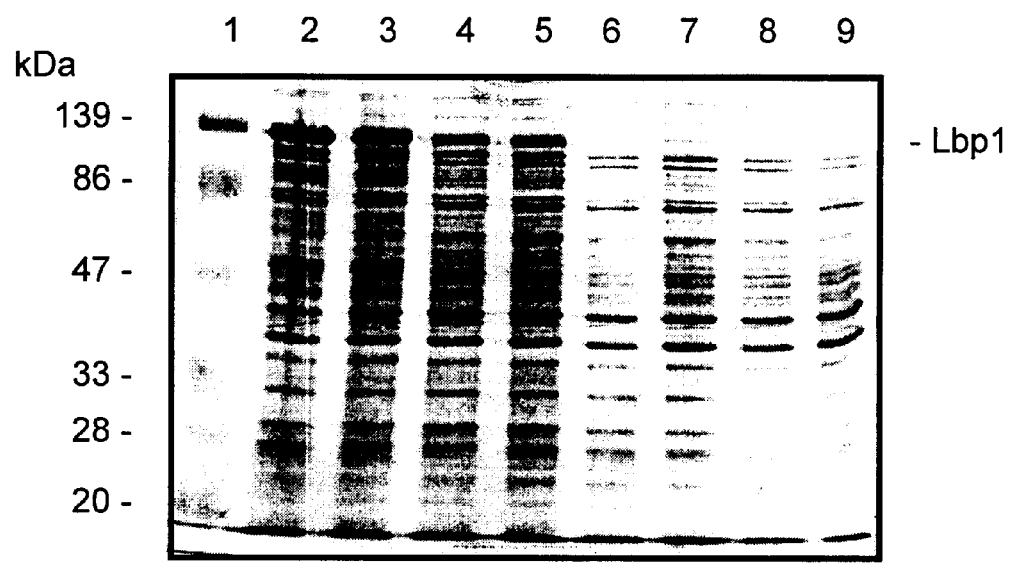
B. 4223 rLbp1
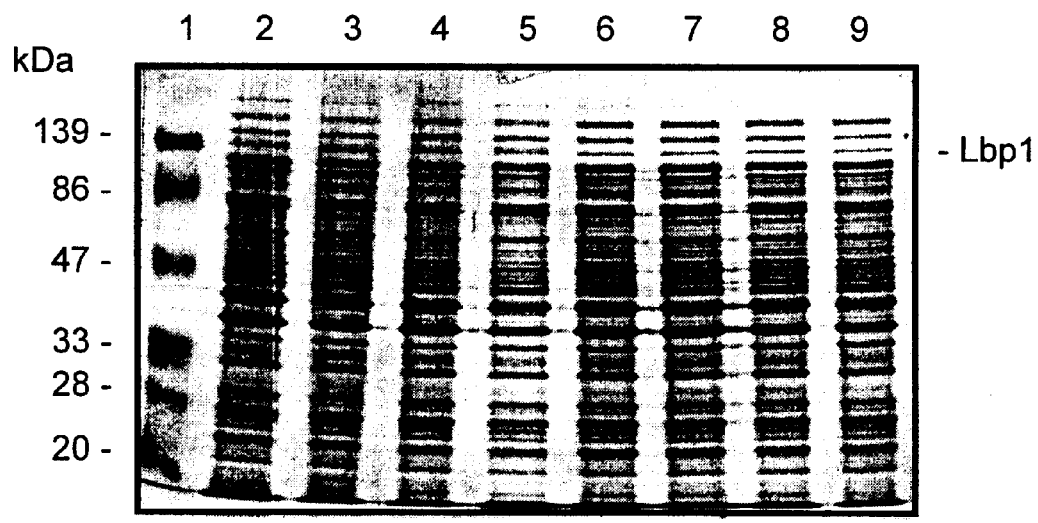

Purification scheme for rLbp1 expressed from E.coli

Purification of Q8 rLbp1 from *E. coli*

1. *E. coli* whole cells
2. Soluble proteins in 50 mM Tris/ NaCl extraction
3. Soluble proteins in Tris/ Triton X-100 extraction
4. Soluble proteins in Tris/ octylglucoside extraction
5. rLbp1 inclusion bodies
6. rLbp1

LACTOFERRIN RECEPTOR GENES OF MORAXELLA

FIELD OF INVENTION

The present invention relates to the molecular cloning of genes encoding lactoferrin receptor (LfR) proteins and, in particular, to the cloning of lactoferrin receptor genes (lbp genes) from *Moraxella (Branhamella) catarrhalis*.

BACKGROUND OF THE INVENTION

*Moraxella (Branhamella) catarrhalis* bacteria are Gram-negative diplococcal pathogens which are carried asymptomatically in the healthy human respiratory tract. However, in recent years, *M. catarrhalis* has been recognized as an important causative agent of otitis media. In addition, *M. catarrhalis* has been associated with sinusitis, conjunctivitis, and urogenital infections, as well as with a number of inflammatory diseases of the lower respiratory tract in children and adults, including pneumonia, chronic bronchitis, tracheitis, and emphysema (refs. 1 to 8). (Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Occasionally, *M. catarrhalis* invades to cause septicaemia, arthritis, endocarditis, and meningitis (refs. 9 to 13).

*M. catarrhalis* colonizes the human upper respiratory tract and is an important cause of otitis media in infants and children as well as lower respiratory tract infections in adults with chronic obstructive pulmonary disease.

Otitis media is one of the most common illnesses of early childhood and approximately 80% of all children suffer at least one middle ear infection before the age of three (ref. 14). Chronic otitis media has been associated with auditory and speech impairment in children, and in some cases, has been associated with learning disabilities. Conventional treatments for otitis media include antibiotic administration and surgical procedures, including tonsillectomies, adenoidectomies, and tympanocentesis. In the United States, treatment costs for otitis media are estimated to be between one and two billion dollars per year.

In otitis media cases, *M. catarrhalis* is commonly co-isolated from middle ear fluid along with *Streptococcus pneumoniae* and non-typable *Haemophilus influenzae*, which are believed to be responsible for 50% and 30% of otitis media infections, respectively. *M. catarrhalis* is believed to be responsible for approximately 20% of otitis media infections (ref. 15). Epidemiological reports indicate that the number of cases of otitis media attributable to *M. catarrhalis* is increasing, along with the number of antibiotic-resistant isolates of *M. catarrhalis*. Thus, prior to 1970, no β-lactamase-producing *M. catarrhalis* isolates had been reported, but since the mid-seventies, an increasing number of β-lactamase-expressing isolates have been detected. Recent surveys suggest that up to 80 to 85% of clinical isolates produce β-lactamase (ref. 16, 22, 23).

Iron-restriction is a general host defence mechanism against microbial pathogens. A number of bacterial species including *Neisseria meningitidis* (ref. 17, 24), *N. gonorrhoeae* (ref. 25) and *M. catarrhalis* (ref. 17), express outer membrane proteins which specifically bind human lactoferrin.

*M. catarrhalis* infection may lead to serious disease. It would be advantageous to provide a recombinant source of lactoferrin binding proteins as antigens in immunogenic preparations including vaccines, carriers for other antigens and immunogens and the generation of diagnostic reagents. The genes encoding lactoferrin binding proteins and fragments thereof are particularly desirable and useful in the specific identification and diagnosis of Moraxella and for immunization against disease caused by *M. catarrhalis* and for the generation of diagnostic reagents.

SUMMARY OF THE INVENTION

The present invention is directed towards the provision of purified and isolated nucleic acid molecules encoding a lactoferrin receptor protein of a strain of Moraxella or a fragment or an analog of the lactoferrin receptor protein. The nucleic acid molecules and isolated and purified lactoferrin binding proteins provided herein are useful for the specific detection of strains of Moraxella and for diagnosis of infection by Moraxella. The purified and isolated nucleic acid molecules provided herein, such as DNA, are also useful for expressing the lbp genes by recombinant DNA means for providing, in an economical manner, purified and isolated lactoferrin receptor proteins free of other Moraxella proteins, as well as subunits, fragments or analogs thereof.

The lactoferrin receptor, subunits or fragments thereof or analogs thereof, as well as nucleic acid molecules encoding the same and vectors containing such nucleic acid molecules, are useful in immunogenic compositions for vaccinating against diseases caused by Moraxella, the diagnosis of infection by Moraxella, and as tools for the generation of immunological reagents.

Monoclonal antibodies or mono-specific antisera (antibodies) raised against the lactoferrin receptor protein produced in accordance with aspects of the present invention are useful for the diagnosis of infection by Moraxella, the specific detection of Moraxella (in, for example, in vitro and in vivo assays) and for the treatment of diseases caused by Moraxella.

In accordance with one aspect of the present invention, there is provided a purified and isolated nucleic acid molecule encoding a lactoferrin receptor protein of a strain of Moraxella, more particularly a strain of *M. catarrhalis*, specifically *M. catarrhalis* strain 4223 or Q8, or a fragment or an analog of the lactoferrin receptor protein.

In one preferred embodiment of the invention, the nucleic acid molecule may encode only the Lbp1 protein of the Moraxella strain or only the Lbp2 protein of the Moraxella strain or only the Lbp3 protein of the Moraxella strain. In another preferred embodiment of the invention, the nucleic acid may encode a fragment of the lactoferrin receptor protein of a strain of Moraxella having a conserved amino acid sequence.

In a further aspect of the present invention, there is provided an isolated and purified nucleic acid molecule encoding at least one lactoferrin binding protein of Moraxella having a restriction map as shown in FIG. 3 for *M. catarrhalis* 4223 or FIG. 5 for *M. catarrhalis* Q8 or the equivalent map from other strains of Moraxella.

In another aspect of the present invention, there is provided a purified and isolated nucleic acid molecule having a DNA sequence selected from the group consisting of (a) a DNA sequence as set out in FIG. 2 or 4 (SEQ ID Nos. 1, 2, 3, 4, 5, 6, 7, 8, 9, 10) or the complimentary DNA sequence thereto; (b) a DNA sequence encoding an amino acid sequence as set out in FIG. 2 or 4 (SEQ ID Nos. 11, 12, 13, 14, 15, 16, 17, 18) or the complimentary DNA sequence thereto; and (c) a DNA sequence which hybridizes under stringent conditions to any one of the DNA sequences defined in (a) or (b).

In an additional aspect, the present invention includes a vector adapted for transformation of a host, comprising a nucleic acid molecule as provided herein and may have the characteristics of a nucleotide sequence contained within vectors pLD3, pLDW3, pLDl-8 and pLDW1.

The vector may be adapted for expression of the encoded lactoferrin receptor protein, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the lactoferrin receptor protein or the fragment or analog of the lactoferrin receptor protein.

In specific embodiments of this aspect of the invention, the nucleic acid molecule may encode substantially all the lactoferrin receptor protein, only the Lbp1 protein of the Moraxella strain, only the Lbp2 protein of the Moraxella strain, only the Lbp3 protein of the Moraxella strain, or fragments of the Lbp1, Lbp2 or Lbp3 proteins.

The expression means may include a nucleic acid portion encoding a leader sequence for secretion from the host of the lactoferrin receptor protein or the fragment or the analog of the lactoferrin receptor protein. The expression means also may include a nucleic acid portion encoding a lipidation signal for expression from the host of a lipidated form of the lactoferrin receptor protein or the fragment or the analog of the lactoferrin receptor protein. The host may be selected from, for example, *Escherichia coli*, Bacillus, Bordetella, Haemophilus, Moraxella, fungi, yeast or baculovirus and Semliki Forest virus expression system may be used. In a particular embodiment, the plasmid adapted for expression of Lbp2 is pRD2A, pRD2B, pQW2A or pQW2B; the plasmid adapted for expression of Lbp1 is pRD1A, pRD1B, PQ1A or pQ1B; and the plasmid adapted for expression of Lbp3 is pLRD3 or pLQW3.

In an additional aspect of the invention, there is provided a transformed host containing an expression vector as provided herein. The invention further includes a recombinant lactoferrin receptor protein or fragment or analog thereof of a strain of Moraxella producible by the transformed host.

Such recombinant lactoferrin receptor protein may be provided in substantially pure form according to a further aspect of the invention, which provides a method of forming a substantially pure recombinant lactoferrin receptor protein, which comprises growing the transformed host provided herein and isolating and purifying the lactoferrin receptor protein, analog or fragment thereof. The lactoferrin receptor protein may be expressed in inclusion bodies, which may be purified free from cellular material and soluble proteins and lactoferrin receptor protein solubilized from the purified inclusion bodies, and the lactoferrin receptor protein purified free from other solubilized materials. The substantially pure recombinant lactoferrin receptor protein may comprise Lbp1 alone, Lbp2 alone, Lbp3 or a mixture of two or more of such proteins. The recombinant protein is generally at least about 70% pure, preferably at least about 90% pure.

Further aspects of the present invention, therefore, provide recombinantly-produced Lbp1 protein (or a fragment or analog thereof) of a strain of Moraxella devoid of the Lbp2 and Lbp3 proteins of the Moraxella strain and any other protein of the Moraxella strain, recombinantly-produced Lbp2 protein (or a fragment or analog thereof) of a strain of Moraxella devoid of the Lbp1 and Lbp3 proteins of the Moraxella strain and any other protein of the Moraxella strain, and recombinantly-produced Lbp3 protein (or a fragment or analog thereof) of a strain of Moraxella devoid of the Lbp1 and Lbp2 proteins of the Moraxella strain and any other protein of the Moraxella strain. The Moraxella strain may be *M. catarrhalis* 4223 or Q8 strain.

The invention further includes, in an additional aspect, a lactoferrin binding protein 3 (Lbp3) of a Moraxella strain or a fragment or analog of the lactoferrin binding protein. The Lbp3 may be from a strain of *M. catarrhalis*, which may be strain 4223 or Q8. The Lbp3 may have a molecular mass of about 60 kDa.

In accordance with another aspect of the invention, an immunogenic composition is provided which comprises at least one active component selected from at least one nucleic acid molecule as provided herein, at least one recombinant protein as provided herein or at least one novel protein as provided herein, and a pharmaceutically acceptable carrier therefor or vector therefor. The at least one active component produces an immune response when administered to a host.

The immunogenic compositions provided herein may be formulated as a vaccine for in vivo administration to a host to provide protection against disease caused by *M. catarrhalis*. For such purpose, the compositions may be formulated as a microparticle, capsule, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants to induce a TH1 response. Advantageous combination of adjuvants are described in copending U.S. patent application Ser. Nos. 08/261,194 filed Jun. 16, 1994 and 08/483,856 filed Jun. 7, 1995, assigned to the assignee hereof and the disclosure of which is incorporated herein by reference (WO 95/34308, published Nov. 21, 1995).

In accordance with another aspect of the invention, there is provided a method for generating an immune response in a host, comprising the step of administering to a susceptible host, such as a human, an effective amount of the immunogenic composition as recited above. The immune response may be humoral or a cell-mediated immune response and may provide protection against disease caused by Moraxella. Hosts in which protection against disease may be conferred include primates, including humans.

In a further aspect, there is provided a live vector for delivery of lactoferrin receptor to a host, comprising a vector containing the nucleic acid molecule as described above. The vector may be selected from Salmonella, BCG, adenovirus, poxvirus, vaccinia and poliovirus.

The nucleic acid molecules provided herein are useful in diagnostic applications. Accordingly, in a further aspect of the invention, there is provided a method of determining the presence, in a sample, of nucleic acid encoding a lactoferrin receptor protein of a strain of Moraxella, comprising the steps of:

a) contacting the sample with a nucleic acid molecule as provided herein to produce duplexes comprising the nucleic acid molecule and any nucleic acid molecule encoding the lactoferrin receptor protein of a strain of Moraxella present in the sample and specifically hybridizable therewith; and b) determining the production of the duplexes.

In addition, the present invention provides a diagnostic kit for determining the presence, in a sample, of nucleic acid encoding a lactoferrin receptor protein of a strain of Moraxella, comprising:

a) a nucleic acid molecule as provided herein;

b) means for contacting the nucleic acid molecule with the sample to produce duplexes comprising the nucleic acid molecule and any such nucleic acid present in the sample and hybridizable with the nucleic acid present in the sample and hydridizable with the nucleic acid molecule; and c) means for determining production of the duplexes.

The invention further includes the use of the nucleic acid molecules and proteins provided herein as medicines. The invention additionally includes the use of the nucleic acid molecules and proteins provided herein in the manufacture of medicaments for protection against disease caused by strains of Moraxella.

Advantages of the present invention include:

an isolated and purified nucleic acid molecule encoding a lactoferrin receptor protein of a strain of Moraxella or a fragment or an analog of the lactoferrin receptor protein;

recombinantly-produced lactoferrin receptor proteins, including Lbp1, Lbp2 and Lbp3 and fragments and analogs thereof free from each other and other Moraxella proteins;

lactoferrin binding protein 3; and diagnostic kits and immunological reagents for specific identification of Moraxella.

BRIEF DESCRIPTION OF DRAWINGS

The present invention will be further understood from the following description with reference to the drawings, in which:

FIG. 1 shows partial sequence of the 2.2 kb PCR amplified fragments of the lbpA genes from *M. catarrhalis* 4223 or Q8, which were used to probe the phage libraries. In the figure, Tbpl is the deduced 4223 Tbp1 sequence (as described in U.S. patent application Ser. No. 08/613,009 filed Mar. 8, 1996, assigned to the assignee hereof and the disclosure of which is incorporated herein by reference) (SEQ ID No: 19), Lbp1 is the deduced full-length 4223 Lbp1 sequence (SEQ ID No: 3) used here solely for aligning the PCR fragments, PCR4 is the 4223 PCR fragment (SEQ ID No: 20), and PCR5 is a partial sequence of the Q8 PCR fragment (SEQ ID No: 21). Only single strand sequence was obtained for the PCR fragments and "X" has been inserted where there was a doubtful sequence. Dashes have been used for maximum alignment. The underlined sequence in Lbp1 (MVQYTYRKGKENKAH—SEQ ID No: 22) represents the position of a CNBr peptide used to generate the 5'-PCR primer.

FIG. 2 shows the nucleotide (SEQ ID No: 1, full sequence; SEQ ID No: 2, Lbp2 coding sequence; SEQ ID No: 3, Lbp1 coding sequence, first methionine; SEQ ID No: 4, Lbp1 coding sequence, second methionine; SEQ ID No: 5, Lbp3 coding sequence) and deduced amino acid sequences (SEQ ID No: 11, Lbp2; SEQ ID No: 12, Lbp1, first methionine; SEQ ID No: 13, Lbp1, second methionine; SEQ ID No: 14, Lbp3) of the putative lfr locus from *M. catarrhalis* 4223. There are three tandem genes in the putative lfr locus identified as lbpB, lbpA and orf3. Potential promoter elements found upstream of the lbpB and lbpA genes are indicated by underlining.

FIG. 4 shows the nucleotide (SEQ ID No: 6, full sequence; SEQ ID No: 7, Lbp2 coding sequence; SEQ ID No: 8, Lbp1 coding sequence, first methionine; SEQ ID No: 9, Lbp1, second methionine; SEQ ID No: 10, Lbp3 coding sequence) and deduced amino acid sequences (SEQ ID No: 15, Lbp2; SEQ ID No: 16, Lbp1, first methionine; SEQ ID No: 17, Lbp1, second methionine; SEQ ID No: 18, Lbp3) of the putative lfr locus from *M. catarrhalis* Q8. There are three tandem genes in the putative lfr locus identified as lbpB, lbpA and orf3. Potential promoter elements found upstream of the lbpB and lbpA genes are indicated by underlining.

FIG. 6 shows a comparison of the amino acid sequences of Lbp1 from *M. catarrhalis* strains 4223 (SEQ ID No: 12) and Q8 (SEQ ID No: 16), *N. meningitidis* strain BNCV (SEQ ID No: 23), and *N. gonorrhoeae* strain FA19 (SEQ ID No: 24). Dots indicate identical residues and dashes have been introduced to achieve maximum sequence alignment.

FIG. 7 shows a comparison of the amino acid sequences of Lbp2 from *M. catarrhalis* strains 4223 (SEQ ID No: 11) and Q8 (SEQ ID No: 15). Dots indicate identical residues. The arrow indicates the lipidated cysteine of a potential mature Lbp2 lipoprotein.

FIG. 8 shows a comparison of the amino acid sequences of Tbp2 (U.S. patent application Ser. No: 08/613,009) (SEQ ID No: 25) and Lbp2 from *M. catarrhalis* strain 4223 (SEQ ID No: 11). Dots indicate identical residues and dashes have been inserted to achieve maximum sequence alignment. The asterisks indicate conserved residues and the putative site of lipidation for both proteins is indicated by the arrow.

FIG. 9 shows a comparison of the amino acid sequences of Lbp3 (ORF3) from *M. catarrhalis* strains 4223 (SEQ ID No: 14) and Q8 (SEQ ID No: 18). Dots indicate identical residues and dashes have been introduced for maximum alignment.

FIG. 11, comprising panels A and B, shows the expression of recombinant Lbp1 (rLbp1) proteins from *E. coli*. Panel A shows the expression of the Q8 Lbp1 proteins and panel B shows the expression of the 4223 Lbp1 proteins. Lane 1, molecular weight marker. Lanes 2 and 3 demonstrate the induced expression of the longer Lbp1 starting from the first methionine residues and lanes 4 and 5 illustrate the expression of the shorter Lbp1 proteins starting from the second methionine residues. Lanes 6, 7, 8 and 9 are uninduced samples.

GENERAL DESCRIPTION OF THE INVENTION

Figure 3A:
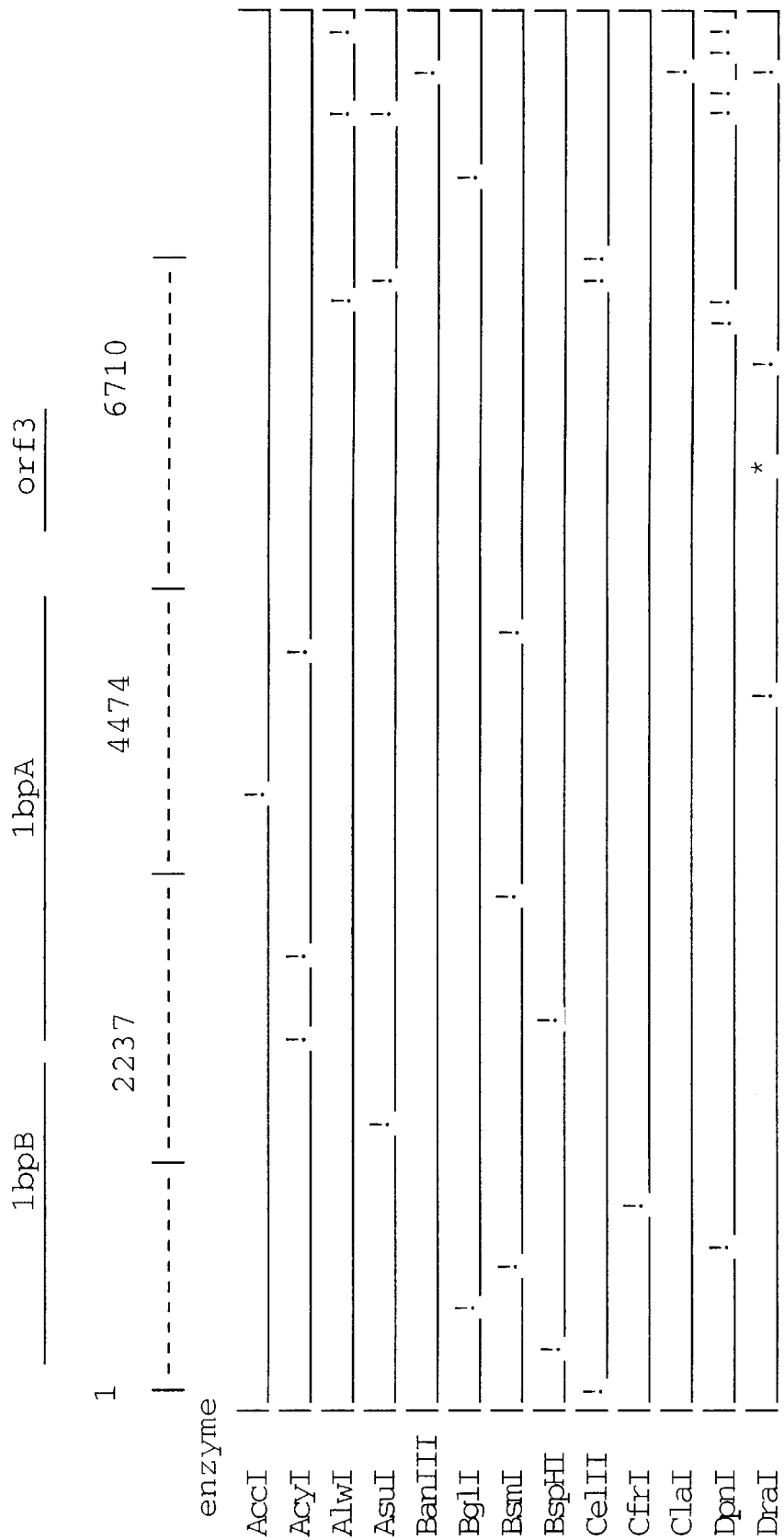
FIG. 3 shows a restriction map of clone pLD1-8 containing the lbpA, lbpB, and orf3 genes from *M. catarrhalis* isolate 4223.

Any Moraxella strain may be conveniently used to provide the purified and isolated nucleic acid, which may be in the form of DNA molecules, comprising at least a portion of the nucleic acid coding for a lactoferrin receptor as typified by embodiments of the present invention. Such strains are generally available from clinical sources and from bacterial culture collections, such as the American Type Culture Collection.

In this application, the terms "lactoferrin receptor" (LfR) and "lactoferrin binding proteins" (Lbp) are used to define a family of Lbp1, Lbp2 and/or Lbp3 proteins which includes those having variations in their amino acid sequences including those naturally occurring in various strains of, for example, Moraxella. The purified and isolated DNA molecules comprising at least a portion coding for lactoferrin receptor of the present invention also includes those encoding functional analogs of lactoferrin receptor proteins Lbp1, Lbp2 and/or Lbp3 of Moraxella. In this application, a first protein is a "functional analog" of a second protein if the first protein is immunologically related to and/or has the same function as the second protein. The functional analog may be, for example, a fragment of the protein, or a substitution, addition or deletion mutant thereof.

Lactoferrin receptor proteins were purified from M. catarrhalis membrane preparations by affinity chromatography on biotinylated human lactoferrin. Cyanogen bromide fragments were generated and amino acid sequence analysis of a 13 kDa fragment provided an internal Lbp1 sequence of MVQYTRKGENKAH (SEQ ID No: 22). The C-terminus of M. catarrhalis Tbp1 (U.S. patent application Ser. No. 08/613,009), N. meningitidis Tbp1 (ref. 27) and H. influenzae Tbp1 (ref. 31) has a conserved LEMKF (SEQ ID No: 26) sequence. Oligonucleotide primers were generated based upon these two sequences and used to PCR amplify an approximately 2.2 kb fragment of the lbpA gene from M. catarrhalis strains 4223 and Q8. Partial sequence analysis demonstrated that the amplified genes were lbpA and not tbpA (see FIG. 1). The 2.2 kb PCR fragments were used to screen genomic libraries.

Chromosomal DNA from 4223 and Q8 was partially digested with Sau3A I and 15 to 23 kb fragments were purified before cloning into BamH I arms of the lambda vector EMBL3. The libraries were screened with the PCR fragment and positive clones were subjected to three rounds of plaque purification. Phage clone 4223LfR.17 containing an approximately 16 kb insert from 4223 and phage clone Q8LfR.13 containing an approximately 16 kb insert from Q8 were selected for further analysis.

Restriction enzyme and Southern blot analyses revealed that an internal Hind III fragment of approximately 9 kb contained at least a portion of the lbpA gene for both phage clones. The approximately 9 kb Hind III fragments were subcloned into pUC or pBluescript-based plasmids and sequenced. In each case, they contained the complete lbpA gene as well as an upstream gene identified as lbpB, and a downstream gene designated as orf3. The lbpB-lbpA gene arrangement is the same as present for Neisseria strains, but there has been no identification of a third gene for these organisms.

The gene arrangement is different than that observed for the M. catarrhalis tfr operon which was tbpA-orf-tbpB (U.S. patent application Ser. No. 08/613,009). There are promoter elements found upstream of both the lbpB and lbpA genes from strains 4223 and Q8. The third ORF is located immediately downstream of lbpA, separated by a single nucleotide and there are no obvious promoter elements upstream of it within the lbpA gene.

By analogy with the N. meningitidis and N. gonorrhoeae transferrin receptor operons (ref. 26, 27, 28), the lactoferrin receptor operon was presumed to consist of two genes encoding lactoferrin binding proteins 1 and 2 (Lbp1 and Lbp2) (ref. 29). However, we report here that, for M. catarrhalis, there also appears to be a third gene located immediately downstream of lbpA encoding a lactoferrin binding protein 3 (Lpb3).

The M. catarrhalis 4223 and Q8 lbpA genes encode proteins of molecular mass about 110 kDa and that are highly conserved with only seven residues difference between them. The N-terminal sequence of the native Lbp protein is unknown and there are two possible ATG start codons at positions 1 or 16. The first of these is adjacent to consensus sequences for promoter elements and the second is followed by a putative signal sequence. The exact peptide sequence used to design the PCR amplification primers was not found. When compared with other known Lbp1 sequences from N. meningitidis (refs. 31, 24) or N. gonorrhoeae (ref. 25) there is about 32% sequence identity and about 50% sequence homology between the M. catarrhalis and the Neisseria proteins. There is some homology between the M. catarrhalis Lbp1 and Tbp1 proteins as shown in FIG. 1, but it is very scattered.

The M. catarrhalis 4223 and Q8 lbpB genes encode 898 and 894 amino acid proteins, respectively. The M. catarrhalis Lbp2 proteins are 92% identical and 95% homologous. There is a consensus sequence for lipidation at the $Cys^{32}$ residue, suggesting that Lbp2 is a lipoprotein like Tbp2. There is little homology between the M. catarrhalis Lbp2 and Tbp2 proteins (FIG. 8) with the exception of a previously identified peptide sequence (LEGGFY (SEQ ID No: 27)) that is also found in N. meningitidis and H. influenzae Tbp2 (ref. 30).

The sequence of the proposed M. catarrhalis lfr-related downstream orf3 is conserved between strains 4223 and Q8. The encoded 4223 and Q8 Lbp3 proteins when compared to the PIR and Swiss Prok protein databases were found to be previously unknown. The Lbp3 protein may bind lactoferrin itself or may be an associated or regulatory protein for Lbp1 and/or Lbp2.

Results shown in Table 1 below illustrate the ability of anti-Lbp1 guinea pig antiserum, produced by immunization with affinity purified Lbp1 to lyse M. catarrhalis. The results show that the antisera produced by immunization with Lbp1 protein isolated from *M. catarrhalis* isolate 4223 was bactericidal against a homologous non-clumping *M. catarrhalis* strain RH408 (a strain previously deposited in connection with U.S. patent application Ser No. 08/328,589, assigned to the assignee hereof (WO 96/12733 published May 2, 1996) derived from isolate 4223. In addition, antisera produced by immunization with Lbp1 protein isolated from *M. catarrhalis* 4223 were bactericidal against the heterologous non-clumping strain Q8. The ability of isolated and purified lactoferrin binding protein to generate bactericidal antibodies is in vivo evidence of utility of these proteins as vaccines to protect against disease caused by Moraxella.

Thus, in accordance with another aspect of the present invention, there is provided a vaccine against Moraxella comprising an immunogenically-effective amount of lactoferrin binding protein or fragment or analog thereof, or a nucleic acid molecule (DNA or RNA) encoding the lactoferrin binding protein or fragment or analog thereof, and a physiologically-acceptable carrier therefor. The lactoferrin binding protein or fragment or analog thereof provided herein may also be used as a carrier protein for haptens, polysaccharide or peptides to make conjugate vaccines against antigenic determinants unrelated to lactoferrin binding proteins.

In additional embodiments of the present invention, therefore, the lactoferrin binding protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitidis, Salmonella typhi, Streptococcus mutans, Cryptococcus neoformans,* Klebsiella, *Staphylococcus aureus* and *Pseudomonas aeruginosa*. Particular antigens which can be conjugated to lactoferrin binding protein and methods to achieve such conjugations are described in U.S. patent application Ser. No. 08/433,522 filed Nov. 23, 1993 (WO 94/12641), assigned to the assignee hereof and the disclosure of which is hereby incorporated by reference thereto.

In another embodiment, the carrier function of lactoferrin binding protein may be used, for example, to induce an immune response against abnormal polysaccharides of tumour cells, or to produce anti-tumour antibodies that can be conjugated to chemotherapeutic or bioactive agents.

The lactoferrin binding protein provided herein is useful as a diagnostic reagent, as an antigen or for the generation of anti-lactoferrin protein binding antibodies, antigen for vaccination against disease caused by species of Moraxella and for detecting infection by Moraxella and other such bacteria The invention extends to lactoferrin binding proteins or fragments or analogs thereof or nucleic acid molecules encoding the same from *Moraxella catarrhalis* for use as an active ingredient in a vaccine against disease caused by infection with Moraxella. The invention also extends to a pharmaceutical vaccinal composition containing lactoferrin binding proteins or fragments or analogs thereof or nucleic acid molesules encoding the same from *Moraxella catarrhalis* and optionally, a pharmaceutically acceptable carrier and/or diluent.

In a further aspect the invention provides the use of lactoferrin binding proteins or fragments or analogs thereof or nucleic acid molesules encoding the same for the preparation of a pharmaceutical vaccinal composition for immunization against disease caused by infection with Moraxella.

It is clearly apparent to one skilled in the art, that the various embodiments of the present invention have many applications in the fields of vaccination, diagnosis, treatment of, for example, Moraxella infections and the generation of immunological and other diagnostic reagents. A further non-limiting discussion of such uses is further presented below.

1. Vaccine Preparation and Use

Immunogenic compositions, suitable to be used as vaccines, may be prepared from immunogenic lactoferrin receptor proteins, analogs and fragments thereof encoded by the nucleic acid molecules as well as the nucleic acid molecules disclosed herein. The vaccine elicits an immune response which produces antibodies, including anti-lactoferrin receptor antibodies and antibodies that are opsonizing or bactericidal. Should the vaccinated subject be challenged by Moraxella, the antibodies bind to the lactoferrin receptor and thereby prevent access of the bacteria to an iron source which is required for viability. Furthermore, opsonizing or bactericidal anti-lactoferrin receptor antibodies may also provide protection by alternative mechanisms.

Immunogenic compositions, including vaccines, may be prepared as injectables, as liquid solutions or emulsions. The lactoferrin receptor proteins, analogs and fragments thereof and encoding nucleic acid molecules as well as the nucleic acid molecules described herein may be mixed with pharmaceutically acceptable excipients which are compatible with the lactoferrin receptor proteins, fragments, analogs or nucleic acid molecules. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants, to enhance the effectiveness of the vaccines. Immunogenic compositions and vaccines may be administered parenterally, by injection subcutaneously, intradermally or intramuscularly. Alternatively, the immunogenic compositions provided according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration, including suppositories and oral formulations, may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain about 1 to 95% of the lactoferrin receptor proteins, fragments, analogs and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and, if needed, to produce a cell-mediated immune response. Precise amounts of active ingredient required to be administered depend on the judgement of the practitioner. However, suitable dosage ranges are readily determinable by one skilled in the art and may be of the order of micrograms of the lactoferrin receptor proteins, analogs and fragments thereof and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the lactoferrin receptor of Moraxella may be used directly for immunization by administration of the DNA directly, for example, by injection for genetic immunization or by constructing a live vector, such as Salmonella, BCG, adenovirus, poxvirus, vaccinia or poliovirus containing the nucleic acid molecules. A discussion of some live vectors that have been used to carry heterologous antigens to the immune system is contained in, for example, O'Hagan (ref. 18). Processes for the direct injection of DNA into test subjects for genetic immunization are described in, for example, Ulmer et al. (ref. 19).

Immunogenicity can be significantly improved if the antigens are co-administered with adjuvants, commonly used as an 0.05 to 1.0 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989, which is incorporated herein by reference thereto, teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 20) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, (ref. 21) reported that octadecyl esters of aromatic amino acids complexed with a recombinant hepatitis B surface antigen, enhanced the host immune responses against hepatitis B virus.

2. Immunoassays

The lactoferrin receptor proteins, analogs and/or fragments thereof of the present invention are useful as immunogens, as antigens in immunoassays including enzyme-linked immunosorbent assays (ELISA), RIAs and other non-enzyme linked antibody binding assays or procedures known in the art for the detection of anti-Moraxella, lactoferrin receptor protein antibodies. In ELISA assays, the lactoferrin receptor protein, analogs and/or fragments corresponding to portions of Lfr protein, are immobilized onto a selected surface, for example, a surface capable of binding proteins or peptides such as the wells of a polystyrene microtiter plate. After washing to remove incompletely adsorbed lactoferrin receptor, analogs and/or fragments, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by non-specific bindings of antisera onto the surface.

The immobilizing surface is then contacted with a sample, such as clinical or biological materials, to be tested in a manner conducive to immune complex (antigen/antibody)

formation. This procedure may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween or a borate buffer.

Following formation of specific immunocomplexes between the test sample and the bound lactoferrin receptor protein, analogs and/or fragments and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a spectrophotometer.

3. Use of Sequences as Hybridization Probes

The nucleotide sequences of the present invention, comprising the sequence of the lactoferrin receptor gene, now allow for the identification and cloning of the lactoferrin receptor genes from any species of Moraxella.

The nucleotide sequences comprising the sequence of the lactoferrin receptor genes of the present invention are useful for their ability to selectively form duplex molecules with complementary stretches of other lfr genes. Depending on the application, a variety of hybridization conditions may be employed to achieve varying degrees of selectivity of the probe toward the other lfr genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the lfr genes of the present invention may be used in combination with an appropriate means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing lfr gene sequences.

The nucleic acid sequences of lfr genes of the present invention are useful as hybridization probes in solution hybridizations and in embodiments employing solid-phase procedures. In embodiments involving solidphase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the lfr genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Moraxella. The selected probe may be at least 18 bp and may be in the range of about 30 to 90 bp.

4. Expression of the Lactoferrin Receptor Genes

Plasmid vectors containing replicon and control sequences which are derived from species compatible with the host cell may be used for the expression of the lactoferrin receptor genes in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the lactoferrin receptor genes, fragments or analogs thereof, may include E. coli, Bacillus species, Haemophilus, fungi, yeast, Moraxella, Bordetella, or the baculovirus expression system may be used.

In accordance with this invention, it is preferred to produce the lactoferrin receptor protein, fragment or analog thereof, by recombinant methods, particularly since the naturally occurring LfR protein as purified from a culture of a species of Moraxella may include trace amounts of toxic materials or other contaminants. This problem can be avoided by using recombinantly produced LfR protein in heterologous systems which can be isolated from the host in a manner to minimize contaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic lactoferrin receptor proteins, fragments or analogs thereof. Furthermore, recombinant methods of production permit the manufacture of Lbp1 or Lbp2 or Lbp3 or respective analogs or fragments thereof, separate from one another which is distinct from the normal combined proteins present in Moraxella.

Biological Deposits

Certain vectors that contain at least a portion coding for a lactoferrin receptor protein from strains of *Moraxella catarrhalis* strain 4223 and Q8 and a strain of *M. catarrhalis* RH408 that are described and referred to herein have been deposited with the American Type Culture Collection (ATCC) located at 10801 University Boulevard Manassas, Va. 2011-2209, USA, pursuant to the Budapest Treaty and prior to the filing of this application. Samples of the deposited vectors and bacterial strain will become available to the public and the restrictions imposed on access to the deposits will be removed upon grant of a patent based upon this United States patent application. In addition, the deposit will be replaced if viable samples cannot be dispensed by the Depository. The invention described and claimed herein is not to be limited in scope by the biological materials deposited, since the deposited embodiment is intended only as an illustration of the invention. Any equivalent or similar vectors or strains that encode similar or equivalent antigens as described in this application are within the scope of the invention.

Deposit Summary

| Deposit | ATCC Designation | Date deposited |
| --- | --- | --- |
| Plasmid pLD1-8 | 97,997 | April 23, 1997 |
| Plasmid pLDW1 | 97,998 | April 23, 1997 |
| Strain RH408 | 55,637 | Dec. 9, 1994 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

Example 1

This Example illustrates the generation of oligonucleotide primers for PCR amplification of *M. catarrhalis* lbpA.

Native Lbp1 was purified by affinity chromatography as described in U.S. Patent application Ser. No. 08/552,232, assigned to the assignee hereof and the disclosure of which is incorporated herein by reference.

Lactoferrin-Sepharose columns were prepared from the lactoferrin preparations by coupling a 10 mg/ml solution of lactoferrin to activated Sepharose (Pharmacia, Uppsala, Sweden) according to the manufacturer's instruction for coupling ligands to cyanogenbromide-activated Sepharose (CNBr-Sepharose). The resulting column was washed with 2 column volumes of 50 mM Tris buffer (pH 8.0) containing 6 M guanidine hydrochloride to remove non-covalently bound lactoferrin.

Bacterial cells resuspended from fresh cultures on chocolate plates were used to inoculate prewarmed Brian Heart Infusion broth containing 100 $\mu$M EDDA (ethylenediaminedi(O-hydroxyphenyl)acetic acid) to a starting $A_{600}$ of 0.02. The resulting culture was incubated at 37° C. with shaking for 16 hours prior to harvest by centrifugation at 9,000×g for 15 minutes. The cells were resuspended to 0.2 gm/ml in 50 mM TrisHCl, pH 8 buffer containing 50 $\mu$g/ml phenylmethylsulfonyl fluoride. The cells were lysed by passing the suspension through a French pressure cell at 16,000 lb/in$_2$ and cell debris was removed by centrifugation at 9,000×g for 15 minutes. Crude total membranes were collected by centrifugation at 140,000×g for 1 hour and resuspended in 50 mM TrisHCl, pH 8 buffer.

Ten mg of crude membrane protein was diluted in 1 ml of 50 mM Tris-HCl, 1 M NaCl, 20 mM EDTA (pH 8.0) buffer containing 0.75% Sarkosyl NL37. The solubilized membrane preparation was centrifuged at 10,000 rpm for 10 minutes to remove cell debris. The supernatant containing outer membrane components was mixed with 10 $\mu$l of the lactoferrin-Sepharose resin and incubated for 1 hour to allow the binding of lactoferrin receptor protein to its respective ligand. The resin was collected by centrifugation at 500×g for 10 minutes and resuspended in 50 mM TrisHCl, 1 M NaCl, 10 mM EDTA, 0.75% "SARKOSYL", pH 8 buffer. The resin was again collected by centrifugation and washed two more times in the above buffer. After the final wash, the resin was resuspended in 20 mls of the above buffer and poured into 1 cm diameter chromatography column. The packed resin was washed with an additional 10 mls of 50 mM TrisHCl, 1 M NaCl, 10 mM EDTA, 0.5% "SARKOSYL" and the receptor proteins were eluted by application of a 60 ml gradient of 1 to 3 M guanidine hydrochloride in 50 mM TrisHCl, 1 M NaCl, 10 mM EDTA, 0.05% "SARKOSYL". The fractions containing receptor proteins were pooled and dialyzed against two changes of 3 liters of 50 mM TrisHCl, pH 7.5 buffer and one change of phosphate buffered saline (50 mM sodium phosphate, 150 mM NaCl, pH 7.4) and concentrated by ultrafiltration.

The purified Lbp1 protein was digested overnight with cyanogen bromide, then fragments separated by SDS PAGE and submitted to sequence analysis. A 13 kDa protein fragment was found to have the N-terminal sequence MVQYTRKGENKAH (SEQ ID No: 67). A degenerate oligonucleotide primer (4393.RD) was prepared based upon this sequence:

```
    Q   Y   T   R   K   G   E   N   K   A       (SEQ ID No: 28)

5'                                      3'

CAA TAT ACI CGT AAA GGT GAA AAT AAA GC      (SEQ ID No: 29)
```

```
CAA TAT ACI CGT AAA GGC GAA AAC AAA GC      (SEQ ID No: 30)

CAA TAT ACI CGT AAA GGT GAA AAC AAA GC      (SEQ ID No: 31)

CAA TAT ACI CGT AAA GGC GAA AAT AAA GC      (SEQ ID No: 32)

CAA TAT ACI CGC AAA GGC GAA AAC AAA GC      (SEQ ID No: 33)

CAA TAT ACI CGC AAA GGC GAA AAT AAA GC      (SEQ ID No: 34)

CAA TAT ACI CGC AAA GGT GAA AAT AAA GC      (SEQ ID No: 35)

CAA TAT ACI CGC AAA GGT GAA AAC AAA GC      (SEQ ID No: 36)
```

There is a conserved C-terminal pentapeptide found in all known Lbp1 and Tbp1 protein sequences: LEMKF (SEQ ID No. 26). An oligonucleotide primer (4572.RD) was prepared based upon the complementary DNA sequence encoding this pentapeptide:

```
     L    E    M    K    F    *
5' CTT  GAA  ATG  AAG  TTT  TAA 3'          (SEQ ID NO: 37)

3' GAA  CTT  TAC  TTC  AAA  ATT 5'   4572.RD (SEQ ID No: 38)
```

Example 2

This Example illustrates the preparation of chromosomal DNA from M. catarrhalis strains 4223 and Q8.

M. catarrhalis isolate 4223 was inoculated into 100 ml of BHI broth, and incubated for 18 hr at 37° C. with shaking. The cells were harvested by centrifugation at 10,000×g for 20 min. The pellet was used for extraction of M. catarrhalis 4223 chromosomal DNA.

The cell pellet was resuspended in 20 ml of 10 MM Tris-HCl (pH 7.5)–1.0 mM EDTA (TE). Pronase and SDS were added to final concentrations of 500 µg/ml and 1.0%, respectively, and the suspension was incubated at 37° C. for 2 hr. After several sequential extractions with phenol, phenol:chloroform (1:1), and chloroform:isoamyl alcohol (24:1), the aqueous extract was dialysed, at 4° C., against 1.0 M NaCl for 4 hr. and against TE (pH 7.5) for a further 48 hr with three buffer changes. Two volumes of ethanol were added to the dialysate, and the DNA was spooled onto a glass rod. The DNA was allowed to air-dry, and was dissolved in 3.0 ml of water. Concentration was estimated, by UV spectrophotometry, to be about 290 µg/ml.

M. catarrhalis strain Q8 was grown in BHI broth. Cells were pelleted from 50 ml of culture by centrifugation at 5000 rpm for 20 minutes, at 4° C. The cell pellet was resuspended in 10 ml of TE (10 mM Tris-HCl, 1 mM EDTA, pH 7.5) and proteinase K and SDS were added to final concentrations of 500 µg/ml and 1%, respectively. The sample was incubated at 37° C. for 4 hours until a clear lysate was obtained. The lysate was extracted twice with Tris-saturated phenol/chloroform (1:1), and twice with chloroform. The final aqueous phase was dialysed for 24 hours against 2×1000 ml of 1 M NaCl at 4° C., changing the buffer once, and for 24 hours against 2×1000 ml of TE at 4°, changing the buffer once. The final dialysate was precipitated with two volume of 100% ethanol. The DNA was spooled, dried and resuspended in 5 to 10 ml of TE buffer.

Example 3

This Example illustrates the PCR amplification of a fragment of M. catarrhalis lbpA and the generation of probes for screening libraries.

PCR amplification was performed on chromosomal DNA isolated in Example 2 using primers 4393.RD and 4572.RD under the following cycling conditions: 25 cycles of 94° C. for 1 min, 47° C. for 30 sec and 72° C. for 1 min. PCR4 is the amplification of the 4223 lbpA fragment and PCR5 is the amplification of the Q8 lbpA fragment. A specific band of about 2.2 kb was amplified and partial sequence analysis was performed to ensure that the gene product was related to lbpA and was not tbpA. The derived amino acid sequences are shown in FIG. 1 and have been aligned with the complete 4223 Lbp1 sequence to show their placement and the 4223 Tbp1 sequence (U.S. application Ser. No. 08/613,009) to indicate their uniqueness.

The full-length 2.2 kb gene fragment was randomly labeled with $_{32}$P and used to probe genomic libraries.

Example 4

This Example illustrates the generation and screening of the EMBL 3 libraries.

Chromosomal DNA was prepared as described in Example 2.

A series of Sau3AI restriction digests of chromosomal DNA, in final volumes of 10 µL each, were carried out in order to optimize the conditions necessary to generate maximal amounts of restriction fragments within a 15 to 23 kb size range. Using the optimized digestion conditions, a large-scale digestion was set up in a 100 µL volume, containing the following: 50 µL of chromosomal DNA (290 µg/ml), 33 µL water, 10 µL 10X Sau3A buffer (New England Biolabs), 1.0 µL BSA (10 mg/ml, New England Biolabs), and 6.3 µL Sau3A (0.04 U/µL). Following a 15 min. incubation at 37° C., the digestion was terminated by the addition of 10 µL of 100 mM Tris-HCl (pH 8.0)–10 mM EDTA-0.1% bromophenol blue-50% glycerol (loading buffer). Digested DNA was electrophoresed through a 0.5% agarose gel in 40 mM Tris acetate-2 mM Na$_2$EDTA.2H$_2$O (pH 8.5)(TAE buffer) at 50 V for 6 hr. The region containing restriction fragments within a 15 to 23 kb molecular size range was excised from the gel, and placed into dialysis tubing containing 3.0 ml of TAE buffer. DNA was electroeluted from the gel fragment by applying a field strength of 1.0 V/cm for 18 hr. Electroeluted DNA was extracted once each with phenol and phenol:chloroform (1:1), and precipitated with ethanol. The dried DNA was dissolved in 5.0 µL water.

Size-fractionated chromosomal DNA was ligated with BamHI-digested EMBL3 arms (Promega), using T4 DNA ligase in a final volume of 9 μL. The entire ligation mixture was packaged into lambda phage using a commercial packaging kit (Amersham), following manufacturer's instructions.

The packaged DNA library was amplified on solid media. 0.1 ml aliquots of Escherichia coli strain NM539 in 10 mM MgSO$_4$ (OD$_{260}$=0.5) were incubated at 37° C. for 15 min. with 15 to 25 μL of the packaged DNA library. Samples were mixed with 3 ml of 0.6% agarose containing 1.0% BBL trypticase peptone-0.5% NaCl (BBL top agarose), and mixtures were plated onto 1.5% agar plates containing 1.0% BBL trypticase peptone-0.5% NaCl, and incubated at 37° C. for 18 hr. 3 ml quantities of 50 mM Tris-HCl (pH 7.5)–8 mM magnesium sulfate heptahydrate-100 mM NaCl-0.01% (w/v) gelatin (SM buffer) were added to each plate, and plates were left at 4° C. for 7 hr. SM buffer containing phage was collected from the plates, pooled together, and stored in a screwcap tube at 4° C., with chloroform.

Ten μL aliquots of phage stock were combined each with 100 μL of E. coli strain LE392 in 10 mM MgSO4 (OD$_{260}$= 0.5) (plating cells), and incubated at 37° C. for 15 min. The samples were mixed with 3 ml each of BBL top agarose, and the mixtures were poured onto 1.5% agarose plates containing 1% bacto tryptone-0.5% bacto yeast extract-0.05% NaCl (LB agarose; Difco) and supplemented with 200 μM EDDA. The plates were incubated at 37° C. for 18 hr. Plaques were lifted onto nitrocellulose filters (Amersham Hybond-C Extra) which were hybridized with the 32P-labelled 2.2 kb PCR fragment. Several putative phage clones were obtained from each library and clones 4223LfR.17 and Q8LfR.13 were chosen for further analysis.

Example 5

This Example illustrates the subcloning of the phage clones containing M. catarrhalis lfr genes.

Restriction enzyme analysis and Southern blotting using the screening probes, indicated that at least a portion of lbpA was localized to an about 9 kb Hind III fragment from each phage clone. The about 9 kb Hind III fragment from 4223LfR.17 was subcloned into pUC 18, generating clone pLD1-8. The about 9 kb Hind III fragment from Q8LfR.13 was subcloned into pBluescript, generating plasmid pLDW1. Internal about 5.5 kb EcoR V fragments were subcloned generating plasmids pLD3 and pLDW3 for the 4223 and Q8 genes, respectively.

Example 6

This Example illustrates the sequence analysis of clones containing the M. catarrhalis lfr genes from strains 4223 and Q8.

Figure 5A:
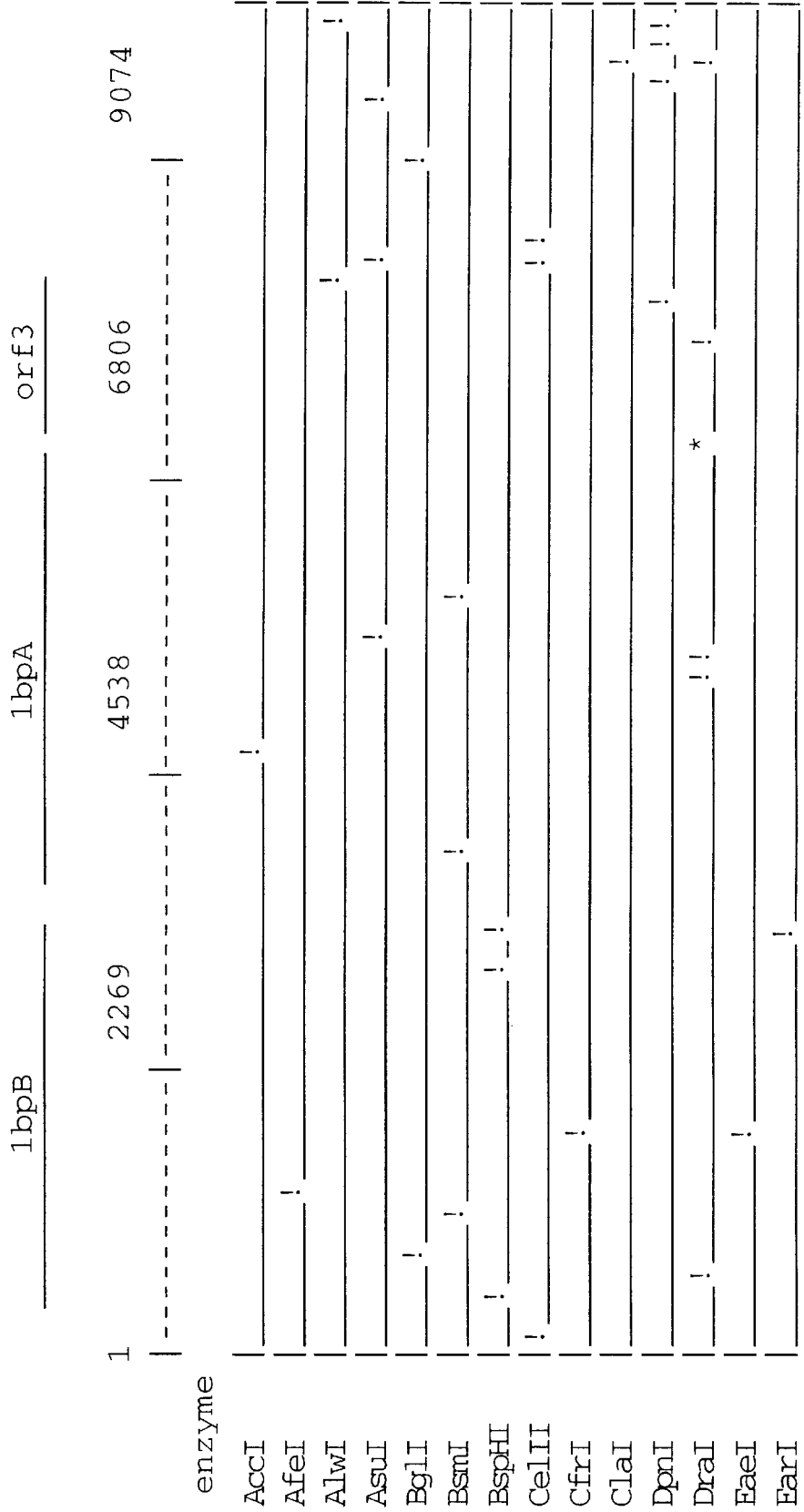
FIG. 5 shows a restriction map of clone pLDW1 containing the lbpA, lbpB and orf3 genes from *M. catarrhalis* isolate Q8.
Figure 5B:
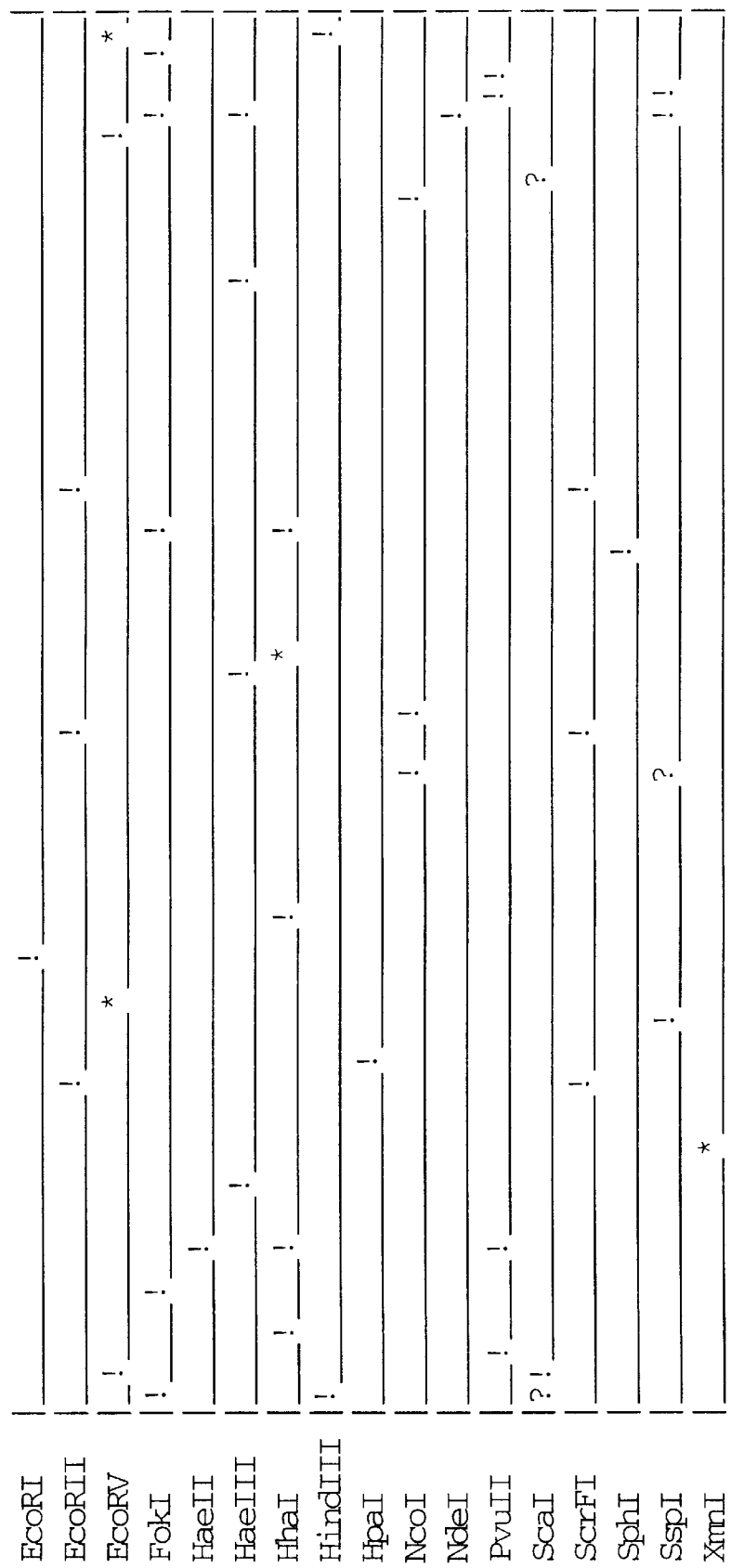

Sequence analysis of the 5.5 kb EcoR V fragments from pLD3 and pLDW3, revealed that they each contained the 3'-end of lbpB, the complete lbpA gene, and a third complete gene designated orf3. The remainder of the lbpB genes was found on the about 9 kb Hind III fragments from pLD1-8 and pLDW1. Partial restriction enzyme analysis of the 4223 lbpA, lbpb, and orf3 genes, based upon the nucleotide sequences is shown in FIG. 3. Partial restriction enzyme analysis of the Q8 lbpA, lbpB, and orf3 genes, based upon the nucleotide sequences is shown in FIG. 5. The complete sequences of the lbpb, lbpA, and orf3 genes comprising the putative lfr locus from M. catarrhalis 4223 and Q8 is shown in FIGS. 2 and 4, respectively. The intergenic distance between the lbpB and lbpA genes is 184 nucleotides, while a single nucleotide separates the lbpA and orf3 genes. A putative promoter and ribosome binding site is indicated by underlining upstream of both lbpB and lbpA. A fourth potential gene was cloned on the approximately 9 kb Hind III fragments.

The N-terminal sequence of the native Lbp1 protein is unknown. Examination of the deduced amino acid sequence of the lbpA gene indicates that there are two possible ATG start codons at positions 1 and 16. The first position is downstream of strong promoter elements found in the lbpB-lbpA intergenic region and the second position is followed by a putative signal sequence. The M. catarrhalis 4223 and Q8 Lbp1 proteins (from the first ATG) have molecular mass values of about 110 kDa and are 99% identical. The deduced Lbp1 protein sequences from M. catarrhalis strains 4223 and Q8 are compared in FIG. 6. They are also compared with the iroA/lbpA gene from N. meningitidis strain BNCV (ref. 24) and the lbpA gene from N. gonorrhoeae strain FA19 (ref. 25). The M. catarrhalis proteins are found to be about 32% identical and about 50% similar to the Neisseria proteins. As shown in FIG. 1, there is very limited sequence homology between the M. catarrhalis Tbp1 and Lbp1 sequences.

The deduced Lbp2 protein sequences from M. catarrhalis strains 4223 and Q8 are compared in FIG. 7. The 4223 and Q8 Lbp2 proteins both have molecular masses of about 99 kDa and are 92% identical and 95% similar to each other. A comparison to the M. catarrhalis Tbp2 proteins shows very little homology except the LEGGFY (SEQ ID No: 27) epitope previously identified in H. influenzae and N. meningitidis Tbp2 proteins (FIG. 8). A cysteine residue at position 32 is preceded by a consensus sequence for lipoproteins suggesting that Lbp2, like Tbp2, is a lipoprotein. An unusual feature of the Lbp2 proteins is the high combined aspartic acid and asparagine content which is nearly 20%. In addition, the 4223 Lbp2 amino acid composition from residues 698 to 751 is about 52% aspartic acid.

The 4223 and Q8 lfr orf3 genes would encode proteins (Lbp3) of molecular mass about 60 kDa, respectively. A notable feature of the Lbp3 protein is a potential signal sequence, a terminal phenylalanine which is often associated with membrane anchored proteins, an internal repeat sequence of DGLG (SEQ ID No: 39), and a high leucine content of 15%. The deduced Lbp3 protein sequences are compared in FIG. 9. These proteins are 98% identical and 99% similar.

Example 7

This Example illustrates the construction of vectors to express M. catarrhalis Lbp1 from the first methionine in E. coli.

Figure 10:
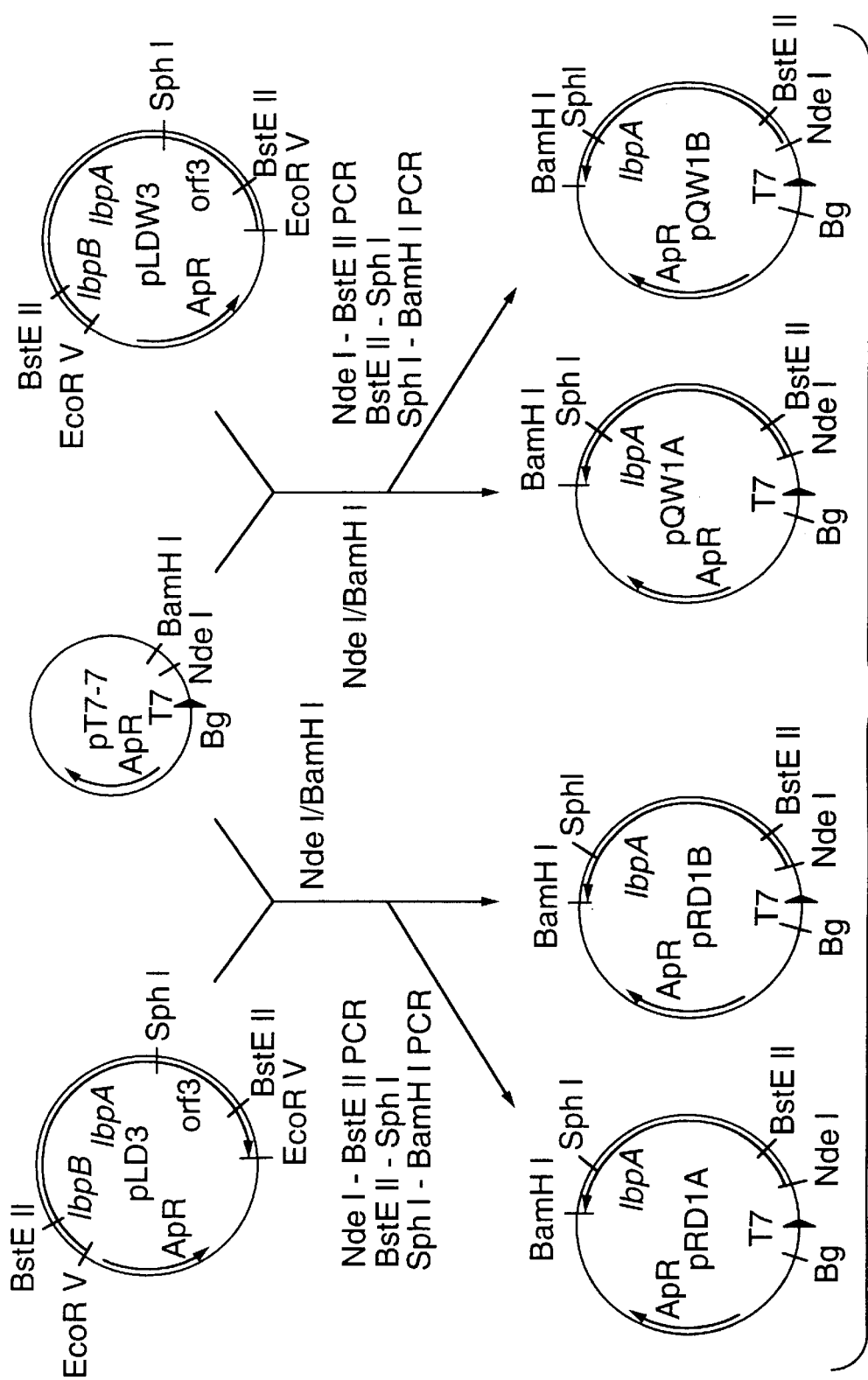
FIG. 10 shows the construction of plasmids for expression of recombinant Lbp1 protein from *E. coli*. Plasmids pRD1A and pRD1B express 4223 Lbp1 from the first or second methionine residues, respectively. Plasmids pQW1A and pQW1B express Q8 Lbp1 from the first or second methionine residues, respectively.

There are two possible start codons at the beginning of the lbpA gene and hence two expression constructs were made. The construction scheme for 4223 or Q8 lbpA expressed from the first methionine is shown in FIG. 10. An approximately 200 bp fragment of the 5'-end of lbpA from the ATG to a BstE II site was PCR amplified using primers 5405.RD and 5407.RD. An Nde I site was engineered at the 5'-end to facilitate cloning into the pT7-7 vector.

```
NdeI
            M   S   K   S   I   T              (SEQ ID No: 40)

5'   GGAATTCCAT ATG TCA AAA TCT ATC ACA AA 3'  5405.RD    (SEQ ID No: 41)

BstE II
        L   D   A   I   T   V   T   A          (SEQ ID No: 42)

5'   T TTA GAT GCC ATC ACG GTA ACC GCC GCC CC  3'         (SEQ ID No: 43)

3'   A AAT CTA CGG TAG TGC CAT GGC CGG CGG GG  5'  5407.RD (SEQ ID No: 44)
```

In order to subclone the lbpA gene into pT7-7, a approximately 515 bp fragment of the 3'-end of the gene from an Sph I site to the stop codon was PCR amplified using primers 5281.RD and 5282.RD and a BamH1 site was engineered at 3'-end.

```
                    Sph I
        G   K   L   D   L   H   A   M   T   S      (SEQ ID No: 45)

5'   GGC AAA CTG GAT TTG CAT GCC ATG ACA TCA  3' 5281.RD   (SEQ ID No: 46)

S   L   E   M   K   F   *                  (SEQ ID No: 47)

5'   AGT CTT GAA ATG AAG TTT AAA            3'     (SEQ ID No: 48)

3'   TCA GAA CTT TAC TTC AAA AAT GCC CTA GGG C 5' 5282.RD  (SEQ ID No: 49)
                                    BamH I
```

For the Q8 subclone, plasmid pLDW3, prepared as described in Example 5, was digested with BstE II and Sph I generating a 2.3 kb fragment of lbpA which was ligated with the Nde I-BstE II and SphI-BamH I FCR fragments and cloned into pT7-7 digested with NdeI and BamH I. The resulting plasmid pQW1A thus contains the full-length Q8 lbpA gene from the first methionine, under the control of the T7 promoter. DNA from pQW1A was purified and transformed by electroporation into electrocompetent BL21(DE3) cells to generate strain QW1A which was grown and induced using IPTG. Expressed proteins were resolved by SDS-PAGE and the induced Lbp1 protein was visualized by Coomassie blue staining (FIG. 11).

For the 4223 subclone, plasmid pLD3, prepared as described in Example 5 was digested with BstEII and SphI, generating a 2.3 kb fragment of lbpA, which was ligated with the Nde I-BstE II and SphI-BamH I PCR fragments and cloned into pT7-7 digested with NdeI and BamH I. The resulting plasmid pRD1A thus contains the full-length 4223 lbpA gene from the first possible methionine under the control of the T7 promoter. DNA from pRD1A was purified and transformed by electroporation into electrocompetent BL21(DE3) cells to generate strain RD1A which was grown and induced using IPTG. Expressed proteins were resolved by SDS-PAGE and the induced Lbp1 protein was visualized by Coomassie blue staining (FIG. 11).

The Q8 Lbp1 protein was expressed at very high levels but the 4223 Lbp1 protein was expressed at substantially lower levels.

Example 8

Figure 14:
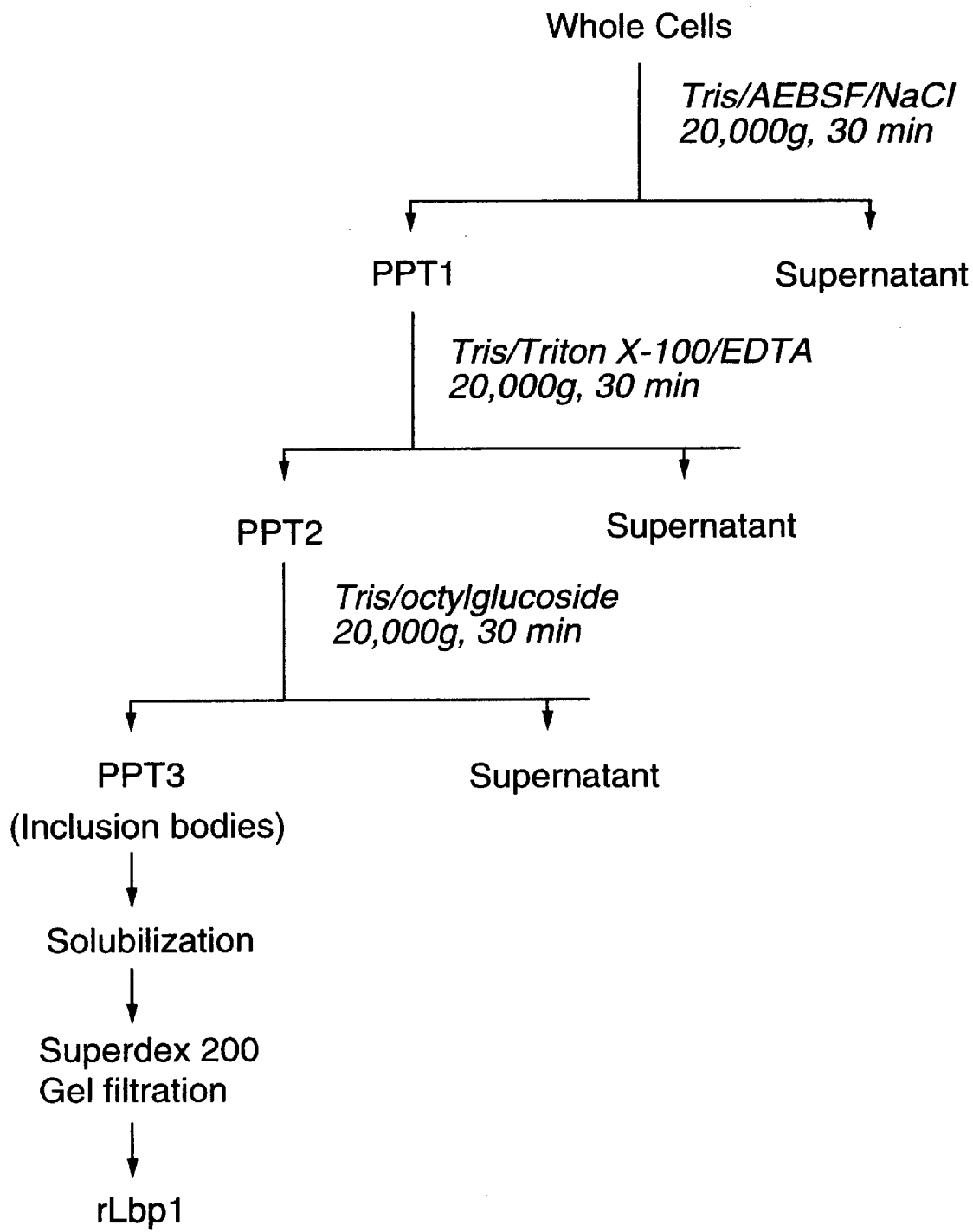
FIG. 14 shows a purification scheme for rLbp1 expressed from E. coli.

This Example illustrates the extraction and purification of rLbp1 from E. coli. The procedure is illustrated generally in FIG. 14.

E. coli cells from a 500 ml culture, prepared as described in Example 7, were resuspended in 40 ml of 50 mM Tris-HCl, pH 8.0 containing 5 mM AEBSF (protease inhibitor) and 0.1 M NaCl, and disrupted by sonication (3×10 min, 70% duty circle). The extract was centrifuged at 20,000×g for 30 min and the resultant supernatant, which contained greater than 95% of the soluble proteins from E. coli, was discarded. The remaining pellet (FIG. 14, PPT1) was further extracted in 40 ml of 50 mM Tris, pH 8.0 containing 0.5% Triton X-100 and 10 mM EDTA. The mixture was stirred at 4° C. for at least 1 hour and then centrifuged at 20,000×g for 30 min and the supernatant containing residual soluble proteins and the majority of the membrane proteins was discarded. The resultant pellet (FIG. 14, PPT2) was further extracted in 40 ml of 50 mM Tris, pH 8.0 containing 1% octylglucoside. The mixture was stirred at 4° C. for at least 1 hour and then centrifuged at 20,000×g for 30 min. The supernatant containing residual contaminating proteins was discarded. The resultant pellet (FIG. 14, PPT3) obtained after the above extractions contained the Lbp1 protein as inclusion bodies.

Figure 15:
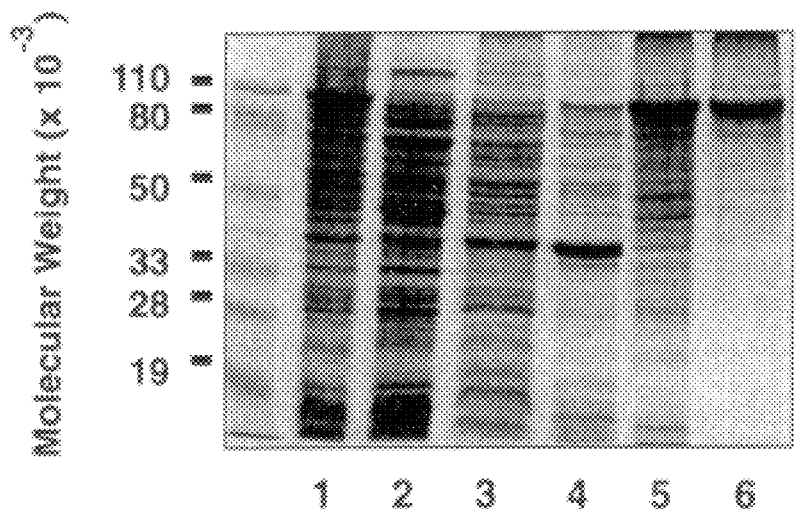
FIG. 15 shows an SDS PAGE gel of the purification of Q8 Lbp1 from E. coli. Lane 1, BL21(DE3) lysate; lane 2, soluble proteins after 50 mM Tris/5 mM AEBSF/0.5 M NaCl, pH 8.0 extraction; lane 3, soluble proteins after 50 mM Tris/0.5% Triton X-100/10 mM EDTA, pH 8.0 extraction; lane 4, soluble proteins after 50 mM Tris-HCl/1% octylglucoside, pH 8.0 extraction; lane 5, solubilized inclusion bodies; lane 6, purified Lbp1.

The rLbp1 protein was solubilized from the inclusion bodies in 50 mM Tris, pH 8.0, containing 6 M guanidine and 5 mM DTT. After centrifugation, the resultant supernatant was further purified on a Superdex 200 gel filtration column equilibrated in 50 mM Tris-HCl, pH 8.0, containing 2 M guanidine and 5 mM DTT. The fractions were analysed by SDS-PAGE and those containing purified rLbp1 were pooled. Triton X-100 was added to the pooled rLbp1 fraction to a final concentration of 0.1%. The fraction was dialysed overnight at 4° C. against PBS, and then centrifuged at 20,000×g for 30 min. The purified rLbp1 was stored at −20° C. Samples from the purification were analyzed by SDS-PAGE (FIG. 15).

Example 9

This Example illustrates the construction of vectors to express M. catarrhalis Lbp1 from the second methionine in E. coli.

The construction scheme for 4223 or Q8 lbpA expressed from the second methionine is shown in FIG. 10. An approximately 200 bp fragment of the 5'-end of lbpA from the ATG to a BstE II site was PCR amplified using primers 5406.RD and 5407.RD. An Nde I site was engineered at the 5'-end to facilitate cloning into the pT7-7 vector.

and Q8. The 5'-end of the lbpB gene was PCR amplified from the ATG start codon through the first BspH I site generating an approximately 201 bp fragment. An NdeI site was engineered at the ATG to facilitate cloning into the pT7-7 expression vector. The oligonucleotides used for amplification are illustrated below:

```
        NdeI

M    T    T    H    R    L                (SEQ ID No: 50)
5'  GGAATTCCAT ATG  ACC  ACG  CAC  CGC  TTA  AA  3'  5406.RD  (SEQ ID No: 51)

BstE II
        L    D    A    I    T    V    T    A    A
5'   T  TTA  GAT  GCC  ATC  ACG GTA ACC  GCC  GCC  CC   3'
3'   A  AAT  CTA  CGG  TAG  TGC  CAT  TGG  CGG  CGG  GG   5'      5407.RD
```

The 3'-end of the lbpA gene was PCR amplified from the SphI restriction site to the stop codon using primers 5281.RD and 5282.RD as described in Example 8.

The 2.3 kb BstE II-Sph I fragments described in Example 8 were ligated to the Nde I-BstE II and Sph I-BamH I PCR fragments and cloned into pT7-7 that had been digested with NdeI and BamH I. Plasmid pQW1B thus contains a full-length Q8 lbpA gene from the second methionine and plasmid pRD1B contains a full-length 4223 lbpA gene from the second methionine under the direction of the T7 promoter. DNA was purified and transformed by electroporation into electrocompetent BL21(DE3) cells to generate recombinant strains which were grown and induced using IPTG. Expressed proteins were resolved by SDS-PAGE and the induced Lbp1 proteins were visible by Coomassie blue staining (FIG. 11).

As seen for the longer protein in Example 8, the shorter Lbp1 from Q8 was expressed to much higher levels than the corresponding 4223 protein. coli.

```
        NdeI

M    S    T    V    K    T    P    H    I         (SEQ ID No: 52)
5'  GGAATTCCAT ATG  AGT  ACT  GTC  AAA  ACC  CCC  CAC  A  3'  5533.RD  (SEQ ID No: 53)

BspH I
        I    P    N    T    G    H    D    N    T    N         (SEQ ID No: 54)
5'     A  ATA  CCG  AAC  ACA  GGT CAT GAC  AAC  ACC  AAT   3'           (SEQ ID No: 55)
       T  TAT  GGC  TTG  TGT  CCA  GTA  CTG  TTG  TGG  TTA  5'  5534.RD  (SEQ ID No: 56)
```

Example 10

This Example illustrates the construction of vectors to express *M. catarrhalis* Lbp2 with a leader sequence from *E.*

Figure 12:
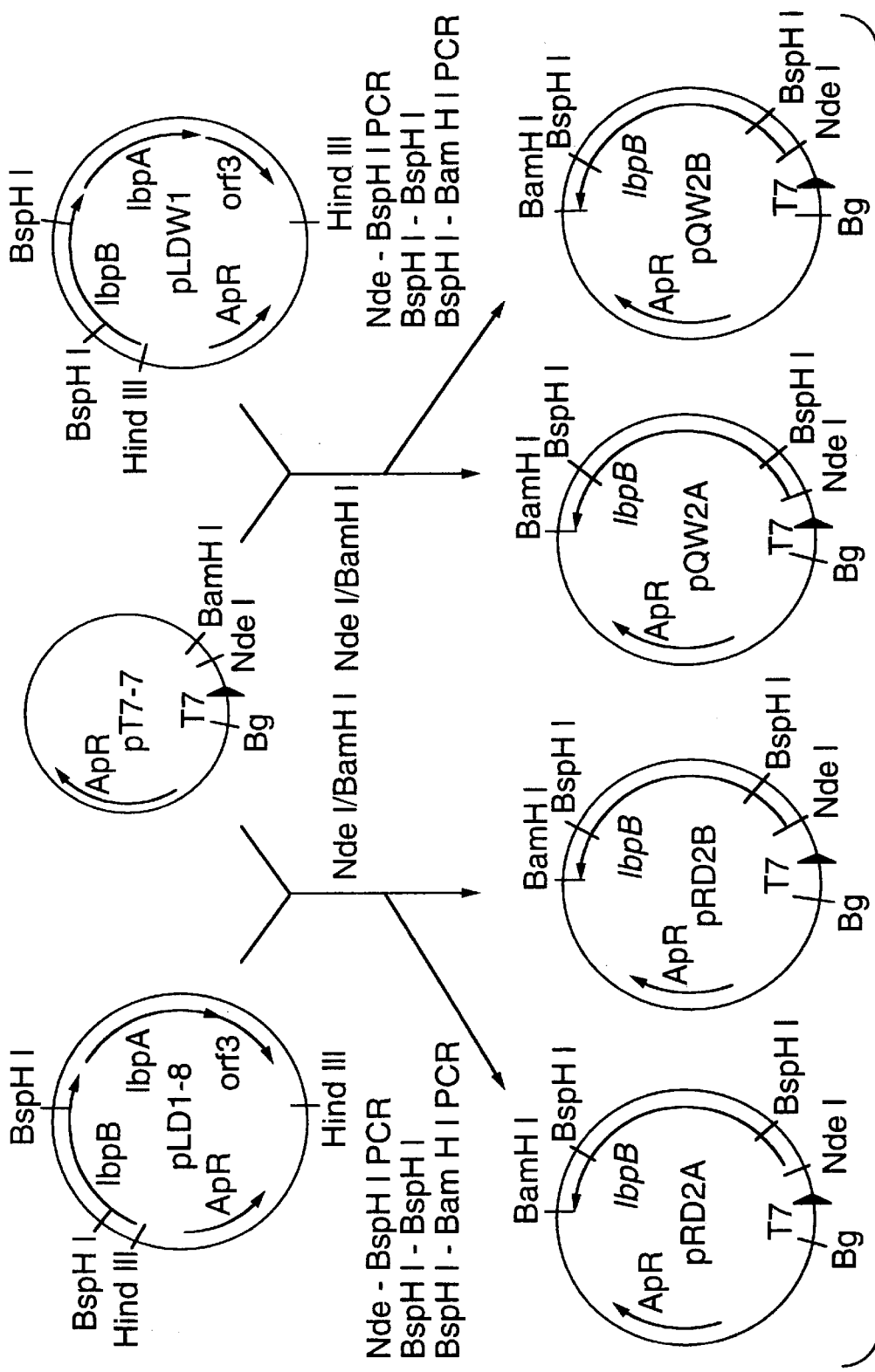
FIG. 12 shows the construction of plasmids for expression of recombinant Lbp2 (rLbp2) protein from *E. coli*. Plasmids pRD2A and pRD2B express 4223 Lbp2 with or without the native leader sequence, respectively. Plasmids pQW2A and pQW2B express Q8 Lbp2 with or without the native leader sequence, respectively.

The construction scheme is illustrated in FIG. 12. There are two BspH I sites within the lbpB genes of strains 4223

The 3'-end of the lbpB gene was PCR amplified from the second BspH I site to the TAA stop codon generating a 381 bp fragment. A BamH I site was introduced after the stop codon for cloning purposes. The oligonucleotides used for amplification are illustrated below:

```
        N    E    P    T    H    E    K    T    F    A              (SEQ ID No: 57)
5'  AAT  GAG  CCT  ACT  CAT  GAA  AAA  ACC  TTT  GCC  3'  5535.RD  (SEQ ID No: 58)
```

```
                           -continued
     G   A   V   F   G   A   V   K   D   K   *                 (SEQ ID No: 59)

5' GG GCT GTC TTT GGG GCT GTT AAA GAT AAA TAA  3'              (SEQ ID No: 60)

CC CGA CAG AAA CCC CGA CAA TTT CTA TTT ATT CCTAGGGC 5' 5536.RD (SEQ ID No: 61)
                                               BamH I
```

Plasmids pLD1-8 or pLDW1, prepared as described in Example 4, were digested with BspH I to release a 2.1 kb internal fragment of the lbpB gene which was ligated with the 5'- and 3'-PCR fragments and cloned into pT7-7 that had been digested with NdeI and BamH I. The resulting plasmids, pLD2A and pLDW2A, contain the full-length 4223 and Q8 lbpB genes under the control of the T7 promoter, respectively.

Example 11

This Example illustrates the construction of vectors to express the mature *M. catarrhalis* Lbp2 proteins from *E. coli*.

The construction scheme is illustrated in FIG. 12. The putative mature Lbp2 lipoproteins start at the $Cys^{32}$ residue. A scheme similar to that described in Example 10 can be used to generate expression clones. To amplify the 5'-end of the lbpB gene, a sense PCR primer is designed that includes an NdeI site for subsequent cloning and an ATG start codon for initiation of translation followed immediately by the $Cys^{32}$ residue. The antisense primer is the same as that described in Example 9 (5534.RD) and includes the BspH I cloning site. The amplified fragment is ~112 bp long. The oligonucleotides are illustrated below:

fragments with the 2.1 kb BspH I fragment and vector pT7-7 digested with NdeI and BamH I. The resulting plasmids, pLD2B and pLDW2B, contain the lbpB gene encoding the mature Lbp2 proteins from strains 4223 and Q8 under the direction of the T7 promoter, respectively.

Example 12

This Example illustrates the construction of a vector to express the *M. catarrhalis* lfr Lbp3 from *E. coli*.

Figure 13:
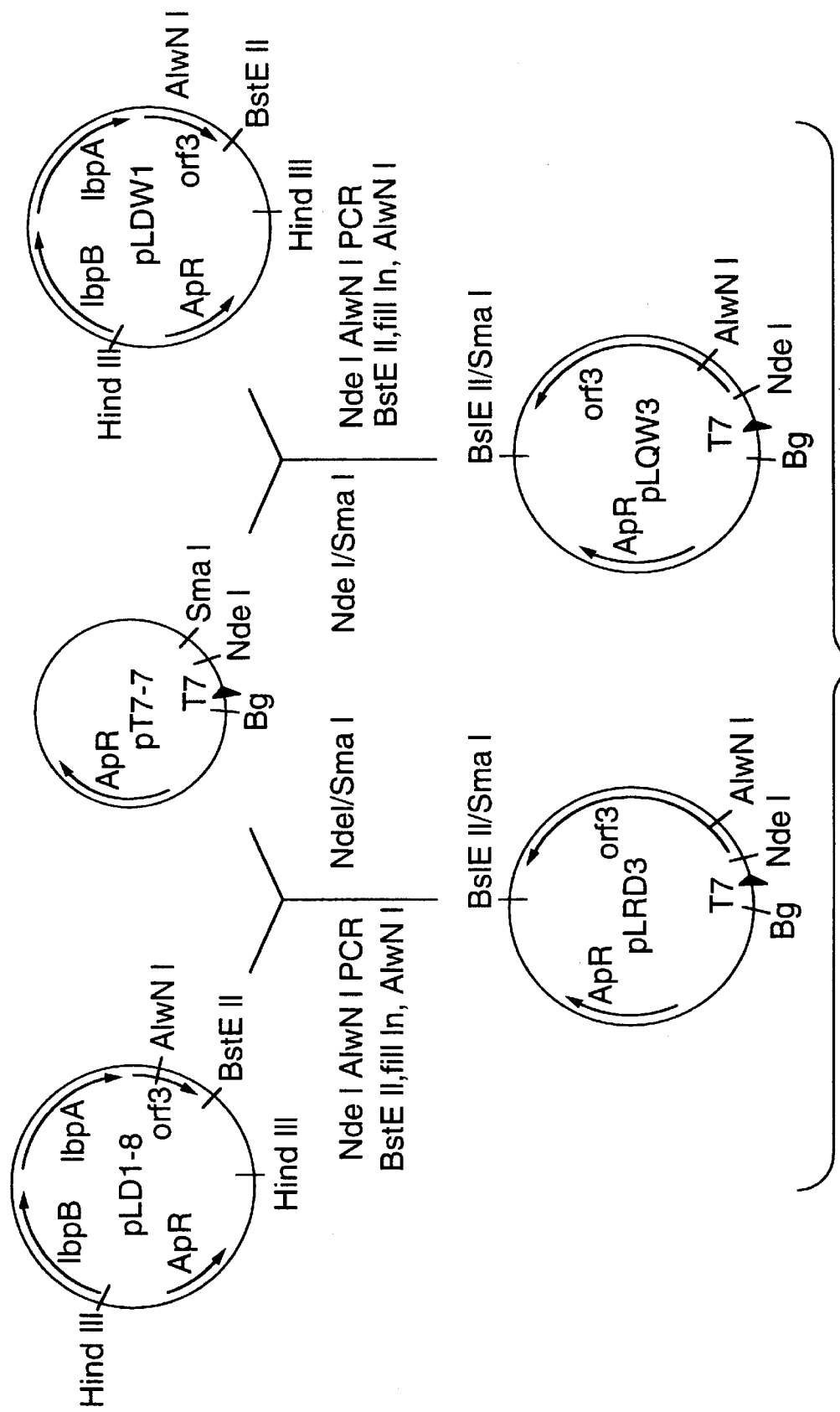
FIG. 13 shows the construction of a plasmid for expression of the recombinant Lbp3 (rLbp3) proteins from E. coli. Plasmid pLRD3 expresses 4223 Lbp3 and plasmid pLQW3 expresses Q8 Lbp3.

The construction scheme is illustrated in FIG. 13. Oligonucleotides were used to generate the 5'-end of the orf3 gene from the ATG start codon to an AlwN I site. An NdeI site was engineered at the 5'-end for subsequent cloning into pT7-7. The oligonucleotides are shown below:

```
         NdeI
              M   C   R   S   D   D   I   S   V   N         (SEQ ID No: 62)
5' GGAATTCCAT ATG TGC CGC TCT GAT GAC ATC AGC GTC AAT 3'  .RD (SEQ ID No: 63)

BspH I
         I  P  N  T  G  H  D  N  T  N                      (SEQ ID No: 54)
5'    A ATA CCG AAC ACA GGT CAT GAC AAC ACC AAT      3'    (SEQ ID No: 55)
      T TAT GGC TTG TGT CCA GTA CTG TTG TGG TTA 5'  5534.RD (SEQ ID No: 56)
```

The BspH I-BamH I 3'-end of the lbpB gene is PCR amplified as in Example 9 and the plasmid expressing mature Lbp2 is constructed by ligating the 5'- and 3'-PCR

```
      NdeI
         M   T   C   L   P   K   T   N   P   A   L   K   V   K   H   R   (SEQ ID No: 64)
5'  T ATG ACC TGT TTA CCA AAG ACC AAC CCT GCT TTA AAA GTC AAG CAC AGA (SEQ ID No: 65)
3'    AC TGG ACA AAT GGT TTC TGG TTG GGA CGA AAT TTT CAG TTC GTG TCT (SEQ ID No: 66)
                AlwN I
         F   L   K   Q   V
         TTT TTA AAG CAG GTG      3'      5532.RD
         AAA AAT TTC GTC          5'      5457.RD
```

The pLD1-8 or pLDW1 plasmid, prepared as described in Example 5, was digested with BstE II generating a 4.6 kb fragment which was filled in with Klenow polymerase before being digested with AlwNI. The resultant 1.8 kb fragment was ligated with the annealed NdeI-AlwN I oligonucleotides and cloned into pT7-7 that had been digested with NdeI and SmaI. The resulting plasmids, pLRD3 and pLQW3, contain the full-length orf3 genes from strains 4223 and Q8 under the direction of the T7 promoter, respectively.

SUMMARY OF THE DISCLOSURE

In summary of this disclosure, the present invention provides purified and isolated DNA molecules containing lactoferrin receptor genes from Moraxella catarrhalis, the sequences of these lactoferrin receptor genes, and the derived amino acid sequences thereof. The genes and DNA sequences are useful for diagnosis, immunization, and the generation of diagnostic and immunological reagents. Immunogenic compositions, including vaccines, based upon expressed recombinant Lbp1 and/or Lbp2 and/or Lbp3, portions thereof, or analogs thereof, can be prepared for prevention of diseases caused by Moraxella. Modifications are possible within the scope of this invention.

TABLE 1

| Bactericidal antibody titres for anti-Lbp1 | | | | |
|---|---|---|---|---|
| | Bactericidal titre - RH408 | | Bactericidal titre - Q8 | |
| Antibody | Pre-immune | Immune | Pre-immune | Immune |
| Anti-4223 Lbp1 | <8 | 114–330 | <8 | 128–512 |

Bactericidal titres are expressed as the reciprocal dilution of antiserum capable of killing 50% of M. catarrhalis cells

REFERENCES

1. Brorson, J-E., A. Axelsson, and S. E. Holm. 1976. Studies on Branhamella catarrhalis (Neisseria catarrhalis) with special reference to maxillary sinusitis. Scan. J. Infect. Dis. 8:151–155.
2. Catlin, B. W., 1990. Branhamella catarrhalis: an organism gaining respect as a pathogen. Clin. Microbiol. Rev. 3: 293–320.
3. Hager, H., A. Verghese, S. Alvarez, and S. L. Berk. 1987. Branhamella catarrhalis respiratory infections. Rev. Infect. Dis. 9:1140–1149.
4. McLeod, D. T., F. Ahmad, M. J. Croughan, and M. A. Calder. 1986. Bronchopulmonary infection due to M. catarrhalis. Clinical features and therapeutic response. Drugs 31(Suppl.3):109–112.
5. Nicotra, B., M. Rivera, J. I. Luman, and R. J. Wallace. 1986. Branhamella catarrhalis as a lower respiratory tract pathogen in patients with chronic lung disease. Arch.In- tern.Med. 146:890–893.
6. Ninane, G., J. Joly, and M. Kraytman. 1978. Bronchopulmonary infection due to Branhamella catarrhalis 11 cases assessed by transtracheal puncture. Br.Med.Jr. 1:276–278.
7. Srinivasan, G., M. J. Raff, W. C. Templeton, S. J. Givens, R. C. Graves, and J. C. Mel. 1981. Branhamella catarrhalis pneumonia. Report of two cases and review of the literature. Am. Rev. Respir. Dis. 123:553–555.
8. West, M., S. L. Berk, and J. K. Smith. 1982. Branhamella catarrhalis pneumonia., South. Med. J. 75:1021–1023.
9. Christensen, J. J., and B. Bruun. 1985. Bacteremia caused by a beta-lactamase producing strain of Branhamella catarrhalis. Acta. Pathol. Microbiol. Immunol. Scand. Sect. B 93:273–275.
10. Craig, D. B., and P. A. Wehrle. 1983. Branhamella catarrhalis septic arthritis. J. Rheumatol. 10:985–986.
11. Guthrie, R., K. Bakenhaster, R. Nelson, and R. Woskobnick. 1988. Branhamella catarrhalis sepsis: a case report and review of the literature. J. Infect. Dis. 158:907–908.
12. Hiroshi, S., E. J. Anaissie, N. Khardori, and G. P. Bodey. 1988. Branhamella catarrhalis septicemia in patients with leukemia. Cancer 61:2315–2317.
13. O'Neill, J. H., and P. W. Mathieson. 1987. Meningitis due to Branhamella catarrhalis. Aust. N. Z. J. Med. 17:241–242.
14. Murphy, T. F. 1989. The surface of Branhamella catarrhalis: a systematic approach to the surface antigens of an emerging pathogen. Pediatr. Infect. Dis. J. 8:S75–S77.
15. Van Hare, G. F., P. A. Shurin, C. D. Marchant, N. A. Cartelli, C. E. Johnson, D. Fulton, S. Carlin, and C. H. Kim. Acute otitis media caused by Branhamella catarrhalis: biology and therapy. Rev. Infect. Dis. 9:16–27.
16. Jorgensen, J. H., Doern, G. V., Maher, L. A., Howell, A. W., and Redding, J. S., 1990 Antimicrobial resistance among respiratory isolates of Haemophilus influenza, Moraxella catarrhalis, and Streptococcus pneumoniae in the United States. Antibicrob. Agents Chemother. 34: 2075–2080.
17. Schryvers, A. B. and Lee, B. C. (1988) Comparative analysis of the transferrin and lactoferrin binding proteins in the family Neisseriaceae. Can. J. Microbiol. 35, 409–415.
18. O'Hagan, DT. 1992. Oral deleivery of vaccines. Formulation and clinical pharmaco kinetic considerations. Clin. Pharmacokinet 22(t):1–10.
19. Ulmer et al. 1993. Curr. Opinion Invest. Drugs 2:983–989.
20. Lockhoff, O., 1991. Glycolipids as immunomodulators: Synthesis and properties.
21. Nixon-George A., et al., 1990. The adjuvant effect of stearyl tyrosine on a recombinant subunit hepatitis B surface antigen. J Immunol 144 (12):4798–4802.
22. Wallace, R. J. et al., 1990. Antibiotic susceptibilites and drug resistance in Moraxella (Branhaemella) catarrhalis. Am. J. Med. 88(5A):465–505.
23. Nissinen A, et al., 1995. Development of beta-lactamase-mediated resistance to penicillin in middle-ear isolates of Moraxella catarrhalis in Finnish children, 1978–1993. Clin Infect Dis 21 (5):1193–1196.
24. Pettersson, A., et al., 1994. Identification of iroa Gene Product of Neisseria meningitides as a Lactoferrin Receptor. J. Bacteriol. 176(6):1764–1766.
25. Biswas G D, Sparring P F. 1995. Characterization of lbpa, the structural gene for a lactoferrin receptor in Neisseria gonorrhoeae. Infect Inimun 63 (8):2958–2967.
26. Legrain M, et al. 1993. Cloning and characterization of Neisseria meningitides genes encoding the transferrin-binding proteins Tbp1 and Tbp2. Gene 130 (1):73–80.
27. Cornelissen C N, Biswas G D, Sparling P F. 1993. Expression of gonococcal transferrin-binding protein 1 causes Escherichia coli to bind human transferrin. J Bacteriol 175 (8):2448–2450.
28. Anderson J E, Sparling P F, Cornelissen C N. 1994. Gonococcal transferrin-binding protein 2 facilitates but is not essential for transferrin utilization. J Bacteriol 176 (11):3162–3170.
29. Ogunnariwo J A, Schryvers A B. 1996. Rapid identification and cloning of bacterial transferrin and lactoferrin receptor protein genes. J Bacteriol 178 (24):7326–7328.

30. Loosmore S M, et al. 1996. Cloning and expression of the Haemophilus influenzae transferrin receptor genes. Mol Microbiol 19 (3):575–586.

31. Pettersson, A. et al. 1993. Molecular Characterization of the 98-Kilodalton Iron-Regulated Outer membrane Protein of Neisseria meningitides. Infect. Immun. 61 (ti): 4724–4733.

SEQUENCE LISTING (1) GENERAL INFORMATION:

(iii) NUMBER OF SEQUENCES: 67

(2) INFORMATION FOR SEQ ID NO:1:

(i) SEQUENCE CHARACTERISTICS:
      (A) LENGTH: 7650 base pairs
      (B) TYPE: nucleic acid
      (C) STRANDEDNESS: single
      (D) TOPOLOGY: linear (xi) SEQUENCE DESCRIPTION: SEQ ID NO:1:

```
AAGCTTAGCA TGATGGCATC GGCTGATTGT CTTTTTGCCT TGTTGTGTGT TTGTGGGAGT      60

TGATTGTACT TACCTTAGTG GTGGATGCTT GGGCTGATTT AATAAAGCGG TCTTCACAAC     120

ACACCAAACG AGATATCACC ATGAGTACTG TCAAAACCCC CCACATTTTC TACCAAAAAC     180

GCACCCTTAG CCTTGCCATC GCCAGTATTT TTGCTGCCTT GGTGATGACA GGCTGCCGCT     240

CTGATGACAT CAGCGTCAAT GCACCCAATG TTACCCAACT GCCCCAAGGC ACGGTTTCAC     300

CAATACCGAA CACAGGTCAT GACAACACCA ATAACACCAA CAATCAGGGC AACAACACGG     360

ATAACAGCAC CAGCACAACT GACCCAAATG GCGATAACAA CCAACTGACA CAAGCACAAA     420

AGACCGCCGC TGCCGCAGGG TTTTTTGTGA TGGGTAAAAT TCGTGATACC AGCCCAAAAA     480

ATGACCCAGA TTATAGCAAT GATTTAGTAC AGCAGTGGCA AGGCAAATTA TATGTTGGTA     540

TTGATGCCCA TCGCCCAGAT GGCATCGGCA CAGGTAAAAA CTTGCGTCAG CCCATCACCG     600

CCAATGACAT CAAACCCTTG TATTTTAACA AATTCCCTGC ATTGTCTGAT TTGCATTTAG     660

ACAGTGAACG CCACCGTTTT GACCCCAAAA AGCTAAACAC CATTAAAGTG TATGGTTATG     720

GCAACTTAAC AACACCCTCT AAAAACAACA CTTACATCAA TCATCAGCAA GCTGATAATA     780

AGAAAAATAA CAAGCCTGTT GACCCTTATG AAAATATCCG TTTTGGGTAT CTTGAACTAC     840

AAGGAAGCAG TCTGACCCAA AAAAATGCCG ATACTCCAAA TGACAAAGAC CGCATTCCCA     900

AACCCATGCC CATTTTGTTT TATCACGGAG AAAACGCCAG CAGCCAGCTG CCCAGTGCTG     960

GTAAATTTAA CTACACAGGC AACTGGCTGT ACCTAAGTGA TGTCAAAAAA CGCCCTGCAC    1020

TTTCAGCATC AGATGATCGA GTGGGGGTCT ATCTCAATGC CAGTGGCAAA TCCAATGAGG    1080

GCGATGTCGT CAGTGCCGCC CACATTTATC TAAACGGCTT TCAATATAAG CACACGCCTG    1140

CCACTTATCA GGTGGATTTT GACACAAACT CATTAACAGG CAAGCTGTCT TATTATGACA    1200

ATCCCAACCA GCAAACTGCC CAAGGCAAAT ACATCAAAAG CCAATTTGAC ACTACCAAAA    1260

AAGTCAATGA AACCGATGTG TATCAAATTG ATGCCAAAAT CAACGGCAAC CGCTTCGTCG    1320

GTACGGCCAA ATCTTTGGTT AATGAGAACA CAGAAACCGC ACCTTTTATC AAAGAGCTGT    1380

TCTCCAAAAA AGCCAATCCC AATAACCCAA ACCCTAATTC AGACACGCTA GAAGGCGGGT    1440

TTTATGGTGA GTCGGGCGAT GAGCTGGCGG GTAAATTTTT ATCCAATGAC AACGCATCTT    1500

ATGTGGTCTT TGGTGGTAAA CGAGACAAAA CAGACAAACC TGTCGCCACA AAAACGGTGT    1560

ATTTTAGTGC AGGCTTTGAA AAACCTAGCA CCAGTTTTGT GGATAATGAA ACGATTGGCA    1620

GAATTATTAA CAGCAAAAAG TTAAATGATG CGGTGAATGA GAAAATTGAT AATGGTGATA    1680
```

```
TTCCTACCAG TGATGAACGC TATGATGAAT TCCTTGGGG CGAAAAAAAA GCAGAATTCA    1740

CCAAAAAAGT CAGCAGCAGC ACCCAAGCCG TGCCAGCTTA TTTTGGGCAA CATGATAAAT    1800

TTTATTTTAA TGGCAACTAT TATGACCTAT CAGCCAGCAG TGTTGATAAA TTGGCCCCTG    1860

CCGATGCTGT CAAAGCCAAC CAATCCATTA AGAAAAATA CCCTAATGCC ACACTAAATA     1920

AGGACAACCA AGTTACCGCC ATCGTGCTAC AAGAAGCCAA AGATAATAAG CCTTATACCG    1980

CCATTCGTGC CAAAAGCTAT CAGCACATCA GTTTTGGCGA GACGCTGTAT AACGATGCCA   2040

ACCAAACCCC AACACGCAGT TATTTTGTGC AAGGCGGTAG GGCAGATACC AGCACCACGC   2100

TGCCCAAGGC AGGTAAATTC ACTTACAACG GTCTTTGGGC AGGCTATCTT ATCCAAAAAA   2160

AGGACAAAGG TTATAGCAAT AATGAAGAAA CCATCAAGAA AAAAGGCCAT CAAGATTATC   2220

TGTTAACCGA AGACTTCACC CCAGAAGATG ATGACGATGA TTTGACCGCA TCTGATGATT   2280

CACAAGATGA TGATGCACAT GGCGATGATG ATTTGATTGC ATCTGATGAT TCACAAGATG   2340

ATGACGCAGA TGGCGATGAC GATTCAGATG ATTTGGGTGA TGGTGCAGAT GACGCCGCCG   2400

CAGGCAAAGT GTATCATGCA GGTAATATTC GCCCTGAATT TGAAAACAAA TACTTGCCCA   2460

TTAATGAGCC TACTCATGAA AAAACCTTTG CCCTAGATGG TAAAAATAAA GCTAAGTTTG   2520

ATGTGGATTT TGACACCAAC AGCCTAACTG GTAAATTAAA CGATGAGAGA GGTGATATCG   2580

TCTTTGATAT CAAAAATGGC AAAATTGATG GCACAGGCTT TACCGCCAAA GCCGATGTGC   2640

CAAACTATCG TGAAGAAGTG GGTAACAACC AAGGTGGCGG TTTCTTATAC AACATCAAAG   2700

ATATTGATGT CAAGGGGCAA TTTTTTGGCA CAAATGGCGA AGAGTTGGCA GGGCAGTTAC   2760

AGTACGACAA AGGCGATGGC ATCAATGACA CCGCCGAAAA AGCAGGGGCT GTCTTTGGGG   2820

CTGTTAAAGA TAAATAAAGC CCCCTTCATC ATCGTTTAGT CGCTTGACCG ACAGTTGATG   2880

ACGCCCTTGG CAATGTCTTA AAACAGCACT TTGAAACAGT GCCTTGGGCG AATTCTTGGA   2940

TAAATGCACC AGATTTGCCT TGGGCTAATA TCTTGATAAA ACATCGCCAT AAAATAGAAA   3000

ATAAAGTTTA GGATTTTTTT ATGTCAAAAT CTATCACAAA AACACAAACA CCATCAGTCC   3060

ATACCATGAC CACGCACCGC TTAAACCTTG CCATCAAAGC GGCGTTATTT GGTGTGGCAG   3120

TTTTACCCCT ATCCGTCTGG GCGCAAGAGA ACACTCAGAC AGATGCCAAC TCTGATGCCA   3180

AAGACACAAA AACCCCTGTC GTCTATTTAG ATGCCATCAC GGTAACCGCC GCCCCATCTG   3240

CCCCTGTTTC TCGGTTTGAC ACCGATGTAA CAGGGCTTGG CAAAACGGTC AAAACCGCTG   3300

ACACGCTGGC AAAAGAACAA GTGCAGGGCA TTCGTGATTT GGTGCGTTAT GAAACTGGGG   3360

TGAGTGTGGT TGAGCAGGGG CGTGGTGGCA GCAGCGGATT TGCCATTCAT GGCGTGGATA   3420

AAAACCGAGT GGGCATTACC GTAGATGGCA TTGCCCAAAT TCAATCCTAC AAAGATGAAT   3480

CCACCAAACG AGCTGGTGCA GGCTCTGGGG CGATGAATGA GATAGAGATT GAAACATTG    3540

CCGCCGTTGC CATCAATAAA GGTGGTAATG CCCTAGAAGC AGGCTCTGGT GCGTTGGGCG   3600

GTTCGGTGGC GTTTCATACC AAAGATGTGA GCGATGTCTT AAAATCTGGT AAAAATCTTG   3660

GCGCTCAAAG CAAAACCACT TATAACAGCA AAAATGACCA TTTTAGTCAG ACGCTGGCAG   3720

CGGCAGGTAA AACCGAGCGT GTGGAAGCGA TGGTGCAATA TACCTACCGT AAAGGCAAAG   3780

AAAACAAAGC ACACAGCGAC CTAAATGGCA TCAACCAAAG CCTATATCGC TTGGGTGCAT   3840

GGCAACAAAA ATATGATTTA AGAAAGCCCA ATGAACTGTT TGCAGGCACA AGCTACATCA   3900

CCGAAAGCTG TTTGGCAAGT GATGACCCAA AAAGCTGCGT ACAATACCCT TATGTCTACA   3960

CCAAAGCCCG ACCAGATGGC ATCGGCAATC GCAATTTTTC TGAGTTAAGC GATGCTGAAA   4020

AAGCACAATA TTTGGCATCC ACGCACCCCC ATGAGGTTGT CTCTGCCAAA GATTATACAG   4080
```

```
GCATTTATCG GTTGTTACCT GACCCCATGG ACTATCGTTC AGACTCGTAT TTGGCACGCC    4140

TTAACATCAA AATCACCCCA AATCTGGTCA GTAAACTGTT ATTAGAAGAC ACCAAGCAAA    4200

CATACAACAT TCGTGATATG CGTCATTGTA GTTACCATGG GGCAAGATTG GGCAATGATG    4260

GTAAGCCTGC CAATGGTGGC TCCATTGTTC TTTGCGATGA TTATCAAGAG TATCTAAACG    4320

CCAATGACGC ATCACAAGCA TTATTTAGAC CAGGTGCTAA TGATGCCCCC ATTCCAAAAC    4380

TGGCTTATGC CAGAAGCAGT GTGTTTAACC AAGAGCATGG CAAAACTCGC TATGGGTTAA    4440

GTTTTGAGTT TAAGCCTGAC ACGCCATGGT TTAAGCAAGC AAAATTAAAC CTACACCAAC    4500

AAAATATCCA AATCATTAAC CATGACATTA AAAAATCGTG CAGCCAATAT CCTAAGGTGG    4560

ATTTAAATTG TGGCATCAGT GAAATTGGGC ATTATGAATA TCAAAATAAT TACCGTTATA    4620

AAGAAGGGCG TGCCAGCTTG ACAGGCAAAC TTGATTTTAA TTTTGACCTG CTGGGTCAGC    4680

ACGATTTGAC GGTGTTGGCT GGTGCAGATA AAGTTAAAAG CCAATTTCGT GCCAACAACC    4740

CCAGACGCAC AATCATTGAC ACCACCCAAG GCGATGCCAT CATTGATGAA AGCACGCTGA    4800

CAGCACAGGA GCAAGCCAAA TTTAAGCAAT CGGGGGCGGC ATGGATTGTC AAAAATCGCC    4860

TTGGACGCTT AGAAGAAAAA GACGCCTGTG GCAATGCCAA TGAATGTGAA CGCGCCCCCA    4920

TTCATGGCAG TAACCAATAT GTGGGCATTA ACAACCTTTA TACACCAAAT GATTATGTGG    4980

ATTTAAGTTT TGGTGGACGC TTGGATAAAC AACGCATTCA CAGCACCGAT TCAAACATCA    5040

TCAGCAAAAC TTACACCAAC AAAAGCTATA ATTTTGGAGC GGCGGTTCAT CTGACACCTG    5100

ATTTTAGCCT GTTGTATAAA ACTGCCAAAG GCTTTCGTAC GCCAAGTTTT TATGAACTGT    5160

ACAACTATAA CAGCACCGCC GCCCAGCATA AAAATGACCC TGATGTGTCT TTTCCCAAAC    5220

GAGCGGTTGA TGTCAAACCT GAAACTTCCA ATACCAATGA ATACGGCTTT CGCTATCAGC    5280

ACCCTTGGGG GGATGTTGAG ATGAGCATGT TCAAAAGCCG TTACAAGGAC ATGTTAGATA    5340

AAGCCATACC GAACCTAACC AAAGCCCAAC AAGAGTATTG TAAGGCTCAT TTGGATTCCA    5400

ATGAATGTGT TGGCAATCCG CCCACGCCCA AAACCAGTGA TGAGGTATTT GCCAACTTAT    5460

ATAATGCCAC CATCAAAGGG GTGAGTGTCA AAGGCAAACT GGATTTGCAT GCCATGACAT    5520

CAAAACTGCC AGATGGTCTT GAAATGACCT TGGGTTATGG TCATACCAAA TTGGGGAAAT    5580

TTGATTACAT TGCACCCAAA GATGCCGATG GTTGGTATCA GGCTCGCCCT GCTTTTTGGG    5640

ATGCCATCAC CCCAGCGCGC TATGTGGTCG GTCTAAACTA TGACCACCCC AGTCAAGTAT    5700

GGGGCATTGG CACAACTTTA ACGCACAGCA AACAAAAAGA TGAAAATGAG CTAAGTGCCC    5760

TTAGAATCCG AAATGGCAAA AGAGAAACAC AAACCTTAAC GCACACAATA CCCAAAGCCT    5820

ATACCTTACT GGACATGACA GGCTATTATA GCCCAACTGA GAGCATCACC GCTCGTCTTG    5880

GTATCAACAA TGTATTAAAC ACCCGCTACA CCACATGGGA AGCGGCACGC CAACTGCCCA    5940

GCGAAGCTGC AAGCAGTACC CAATCAACCC GTTACATTGC ACCAGGTCGC AGTTACTTTG    6000

CCAGTCTTGA AATGAAGTTT TAATATGACC TGTTTACCAA AGACCAACCC TGCTTTAAAA    6060

GTCAAGCACA GATTTTTAAA GCAGGTGCTG TTATTGCTTT GTGTTGATAC ATTAACAGCA    6120

CAGGCGTACG CCCACAGCCA TCATACGCCC ATTCATACAC CCACGCATGA GCTGCCATCT    6180

GCTGATGCTT TATCAGATGA AGGCTTGGGT AAGGATTTGG GCAGTTTGGA CAGTTTGGAT    6240

AGCCCAGATG GTTTGGGTGA TGGTTTAGGC GATGGTTTGG GTGATGGCTT AAAAAGTGAT    6300

AAAGCCCCTT TACCCATCAA CGCCTTGACC GCCCATCAGA CCAATGAGAG CCAGCCTGCC    6360

CCACCGAGCG TAGATGTCAA TTTTTTACTT GCCCAGCCAG AGGCATTTTA TCATGTCTTT    6420

CATCAAGCGA TTGTGCAAGA TGATGTGGCA ACATTACGCT TGTTATTGCC ATTTTATGAC    6480
```

```
CGCCTGCCTG ATGATTATCA AGATGATGTT TTGTTGTTAT TTGCCCAAAG TAAACTTGCC       6540

CTAAGTGATG GCAATACCAA ATTGGCATTG AATCTGCTGA CCGATTTGAG TAACAAAGAG       6600

CCAACACTTA CGGCGGTAAA ATTACAACTT GCTTCCTTGT TGCTGACCAA CAAGCACGAT       6660

AAACACGCCC AAATGGTGCT AGATGAACTC AAAGATGATG CCCACTTTTT AAAATTAAGC       6720

AAAAAAGAGC AAAGATGGGT GCTATCGCAA AGTCGCTATT TACATAAAAA ATATAAAATG       6780

GGCTTGGATT TGGGCATCAA CTATCTGCAT TTGGATAATA TCAACGCCGC CTCCACCATC       6840

ACCCAGCCCA ATATTAAAAA AGATGCCCCA AAACCTGCTC ATGGGCTTGC CTTATCGCTT       6900

GGTGTGAATA ATACACGCC GCTTAGTCAT GGCATGAGTA TTTATACAGC CCTAGATGTT       6960

GATGGTAAAT TTTATGATGA CAAAAGCCAC AATGAACTGG CGGTTTTTGC TCATGCTGGA       7020

CTAAGAAAAG ATCACCAAAA AGGTTATGTT GATGTCGTAC CTTTTGTTGG GCGTATTTTT       7080

GCCACCAATC AGCAGCATGG CAGATTATCC CCCAGAAAAA ACAGTCAGGG CGTGGCGTTT       7140

GGCAGCCATC ATCGGATCAA TGATAAATGG CAAAATGCGT TTTTTGCACG CATGGAAAAA       7200

GGCAATTATA CCGAGCGTTA TCAAGGTTAT GATGGCAAGC GTTATCATGT GAATGACACC       7260

ATTTTGTTGC AAGATGGCCC AAATCGTCGT TACTCTTTGG GCGTGGGGTA TCAGCTTAGC       7320

CATCTGCAAG ATGCAACAAA AAGCAGTCAT GCCACAAAGA TACATTTTGG GGTGTTGCAA       7380

AGATTGCCAA ATGGTCTGAC CGTGCAAGGT AGAGTGAGTG CTGAGCGTGA GCGTTATCAT       7440

GGTAAATTAT TGCGTCTGGT TAATCCTGAT GATGTGTATC GCACAGATAA AACCCTAACC       7500

CTACAAACCT CCATTTGGCA CAAAGACATT CACTGGCTTG GATTAACGCC AAAGCTGACT       7560

TATCGTTACA GTAAAAATAA CAGTAACTTA CCAGCACTTT ATAGCCATAA CAAACAAAAT       7620

TTTTATTTGG AGCTTGGTCG GTCGTTTTAA                                        7650

(2) INFORMATION FOR SEQ ID NO:2:

(i) SEQUENCE CHARACTERISTICS:
        (A) LENGTH: 2694 base pairs
        (B) TYPE: nucleic acid
        (C) STRANDEDNESS: single
        (D) TOPOLOGY: linear (xi) SEQUENCE DESCRIPTION: SEQ ID NO:2:

ATGAGTACTG TCAAAACCCC CCACATTTTC TACCAAAAAC GCACCCTTAG CCTTGCCATC         60

GCCAGTATTT TTGCTGCCTT GGTGATGACA GGCTGCCGCT CTGATGACAT CAGCGTCAAT        120

GCACCCAATG TTACCCAACT GCCCCAAGGC ACGGTTTCAC CAATACCGAA CACAGGTCAT        180

GACAACACCA ATAACACCAA CAATCAGGGC AACAACACGG ATAACAGCAC CAGCACAACT        240

GACCCAAATG GCGATAACAA CCAACTGACA CAAGCACAAA AGACCGCCGC TGCCGCAGGG        300

TTTTTTGTGA TGGGTAAAAT TCGTGATACC AGCCCAAAAA ATGACCCAGA TTATAGCAAT        360

GATTTAGTAC AGCAGTGGCA AGGCAAATTA TATGTTGGTA TTGATGCCCA TCGCCCAGAT        420

GGCATCGGCA CAGGTAAAAA CTTGCGTCAG CCCATCACCG CCAATGACAT CAAACCCTTG        480

TATTTTAACA AATTCCCTGC ATTGTCTGAT TTGCATTTAG ACAGTGAACG CCACCGTTTT        540

GACCCCAAAA AGCTAAACAC CATTAAAGTG TATGGTTATG CAACTTAAC AACACCCTCT        600

AAAAACAACA CTTACATCAA TCATCAGCAA GCTGATAATA AGAAAAATAA CAAGCCTGTT        660

GACCCTTATG AAAATATCCG TTTTGGGTAT CTTGAACTAC AAGGAAGCAG TCTGACCCAA        720

AAAAATGCCG ATACTCCAAA TGACAAAGAC CGCATTCCCA AACCCATGCC CATTTTGTTT        780

TATCACGGAG AAAACGCCAG CAGCCAGCTG CCCAGTGCTG GTAAATTTAA CTACACAGGC        840
```

```
AACTGGCTGT ACCTAAGTGA TGTCAAAAAA CGCCCTGCAC TTTCAGCATC AGATGATCGA      900

GTGGGGGTCT ATCTCAATGC CAGTGGCAAA TCCAATGAGG GCGATGTCGT CAGTGCCGCC      960

CACATTTATC TAAACGGCTT TCAATATAAG CACACGCCTG CCACTTATCA GGTGGATTTT     1020

GACACAAACT CATTAACAGG CAAGCTGTCT TATTATGACA ATCCCAACCA GCAAACTGCC     1080

CAAGGCAAAT ACATCAAAAG CCAATTTGAC ACTACCAAAA AAGTCAATGA AACCGATGTG     1140

TATCAAATTG ATGCCAAAAT CAACGGCAAC CGCTTCGTCG GTACGGCCAA ATCTTTGGTT     1200

AATGAGAACA CAGAAACCGC ACCTTTTATC AAAGAGCTGT TCTCCAAAAA AGCCAATCCC     1260

AATAACCCAA ACCCTAATTC AGACACGCTA GAAGGCGGGT TTTATGGTGA GTCGGGCGAT     1320

GAGCTGGCGG GTAAATTTTT ATCCAATGAC AACGCATCTT ATGTGGTCTT TGGTGGTAAA     1380

CGAGACAAAA CAGACAAACC TGTCGCCACA AAAACGGTGT ATTTTAGTGC AGGCTTTGAA     1440

AAACCTAGCA CCAGTTTTGT GGATAATGAA ACGATTGGCA GAATTATTAA CAGCAAAAAG     1500

TTAAATGATG CGGTGAATGA GAAAATTGAT AATGGTGATA TTCCTACCAG TGATGAACGC     1560

TATGATGAAT TCCTTGGGG CGAAAAAAAA GCAGAATTCA CCAAAAAAGT CAGCAGCAGC     1620

ACCCAAGCCG TGCCAGCTTA TTTTGGGCAA CATGATAAAT TTTATTTTAA TGGCAACTAT     1680

TATGACCTAT CAGCCAGCAG TGTTGATAAA TTGGCCCCTG CCGATGCTGT CAAAGCCAAC     1740

CAATCCATTA AGAAAAATA CCCTAATGCC ACACTAAATA AGGACAACCA AGTTACCGCC     1800

ATCGTGCTAC AAGAAGCCAA AGATAATAAG CCTTATACCG CCATTCGTGC CAAAAGCTAT     1860

CAGCACATCA GTTTTGGCGA GACGCTGTAT AACGATGCCA ACCAAACCCC AACACGCAGT     1920

TATTTTGTGC AAGGCGGTAG GGCAGATACC AGCACCACGC TGCCCAAGGC AGGTAAATTC     1980

ACTTACAACG GTCTTTGGGC AGGCTATCTT ATCCAAAAAA AGGACAAAGG TTATAGCAAT     2040

AATGAAGAAA CCATCAAGAA AAAGGCCAT CAAGATTATC TGTTAACCGA AGACTTCACC     2100

CCAGAAGATG ATGACGATGA TTTGACCGCA TCTGATGATT CACAAGATGA TGATGCACAT     2160

GGCGATGATG ATTTGATTGC ATCTGATGAT TCACAAGATG ATGACGCAGA TGGCGATGAC     2220

GATTCAGATG ATTTGGGTGA TGGTGCAGAT GACGCCGCCG CAGGCAAAGT GTATCATGCA     2280

GGTAATATTC GCCCTGAATT TGAAAACAAA TACTTGCCCA TTAATGAGCC TACTCATGAA     2340

AAAACCTTTG CCCTAGATGG TAAAAATAAA GCTAAGTTTG ATGTGGATTT TGACACCAAC     2400

AGCCTAACTG GTAAATTAAA CGATGAGAGA GGTGATATCG TCTTTGATAT CAAAAATGGC     2460

AAAATTGATG GCACAGGCTT TACCGCCAAA GCCGATGTGC CAAACTATCG TGAAGAAGTG     2520

GGTAACAACC AAGGTGGCGG TTTCTTATAC AACATCAAAG ATATTGATGT CAAGGGGCAA     2580

TTTTTTGGCA CAAATGGCGA AGAGTTGGCA GGGCAGTTAC AGTACGACAA AGGCGATGGC     2640

ATCAATGACA CCGCCGAAAA AGCAGGGGCT GTCTTTGGGG CTGTTAAAGA TAAA            2694

(2) INFORMATION FOR SEQ ID NO:3:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (xi) SEQUENCE DESCRIPTION: SEQ ID NO:3:

ATGTCAAAAT CTATCACAAA AACACAAACA CCATCAGTCC ATACCATGAC CACGCACCGC       60

TTAAACCTTG CCATCAAAGC GGCGTTATTT GGTGTGGCAG TTTTACCCCT ATCCGTCTGG      120

GCGCAAGAGA ACACTCAGAC AGATGCCAAC TCTGATGCCA AAGACACAAA AACCCCTGTC      180

GTCTATTTAG ATGCCATCAC GGTAACCGCC GCCCCATCTG CCCCTGTTTC TCGGTTTGAC      240
```

```
ACCGATGTAA CAGGGCTTGG CAAAACGGTC AAAACCGCTG ACACGCTGGC AAAAGAACAA    300
GTGCAGGGCA TTCGTGATTT GGTGCGTTAT GAAACTGGGG TGAGTGTGGT TGAGCAGGGG    360
CGTGGTGGCA GCAGCGGATT TGCCATTCAT GGCGTGGATA AAAACCGAGT GGGCATTACC    420
GTAGATGGCA TTGCCCAAAT TCAATCCTAC AAAGATGAAT CCACCAAACG AGCTGGTGCA    480
GGCTCTGGGG CGATGAATGA GATAGAGATT GAAAACATTG CCGCCGTTGC CATCAATAAA    540
GGTGGTAATG CCCTAGAAGC AGGCTCTGGT GCGTTGGGCG GTTCGGTGGC GTTTCATACC    600
AAAGATGTGA GCGATGTCTT AAAATCTGGT AAAAATCTTG GCGCTCAAAG CAAAACCACT    660
TATAACAGCA AAAATGACCA TTTTAGTCAG ACGCTGGCAG CGGCAGGTAA AACCGAGCGT    720
GTGGAAGCGA TGGTGCAATA TACCTACCGT AAAGGCAAAG AAAACAAAGC ACACAGCGAC    780
CTAAATGGCA TCAACCAAAG CCTATATCGC TTGGGTGCAT GGCAACAAAA ATATGATTTA    840
AGAAAGCCCA ATGAACTGTT TGCAGGCACA AGCTACATCA CCGAAAGCTG TTTGGCAAGT    900
GATGACCCAA AAAGCTGCGT ACAATACCCT TATGTCTACA CCAAAGCCCG ACCAGATGGC    960
ATCGGCAATC GCAATTTTTC TGAGTTAAGC GATGCTGAAA AAGCACAATA TTTGGCATCC   1020
ACGCACCCCC ATGAGGTTGT CTCTGCCAAA GATTATACAG GCATTTATCG GTTGTTACCT   1080
GACCCCATGG ACTATCGTTC AGACTCGTAT TTGGCACGCC TTAACATCAA AATCACCCCA   1140
AATCTGGTCA GTAAACTGTT ATTAGAAGAC ACCAAGCAAA CATACAACAT TCGTGATATG   1200
CGTCATTGTA GTTACCATGG GGCAAGATTG GGCAATGATG GTAAGCCTGC CAATGGTGGC   1260
TCCATTGTTC TTTGCGATGA TTATCAAGAG TATCTAAACG CCAATGACGC ATCACAAGCA   1320
TTATTTAGAC CAGGTGCTAA TGATGCCCCC ATTCCAAAAC TGGCTTATGC CAGAAGCAGT   1380
GTGTTTAACC AAGAGCATGG CAAAACTCGC TATGGGTTAA GTTTTGAGTT TAAGCCTGAC   1440
ACGCCATGGT TTAAGCAAGC AAAATTAAAC CTACACCAAC AAAATATCCA AATCATTAAC   1500
CATGACATTA AAAAATCGTG CAGCCAATAT CCTAAGGTGG ATTTAAATTG TGGCATCAGT   1560
GAAATTGGGC ATTATGAATA TCAAAATAAT TACCGTTATA AGAAGGGCG TGCCAGCTTG   1620
ACAGGCAAAC TTGATTTTAA TTTTGACCTG CTGGGTCAGC ACGATTTGAC GGTGTTGGCT   1680
GGTGCAGATA AAGTTAAAAG CCAATTTCGT GCCAACAACC CCAGACGCAC AATCATTGAC   1740
ACCACCCAAG GCGATGCCAT CATTGATGAA AGCACGCTGA CAGCACAGGA GCAAGCCAAA   1800
TTTAAGCAAT CGGGGGCGGC ATGGATTGTC AAAAATCGCC TTGGACGCTT AGAAGAAAAA   1860
GACGCCTGTG GCAATGCCAA TGAATGTGAA CGCGCCCCCA TTCATGGCAG TAACCAATAT   1920
GTGGGCATTA ACAACCTTTA TACACCAAAT GATTATGTGG ATTTAAGTTT TGGTGGACGC   1980
TTGGATAAAC AACGCATTCA CAGCACCGAT TCAAACATCA TCAGCAAAAC TTACACCAAC   2040
AAAAGCTATA ATTTTGGAGC GGCGGTTCAT CTGACACCTG ATTTTAGCCT GTTGTATAAA   2100
ACTGCCAAAG GCTTTCGTAC GCCAAGTTTT TATGAACTGT ACAACTATAA CAGCACCGCC   2160
GCCCAGCATA AAAATGACCC TGATGTGTCT TTTCCCAAAC GAGCGGTTGA TGTCAAACCT   2220
GAAACTTCCA ATACCAATGA ATACGGCTTT CGCTATCAGC ACCCTTGGGG GGATGTTGAG   2280
ATGAGCATGT TCAAAAGCCG TTACAAGGAC ATGTTAGATA AAGCCATACC GAACCTAACC   2340
AAAGCCCAAC AAGAGTATTG TAAGGCTCAT TTGGATTCCA ATGAATGTGT TGGCAATCCG   2400
CCCACGCCCA AAACCAGTGA TGAGGTATTT GCCAACTTAT ATAATGCCAC CATCAAAGGG   2460
GTGAGTGTCA AAGGCAAACT GGATTTGCAT GCCATGACAT CAAAACTGCC AGATGGTCTT   2520
GAAATGACCT TGGGTTATGG TCATACCAAA TTGGGGAAAT TTGATTACAT TGCACCCAAA   2580
GATGCCGATG GTTGGTATCA GGCTCGCCCT GCTTTTTGGG ATGCCATCAC CCCAGCGCGC   2640
```

```
TATGTGGTCG GTCTAAACTA TGACCACCCC AGTCAAGTAT GGGGCATTGG CACAACTTTA    2700

ACGCACAGCA AACAAAAAGA TGAAAATGAG CTAAGTGCCC TTAGAATCCG AAATGGCAAA    2760

AGAGAAACAC AAACCTTAAC GCACACAATA CCCAAAGCCT ATACCTTACT GGACATGACA    2820

GGCTATTATA GCCCAACTGA GAGCATCACC GCTCGTCTTG GTATCAACAA TGTATTAAAC    2880

ACCCGCTACA CCACATGGGA AGCGGCACGC CAACTGCCCA GCGAAGCTGC AAGCAGTACC    2940

CAATCAACCC GTTACATTGC ACCAGGTCGC AGTTACTTTG CCAGTCTTGA AATGAAGTTT    3000

(2) INFORMATION FOR SEQ ID NO:4:

(i) SEQUENCE CHARACTERISTICS:
        (A) LENGTH: 2955 base pairs
        (B) TYPE: nucleic acid
        (C) STRANDEDNESS: single
        (D) TOPOLOGY: linear (xi) SEQUENCE DESCRIPTION: SEQ ID NO:4:

ATGACCACGC ACCGCTTAAA CCTTGCCATC AAAGCGGCGT TATTTGGTGT GGCAGTTTTA      60

CCCCTATCCG TCTGGGCGCA AGAGAACACT CAGACAGATG CCAACTCTGA TGCCAAAGAC     120

ACAAAAACCC CTGTCGTCTA TTTAGATGCC ATCACGGTAA CCGCCGCCCC ATCTGCCCCT     180

GTTTCTCGGT TTGACACCGA TGTAACAGGG CTTGGCAAAA CGGTCAAAAC CGCTGACACG     240

CTGGCAAAAG AACAAGTGCA GGGCATTCGT GATTTGGTGC GTTATGAAAC TGGGGTGAGT     300

GTGGTTGAGC AGGGGCGTGG TGGCAGCAGC GGATTTGCCA TTCATGGCGT GGATAAAAAC     360

CGAGTGGGCA TTACCGTAGA TGGCATTGCC CAAATTCAAT CCTACAAAGA TGAATCCACC     420

AAACGAGCTG GTGCAGGCTC TGGGGCGATG AATGAGATAG AGATTGAAAA CATTGCCGCC     480

GTTGCCATCA ATAAAGGTGG TAATGCCCTA GAAGCAGGCT CTGGTGCGTT GGGCGGTTCG     540

GTGGCGTTTC ATACCAAAGA TGTGAGCGAT GTCTTAAAAT CTGGTAAAAA TCTTGGCGCT     600

CAAAGCAAAA CCACTTATAA CAGCAAAAAT GACCATTTTA GTCAGACGCT GGCAGCGGCA     660

GGTAAAACCG AGCGTGTGGA AGCGATGGTG CAATATACCT ACCGTAAAGG CAAAGAAAAC     720

AAAGCACACA GCGACCTAAA TGGCATCAAC CAAAGCCTAT ATCGCTTGGG TGCATGGCAA     780

CAAAAATATG ATTTAAGAAA GCCCAATGAA CTGTTTGCAG GCACAAGCTA CATCACCGAA     840

AGCTGTTTGG CAAGTGATGA CCCAAAAAGC TGCGTACAAT ACCCTTATGT CTACACCAAA     900

GCCCGACCAG ATGGCATCGG CAATCGCAAT TTTTCTGAGT TAAGCGATGC TGAAAAAGCA     960

CAATATTTGG CATCCACGCA CCCCCATGAG GTTGTCTCTG CCAAAGATTA TACAGGCATT    1020

TATCGGTTGT TACCTGACCC CATGGACTAT CGTTCAGACT CGTATTTGGC ACGCCTTAAC    1080

ATCAAAATCA CCCCAAATCT GGTCAGTAAA CTGTTATTAG AAGACACCAA GCAAACATAC    1140

AACATTCGTG ATATGCGTCA TTGTAGTTAC CATGGGGCAA GATTGGGCAA TGATGGTAAG    1200

CCTGCCAATG GTGGCTCCAT TGTTCTTTGC GATGATTATC AAGAGTATCT AAACGCCAAT    1260

GACGCATCAC AAGCATTATT TAGACCAGGT GCTAATGATG CCCCCATTCC AAAACTGGCT    1320

TATGCCAGAA GCAGTGTGTT TAACCAAGAG CATGGCAAAA CTCGCTATGG GTTAAGTTTT    1380

GAGTTTAAGC CTGACACGCC ATGGTTTAAG CAAGCAAAAT TAAACCTACA CCAACAAAAT    1440

ATCCAAATCA TTAACCATGA CATTAAAAAA TCGTGCAGCC AATATCCTAA GGTGGATTTA    1500

AATTGTGGCA TCAGTGAAAT TGGGCATTAT GAATATCAAA ATAATTACCG TTATAAAGAA    1560

GGGCGTGCCA GCTTGACAGG CAAACTTGAT TTTAATTTTG ACCTGCTGGG TCAGCACGAT    1620

TTGACGGTGT TGGCTGGTGC AGATAAAGTT AAAAGCCAAT TTCGTGCCAA CAACCCCAGA    1680
```

-continued

| | |
|---|---|
| CGCACAATCA TTGACACCAC CCAAGGCGAT GCCATCATTG ATGAAAGCAC GCTGACAGCA | 1740 |
| CAGGAGCAAG CCAAATTTAA GCAATCGGGG GCGGCATGGA TTGTCAAAAA TCGCCTTGGA | 1800 |
| CGCTTAGAAG AAAAAGACGC CTGTGGCAAT GCCAATGAAT GTGAACGCGC CCCCATTCAT | 1860 |
| GGCAGTAACC AATATGTGGG CATTAACAAC CTTTATACAC CAAATGATTA TGTGGATTTA | 1920 |
| AGTTTTGGTG GACGCTTGGA TAAACAACGC ATTCACAGCA CCGATTCAAA CATCATCAGC | 1980 |
| AAAACTTACA CCAACAAAAG CTATAATTTT GGAGCGGCGG TTCATCTGAC ACCTGATTTT | 2040 |
| AGCCTGTTGT ATAAAACTGC CAAAGGCTTT CGTACGCCAA GTTTTTATGA ACTGTACAAC | 2100 |
| TATAACAGCA CCGCCGCCCA GCATAAAAAT GACCCTGATG TGTCTTTTCC CAAACGAGCG | 2160 |
| GTTGATGTCA AACCTGAAAC TTCCAATACC AATGAATACG GCTTTCGCTA TCAGCACCCT | 2220 |
| TGGGGGGATG TTGAGATGAG CATGTTCAAA AGCCGTTACA AGGACATGTT AGATAAAGCC | 2280 |
| ATACCGAACC TAACCAAAGC CCAACAAGAG TATTGTAAGG CTCATTTGGA TTCCAATGAA | 2340 |
| TGTGTTGGCA ATCCGCCCAC GCCCAAAACC AGTGATGAGG TATTTGCCAA CTTATATAAT | 2400 |
| GCCACCATCA AAGGGGTGAG TGTCAAAGGC AAACTGGATT TGCATGCCAT GACATCAAAA | 2460 |
| CTGCCAGATG GTCTTGAAAT GACCTTGGGT TATGGTCATA CCAAATTGGG GAAATTTGAT | 2520 |
| TACATTGCAC CCAAAGATGC CGATGGTTGG TATCAGGCTC GCCCTGCTTT TTGGGATGCC | 2580 |
| ATCACCCCAG CGCGCTATGT GGTCGGTCTA AACTATGACC ACCCCAGTCA AGTATGGGGC | 2640 |
| ATTGGCACAA CTTTAACGCA CAGCAAACAA AAAGATGAAA ATGAGCTAAG TGCCCTTAGA | 2700 |
| ATCCGAAATG GCAAAAGAGA AACACAAACC TTAACGCACA CAATACCCAA AGCCTATACC | 2760 |
| TTACTGGACA TGACAGGCTA TTATAGCCCA ACTGAGAGCA TCACCGCTCG TCTTGGTATC | 2820 |
| AACAATGTAT TAAACACCCG CTACACCACA TGGGAAGCGG CACGCCAACT GCCCAGCGAA | 2880 |
| GCTGCAAGCA GTACCCAATC AACCCGTTAC ATTGCACCAG GTCGCAGTTA CTTTGCCAGT | 2940 |
| CTTGAAATGA AGTTT | 2955 |

(2) INFORMATION FOR SEQ ID NO:5:

(i) SEQUENCE CHARACTERISTICS:
        (A) LENGTH: 1623 base pairs
        (B) TYPE: nucleic acid
        (C) STRANDEDNESS: single
        (D) TOPOLOGY: linear (xi) SEQUENCE DESCRIPTION: SEQ ID NO:5:

| | |
|---|---|
| ATGACCTGTT TACCAAAGAC CAACCCTGCT TTAAAAGTCA AGCACAGATT TTTAAAGCAG | 60 |
| GTGCTGTTAT TGCTTTGTGT TGATACATTA ACAGCACAGG CGTACGCCCA CAGCCATCAT | 120 |
| ACGCCCATTC ATACACCCAC GCATGAGCTG CCATCTGCTG ATGCTTTATC AGATGAAGGC | 180 |
| TTGGGTAAGG ATTTGGGCAG TTTGGACAGT TTGGATAGCC CAGATGGTTT GGGTGATGGT | 240 |
| TTAGGCGATG GTTTGGGTGA TGGCTTAAAA AGTGATAAAG CCCCTTTACC CATCAACGCC | 300 |
| TTGACCGCCC ATCAGACCAA TGAGAGCCAG CCTGCCCCAC CGAGCGTAGA TGTCAATTTT | 360 |
| TTACTTGCCC AGCCAGAGGC ATTTTATCAT GTCTTTCATC AAGCGATTGT GCAAGATGAT | 420 |
| GTGGCAACAT TACGCTTGTT ATTGCCATTT TATGACCGCC TGCCTGATGA TTATCAAGAT | 480 |
| GATGTTTTGT TGTTATTTGC CCAAAGTAAA CTTGCCCTAA GTGATGGCAA TACCAAATTG | 540 |
| GCATTGAATC TGCTGACCGA TTTGAGTAAC AAAGAGCCAA CACTTACGGC GGTAAAATTA | 600 |
| CAACTTGCTT CCTTGTTGCT GACCAACAAG CACGATAAAC ACGCCCAAAT GGTGCTAGAT | 660 |
| GAACTCAAAG ATGATGCCCA CTTTTTAAAA TTAAGCAAAA AAGAGCAAAG ATGGGTGCTA | 720 |
| TCGCAAAGTC GCTATTTACA TAAAAAATAT AAAATGGGCT TGGATTTGGG CATCAACTAT | 780 |

```
CTGCATTTGG ATAATATCAA CGCCGCCTCC ACCATCACCC AGCCCAATAT TAAAAAAGAT      840

GCCCCAAAAC CTGCTCATGG GCTTGCCTTA TCGCTTGGTG TGAATAAATA CACGCCGCTT      900

AGTCATGGCA TGAGTATTTA TACAGCCCTA GATGTTGATG GTAAATTTTA TGATGACAAA      960

AGCCACAATG AACTGGCGGT TTTTGCTCAT GCTGGACTAA GAAAAGATCA CCAAAAAGGT     1020

TATGTTGATG TCGTACCTTT TGTTGGGCGT ATTTTTGCCA CCAATCAGCA GCATGGCAGA     1080

TTATCCCCCA GAAAAGACAG TCAGGGCGTG GCGTTTGGCA GCCATCATCG GATCAATGAT     1140

AAATGGCAAA ATGCGTTTTT TGCACGCATG GAAAAAGGCA ATTATACCGA GCGTTATCAA     1200

GGTTATGATG GCAAGCGTTA TCATGTGAAT GACACCATTT TGTTGCAAGA TGGCCCAAAT     1260

CGTCGTTACT CTTTGGGCGT GGGGTATCAG CTTAGCCATC TGCAAGATGC AACAAAAAGC     1320

AGTCATGCCA CAAAGATACA TTTTGGGGTG TTGCAAAGAT TGCCAAATGG TCTGACCGTG     1380

CAAGGTAGAG TGAGTGCTGA GCGTGAGCGT TATCATGGTA AATTATTGCG TCTGGTTAAT     1440

CCTGATGATG TGTATCGCAC AGATAAAACC CTAACCCTAC AAACCTCCAT TTGGCACAAA     1500

GACATTCACT GGCTTGGATT AACGCCAAAG CTGACTTATC GTTACAGTAA AAATAACAGT     1560

AACTTACCAG CACTTTATAG CCATAACAAA CAAAATTTTT ATTTGGAGCT TGGTCGGTCG     1620

TTT                                                                  1623

(2) INFORMATION FOR SEQ ID NO:6:

(i) SEQUENCE CHARACTERISTICS:
        (A) LENGTH: 7641 base pairs
        (B) TYPE: nucleic acid
        (C) STRANDEDNESS: single
        (D) TOPOLOGY: linear (xi) SEQUENCE DESCRIPTION: SEQ ID NO:6:

AAGCTTAGCA TGATGGCATC GGCTGATTGT CTTTTTGCCT TGTTGTGTGT TTGTGGGAGT       60

TGATTGTACT TACCTTAGTG GTGGATGCTT GGGCTGATTT AATTAAATTT AATCAAAGCG      120

GTCTTCACAA CACACCAAAC GAGATATCAC CATGAGTACT GTCAAAACCC CCATATTTT       180

CTACCAAAAA CGCACCCTTA GCCTTGCCAT CGCCAGTATT TTTGCTGCCT TGGTGATGAC      240

AGGCTGCCGC TCTGATGACA TCAGCGTCAA TGCACCCAAT GTTACCCAGC TGCCCCAAGG      300

CACGGTTTCA CCAACGCCGA ACACAGGTCA TGACAACGCC AATAACACCA ACAATCAGGG      360

CAACAACACG GATAACAGCA CCAGCACAAC TGACCCAAAT GGCGATAACA ACCAACTGAC      420

ACAAGCGCAA AAAACTGCCG CCGCCGCAGG GTTTTTTGTG ATGGGTAAAA TTCGTGATAC      480

CAGCGAAAAA AATGACCCAG ATTATAGTGA TGATTTAAAA CAGCAGTGGC TGGGCAAATT      540

ATATGTTGGT ATTGATGCCC ATCGCCCAGA TGGCATCGGA AAAGGTAAAA ACTTGCGTCA      600

GCCCATCACC GCCAATGACA TCAAACCCTT GTATTTTAAC AAATTCCCTG CATTGTCTGA      660

TTTGCACTTA GACAGTGAAC GCCATCGTTT TGACCCCCAA AAGATAAACA CCATTAAAGT      720

GTATGGTTAT GGTAACTTAA CAACACCATC CAACAACAAC ACTCACATCA ATCATCAGCA      780

AGCTGATAAT AAGAAAAATA ACAAGCCTGT TGACCCTTAT GAAAATATCC GTTTTGGGTA      840

TCTTGAACTA CAAGGAAGCA GCCTGACCCA AAAAAATGCC GATAATCAAA ATGAGCAAGA      900

CCGCATTCCC AAACCCATGC CCATTTTGTT TTATCATGGA GAAACGCCA GCAGCCAGCT       960

GCCCAGCGCT GGTAAATTTA ACTACACAGG CAACTGGCTG TACCTAAGTG ATGTCAAAAA     1020

ACGCCCTGCC CTTTCAGCAT CAGATGAGCG AGTGGGGGTC TATCTCAATG CCAGTGGCAA     1080

AGCCAACGAG GGCGATGTCG TCAGTGCCGC CCACATTTAT CTAAACGGCT TTCAATATAA     1140
```

```
GCACACGCCT GCCACTTATC AGGTGGATTT TGACACAAAC TCATTAACAG GCAAGCTGTC      1200

CTATTATGAC AATCCCAATC AGCAAAATAA TAAAGGCGAA TATCTCAAAA GCCAATTTGA      1260

CACTACCAAA AAAGTCAATG AAACCGATGT GTATCAAATT GATGCCAAAA TCAACGGTAA      1320

CCGCTTTGTC GGTACGGCCA AATCTTTGGT TAATGAGAAA ACACAAACCG CACCTTTTAT      1380

CAAAGAGCTG TTCTCCAAAA AAGCCAACCC CAATAACCCA AACCCTAATT CAGACACGCT      1440

AGAAGGCGGA TTTTATGGTG AGTCGGGCGA TGAGCTGGCG GGTAAATTTT TATCCAATGA      1500

CAACGCATCT TATGTGGTCT TTGGTGGCAA ACGAGACAAA ACGACTAAAC CTGTCGCCAC      1560

AAAAACGGTG TATTTTAGTG CAGGCTTTGA AAAACCCAGC ACCAGTTTTG TGGATAATGA      1620

AACGATTGGT GGAATTATTG ACCGTAAAGG GTTAAATAAT CACATTAATG AAGATGAAAT      1680

TATTCCCAGT GATGATAGTT ATTATGGATA TACTTGGGGC AAGCCAGAGA AGCAGTTCAC      1740

CAAAAAAGTC AGCAGCAGCA CCCAAGTCGT GCCAGCTTAT TTTGGGCAAC ATGATAAATT      1800

TTATTTTAAT GGCAACTATT ATGACCTATC AGCCAGTCGT GTTGATAAAT TAGCCCCTGC      1860

CGATGCTGTC AAAGCCAACC AATCCATTAA AGAAAAATAC CCTAATGCCA CACTAAATAA      1920

GGACAACCAA GTTACCGCCA TCGTGCTACA AGAAGCCAAA GATAATAAGC CTTATACCGC      1980

CATTCGTGCC AAAAGCTATC AGCACATCAG TTTTGGCGAG ACGCTGTATA ACGATGCCAA      2040

CCAAACCCCA ACACGCAGTT ATTTTGTGCA AGGCGGTAGG GCAGATACCA GCACAACTTT      2100

GCCCCAGGCA GGTAAATTCA CTTACAACGG TCTTTGGGCA GGCTACCTGA CCCAAAAAAA      2160

GGACAAAGGT TATAGCGATA ATGCAGAAAC CATCAAGGAA AAAGGTCATC CAGGTTATCT      2220

GTTAACCGAA AACTTCACCC CAGAAGATGA TGACGATGAT TTGACCGCAT CTGATGATTC      2280

ACAAGATGAT AATACACATG GCGATGATGA TTTGATTGCA TCTGATGATT CACAAGATGA      2340

TGACGCAGAT GGAGATGACG ATTCAGATGA TTTGGGTGAT GGTGCAGATG ATGACGCCGC      2400

AGGCAAAGTG TATCATGCAG GTAATATTCG CCCTGAATTT GAAAACAAAT ACTTGCCCAT      2460

TAATGAGCCT ACTCATGAAA AAACCTTTGC CCTAGATGGT AAAAATAAAG CTAAGTTTGA      2520

AGTGGATTTT AACACCAACA GCCTAACTGG TAAATTAAAC GATGAGAGAG GTGATATCGT      2580

CTTTGATATC AAAAATGGCA AAATTGATGG CACAGGATTT ACCGCCAAAG CCGATGTGCC      2640

AAACTATCGT GAAGAAGTGG GTAACAACCA AGGTGGCGGT TCTTATACA ACATCAAAGA      2700

TATTGATGTT AAGGGGCAAT TTTTTGGCAC AAATGGCGAA GAGTTGGCAG ACAGTTACA      2760

TCATGACAAA GGCGATGGCA TCAATGCACA CGCCGAAAAA GCAGGGGCTG TCTTTGGGGC      2820

TGTTAAAGAT AAATAAAGCC CCCCTTCATC ATCGTTTAGT CGCTTGACCG ACAGTTGATG      2880

ACGCCCTTGG CAATGTCTTA AAACAGCACT TTGAAACAGT GCCTTGGGCG AATTCTTGGA      2940

TAAATGCACC AGATTTGCCT TGGGCTAATA TCTTGATAAA ACATCGCCAT AAAATAGAAA      3000

ATAAAGTTTA GGATTTTTTT ATGTCAAAAT CTATCACAAA AACACAAACA CCATCAGTCC      3060

ATACCATGAC CACGCACCGC TTAAACCTTG CCATCAAAGC GGCGTTATTT GGTGTGGCAG      3120

TTTTACCCCT ATCCGTCTGG GCGCAAGAGA ACACTCAGAC AGATGCCAAC TCTGATGCCA      3180

AAGACACAAA AACCCCTGTC GTCTATTTAG ATGCCATCAC GGTAACCGCC GCCCCATCTG      3240

CCCCTGTTTC TCGGTTTGAC ACCGATGTAA CAGGGCTTGG CAAAACCGTC AAAACCGCTG      3300

ACACGCTGGC AAAAGAACAA GTACAGGGCA TTCGTGATTT GGTGCGTTAT GAAACTGGGG      3360

TGAGTGTGGT TGAGCAGGGG CGTGGTGGCA GCAGCGGATT TGCCATTCAT GGCGTGGATA      3420

AAAACCGAGT GGGCATTACC GTAGATGGCA TTGCCCAAAT TCAATCCTAC AAAGACGAAT      3480

CCACTAAGCG AGCTGGGGCA GGCTCTGGGG CGATGAACGA GATAGAGATT GAAAACATTG      3540
```

```
CCGCCGTTGC CATCAATAAA GGCGGTAATG CCTTAGAAGC AGGCTCTGGT GCGTTGGGTG    3600

GTTCGGTGGC GTTTCATACC AAAGATGTGA GCGATGTCTT AAAATCTGGT AACAATCTTG    3660

GTGCTCAAAG CAAAACCACT TATAACAGCA AAAATGACCA TTTTAGTCAG ACGCTGGCAG    3720

CGGCAGGTAA AACCGAGCGT GTGGAAGCGA TGGTGCAATA TACCTACCGT AAAGGCAAAG    3780

AAAACAAAGC ACACAGCGAC CTAAATGGCA TCAACCAAAG CCTATATCGC TTGGGTGCAT    3840

GGCAACAAAA ATATGATTTA AGAAAGCCTA ACGAACTGTT TGCAGGCACA AGCTATATCA    3900

CCGAAAGCTG TTTGGCAAGT GATGACCCAA AAAGCTGCGT ACAATACCCT TATGTCTACA    3960

CCAAAGCCCG ACCAGATGGT ATCGGCAATC GCAATTTTTC TGAGTTAAGC GATGCTGAAA    4020

AAGCACAATA TTTGGCGTCC ACGCACCCCC ATGAGGTTGT CTCTGCCAAA GATTATACAG    4080

GCACTTATCG GTTGTTACCT GACCCCATGG ACTATCGTTC AGACTCGTAT TTGGCACGCC    4140

TTAACATCAA AATCACCCCA AATTTGGTCA GTAAACTGTT ATTAGAAGAC ACCAAGCAAA    4200

CATACAACAT TCGTGATATG CGTCATTGTA GTTATCATGG GGCAAGATTG GGCAATGACG    4260

GTAAGCCTGC CAATGGCGGC TCCATTGTCC TTTGCGATGA TTATCAAGAG TATCTAAATG    4320

CCAATGACGC ATCACAAGCA TCATTTAGAC CAGGGGCTAA TGACGCCCCC ATTCCAAAAC    4380

TGGCTTATGC CAGAAGCAGT GTGTTTAACC AAGAGCATGG CAAAACTCGC TATGGGTTAG    4440

GTTTTGAGTT TAAGCCTGAC ACGCCATGGT TTAAACAAGC AAAATTAAAC CTACATCAAC    4500

AAAATATCCA AATCATTAAC CATGACATTA AAAATCGTG CAGCCAATAT CCCAAGGTGG    4560

ATTTAAATTG TGGCATCAGT GAAATTGGGC ATTATGAATA TCAAAACAAT TACCGTTATA    4620

AGAAGGGCG TACCAGTTTG ACAGGCAAAC TTGATTTTAA TTTTGACCTG CTGGGCCAGC    4680

ACGATTTGAC GGTGTTGGCT GGTGCAGATA AGTTAAAAG CCAATTTCGT GCCAACAACC    4740

CCAGACGCAC AATCATTGAC ACCACCCAAG GCGATGCCAT CATTGATGAA AGCACGCTGA    4800

CAGCACAGGA GCAAGCCAAA TTTAAGCAAT CAGGGGCAGC ATGGATTGTC AAAAATCGCT    4860

TAGGACGCTT AGAAGAAAAA GACGCCTGTG GCAATGCCAA TGAATGTGAA CGCGCGCCCA    4920

TTCATGGCAG TAACCAATAT GTGGGCATTA ACAACCTTTA TACACCAAAT GATTATGTGG    4980

ATTTAAGTTT TGGTGGACGC TTGGATAAAC AACGCATTCA CAGCACCGAT TCAAACATCA    5040

TCAGCAAAAC TTACACCAAC AAAAGCTATA ATTTTGGAGC GGCGGTTCAT CTGACACCTG    5100

ATTTTAGCCT GTTGTATAAA ACTGCCAAAG GCTTTCGTAC GCCAAGTTTT TATGAACTGT    5160

ACAACTATAA CAGCACCGCC GCCCAGCATA AAAATGACCC TGATGTGTCT TTTCCCAAAC    5220

GAGCGGTTGA TGTCAAACCT GAAACTTCCA ATACCAATGA ATACGGCTTT CGCTATCAGC    5280

ACCCTTGGGG GGATATTGAG ATGAGCATGT TCAAAAGCCG TTACAAGGAC ATGTTAGATA    5340

AAGCCATACC GAACCTAACC AAAGCCCAGC AAGAGTATTG TAAGGCTCAT TTGGATTCCA    5400

ATGAATGTGT TGGTAATCCA CCCACGCCCA AAACCAGTGA TGAGGTATTT GCCAACTTAT    5460

ATAATGCCAC CATCAAAGGG GTGAGTGTCA AAGGCAAACT GGATTTGCAT GCCATGACAT    5520

CAAAACTGCC AGATGGTCTT GAAATGACCT TGGGTTATGG TCATACCAAA TTGGGGAAAT    5580

TTGATTACAT TGCACCCAAA GATGCCGATG GTTGGTATCA GGCTCGCCCT GCTTTTTGGG    5640

ATGCCATCAC CCCAGCGCGC TATGTGGTCG GTCTAAACTA TGACCACCCC AGTCAAGTAT    5700

GGGGCATTGG CACAACTTTA ACGCACAGCA AACAAAAAGA TGAAAATGAG CTAAGTGCCC    5760

TTAGAATCCG AAATGGCAAA AGAGAAATAC AAACCTTAAC GCACACAATA CCCAAAGCCT    5820

ATACCTTACT GGACATGACA GGCTATTATA GCCCAACTGA GAGCATCACC GCTCGTCTTG    5880

GTATCAACAA TGTATTAAAC ACCCGCTACA CCACATGGGA AGCGGCACGC CAACTGCCCA    5940
```

```
GCGAAGCTGC AAGCAGTACC CAATCAACCC GTTACATTGC ACCAGGTCGC AGTTACTTTG      6000

CCAGTCTTGA AATGAAGTTT TAATATGACC TGTTTACCAA AGACCAACCC TGCTTTAAAA      6060

GTCAAGCACA GATTTTTAAA GCAGGTGCTG TTATTGCTTT GTGTTGATAC ATTAACAGCA      6120

CAGGCGTACG CCCACAGCCA TCATACGCCC ATTCATACAC CCACGCATGA GCTGTCATCT      6180

GCTGATGCTT TATCAGATGA AGGCTTGGGT AAGGATTTGG GCAGTTTGGA CAGCCCAGAT      6240

GGTTTGGGTG ATGGTTTAGG CGATGGTTTG GGTGATGGCT TAAAAAGTGA TAAAACCCCT      6300

TTACCCATCA ACGCCTTGAC CGTTAATCAG AGCAATGAGA GCCAGCCTGC CCCACCGAGC      6360

GTAGATGTCA ATTTTTTACT TGCCCAGCCA GAGGCATTTT ATCATGTCTT TCATCAAGCG      6420

ATTGTGCAAG ATGATGTGGC AACATTACGC TTGTTATTGC CATTTTATGA CCGCCTGCCT      6480

GATGATTATC AAGATGATGT TTTGTTGTTA TTTGCCCAAA GTAAACTTGC CCTAAGTGAT      6540

GGCAATACCA AATTGGCATT GAATCTGCTG ACCGATTTGA GTAACAAAGA GCCAACACTT      6600

ACGGCGGTAA AATTACAACT TGCTTCCTTG TTGCTGACCA ACAAGCACGA TAAACACGCC      6660

CAAATGGTGC TAGATGAACT CAAAGATGAT GCCCACTTTT TAAAATTAAG CAAAAAAGAG      6720

CAAAGATGGG TGCTATCGCA AAGTCGCTAT TTACATAAAA AATATAAAAT GGGCTTGGAT      6780

TTGGGCATCA ACTATCTGCA TTTGGATAAT ATCAACGCCG CCTCCACCAT CACCCAGCCC      6840

AACATTAAAA AAGATGCCCC AAAACCTGCT CATGGGCTTG CCTTATCGCT TGGTGTGAAT      6900

AAATACACGC CGCTTAGTCA TGGCATGAGT ATTTATACAG CCCTAGATGT TGATGGTAAA      6960

TTTTATGATG ACAAAAGCCA CAATGAACTG GCGGTTTTTG CTCATGCTGG ACTAAGAAAA      7020

GATCACCAAA AAGGTTATGT TGATGTCGTA CCTTTTGTTG GGCGTATTTT TGCCACCAAT      7080

CAGCAGCATG GCAGATTATC CCCCAGAAAA GACAGTCAGG GCGTGGCGTT TGGCAGCCAT      7140

CATCGGATCA ATGATAAATG GCAAAATGCG TTTTTTGCAC GCATGGAAAA AGGCAATTAT      7200

ACCGAGCATT ATCAAGGTTA TGATGGCAAG CGTTATCATG TGAATGACAC CATTTTGTTG      7260

CAAGATGGCC CAAATCGTCG TTACTCTTTG GGCGTGGGGT ATCAGCTTAG CCATCTGCAA      7320

GATGCAACAA AAAGCAGTCA TGCCACAAAG ATACATTTTG GGGTGTTGCA AAGATTGCCA      7380

AATGGTCTGA CCGTGCAAGG TAGAGTGAGT GCTGAGCGTG AGCGTTATCA TGGTAAATTA      7440

TTGCGTCTGG TTAATCCTGA TGATGTGTAT CGCACAGATA AAACCCTAAC CTACAAACC       7500

TCCATTTGGC ACAAAGACAT TCACTGGCTT GGATTAACGC CAAAGCTGAC TTATCGTTAC      7560

AGTAAAAATA ACAGTAACTT ACCAGCACTT TATAGCCATA ACAAACAAAA TTTTTATTTG      7620

GAGCTTGGTC GGTCGTTTTA A                                                7641

(2) INFORMATION FOR SEQ ID NO:7:

(i) SEQUENCE CHARACTERISTICS:
            (A) LENGTH: 2682 base pairs
            (B) TYPE: nucleic acid
            (C) STRANDEDNESS: single
            (D) TOPOLOGY: linear (xi) SEQUENCE DESCRIPTION: SEQ ID NO:7:

ATGAGTACTG TCAAAACCCC CCATATTTTC TACCAAAAAC GCACCCTTAG CCTTGCCATC        60

GCCAGTATTT TTGCTGCCTT GGTGATGACA GGCTGCCGCT CTGATGACAT CAGCGTCAAT       120

GCACCCAATG TTACCCAGCT GCCCCAAGGC ACGGTTTCAC CAACGCCGAA CACAGGTCAT       180

GACAACGCCA ATAACACCAA CAATCAGGGC AACAACACGG ATAACAGCAC CAGCACAACT       240

GACCCAAATG GCGATAACAA CCAACTGACA CAAGCGCAAA AAACTGCCGC CGCCGCAGGG       300

TTTTTTGTGA TGGGTAAAAAT TCGTGATACC AGCGAAAAAA ATGACCCAGA TTATAGTGAT       360
```

```
GATTTAAAAC AGCAGTGGCT GGGCAAATTA TATGTTGGTA TTGATGCCCA TCGCCCAGAT      420

GGCATCGGAA AAGGTAAAAA CTTGCGTCAG CCCATCACCG CCAATGACAT CAAACCCTTG      480

TATTTTAACA AATTCCCTGC ATTGTCTGAT TTGCACTTAG ACAGTGAACG CCATCGTTTT      540

GACCCCCAAA AGATAAACAC CATTAAAGTG TATGGTTATG GTAACTTAAC AACACCATCC      600

AACAACAACA CTCACATCAA TCATCAGCAA GCTGATAATA AGAAAAATAA CAAGCCTGTT      660

GACCCTTATG AAAATATCCG TTTTGGGTAT CTTGAACTAC AAGGAAGCAG CCTGACCCAA      720

AAAAATGCCG ATAATCAAAA TGAGCAAGAC CGCATTCCCA AACCCATGCC CATTTTGTTT      780

TATCATGGAG AAAACGCCAG CAGCCAGCTG CCCAGCGCTG GTAAATTTAA CTACACAGGC      840

AACTGGCTGT ACCTAAGTGA TGTCAAAAAA CGCCCTGCCC TTTCAGCATC AGATGAGCGA      900

GTGGGGGTCT ATCTCAATGC CAGTGGCAAA GCCAACGAGG GCGATGTCGT CAGTGCCGCC      960

CACATTTATC TAAACGGCTT TCAATATAAG CACACGCCTG CCACTTATCA GGTGGATTTT     1020

GACACAAACT CATTAACAGG CAAGCTGTCC TATTATGACA ATCCCAATCA GCAAAATAAT     1080

AAAGGCGAAT ATCTCAAAAG CCAATTTGAC ACTACCAAAA AAGTCAATGA AACCGATGTG     1140

TATCAAATTG ATGCCAAAAT CAACGGTAAC CGCTTTGTCG GTACGGCCAA ATCTTTGGTT     1200

AATGAGAAAA CACAAACCGC ACCTTTTATC AAAGAGCTGT TCTCCAAAAA AGCCAACCCC     1260

AATAACCCAA ACCCTAATTC AGACACGCTA GAAGGCGGAT TTTATGGTGA GTCGGGCGAT     1320

GAGCTGGCGG GTAAATTTTT ATCCAATGAC AACGCATCTT ATGTGGTCTT TGGTGGCAAA     1380

CGAGACAAAA CGACTAAACC TGTCGCCACA AAAACGGTGT ATTTTAGTGC AGGCTTTGAA     1440

AAACCCAGCA CCAGTTTTGT GGATAATGAA ACGATTGGTG GAATTATTGA CCGTAAAGGG     1500

TTAAATAATC ACATTAATGA AGATGAAATT ATTCCCAGTG ATGATAGTTA TTATGGATAT     1560

ACTTGGGGCA AGCCAGAGAA GCAGTTCACC AAAAAAGTCA GCAGCAGCAC CCAAGTCGTG     1620

CCAGCTTATT TTGGGCAACA TGATAAATTT TATTTTAATG GCAACTATTA TGACCTATCA     1680

GCCAGTCGTG TTGATAAATT AGCCCCTGCC GATGCTGTCA AAGCCAACCA ATCCATTAAA     1740

GAAAAATACC CTAATGCCAC ACTAAATAAG GACAACCAAG TTACCGCCAT CGTGCTACAA     1800

GAAGCCAAAG ATAATAAGCC TTATACCGCC ATTCGTGCCA AAAGCTATCA GCACATCAGT     1860

TTTGGCGAGA CGCTGTATAA CGATGCCAAC CAAACCCCAA CACGCAGTTA TTTTGTGCAA     1920

GGCGGTAGGG CAGATACCAG CACAACTTTG CCCCAGGCAG GTAAATTCAC TTACAACGGT     1980

CTTTGGGCAG GCTACCTGAC CCAAAAAAAG GACAAAGGTT ATAGCGATAA TGCAGAAACC     2040

ATCAAGGAAA AAGGTCATCC AGGTTATCTG TTAACCGAAA ACTTCACCCC AGAAGATGAT     2100

GACGATGATT TGACCGCATC TGATGATTCA CAAGATGATA ATACACATGG CGATGATGAT     2160

TTGATTGCAT CTGATGATTC ACAAGATGAT GACGCAGATG GAGATGACGA TTCAGATGAT     2220

TTGGGTGATG GTGCAGATGA TGACGCCGCA GGCAAAGTGT ATCATGCAGG TAATATTCGC     2280

CCTGAATTTG AAAACAAATA CTTGCCCATT AATGAGCCTA CTCATGAAAA AACCTTTGCC     2340

CTAGATGGTA AAAATAAAGC TAAGTTTGAA GTGGATTTTA ACACCAACAG CCTAACTGGT     2400

AAATTAAACG ATGAGAGAGG TGATATCGTC TTTGATATCA AAAATGGCAA AATTGATGGC     2460

ACAGGATTTA CCGCCAAAGC CGATGTGCCA AACTATCGTG AAGAAGTGGG TAACAACCAA     2520

GGTGGCGGTT TCTTATACAA CATCAAAGAT ATTGATGTTA AGGGGCAATT TTTTGGCACA     2580

AATGGCGAAG AGTTGGCAGG ACAGTTACAT CATGACAAAG GCGATGGCAT CAATGACACC     2640

GCCGAAAAAG CAGGGGCTGT CTTTGGGGCT GTTAAAGATA AA                        2682
```

(2) INFORMATION FOR SEQ ID NO:8:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (xi) SEQUENCE DESCRIPTION: SEQ ID NO:8:

```
ATGTCAAAAT CTATCACAAA AACACAAACA CCATCAGTCC ATACCATGAC CACGCACCGC      60

TTAAACCTTG CCATCAAAGC GGCGTTATTT GGTGTGGCAG TTTTACCCCT ATCCGTCTGG     120

GCGCAAGAGA ACACTCAGAC AGATGCCAAC TCTGATGCCA AAGACACAAA AACCCCTGTC     180

GTCTATTTAG ATGCCATCAC GGTAACCGCC GCCCCATCTG CCCCTGTTTC TCGGTTTGAC     240

ACCGATGTAA CAGGGCTTGG CAAAACCGTC AAAACCGCTG ACACGCTGGC AAAAGAACAA     300

GTACAGGGCA TTCGTGATTT GGTGCGTTAT GAAACTGGGG TGAGTGTGGT TGAGCAGGGG     360

CGTGGTGGCA GCAGCGGATT TGCCATTCAT GGCGTGGATA AAACCGAGT GGGCATTACC      420

GTAGATGGCA TTGCCCAAAT TCAATCCTAC AAAGACGAAT CCACTAAGCG AGCTGGGGCA     480

GGCTCTGGGG CGATGAACGA GATAGAGATT GAAAACATTG CCGCCGTTGC CATCAATAAA     540

GGCGGTAATG CCTTAGAAGC AGGCTCTGGT GCGTTGGGTG GTTCGGTGGC GTTTCATACC     600

AAAGATGTGA GCGATGTCTT AAAATCTGGT AACAATCTTG GTGCTCAAAG CAAAACCACT     660

TATAACAGCA AAAATGACCA TTTTAGTCAG ACGCTGGCAG CGGCAGGTAA AACCGAGCGT     720

GTGGAAGCGA TGGTGCAATA TACCTACCGT AAAGGCAAAG AAAACAAAGC ACACAGCGAC     780

CTAAATGGCA TCAACCAAAG CCTATATCGC TTGGGTGCAT GGCAACAAAA ATATGATTTA     840

AGAAAGCCTA ACGAACTGTT TGCAGGCACA AGCTATATCA CCGAAAGCTG TTTGGCAAGT     900

GATGACCCAA AAAGCTGCGT ACAATACCCT TATGTCTACA CCAAAGCCCG ACCAGATGGT     960

ATCGGCAATC GCAATTTTTC TGAGTTAAGC GATGCTGAAA AAGCACAATA TTTGGCGTCC    1020

ACGCACCCCC ATGAGGTTGT CTCTGCCAAA GATTATACAG GCACTTATCG GTTGTTACCT    1080

GACCCCATGG ACTATCGTTC AGACTCGTAT TTGGCACGCC TTAACATCAA AATCACCCCA    1140

AATTTGGTCA GTAAACTGTT ATTAGAAGAC ACCAAGCAAA CATACAACAT TCGTGATATG    1200

CGTCATTGTA GTTATCATGG GGCAAGATTG GGCAATGACG GTAAGCCTGC CAATGGCGGC    1260

TCCATTGTCC TTTGCGATGA TTATCAAGAG TATCTAAATG CCAATGACGC ATCACAAGCA    1320

TCATTTAGAC CAGGGGCTAA TGACGCCCCC ATTCCAAAAC TGGCTTATGC CAGAAGCAGT    1380

GTGTTTAACC AAGAGCATGG CAAAACTCGC TATGGGTTAG GTTTTGAGTT TAAGCCTGAC    1440

ACGCCATGGT TTAAACAAGC AAAATTAAAC CTACATCAAC AAAATATCCA AATCATTAAC    1500

CATGACATTA AAAAATCGTG CAGCCAATAT CCCAAGGTGG ATTTAAATTG TGGCATCAGT    1560

GAAATTGGGC ATTATGAATA TCAAAACAAT TACCGTTATA AGAAGGGCG TACCAGTTTG      1620

ACAGGCAAAC TTGATTTTAA TTTTGACCTG CTGGGCCAGC ACGATTTGAC GGTGTTGGCT    1680

GGTGCAGATA AAGTTAAAAG CCAATTTCGT GCCAACAACC CCAGACGCAC AATCATTGAC    1740

ACCACCCAAG GCGATGCCAT CATTGATGAA AGCACGCTGA CAGCACAGGA GCAAGCCAAA    1800

TTTAAGCAAT CAGGGGCAGC ATGGATTGTC AAAAATCGCT TAGGACGCTT AGAAGAAAAA    1860

GACGCCTGTG GCAATGCCAA TGAATGTGAA CGCGCGCCCA TTCATGGCAG TAACCAATAT    1920

GTGGGCATTA ACAACCTTTA TACACCAAAT GATTATGTGG ATTTAAGTTT TGGTGGACGC    1980

TTGGATAAAC AACGCATTCA CAGCACCGAT TCAAACATCA TCAGCAAAAC TTACACCAAC    2040

AAAAGCTATA ATTTTGGAGC GGCGGTTCAT CTGACACCTG ATTTTAGCCT GTTGTATAAA    2100
```

```
ACTGCCAAAG GCTTTCGTAC GCCAAGTTTT TATGAACTGT ACAACTATAA CAGCACCGCC    2160

GCCCAGCATA AAAATGACCC TGATGTGTCT TTTCCCAAAC GAGCGGTTGA TGTCAAACCT    2220

GAAACTTCCA ATACCAATGA ATACGGCTTT CGCTATCAGC ACCCTTGGGG GGATATTGAG    2280

ATGAGCATGT TCAAAAGCCG TTACAAGGAC ATGTTAGATA AAGCCATACC GAACCTAACC    2340

AAAGCCCAGC AAGAGTATTG TAAGGCTCAT TTGGATTCCA ATGAATGTGT TGGTAATCCA    2400

CCCACGCCCA AAACCAGTGA TGAGGTATTT GCCAACTTAT ATAATGCCAC CATCAAAGGG    2460

GTGAGTGTCA AAGGCAAACT GGATTTGCAT GCCATGACAT CAAAACTGCC AGATGGTCTT    2520

GAAATGACCT TGGGTTATGG TCATACCAAA TTGGGGAAAT TTGATTACAT TGCACCCAAA    2580

GATGCCGATG GTTGGTATCA GGCTCGCCCT GCTTTTTGGG ATGCCATCAC CCCAGCGCGC    2640

TATGTGGTCG GTCTAAACTA TGACCACCCC AGTCAAGTAT GGGGCATTGG CACAACTTTA    2700

ACGCACAGCA AACAAAAAGA TGAAAATGAG CTAAGTGCCC TTAGAATCCG AAATGGCAAA    2760

AGAGAAATAC AAACCTTAAC GCACACAATA CCCAAAGCCT ATACCTTACT GGACATGACA    2820

GGCTATTATA GCCCAACTGA GAGCATCACC GCTCGTCTTG GTATCAACAA TGTATTAAAC    2880

ACCCGCTACA CCACATGGGA AGCGGCACGC CAACTGCCCA GCGAAGCTGC AAGCAGTACC    2940

CAATCAACCC GTTACATTGC ACCAGGTCGC AGTTACTTTG CCAGTCTTGA AATGAAGTTT    3000

(2) INFORMATION FOR SEQ ID NO:9:

(i) SEQUENCE CHARACTERISTICS:
        (A) LENGTH: 2955 base pairs
        (B) TYPE: nucleic acid
        (C) STRANDEDNESS: single
        (D) TOPOLOGY: linear (xi) SEQUENCE DESCRIPTION: SEQ ID NO:9:

ATGACCACGC ACCGCTTAAA CCTTGCCATC AAAGCGGCGT TATTTGGTGT GGCAGTTTTA      60

CCCCTATCCG TCTGGGCGCA AGAGAACACT CAGACAGATG CCAACTCTGA TGCCAAAGAC     120

ACAAAAACCC CTGTCGTCTA TTTAGATGCC ATCACGGTAA CCGCCGCCCC ATCTGCCCCT     180

GTTTCTCGGT TTGACACCGA TGTAACAGGG CTTGGCAAAA CCGTCAAAAC CGCTGACACG     240

CTGGCAAAAG AACAAGTACA GGGCATTCGT GATTTGGTGC GTTATGAAAC TGGGGTGAGT     300

GTGGTTGAGC AGGGGCGTGG TGGCAGCAGC GGATTTGCCA TTCATGGCGT GGATAAAAAC     360

CGAGTGGGCA TTACCGTAGA TGGCATTGCC CAAATTCAAT CCTACAAAGA CGAATCCACT     420

AAGCGAGCTG GGGCAGGCTC TGGGGCGATG AACGAGATAG AGATTGAAAA CATTGCCGCC     480

GTTGCCATCA ATAAAGGCGG TAATGCCTTA GAAGCAGGCT CTGGTGCGTT GGGTGGTTCG     540

GTGGCGTTTC ATACCAAAGA TGTGAGCGAT GTCTTAAAAT CTGGTAACAA TCTTGGTGCT     600

CAAAGCAAAA CCACTTATAA CAGCAAAAAT GACCATTTTA GTCAGACGCT GGCAGCGGCA     660

GGTAAAACCG AGCGTGTGGA AGCGATGGTG CAATATACCT ACCGTAAAGG CAAAGAAAAC     720

AAAGCACACA GCGACCTAAA TGGCATCAAC CAAAGCCTAT ATCGCTTGGG TGCATGGCAA     780

CAAAAATATG ATTTAAGAAA GCCTAACGAA CTGTTTGCAG GCACAAGCTA TATCACCGAA     840

AGCTGTTTGG CAAGTGATGA CCCAAAAAGC TGCGTACAAT ACCCTTATGT CTACACCAAA     900

GCCCGACCAG ATGGTATCGG CAATCGCAAT TTTTCTGAGT TAAGCGATGC TGAAAAAGCA     960

CAATATTTGG CGTCCACGCA CCCCCATGAG GTTGTCTCTG CCAAAGATTA TAGGCACT    1020

TATCGGTTGT TACCTGACCC CATGGACTAT CGTTCAGACT CGTATTTGGC ACGCCTTAAC    1080

ATCAAAATCA CCCCAAATTT GGTCAGTAAA CTGTTATTAG AAGACACCAA GCAAACATAC    1140

AACATTCGTG ATATGCGTCA TTGTAGTTAT CATGGGGCAA GATTGGGCAA TGACGGTAAG    1200
```

```
CCTGCCAATG GCGGCTCCAT TGTCCTTTGC GATGATTATC AAGAGTATCT AAATGCCAAT    1260

GACGCATCAC AAGCATCATT TAGACCAGGG GCTAATGACG CCCCCATTCC AAAACTGGCT    1320

TATGCCAGAA GCAGTGTGTT TAACCAAGAG CATGGCAAAA CTCGCTATGG GTTAGGTTTT    1380

GAGTTTAAGC CTGACACGCC ATGGTTTAAA CAAGCAAAAT TAAACCTACA TCAACAAAAT    1440

ATCCAAATCA TTAACCATGA CATTAAAAAA TCGTGCAGCC AATATCCCAA GGTGGATTTA    1500

AATTGTGGCA TCAGTGAAAT TGGGCATTAT GAATATCAAA ACAATTACCG TTATAAAGAA    1560

GGGCGTACCA GTTTGACAGG CAAACTTGAT TTTAATTTTG ACCTGCTGGG CCAGCACGAT    1620

TTGACGGTGT TGGCTGGTGC AGATAAAGTT AAAAGCCAAT TTCGTGCCAA CAACCCCAGA    1680

CGCACAATCA TTGACACCAC CCAAGGCGAT GCCATCATTG ATGAAAGCAC GCTGACAGCA    1740

CAGGAGCAAG CCAAATTTAA GCAATCAGGG GCAGCATGGA TTGTCAAAAA TCGCTTAGGA    1800

CGCTTAGAAG AAAAAGACGC CTGTGGCAAT GCCAATGAAT GTGAACGCGC GCCCATTCAT    1860

GGCAGTAACC AATATGTGGG CATTAACAAC CTTTATACAC AAATGATTA TGTGGATTTA    1920

AGTTTTGGTG GACGCTTGGA TAAACAACGC ATTCACAGCA CCGATTCAAA CATCATCAGC    1980

AAAACTTACA CCAACAAAAG CTATAATTTT GGAGCGGCGG TTCATCTGAC ACCTGATTTT    2040

AGCCTGTTGT ATAAAACTGC CAAAGGCTTT CGTACGCCAA GTTTTTATGA ACTGTACAAC    2100

TATAACAGCA CCGCCGCCCA GCATAAAAAT GACCCTGATG TGTCTTTTCC CAAACGAGCG    2160

GTTGATGTCA AACCTGAAAC TTCCAATACC AATGAATACG GCTTTCGCTA TCAGCACCCT    2220

TGGGGGGATA TTGAGATGAG CATGTTCAAA AGCCGTTACA AGGACATGTT AGATAAAGCC    2280

ATACCGAACC TAACCAAAGC CCAGCAAGAG TATTGTAAGG CTCATTTGGA TTCCAATGAA    2340

TGTGTTGGTA ATCCACCCAC GCCCAAAACC AGTGATGAGG TATTTGCCAA CTTATATAAT    2400

GCCACCATCA AAGGGGTGAG TGTCAAAGGC AAACTGGATT TGCATGCCAT GACATCAAAA    2460

CTGCCAGATG GTCTTGAAAT GACCTTGGGT TATGGTCATA CCAAATTGGG GAAATTTGAT    2520

TACATTGCAC CCAAAGATGC CGATGGTTGG TATCAGGCTC GCCCTGCTTT TTGGGATGCC    2580

ATCACCCCAG CGCGCTATGT GGTCGGTCTA AACTATGACC ACCCCAGTCA AGTATGGGGC    2640

ATTGGCACAA CTTTAACGCA CAGCAAACAA AAAGATGAAA ATGAGCTAAG TGCCCTTAGA    2700

ATCCGAAATG GCAAAAGAGA AATACAAACC TTAACGCACA CAATACCCAA AGCCTATACC    2760

TTACTGGACA TGACAGGCTA TTATAGCCCA ACTGAGAGCA TCACCGCTCG TCTTGGTATC    2820

AACAATGTAT TAAACACCCG CTACACCACA TGGGAAGCGG CACGCCAACT GCCCAGCGAA    2880

GCTGCAAGCA GTACCCAATC AACCCGTTAC ATTGCACCAG GTCGCAGTTA CTTTGCCAGT    2940

CTTGAAATGA AGTTT                                                    2955
```

(2) INFORMATION FOR SEQ ID NO:10:

(i) SEQUENCE CHARACTERISTICS:
        (A) LENGTH: 1614 base pairs
        (B) TYPE: nucleic acid
        (C) STRANDEDNESS: single
        (D) TOPOLOGY: linear (xi) SEQUENCE DESCRIPTION: SEQ ID NO:10:

```
ATGACCTGTT TACCAAAGAC CAACCCTGCT TTAAAAGTCA AGCACAGATT TTTAAAGCAG     60

GTGCTGTTAT TGCTTTGTGT TGATACATTA ACAGCACAGG CGTACGCCCA CAGCCATCAT    120

ACGCCCATTC ATACACCCAC GCATGAGCTG TCATCTGCTG ATGCTTTATC AGATGAAGGC    180

TTGGGTAAGG ATTTGGGCAG TTTGGACAGC CCAGATGGTT TGGGTGATGG TTTAGGCGAT    240
```

| | | |
|---|---|---|
| GGTTTGGGTG ATGGCTTAAA AAGTGATAAA ACCCCTTTAC CCATCAACGC CTTGACCGTT | 300 | |
| AATCAGAGCA ATGAGAGCCA GCCTGCCCCA CCGAGCGTAG ATGTCAATTT TTTACTTGCC | 360 | |
| CAGCCAGAGG CATTTTATCA TGTCTTTCAT CAAGCGATTG TGCAAGATGA TGTGGCAACA | 420 | |
| TTACGCTTGT TATTGCCATT TTATGACCGC CTGCCTGATG ATTATCAAGA TGATGTTTTG | 480 | |
| TTGTTATTTG CCCAAAGTAA ACTTGCCCTA AGTGATGGCA ATACCAAATT GGCATTGAAT | 540 | |
| CTGCTGACCG ATTTGAGTAA CAAAGAGCCA ACACTTACGG CGGTAAAATT ACAACTTGCT | 600 | |
| TCCTTGTTGC TGACCAACAA GCACGATAAA CACGCCCAAA TGGTGCTAGA TGAACTCAAA | 660 | |
| GATGATGCCC ACTTTTTAAA ATTAAGCAAA AAAGAGCAAA GATGGGTGCT ATCGCAAAGT | 720 | |
| CGCTATTTAC ATAAAAAATA TAAAATGGGC TTGGATTTGG GCATCAACTA TCTGCATTTG | 780 | |
| GATAATATCA ACGCCGCCTC CACCATCACC CAGCCCAACA TTAAAAAAGA TGCCCCAAAA | 840 | |
| CCTGCTCATG GGCTTGCCTT ATCGCTTGGT GTGAATAAAT ACACGCCGCT TAGTCATGGC | 900 | |
| ATGAGTATTT ATACAGCCCT AGATGTTGAT GGTAAATTTT ATGATGACAA AGCCACAAT | 960 | |
| GAACTGGCGG TTTTTGCTCA TGCTGGACTA AGAAAAGATC ACCAAAAAGG TTATGTTGAT | 1020 | |
| GTCGTACCTT TTGTTGGGCG TATTTTTGCC ACCAATCAGC AGCATGGCAG ATTATCCCCC | 1080 | |
| AGAAAAGACA GTCAGGGCGT GGCGTTTGGC AGCCATCATC GGATCAATGA TAAATGGCAA | 1140 | |
| AATGCGTTTT TTGCACGCAT GGAAAAAGGC AATTATACCG AGCATTATCA AGGTTATGAT | 1200 | |
| GGCAAGCGTT ATCATGTGAA TGACACCATT TTGTTGCAAG ATGGCCCAAA TCGTCGTTAC | 1260 | |
| TCTTTGGGCG TGGGGTATCA GCTTAGCCAT CTGCAAGATG CAACAAAAAG CAGTCATGCC | 1320 | |
| ACAAAGATAC ATTTTGGGGT GTTGCAAAGA TTGCCAAATG GTCTGACCGT GCAAGGTAGA | 1380 | |
| GTGAGTGCTG AGCGTGAGCG TTATCATGGT AAATTATTGC GTCTGGTTAA TCCTGATGAT | 1440 | |
| GTGTATCGCA CAGATAAAAC CCTAACCCTA CAAACCTCCA TTTGGCACAA AGACATTCAC | 1500 | |
| TGGCTTGGAT TAACGCCAAA GCTGACTTAT CGTTACAGTA AAAATAACAG TAACTTACCA | 1560 | |
| GCACTTTATA GCCATAACAA ACAAAATTTT TATTTGGAGC TTGGTCGGTC GTTT | 1614 | |

(2) INFORMATION FOR SEQ ID NO:11:

(i) SEQUENCE CHARACTERISTICS:
        (A) LENGTH: 898 amino acids
        (B) TYPE: amino acid
        (C) STRANDEDNESS: single
        (D) TOPOLOGY: linear (xi) SEQUENCE DESCRIPTION: SEQ ID NO:11:

```
Met Ser Thr Val Lys Thr Pro His Ile Phe Tyr Gln Lys Arg Thr Leu
1               5                   10                  15

Ser Leu Ala Ile Ala Ser Ile Phe Ala Ala Leu Val Met Thr Gly Cys
                20                  25                  30

Arg Ser Asp Asp Ile Ser Val Asn Ala Pro Asn Val Thr Gln Leu Pro
            35                  40                  45

Gln Gly Thr Val Ser Pro Ile Pro Asn Thr Gly His Asp Asn Thr Asn
        50                  55                  60

Asn Thr Asn Asn Gln Gly Asn Asn Thr Asp Asn Ser Thr Ser Thr Thr
65                  70                  75                  80

Asp Pro Asn Gly Asp Asn Asn Gln Leu Thr Gln Ala Gln Lys Thr Ala
                85                  90                  95

Ala Ala Ala Gly Phe Phe Val Met Gly Lys Ile Arg Asp Thr Ser Pro
            100                 105                 110

Lys Asn Asp Pro Asp Tyr Ser Asn Asp Leu Val Gln Gln Trp Gln Gly
        115                 120                 125
```

```
Lys Leu Tyr Val Gly Ile Asp Ala His Arg Pro Asp Gly Ile Gly Thr
        130                 135                 140

Gly Lys Asn Leu Arg Gln Pro Ile Thr Ala Asn Asp Ile Lys Pro Leu
145                 150                 155                 160

Tyr Phe Asn Lys Phe Pro Ala Leu Ser Asp Leu His Leu Asp Ser Glu
                165                 170                 175

Arg His Arg Phe Asp Pro Lys Lys Leu Asn Thr Ile Lys Val Tyr Gly
            180                 185                 190

Tyr Gly Asn Leu Thr Thr Pro Ser Lys Asn Thr Tyr Ile Asn His
        195                 200                 205

Gln Gln Ala Asp Asn Lys Lys Asn Asn Lys Pro Val Asp Pro Tyr Glu
    210                 215                 220

Asn Ile Arg Phe Gly Tyr Leu Glu Leu Gln Gly Ser Ser Leu Thr Gln
225                 230                 235                 240

Lys Asn Ala Asp Thr Pro Asn Asp Lys Asp Arg Ile Pro Lys Pro Met
                245                 250                 255

Pro Ile Leu Phe Tyr His Gly Glu Asn Ala Ser Ser Gln Leu Pro Ser
                260                 265                 270

Ala Gly Lys Phe Asn Tyr Thr Gly Asn Trp Leu Tyr Leu Ser Asp Val
        275                 280                 285

Lys Lys Arg Pro Ala Leu Ser Ala Ser Asp Asp Arg Val Gly Val Tyr
        290                 295                 300

Leu Asn Ala Ser Gly Lys Ser Asn Glu Gly Asp Val Val Ser Ala Ala
305                 310                 315                 320

His Ile Tyr Leu Asn Gly Phe Gln Tyr Lys His Thr Pro Ala Thr Tyr
                325                 330                 335

Gln Val Asp Phe Asp Thr Asn Ser Leu Thr Gly Lys Leu Ser Tyr Tyr
            340                 345                 350

Asp Asn Pro Asn Gln Gln Thr Ala Gln Gly Lys Tyr Ile Lys Ser Gln
        355                 360                 365

Phe Asp Thr Thr Lys Lys Val Asn Glu Thr Asp Val Tyr Gln Ile Asp
    370                 375                 380

Ala Lys Ile Asn Gly Asn Arg Phe Val Gly Thr Ala Lys Ser Leu Val
385                 390                 395                 400

Asn Glu Asn Thr Glu Thr Ala Pro Phe Ile Lys Glu Leu Phe Ser Lys
                405                 410                 415

Lys Ala Asn Pro Asn Asn Pro Asn Ser Asp Thr Leu Glu Gly
            420                 425                 430

Gly Phe Tyr Gly Glu Ser Gly Asp Glu Leu Ala Gly Lys Phe Leu Ser
        435                 440                 445

Asn Asp Asn Ala Ser Tyr Val Val Phe Gly Gly Lys Arg Asp Lys Thr
    450                 455                 460

Asp Lys Pro Val Ala Thr Lys Thr Val Tyr Phe Ser Ala Gly Phe Glu
465                 470                 475                 480

Lys Pro Ser Thr Ser Phe Val Asp Asn Glu Thr Ile Gly Arg Ile Ile
                485                 490                 495

Asn Ser Lys Lys Leu Asn Asp Ala Val Asn Glu Lys Ile Asp Asn Gly
            500                 505                 510

Asp Ile Pro Thr Ser Asp Glu Arg Tyr Asp Glu Phe Pro Trp Gly Glu
        515                 520                 525

Lys Lys Ala Glu Phe Thr Lys Leu Val Ser Ser Thr Gln Ala Val
    530                 535                 540

Pro Ala Tyr Phe Gly Gln His Asp Lys Phe Tyr Phe Asn Gly Asn Tyr
```

```
                545                 550                 555                 560
Tyr Asp Leu Ser Ala Ser Ser Val Asp Lys Leu Ala Pro Ala Asp Ala
                    565                 570                 575
Val Lys Ala Asn Gln Ser Ile Lys Glu Lys Tyr Pro Asn Ala Thr Leu
                580                 585                 590
Asn Lys Asp Asn Gln Val Thr Ala Ile Val Leu Gln Glu Ala Lys Asp
                595                 600                 605
Asn Lys Pro Tyr Thr Ala Ile Arg Ala Lys Ser Tyr Gln His Ile Ser
                610                 615                 620
Phe Gly Glu Thr Leu Tyr Asn Asp Ala Asn Gln Thr Pro Thr Arg Ser
625                 630                 635                 640
Tyr Phe Val Gln Gly Gly Arg Ala Asp Thr Ser Thr Thr Leu Pro Lys
                    645                 650                 655
Ala Gly Lys Phe Thr Tyr Asn Gly Leu Trp Ala Gly Tyr Leu Ile Gln
                660                 665                 670
Lys Lys Asp Lys Gly Tyr Ser Asn Asn Glu Glu Thr Ile Lys Lys Lys
                    675                 680                 685
Gly His Gln Asp Tyr Leu Leu Thr Glu Asp Phe Thr Pro Glu Asp Asp
                690                 695                 700
Asp Asp Asp Leu Thr Ala Ser Asp Asp Ser Gln Asp Asp Ala His
705                 710                 715                 720
Gly Asp Asp Leu Ile Ala Ser Asp Ser Gln Asp Asp Ala
                    725                 730                 735
Asp Gly Asp Asp Ser Asp Asp Leu Gly Asp Gly Ala Asp Asp Ala
                    740                 745                 750
Ala Ala Gly Lys Val Tyr His Ala Gly Asn Ile Arg Pro Glu Phe Glu
                755                 760                 765
Asn Lys Tyr Leu Pro Ile Asn Glu Pro Thr His Glu Lys Thr Phe Ala
                770                 775                 780
Leu Asp Gly Lys Asn Lys Ala Lys Phe Asp Val Asp Phe Asp Thr Asn
785                 790                 795                 800
Ser Leu Thr Gly Lys Leu Asn Asp Glu Arg Gly Asp Ile Val Phe Asp
                    805                 810                 815
Ile Lys Asn Gly Lys Ile Asp Gly Thr Gly Phe Thr Lys Ala Asp
                820                 825                 830
Val Pro Asn Tyr Arg Glu Glu Val Gly Asn Asn Gln Gly Gly Phe
                835                 840                 845
Leu Tyr Asn Ile Lys Asp Ile Asp Val Lys Gly Gln Phe Phe Gly Thr
                850                 855                 860
Asn Gly Glu Glu Leu Ala Gly Gln Leu Gln Tyr Asp Lys Gly Asp Gly
865                 870                 875                 880
Ile Asn Asp Thr Ala Glu Lys Ala Gly Ala Val Phe Gly Ala Val Lys
                    885                 890                 895
Asp Lys (2) INFORMATION FOR SEQ ID NO:12:

(i) SEQUENCE CHARACTERISTICS:
        (A) LENGTH: 1000 amino acids
        (B) TYPE: amino acid
        (C) STRANDEDNESS: single
        (D) TOPOLOGY: linear (xi) SEQUENCE DESCRIPTION: SEQ ID NO:12:

Met Ser Lys Ser Ile Thr Lys Thr Gln Thr Pro Ser Val His Thr Met
1               5                   10                  15
```

```
Thr Thr His Arg Leu Asn Leu Ala Ile Lys Ala Ala Leu Phe Gly Val
            20                  25                  30

Ala Val Leu Pro Leu Ser Val Trp Ala Gln Glu Asn Thr Gln Thr Asp
        35                  40                  45

Ala Asn Ser Asp Ala Lys Asp Thr Lys Thr Pro Val Val Tyr Leu Asp
50                  55                  60

Ala Ile Thr Val Thr Ala Ala Pro Ser Ala Pro Val Ser Arg Phe Asp
65                  70                  75                  80

Thr Asp Val Thr Gly Leu Gly Lys Thr Val Lys Thr Ala Asp Thr Leu
                85                  90                  95

Ala Lys Glu Gln Val Gln Gly Ile Arg Asp Leu Val Arg Tyr Glu Thr
            100                 105                 110

Gly Val Ser Val Val Glu Gln Gly Arg Gly Ser Ser Gly Phe Ala
            115                 120                 125

Ile His Gly Val Asp Lys Asn Arg Val Gly Ile Thr Val Asp Gly Ile
        130                 135                 140

Ala Gln Ile Gln Ser Tyr Lys Asp Glu Ser Thr Lys Arg Ala Gly Ala
145                 150                 155                 160

Gly Ser Gly Ala Met Asn Glu Ile Glu Ile Glu Asn Ile Ala Ala Val
                165                 170                 175

Ala Ile Asn Lys Gly Gly Asn Ala Leu Glu Ala Gly Ser Gly Ala Leu
            180                 185                 190

Gly Gly Ser Val Ala Phe His Thr Lys Asp Val Ser Asp Val Leu Lys
            195                 200                 205

Ser Gly Lys Asn Leu Gly Ala Gln Ser Lys Thr Thr Tyr Asn Ser Lys
        210                 215                 220

Asn Asp His Phe Ser Gln Thr Leu Ala Ala Gly Lys Thr Glu Arg
225                 230                 235                 240

Val Glu Ala Met Val Gln Tyr Thr Tyr Arg Lys Gly Lys Glu Asn Lys
                245                 250                 255

Ala His Ser Asp Leu Asn Gly Ile Asn Gln Ser Leu Tyr Arg Leu Gly
            260                 265                 270

Ala Trp Gln Gln Lys Tyr Asp Leu Arg Lys Pro Asn Glu Leu Phe Ala
        275                 280                 285

Gly Thr Ser Tyr Ile Thr Glu Ser Cys Leu Ala Ser Asp Asp Pro Lys
        290                 295                 300

Ser Cys Val Gln Tyr Pro Tyr Val Tyr Thr Lys Ala Arg Pro Asp Gly
305                 310                 315                 320

Ile Gly Asn Arg Asn Phe Ser Glu Leu Ser Asp Ala Glu Lys Ala Gln
                325                 330                 335

Tyr Leu Ala Ser Thr His Pro His Glu Val Val Ser Ala Lys Asp Tyr
            340                 345                 350

Thr Gly Ile Tyr Arg Leu Leu Pro Asp Pro Met Asp Tyr Arg Ser Asp
        355                 360                 365

Ser Tyr Leu Ala Arg Leu Asn Ile Lys Ile Thr Pro Asn Leu Val Ser
        370                 375                 380

Lys Leu Leu Leu Glu Asp Thr Lys Gln Thr Tyr Asn Ile Arg Asp Met
385                 390                 395                 400

Arg His Cys Ser Tyr His Gly Ala Arg Leu Gly Asn Asp Gly Lys Pro
                405                 410                 415

Ala Asn Gly Gly Ser Ile Val Leu Cys Asp Asp Tyr Gln Glu Tyr Leu
            420                 425                 430

Asn Ala Asn Asp Ala Ser Gln Ala Leu Phe Arg Pro Gly Ala Asn Asp
```

```
                435             440             445
Ala Pro Ile Pro Lys Leu Ala Tyr Ala Arg Ser Ser Val Phe Asn Gln
    450                 455                 460
Glu His Gly Lys Thr Arg Tyr Gly Leu Ser Phe Glu Phe Lys Pro Asp
465                 470                 475                 480
Thr Pro Trp Phe Lys Gln Ala Lys Leu Asn Leu His Gln Gln Asn Ile
                485                 490                 495
Gln Ile Ile Asn His Asp Ile Lys Lys Ser Cys Ser Gln Tyr Pro Lys
                500                 505                 510
Val Asp Leu Asn Cys Gly Ile Ser Glu Ile Gly His Tyr Glu Tyr Gln
                515                 520                 525
Asn Asn Tyr Arg Tyr Lys Glu Gly Arg Ala Ser Leu Thr Gly Lys Leu
                530                 535                 540
Asp Phe Asn Phe Asp Leu Leu Gly Gln His Asp Leu Thr Val Leu Ala
545                 550                 555                 560
Gly Ala Asp Lys Val Lys Ser Gln Phe Arg Ala Asn Asn Pro Arg Arg
                565                 570                 575
Thr Ile Ile Asp Thr Thr Gln Gly Asp Ala Ile Ile Asp Glu Ser Thr
                580                 585                 590
Leu Thr Ala Gln Glu Gln Ala Lys Phe Lys Gln Ser Gly Ala Ala Trp
    595                 600                 605
Ile Val Lys Asn Arg Leu Gly Arg Leu Glu Glu Lys Asp Ala Cys Gly
    610                 615                 620
Asn Ala Asn Glu Cys Glu Arg Ala Pro Ile His Gly Ser Asn Gln Tyr
625                 630                 635                 640
Val Gly Ile Asn Asn Leu Tyr Thr Pro Asn Asp Tyr Val Asp Leu Ser
                645                 650                 655
Phe Gly Gly Arg Leu Asp Lys Gln Arg Ile His Ser Thr Asp Ser Asn
                660                 665                 670
Ile Ile Ser Lys Thr Tyr Thr Asn Lys Ser Tyr Asn Phe Gly Ala Ala
                675                 680                 685
Val His Leu Thr Pro Asp Phe Ser Leu Leu Tyr Lys Thr Ala Lys Gly
    690                 695                 700
Phe Arg Thr Pro Ser Phe Tyr Glu Leu Tyr Asn Tyr Asn Ser Thr Ala
705                 710                 715                 720
Ala Gln His Lys Asn Asp Pro Asp Val Ser Phe Pro Lys Arg Ala Val
                725                 730                 735
Asp Val Lys Pro Glu Thr Ser Asn Thr Asn Glu Tyr Gly Phe Arg Tyr
                740                 745                 750
Gln His Pro Trp Gly Asp Val Glu Met Ser Met Phe Lys Ser Arg Tyr
    755                 760                 765
Lys Asp Met Leu Asp Lys Ala Ile Pro Asn Leu Thr Lys Ala Gln Gln
770                 775                 780
Glu Tyr Cys Lys Ala His Leu Asp Ser Asn Glu Cys Val Gly Asn Pro
785                 790                 795                 800
Pro Thr Pro Lys Thr Ser Asp Glu Val Phe Ala Asn Leu Tyr Asn Ala
                805                 810                 815
Thr Ile Lys Gly Val Ser Val Lys Gly Lys Leu Asp Leu His Ala Met
                820                 825                 830
Thr Ser Lys Leu Pro Asp Gly Leu Glu Met Thr Leu Gly Tyr Gly His
                835                 840                 845
Thr Lys Leu Gly Lys Phe Asp Tyr Ile Ala Pro Lys Asp Ala Asp Gly
850                 855                 860
```

```
Trp Tyr Gln Ala Arg Pro Ala Phe Trp Asp Ala Ile Thr Pro Ala Arg
865                 870                 875                 880

Tyr Val Val Gly Leu Asn Tyr Asp His Pro Ser Gln Val Trp Gly Ile
            885                 890                 895

Gly Thr Thr Leu Thr His Ser Lys Gln Lys Asp Glu Asn Glu Leu Ser
        900                 905                 910

Ala Leu Arg Ile Arg Asn Gly Lys Arg Glu Thr Gln Thr Leu Thr His
    915                 920                 925

Thr Ile Pro Lys Ala Tyr Thr Leu Leu Asp Met Thr Gly Tyr Tyr Ser
930                 935                 940

Pro Thr Glu Ser Ile Thr Ala Arg Leu Gly Ile Asn Asn Val Leu Asn
945                 950                 955                 960

Thr Arg Tyr Thr Thr Trp Glu Ala Ala Arg Gln Leu Pro Ser Glu Ala
            965                 970                 975

Ala Ser Ser Thr Gln Ser Thr Arg Tyr Ile Ala Pro Gly Arg Ser Tyr
            980                 985                 990

Phe Ala Ser Leu Glu Met Lys Phe
            995                 1000

(2) INFORMATION FOR SEQ ID NO:13:

(i) SEQUENCE CHARACTERISTICS:
        (A) LENGTH: 985 amino acids
        (B) TYPE: amino acid
        (C) STRANDEDNESS: single
        (D) TOPOLOGY: linear (xi) SEQUENCE DESCRIPTION: SEQ ID NO:13:

Met Thr Thr His Arg Leu Asn Leu Ala Ile Lys Ala Leu Phe Gly
1               5                   10                  15

Val Ala Val Leu Pro Leu Ser Val Trp Ala Gln Glu Asn Thr Gln Thr
            20                  25                  30

Asp Ala Asn Ser Asp Ala Lys Asp Thr Lys Thr Pro Val Val Tyr Leu
            35                  40                  45

Asp Ala Ile Thr Val Thr Ala Ala Pro Ser Ala Pro Val Ser Arg Phe
    50                  55                  60

Asp Thr Asp Val Thr Gly Leu Gly Lys Thr Val Lys Thr Ala Asp Thr
65                  70                  75                  80

Leu Ala Lys Glu Gln Val Gln Gly Ile Arg Asp Leu Val Arg Tyr Glu
                85                  90                  95

Thr Gly Val Ser Val Val Glu Gln Gly Arg Gly Ser Ser Gly Phe
            100                 105                 110

Ala Ile His Gly Val Asp Lys Asn Arg Val Gly Ile Thr Val Asp Gly
    115                 120                 125

Ile Ala Gln Ile Gln Ser Tyr Lys Asp Glu Ser Thr Lys Arg Ala Gly
130                 135                 140

Ala Gly Ser Gly Ala Met Asn Glu Ile Glu Ile Glu Asn Ile Ala Ala
145                 150                 155                 160

Val Ala Ile Asn Lys Gly Gly Asn Ala Leu Glu Ala Gly Ser Gly Ala
            165                 170                 175

Leu Gly Gly Ser Val Ala Phe His Thr Lys Asp Val Ser Asp Val Leu
            180                 185                 190

Lys Ser Gly Lys Asn Leu Gly Ala Gln Ser Lys Thr Thr Tyr Asn Ser
        195                 200                 205

Lys Asn Asp His Phe Ser Gln Thr Leu Ala Ala Ala Gly Lys Thr Glu
    210                 215                 220
```

```
Arg Val Glu Ala Met Val Gln Tyr Thr Tyr Arg Lys Gly Lys Glu Asn
225                 230                 235                 240

Lys Ala His Ser Asp Leu Asn Gly Ile Asn Gln Ser Leu Tyr Arg Leu
            245                 250                 255

Gly Ala Trp Gln Gln Lys Tyr Asp Leu Arg Lys Pro Asn Glu Leu Phe
        260                 265                 270

Ala Gly Thr Ser Tyr Ile Thr Glu Ser Cys Leu Ala Ser Asp Asp Pro
    275                 280                 285

Lys Ser Cys Val Gln Tyr Pro Tyr Val Tyr Thr Lys Ala Arg Pro Asp
290                 295                 300

Gly Ile Gly Asn Arg Asn Phe Ser Glu Leu Ser Asp Ala Glu Lys Ala
305                 310                 315                 320

Gln Tyr Leu Ala Ser Thr His Pro His Glu Val Val Ser Ala Lys Asp
                325                 330                 335

Tyr Thr Gly Ile Tyr Arg Leu Leu Pro Asp Pro Met Asp Tyr Arg Ser
            340                 345                 350

Asp Ser Tyr Leu Ala Arg Leu Asn Ile Lys Ile Thr Pro Asn Leu Val
        355                 360                 365

Ser Lys Leu Leu Leu Glu Asp Thr Lys Gln Thr Tyr Asn Ile Arg Asp
    370                 375                 380

Met Arg His Cys Ser Tyr His Gly Ala Arg Leu Gly Asn Asp Gly Lys
385                 390                 395                 400

Pro Ala Asn Gly Gly Ser Ile Val Leu Cys Asp Asp Tyr Gln Glu Tyr
                405                 410                 415

Leu Asn Ala Asn Asp Ala Ser Gln Ala Leu Phe Arg Pro Gly Ala Asn
            420                 425                 430

Asp Ala Pro Ile Pro Lys Leu Ala Tyr Ala Arg Ser Ser Val Phe Asn
        435                 440                 445

Gln Glu His Gly Lys Thr Arg Tyr Gly Leu Ser Phe Glu Phe Lys Pro
    450                 455                 460

Asp Thr Pro Trp Phe Lys Gln Ala Lys Leu Asn Leu His Gln Gln Asn
465                 470                 475                 480

Ile Gln Ile Ile Asn His Asp Ile Lys Lys Ser Cys Ser Gln Tyr Pro
                485                 490                 495

Lys Val Asp Leu Asn Cys Gly Ile Ser Glu Ile Gly His Tyr Glu Tyr
            500                 505                 510

Gln Asn Asn Tyr Arg Tyr Lys Glu Gly Arg Ala Ser Leu Thr Gly Lys
        515                 520                 525

Leu Asp Phe Asn Phe Asp Leu Leu Gly Gln His Asp Leu Thr Val Leu
    530                 535                 540

Ala Gly Ala Asp Lys Val Lys Ser Gln Phe Arg Ala Asn Asn Pro Arg
545                 550                 555                 560

Arg Thr Ile Ile Asp Thr Thr Gln Gly Asp Ala Ile Ile Asp Glu Ser
                565                 570                 575

Thr Leu Thr Ala Gln Glu Gln Ala Lys Phe Lys Gln Ser Gly Ala Ala
            580                 585                 590

Trp Ile Val Lys Asn Arg Leu Gly Arg Leu Glu Glu Lys Asp Ala Cys
        595                 600                 605

Gly Asn Ala Asn Glu Cys Glu Arg Ala Pro Ile His Gly Ser Asn Gln
    610                 615                 620

Tyr Val Gly Ile Asn Asn Leu Tyr Thr Pro Asn Asp Tyr Val Asp Leu
625                 630                 635                 640

Ser Phe Gly Gly Arg Leu Asp Lys Gln Arg Ile His Ser Thr Asp Ser
                645                 650                 655
```

```
Asn Ile Ile Ser Lys Thr Tyr Thr Asn Lys Ser Tyr Asn Phe Gly Ala
            660                 665                 670

Ala Val His Leu Thr Pro Asp Phe Ser Leu Leu Tyr Lys Thr Ala Lys
            675                 680                 685

Gly Phe Arg Thr Pro Ser Phe Tyr Glu Leu Tyr Asn Tyr Asn Ser Thr
            690                 695                 700

Ala Ala Gln His Lys Asn Asp Pro Asp Val Ser Phe Pro Lys Arg Ala
705                 710                 715                 720

Val Asp Val Lys Pro Glu Thr Ser Asn Thr Asn Glu Tyr Gly Phe Arg
                725                 730                 735

Tyr Gln His Pro Trp Gly Asp Val Glu Met Ser Met Phe Lys Ser Arg
            740                 745                 750

Tyr Lys Asp Met Leu Asp Lys Ala Ile Pro Asn Leu Thr Lys Ala Gln
            755                 760                 765

Gln Glu Tyr Cys Lys Ala His Leu Asp Ser Asn Glu Cys Val Gly Asn
            770                 775                 780

Pro Pro Thr Pro Lys Thr Ser Asp Glu Val Phe Ala Asn Leu Tyr Asn
785                 790                 795                 800

Ala Thr Ile Lys Gly Val Ser Val Lys Gly Lys Leu Asp Leu His Ala
                805                 810                 815

Met Thr Ser Lys Leu Pro Asp Gly Leu Glu Met Thr Leu Gly Tyr Gly
            820                 825                 830

His Thr Lys Leu Gly Lys Phe Asp Tyr Ile Ala Pro Lys Asp Ala Asp
            835                 840                 845

Gly Trp Tyr Gln Ala Arg Pro Ala Phe Trp Asp Ala Ile Thr Pro Ala
            850                 855                 860

Arg Tyr Val Val Gly Leu Asn Tyr Asp His Pro Ser Gln Val Trp Gly
865                 870                 875                 880

Ile Gly Thr Thr Leu Thr His Ser Lys Gln Lys Asp Glu Asn Glu Leu
                885                 890                 895

Ser Ala Leu Arg Ile Arg Asn Gly Lys Arg Glu Thr Gln Thr Leu Thr
            900                 905                 910

His Thr Ile Pro Lys Ala Tyr Thr Leu Leu Asp Met Thr Gly Tyr Tyr
            915                 920                 925

Ser Pro Thr Glu Ser Ile Thr Ala Arg Leu Gly Ile Asn Asn Val Leu
930                 935                 940

Asn Thr Arg Tyr Thr Thr Trp Glu Ala Ala Arg Gln Leu Pro Ser Glu
945                 950                 955                 960

Ala Ala Ser Ser Thr Gln Ser Thr Arg Tyr Ile Ala Pro Gly Arg Ser
                965                 970                 975

Tyr Phe Ala Ser Leu Glu Met Lys Phe
            980                 985

(2) INFORMATION FOR SEQ ID NO:14:

(i) SEQUENCE CHARACTERISTICS:
        (A) LENGTH: 541 amino acids
        (B) TYPE: amino acid
        (C) STRANDEDNESS: single
        (D) TOPOLOGY: linear (xi) SEQUENCE DESCRIPTION: SEQ ID NO:14:

Met Thr Cys Leu Pro Lys Thr Asn Pro Ala Leu Lys Val Lys His Arg
1               5                   10                  15

Phe Leu Lys Gln Val Leu Leu Leu Cys Val Asp Thr Leu Thr Ala
                20                  25                  30
```

```
Gln Ala Tyr Ala His Ser His His Thr Pro Ile His Thr Pro Thr His
         35                  40                  45
Glu Leu Pro Ser Ala Asp Ala Leu Ser Asp Glu Gly Leu Gly Lys Asp
 50                  55                  60
Leu Gly Ser Leu Asp Ser Leu Asp Ser Pro Asp Gly Leu Gly Asp Gly
 65                  70                  75                  80
Leu Gly Asp Gly Leu Gly Asp Gly Leu Lys Ser Asp Lys Ala Pro Leu
                 85                  90                  95
Pro Ile Asn Ala Leu Thr Ala His Gln Thr Asn Glu Ser Gln Pro Ala
                100                 105                 110
Pro Pro Ser Val Asp Val Asn Phe Leu Leu Ala Gln Pro Glu Ala Phe
         115                 120                 125
Tyr His Val Phe His Gln Ala Ile Val Gln Asp Asp Val Ala Thr Leu
         130                 135                 140
Arg Leu Leu Leu Pro Phe Tyr Asp Arg Leu Pro Asp Asp Tyr Gln Asp
145                 150                 155                 160
Asp Val Leu Leu Phe Ala Gln Ser Lys Leu Ala Leu Ser Asp Gly
                165                 170                 175
Asn Thr Lys Leu Ala Leu Asn Leu Leu Thr Asp Leu Ser Asn Lys Glu
                180                 185                 190
Pro Thr Leu Thr Ala Val Lys Leu Gln Leu Ala Ser Leu Leu Leu Thr
         195                 200                 205
Asn Lys His Asp Lys His Ala Gln Met Val Leu Asp Glu Leu Lys Asp
210                 215                 220
Asp Ala His Phe Leu Lys Leu Ser Lys Lys Glu Gln Arg Trp Val Leu
225                 230                 235                 240
Ser Gln Ser Arg Tyr Leu His Lys Lys Tyr Lys Met Gly Leu Asp Leu
                245                 250                 255
Gly Ile Asn Tyr Leu His Leu Asp Asn Ile Asn Ala Ala Ser Thr Ile
                260                 265                 270
Thr Gln Pro Asn Ile Lys Lys Asp Ala Pro Lys Pro Ala His Gly Leu
         275                 280                 285
Ala Leu Ser Leu Gly Val Asn Lys Tyr Thr Pro Leu Ser His Gly Met
         290                 295                 300
Ser Ile Tyr Thr Ala Leu Asp Val Asp Gly Lys Phe Tyr Asp Asp Lys
305                 310                 315                 320
Ser His Asn Glu Leu Ala Val Phe Ala His Ala Gly Leu Arg Lys Asp
                325                 330                 335
His Gln Lys Gly Tyr Val Asp Val Pro Phe Val Gly Arg Ile Phe
                340                 345                 350
Ala Thr Asn Gln Gln His Gly Arg Leu Ser Pro Arg Lys Asp Ser Gln
         355                 360                 365
Gly Val Ala Phe Gly Ser His Arg Ile Asn Asp Lys Trp Gln Asn
         370                 375                 380
Ala Phe Phe Ala Arg Met Glu Lys Gly Asn Tyr Thr Glu Arg Tyr Gln
385                 390                 395                 400
Gly Tyr Asp Gly Lys Arg Tyr His Val Asn Asp Thr Ile Leu Leu Gln
                405                 410                 415
Asp Gly Pro Asn Arg Arg Tyr Ser Leu Gly Val Gly Tyr Gln Leu Ser
                420                 425                 430
His Leu Gln Asp Ala Thr Lys Ser Ser His Ala Thr Lys Ile His Phe
         435                 440                 445
Gly Val Leu Gln Arg Leu Pro Asn Gly Leu Thr Val Gln Gly Arg Val
```

```
            450                 455                 460
Ser Ala Glu Arg Glu Arg Tyr His Gly Lys Leu Leu Arg Leu Val Asn
465                 470                 475                 480

Pro Asp Asp Val Tyr Arg Thr Asp Lys Thr Leu Thr Leu Gln Thr Ser
                485                 490                 495

Ile Trp His Lys Asp Ile His Trp Leu Gly Leu Thr Pro Lys Leu Thr
                500                 505                 510

Tyr Arg Tyr Ser Lys Asn Asn Ser Asn Leu Pro Ala Leu Tyr Ser His
                515                 520                 525

Asn Lys Gln Asn Phe Tyr Leu Glu Leu Gly Arg Ser Phe
530                 535                 540

(2) INFORMATION FOR SEQ ID NO:15:

(i) SEQUENCE CHARACTERISTICS:
        (A) LENGTH: 894 amino acids
        (B) TYPE: amino acid
        (C) STRANDEDNESS: single
        (D) TOPOLOGY: linear (xi) SEQUENCE DESCRIPTION: SEQ ID NO:15:

Met Ser Thr Val Lys Thr Pro His Ile Phe Tyr Gln Lys Arg Thr Leu
1                   5                   10                  15

Ser Leu Ala Ile Ala Ser Ile Phe Ala Ala Leu Val Met Thr Gly Cys
                20                  25                  30

Arg Ser Asp Asp Ile Ser Val Asn Ala Pro Asn Val Thr Gln Leu Pro
            35                  40                  45

Gln Gly Thr Val Ser Pro Thr Pro Asn Thr Gly His Asp Asn Ala Asn
        50                  55                  60

Asn Thr Asn Asn Gln Gly Asn Asn Thr Asp Asn Ser Thr Ser Thr Thr
65                  70                  75                  80

Asp Pro Asn Gly Asp Asn Asn Gln Leu Thr Gln Ala Gln Lys Thr Ala
                85                  90                  95

Ala Ala Ala Gly Phe Phe Val Met Gly Lys Ile Arg Asp Thr Ser Glu
            100                 105                 110

Lys Asn Asp Pro Asp Tyr Ser Asp Asp Leu Lys Gln Gln Trp Leu Gly
            115                 120                 125

Lys Leu Tyr Val Gly Ile Asp Ala His Arg Pro Asp Gly Ile Gly Lys
        130                 135                 140

Gly Lys Asn Leu Arg Gln Pro Ile Thr Ala Asn Asp Ile Lys Pro Leu
145                 150                 155                 160

Tyr Phe Asn Lys Phe Pro Ala Leu Ser Asp Leu His Leu Asp Ser Glu
                165                 170                 175

Arg His Arg Phe Asp Pro Gln Lys Ile Asn Thr Ile Lys Val Tyr Gly
            180                 185                 190

Tyr Gly Asn Leu Thr Thr Pro Ser Asn Asn Thr His Ile Asn His
        195                 200                 205

Gln Gln Ala Asp Asn Lys Lys Asn Asn Lys Pro Val Asp Pro Tyr Glu
        210                 215                 220

Asn Ile Arg Phe Gly Tyr Leu Glu Leu Gln Gly Ser Ser Leu Thr Gln
225                 230                 235                 240

Lys Asn Ala Asp Asn Gln Asn Glu Gln Asp Arg Ile Pro Lys Pro Met
                245                 250                 255

Pro Ile Leu Phe Tyr His Gly Leu Asn Ala Ser Ser Gln Leu Pro Ser
            260                 265                 270

Ala Gly Lys Phe Asn Tyr Thr Gly Asn Trp Leu Tyr Leu Ser Asp Val
```

```
                    275                 280                 285
Lys Lys Arg Pro Ala Leu Ser Ala Ser Asp Glu Arg Val Gly Val Tyr
    290                 295                 300
Leu Asn Ala Ser Gly Lys Ala Asn Glu Gly Asp Val Val Ser Ala Ala
305                 310                 315                 320
His Ile Tyr Leu Asn Gly Phe Gln Tyr Lys His Thr Pro Ala Thr Tyr
                325                 330                 335
Gln Val Asp Phe Asp Thr Asn Ser Leu Thr Gly Lys Leu Ser Tyr Tyr
                340                 345                 350
Asp Asn Pro Asn Gln Gln Asn Asn Lys Gly Glu Tyr Leu Lys Ser Gln
                355                 360                 365
Phe Asp Thr Thr Lys Lys Val Asn Glu Thr Asp Val Tyr Gln Ile Asp
370                 375                 380
Ala Lys Ile Asn Gly Asn Arg Phe Val Gly Thr Ala Lys Ser Leu Val
385                 390                 395                 400
Asn Glu Lys Thr Gln Thr Ala Pro Phe Ile Lys Glu Leu Phe Ser Lys
                405                 410                 415
Lys Ala Asn Pro Asn Asn Pro Asn Pro Asn Ser Asp Thr Leu Glu Gly
                420                 425                 430
Gly Phe Tyr Gly Glu Ser Gly Asp Glu Leu Ala Gly Lys Phe Leu Ser
                435                 440                 445
Asn Asp Asn Ala Ser Tyr Val Val Phe Gly Gly Lys Arg Asp Lys Thr
450                 455                 460
Thr Lys Pro Val Ala Thr Lys Thr Val Tyr Phe Ser Ala Gly Phe Glu
465                 470                 475                 480
Lys Pro Ser Thr Ser Phe Val Asp Asn Glu Thr Ile Gly Gly Ile Ile
                485                 490                 495
Asp Arg Lys Gly Leu Asn Asn His Ile Asn Glu Asp Glu Ile Ile Pro
                500                 505                 510
Ser Asp Asp Ser Tyr Tyr Gly Tyr Thr Trp Gly Lys Pro Glu Lys Gln
                515                 520                 525
Phe Thr Lys Lys Val Ser Ser Ser Thr Gln Val Val Pro Ala Tyr Phe
                530                 535                 540
Gly Gln His Asp Lys Phe Tyr Phe Asn Gly Asn Tyr Tyr Asp Leu Ser
545                 550                 555                 560
Ala Ser Arg Val Asp Lys Leu Ala Pro Ala Asp Ala Val Lys Ala Asn
                565                 570                 575
Gln Ser Ile Lys Glu Lys Tyr Pro Asn Ala Thr Leu Asn Lys Asp Asn
                580                 585                 590
Gln Val Thr Ala Ile Val Leu Gln Glu Ala Lys Asp Asn Lys Pro Tyr
                595                 600                 605
Thr Ala Ile Arg Ala Lys Ser Tyr Gln His Ile Ser Phe Gly Glu Thr
610                 615                 620
Leu Tyr Asn Asp Ala Asn Gln Thr Pro Thr Arg Ser Tyr Phe Val Gln
625                 630                 635                 640
Gly Gly Arg Ala Asp Thr Ser Thr Leu Pro Gln Ala Gly Lys Phe
                645                 650                 655
Thr Tyr Asn Gly Leu Trp Ala Gly Tyr Leu Thr Gln Lys Lys Asp Lys
                660                 665                 670
Gly Tyr Ser Asp Asn Ala Glu Thr Ile Lys Glu Lys Gly His Pro Gly
                675                 680                 685
Tyr Leu Leu Thr Glu Asn Phe Pro Glu Asp Asp Asp Asp Leu
                690                 695                 700
```

-continued

```
Thr Ala Ser Asp Asp Ser Gln Asp Asp Asn Thr His Gly Asp Asp Asp
705                 710                 715                 720

Leu Ile Ala Ser Asp Asp Ser Gln Asp Asp Asp Ala Asp Gly Asp Asp
            725                 730                 735

Asp Ser Asp Asp Leu Gly Asp Gly Ala Asp Asp Ala Ala Gly Lys
        740                 745                 750

Val Tyr His Ala Gly Asn Ile Arg Pro Glu Phe Glu Asn Lys Tyr Leu
            755                 760                 765

Pro Ile Asn Glu Pro Thr His Glu Lys Thr Phe Ala Leu Asp Gly Lys
    770                 775                 780

Asn Lys Ala Lys Phe Glu Val Asp Phe Asn Thr Asn Ser Leu Thr Gly
785                 790                 795                 800

Lys Leu Asn Asp Glu Arg Gly Asp Ile Val Phe Asp Ile Lys Asn Gly
                805                 810                 815

Lys Ile Asp Gly Thr Gly Phe Thr Ala Lys Ala Asp Val Pro Asn Tyr
            820                 825                 830

Arg Glu Glu Val Gly Asn Asn Gln Gly Gly Phe Leu Tyr Asn Ile
                835                 840                 845

Lys Asp Ile Asp Val Lys Gly Gln Phe Phe Gly Thr Asn Gly Glu Glu
    850                 855                 860

Leu Ala Gly Gln Leu His His Asp Lys Gly Asp Gly Ile Asn Asp Thr
865                 870                 875                 880

Ala Glu Lys Ala Gly Ala Val Phe Gly Ala Val Lys Asp Lys
                885                 890
```

(2) INFORMATION FOR SEQ ID NO:16:

(i) SEQUENCE CHARACTERISTICS:
        (A) LENGTH: 1000 amino acids
        (B) TYPE: amino acid
        (C) STRANDEDNESS: single
        (D) TOPOLOGY: linear (xi) SEQUENCE DESCRIPTION: SEQ ID NO:16:

```
Met Ser Lys Ser Ile Thr Lys Thr Gln Thr Pro Ser Val His Thr Met
1               5                   10                  15

Thr Thr His Arg Leu Asn Leu Ala Ile Lys Ala Ala Leu Phe Gly Val
                20                  25                  30

Ala Val Leu Pro Leu Ser Val Trp Ala Gln Glu Asn Thr Gln Thr Asp
            35                  40                  45

Ala Asn Ser Asp Ala Lys Asp Thr Lys Thr Pro Val Tyr Leu Asp
        50                  55                  60

Ala Ile Thr Val Thr Ala Ala Pro Ser Ala Pro Val Ser Arg Phe Asp
65                  70                  75                  80

Thr Asp Val Thr Gly Leu Gly Lys Thr Val Lys Thr Ala Asp Thr Leu
                85                  90                  95

Ala Lys Glu Gln Val Gln Gly Ile Arg Asp Leu Val Arg Tyr Glu Thr
            100                 105                 110

Gly Val Ser Val Val Glu Gln Gly Arg Gly Ser Ser Gly Phe Ala
        115                 120                 125

Ile His Gly Val Asp Lys Asn Arg Val Gly Ile Thr Val Asp Gly Ile
    130                 135                 140

Ala Gln Ile Gln Ser Tyr Lys Asp Glu Ser Thr Lys Arg Ala Gly Ala
145                 150                 155                 160

Gly Ser Gly Ala Met Asn Glu Ile Glu Ile Glu Asn Ile Ala Ala Val
                165                 170                 175
```

-continued

```
Ala Ile Asn Lys Gly Gly Asn Ala Leu Glu Ala Gly Ser Gly Ala Leu
            180                 185                 190

Gly Gly Ser Val Ala Phe His Thr Lys Asp Val Ser Asp Val Leu Lys
        195                 200                 205

Ser Gly Asn Asn Leu Gly Ala Gln Ser Lys Thr Thr Tyr Asn Ser Lys
    210                 215                 220

Asn Asp His Phe Ser Gln Thr Leu Ala Ala Gly Lys Thr Glu Arg
225                 230                 235                 240

Val Glu Ala Met Val Gln Tyr Thr Tyr Arg Lys Gly Lys Glu Asn Lys
                245                 250                 255

Ala His Ser Asp Leu Asn Gly Ile Asn Gln Ser Leu Tyr Arg Leu Gly
            260                 265                 270

Ala Trp Gln Gln Lys Tyr Asp Leu Arg Lys Pro Asn Glu Leu Phe Ala
        275                 280                 285

Gly Thr Ser Tyr Ile Thr Glu Ser Cys Leu Ala Ser Asp Pro Lys
    290                 295                 300

Ser Cys Val Gln Tyr Pro Tyr Val Tyr Thr Lys Ala Arg Pro Asp Gly
305                 310                 315                 320

Ile Gly Asn Arg Asn Phe Ser Glu Leu Ser Asp Ala Glu Lys Ala Gln
                325                 330                 335

Tyr Leu Ala Ser Thr His Pro His Glu Val Val Ser Ala Lys Asp Tyr
            340                 345                 350

Thr Gly Thr Tyr Arg Leu Leu Pro Asp Pro Met Asp Tyr Arg Ser Asp
        355                 360                 365

Ser Tyr Leu Ala Arg Leu Asn Ile Lys Ile Thr Pro Asn Leu Val Ser
    370                 375                 380

Lys Leu Leu Leu Glu Asp Thr Lys Gln Thr Tyr Asn Ile Arg Asp Met
385                 390                 395                 400

Arg His Cys Ser Tyr His Gly Ala Arg Leu Gly Asn Asp Gly Lys Pro
                405                 410                 415

Ala Asn Gly Gly Ser Ile Val Leu Cys Asp Asp Tyr Gln Glu Tyr Leu
            420                 425                 430

Asn Ala Asn Asp Ala Ser Gln Ala Ser Phe Arg Pro Gly Ala Asn Asp
        435                 440                 445

Ala Pro Ile Pro Lys Leu Ala Tyr Ala Arg Ser Ser Val Phe Asn Gln
    450                 455                 460

Glu His Gly Lys Thr Arg Tyr Gly Leu Gly Phe Glu Phe Lys Pro Asp
465                 470                 475                 480

Thr Pro Trp Phe Lys Gln Ala Lys Leu Asn Leu His Gln Asn Ile
                485                 490                 495

Gln Ile Ile Asn His Asp Ile Lys Lys Ser Cys Ser Gln Tyr Pro Lys
            500                 505                 510

Val Asp Leu Asn Cys Gly Ile Ser Glu Ile Gly His Tyr Glu Tyr Gln
        515                 520                 525

Asn Asn Tyr Arg Tyr Lys Glu Gly Arg Thr Ser Leu Thr Gly Lys Leu
    530                 535                 540

Asp Phe Asn Phe Asp Leu Leu Gly Gln His Asp Leu Thr Val Leu Ala
545                 550                 555                 560

Gly Ala Asp Lys Val Lys Ser Gln Phe Arg Ala Asn Asn Pro Arg Arg
                565                 570                 575

Thr Ile Ile Asp Thr Thr Gln Gly Asp Ala Ile Ile Asp Glu Ser Thr
            580                 585                 590

Leu Thr Ala Gln Glu Gln Ala Lys Phe Lys Gln Ser Gly Ala Ala Trp
        595                 600                 605
```

```
Ile Val Lys Asn Arg Leu Gly Arg Leu Glu Lys Asp Ala Cys Gly
    610                 615                 620

Asn Ala Asn Glu Cys Glu Arg Ala Pro Ile His Gly Ser Asn Gln Tyr
625                 630                 635                 640

Val Gly Ile Asn Asn Leu Tyr Thr Pro Asn Asp Tyr Val Asp Leu Ser
                645                 650                 655

Phe Gly Gly Arg Leu Asp Lys Gln Arg Ile His Ser Thr Asp Ser Asn
            660                 665                 670

Ile Ile Ser Lys Thr Tyr Thr Asn Lys Ser Tyr Asn Phe Gly Ala Ala
        675                 680                 685

Val His Leu Thr Pro Asp Phe Ser Leu Leu Tyr Lys Thr Ala Lys Gly
    690                 695                 700

Phe Arg Thr Pro Ser Phe Tyr Glu Leu Tyr Asn Tyr Asn Ser Thr Ala
705                 710                 715                 720

Ala Gln His Lys Asn Asp Pro Asp Val Ser Phe Pro Lys Arg Ala Val
                725                 730                 735

Asp Val Lys Pro Glu Thr Ser Asn Thr Asn Glu Tyr Gly Phe Arg Tyr
            740                 745                 750

Gln His Pro Trp Gly Asp Ile Glu Met Ser Met Phe Lys Ser Arg Tyr
        755                 760                 765

Lys Asp Met Leu Asp Lys Ala Ile Pro Asn Leu Thr Lys Ala Gln Gln
    770                 775                 780

Glu Tyr Cys Lys Ala His Leu Asp Ser Asn Glu Cys Val Gly Asn Pro
785                 790                 795                 800

Pro Thr Pro Lys Thr Ser Asp Glu Val Phe Ala Asn Leu Tyr Asn Ala
                805                 810                 815

Thr Ile Lys Gly Val Ser Val Lys Gly Lys Leu Asp Leu His Ala Met
            820                 825                 830

Thr Ser Lys Leu Pro Asp Gly Leu Glu Met Thr Leu Gly Tyr Gly His
        835                 840                 845

Thr Lys Leu Gly Lys Phe Asp Tyr Ile Ala Pro Lys Asp Ala Asp Gly
    850                 855                 860

Trp Tyr Gln Ala Arg Pro Ala Phe Trp Asp Ala Ile Thr Pro Ala Arg
865                 870                 875                 880

Tyr Val Val Gly Leu Asn Tyr Asp His Pro Ser Gln Val Trp Gly Ile
                885                 890                 895

Gly Thr Thr Leu Thr His Ser Lys Gln Lys Asp Glu Asn Glu Leu Ser
            900                 905                 910

Ala Leu Arg Ile Arg Asn Gly Lys Arg Glu Ile Gln Thr Leu Thr His
        915                 920                 925

Thr Ile Pro Lys Ala Tyr Thr Leu Leu Asp Met Thr Gly Tyr Tyr Ser
    930                 935                 940

Pro Thr Glu Ser Ile Thr Ala Arg Leu Gly Ile Asn Asn Val Leu Asn
945                 950                 955                 960

Thr Arg Tyr Thr Thr Trp Glu Ala Ala Arg Gln Leu Pro Ser Glu Ala
                965                 970                 975

Ala Ser Ser Thr Gln Ser Thr Arg Tyr Ile Ala Pro Gly Arg Ser Tyr
            980                 985                 990

Phe Ala Ser Leu Glu Met Lys Phe
        995                 1000
```

(2) INFORMATION FOR SEQ ID NO:17:

(i) SEQUENCE CHARACTERISTICS:

(A) LENGTH: 985 amino acids
(B) TYPE: amino acid
(C) STRANDEDNESS: single
(D) TOPOLOGY: linear (xi) SEQUENCE DESCRIPTION: SEQ ID NO:17:

```
Met Thr Thr His Arg Leu Asn Leu Ala Ile Lys Ala Ala Leu Phe Gly
1               5                   10                  15

Val Ala Val Leu Pro Leu Ser Val Trp Ala Gln Glu Asn Thr Gln Thr
                20                  25                  30

Asp Ala Asn Ser Asp Ala Lys Asp Thr Lys Thr Pro Val Val Tyr Leu
            35                  40                  45

Asp Ala Ile Thr Val Thr Ala Ala Pro Ser Ala Pro Val Ser Arg Phe
        50                  55                  60

Asp Thr Asp Val Thr Gly Leu Gly Lys Thr Val Lys Thr Ala Asp Thr
65                  70                  75                  80

Leu Ala Lys Glu Gln Val Gln Gly Ile Arg Asp Leu Val Arg Tyr Glu
                85                  90                  95

Thr Gly Val Ser Val Val Glu Gln Gly Arg Gly Gly Ser Ser Gly Phe
                100                 105                 110

Ala Ile His Gly Val Asp Lys Asn Arg Val Gly Ile Thr Val Asp Gly
            115                 120                 125

Ile Ala Gln Ile Gln Ser Tyr Lys Asp Glu Ser Thr Lys Arg Ala Gly
        130                 135                 140

Ala Gly Ser Gly Ala Met Asn Glu Ile Glu Ile Glu Asn Ile Ala Ala
145                 150                 155                 160

Val Ala Ile Asn Lys Gly Gly Asn Ala Leu Glu Ala Gly Ser Gly Ala
                165                 170                 175

Leu Gly Gly Ser Val Ala Phe His Thr Lys Asp Val Ser Asp Val Leu
                180                 185                 190

Lys Ser Gly Asn Asn Leu Gly Ala Gln Ser Lys Thr Thr Tyr Asn Ser
            195                 200                 205

Lys Asn Asp His Phe Ser Gln Thr Leu Ala Ala Gly Lys Thr Glu
            210                 215                 220

Arg Val Glu Ala Met Val Gln Tyr Thr Tyr Arg Lys Gly Lys Glu Asn
225                 230                 235                 240

Lys Ala His Ser Asp Leu Asn Gly Ile Asn Gln Ser Leu Tyr Arg Leu
                245                 250                 255

Gly Ala Trp Gln Gln Lys Tyr Asp Leu Arg Lys Pro Asn Glu Leu Phe
                260                 265                 270

Ala Gly Thr Ser Tyr Ile Thr Glu Ser Cys Leu Ala Ser Asp Asp Pro
            275                 280                 285

Lys Ser Cys Val Gln Tyr Pro Tyr Val Tyr Thr Lys Ala Arg Pro Asp
        290                 295                 300

Gly Ile Gly Asn Arg Asn Phe Ser Glu Leu Ser Asp Ala Glu Lys Ala
305                 310                 315                 320

Gln Tyr Leu Ala Ser Thr His Pro His Glu Val Val Ser Ala Lys Asp
                325                 330                 335

Tyr Thr Gly Thr Tyr Arg Leu Leu Pro Asp Pro Met Asp Tyr Arg Ser
                340                 345                 350

Asp Ser Tyr Leu Ala Arg Leu Asn Ile Lys Ile Thr Pro Asn Leu Val
            355                 360                 365

Ser Lys Leu Leu Leu Glu Asp Thr Lys Gln Thr Tyr Asn Ile Arg Asp
370                 375                 380

Met Arg His Cys Ser Tyr His Gly Ala Arg Leu Gly Asn Asp Gly Lys
```

```
385             390             395             400
Pro Ala Asn Gly Gly Ser Ile Val Leu Cys Asp Asp Tyr Gln Glu Tyr
            405                 410                 415
Leu Asn Ala Asn Asp Ala Ser Gln Ala Ser Phe Arg Pro Gly Ala Asn
            420                 425                 430
Asp Ala Pro Ile Pro Lys Leu Ala Tyr Ala Arg Ser Ser Val Phe Asn
            435                 440                 445
Gln Glu His Gly Lys Thr Arg Tyr Gly Leu Gly Phe Glu Phe Lys Pro
            450                 455                 460
Asp Thr Pro Trp Phe Lys Gln Ala Lys Leu Asn Leu His Gln Gln Asn
465                 470                 475                 480
Ile Gln Ile Ile Asn His Asp Ile Lys Lys Ser Cys Ser Gln Tyr Pro
            485                 490                 495
Lys Val Asp Leu Asn Cys Gly Ile Ser Glu Ile Gly His Tyr Glu Tyr
            500                 505                 510
Gln Asn Asn Tyr Arg Tyr Lys Glu Gly Arg Thr Ser Leu Thr Gly Lys
            515                 520                 525
Leu Asp Phe Asn Phe Asp Leu Leu Gly Gln His Asp Leu Thr Val Leu
            530                 535                 540
Ala Gly Ala Asp Lys Val Lys Ser Gln Phe Arg Ala Asn Asn Pro Arg
545                 550                 555                 560
Arg Thr Ile Ile Asp Thr Thr Gln Gly Asp Ala Ile Ile Asp Glu Ser
                565                 570                 575
Thr Leu Thr Ala Gln Glu Gln Ala Lys Phe Lys Gln Ser Gly Ala Ala
                580                 585                 590
Trp Ile Val Lys Asn Arg Leu Gly Arg Leu Glu Glu Lys Asp Ala Cys
            595                 600                 605
Gly Asn Ala Asn Glu Cys Glu Arg Ala Pro Ile His Gly Ser Asn Gln
            610                 615                 620
Tyr Val Gly Ile Asn Asn Leu Tyr Thr Pro Asn Asp Tyr Val Asp Leu
625                 630                 635                 640
Ser Phe Gly Gly Arg Leu Asp Lys Gln Arg Ile His Ser Thr Asp Ser
                645                 650                 655
Asn Ile Ile Ser Lys Thr Tyr Thr Asn Lys Ser Tyr Asn Phe Gly Ala
                660                 665                 670
Ala Val His Leu Thr Pro Asp Phe Ser Leu Leu Tyr Lys Thr Ala Lys
            675                 680                 685
Gly Phe Arg Thr Pro Ser Phe Tyr Glu Leu Tyr Asn Tyr Asn Ser Thr
            690                 695                 700
Ala Ala Gln His Lys Asn Asp Pro Asp Val Ser Phe Pro Lys Arg Ala
705                 710                 715                 720
Val Asp Val Lys Pro Glu Thr Ser Asn Thr Asn Glu Tyr Gly Phe Arg
                725                 730                 735
Tyr Gln His Pro Trp Gly Asp Ile Glu Met Ser Met Phe Lys Ser Arg
                740                 745                 750
Tyr Lys Asp Met Leu Asp Lys Ala Ile Pro Asn Leu Thr Lys Ala Gln
            755                 760                 765
Gln Glu Tyr Cys Lys Ala His Leu Asp Ser Asn Glu Cys Val Gly Asn
            770                 775                 780
Pro Pro Thr Pro Lys Thr Ser Asp Glu Val Phe Ala Asn Leu Tyr Asn
785                 790                 795                 800
Ala Thr Ile Lys Gly Val Ser Val Lys Gly Lys Leu Asp Leu His Ala
                805                 810                 815
```

```
Met Thr Ser Lys Leu Pro Asp Gly Leu Glu Met Thr Leu Gly Tyr Gly
            820                 825                 830

His Thr Lys Leu Gly Lys Phe Asp Tyr Ile Ala Pro Lys Asp Ala Asp
            835                 840                 845

Gly Trp Tyr Gln Ala Arg Pro Ala Phe Trp Asp Ala Ile Thr Pro Ala
850                 855                 860

Arg Tyr Val Val Gly Leu Asn Tyr Asp His Pro Ser Gln Val Trp Gly
865                 870                 875                 880

Ile Gly Thr Thr Leu Thr His Ser Lys Gln Lys Asp Glu Asn Glu Leu
                885                 890                 895

Ser Ala Leu Arg Ile Arg Asn Gly Lys Arg Glu Ile Gln Thr Leu Thr
            900                 905                 910

His Thr Ile Pro Lys Ala Tyr Thr Leu Leu Asp Met Thr Gly Tyr Tyr
            915                 920                 925

Ser Pro Thr Glu Ser Ile Thr Ala Arg Leu Gly Ile Asn Asn Val Leu
            930                 935                 940

Asn Thr Arg Tyr Thr Thr Trp Glu Ala Ala Arg Gln Leu Pro Ser Glu
945                 950                 955                 960

Ala Ala Ser Ser Thr Gln Ser Thr Arg Tyr Ile Ala Pro Gly Arg Ser
                965                 970                 975

Tyr Phe Ala Ser Leu Glu Met Lys Phe
            980                 985

(2) INFORMATION FOR SEQ ID NO:18:

(i) SEQUENCE CHARACTERISTICS:
        (A) LENGTH: 538 amino acids
        (B) TYPE: amino acid
        (C) STRANDEDNESS: single
        (D) TOPOLOGY: linear (xi) SEQUENCE DESCRIPTION: SEQ ID NO:18:

Met Thr Cys Leu Pro Lys Thr Asn Pro Ala Leu Lys Val Lys His Arg
1               5                   10                  15

Phe Leu Lys Gln Val Leu Leu Leu Cys Val Asp Thr Leu Thr Ala
            20                  25                  30

Gln Ala Tyr Ala His Ser His His Thr Pro Ile His Thr Pro Thr His
            35                  40                  45

Glu Leu Ser Ser Ala Asp Ala Leu Ser Asp Glu Gly Leu Gly Lys Asp
50                  55                  60

Leu Gly Ser Leu Asp Ser Pro Asp Gly Leu Asp Gly Leu Gly Asp
65                  70                  75                  80

Gly Leu Gly Asp Gly Leu Lys Ser Asp Lys Thr Pro Leu Pro Ile Asn
                85                  90                  95

Ala Leu Thr Val Asn Gln Ser Asn Glu Ser Gln Pro Ala Pro Pro Ser
            100                 105                 110

Val Asp Val Asn Phe Leu Leu Ala Gln Pro Glu Ala Phe Tyr His Val
            115                 120                 125

Phe His Gln Ala Ile Val Gln Asp Asp Val Ala Thr Leu Arg Leu Leu
            130                 135                 140

Leu Pro Phe Tyr Asp Arg Leu Pro Asp Tyr Gln Asp Asp Val Leu
145                 150                 155                 160

Leu Leu Phe Ala Gln Ser Lys Leu Ala Leu Ser Asp Gly Asn Thr Lys
                165                 170                 175

Leu Ala Leu Asn Leu Leu Thr Asp Leu Ser Asn Lys Glu Pro Thr Leu
            180                 185                 190
```

```
Thr Ala Val Lys Leu Gln Leu Ala Ser Leu Leu Leu Thr Asn Lys His
        195                 200                 205

Asp Lys His Ala Gln Met Val Leu Asp Glu Leu Lys Asp Asp Ala His
        210                 215                 220

Phe Leu Lys Leu Ser Lys Leu Glu Gln Arg Trp Val Leu Ser Gln Ser
225                 230                 235                 240

Arg Tyr Leu His Lys Lys Tyr Lys Met Gly Leu Asp Leu Gly Ile Asn
                    245                 250                 255

Tyr Leu His Leu Asp Asn Ile Asn Ala Ala Ser Thr Ile Thr Gln Pro
                260                 265                 270

Asn Ile Lys Lys Asp Ala Pro Lys Pro Ala His Gly Leu Ala Leu Ser
            275                 280                 285

Leu Gly Val Asn Lys Tyr Thr Pro Leu Ser His Gly Met Ser Ile Tyr
        290                 295                 300

Thr Ala Leu Asp Val Asp Gly Lys Phe Tyr Asp Asp Lys Ser His Asn
305                 310                 315                 320

Glu Leu Ala Val Phe Ala His Ala Gly Leu Arg Lys Asp His Gln Lys
                    325                 330                 335

Gly Tyr Val Asp Val Val Pro Phe Val Gly Arg Ile Phe Ala Thr Asn
                340                 345                 350

Gln Gln His Gly Arg Leu Ser Pro Arg Lys Asp Ser Gln Gly Val Ala
            355                 360                 365

Phe Gly Ser His His Arg Ile Asn Asp Lys Trp Gln Asn Ala Phe Phe
370                 375                 380

Ala Arg Met Glu Lys Gly Asn Tyr Thr Glu His Tyr Gln Gly Tyr Asp
385                 390                 395                 400

Gly Lys Arg Tyr His Val Asn Asp Thr Ile Leu Leu Gln Asp Gly Pro
                    405                 410                 415

Asn Arg Arg Tyr Ser Leu Gly Val Gly Tyr Gln Leu Ser His Leu Gln
                420                 425                 430

Asp Ala Thr Lys Ser Ser His Ala Thr Lys Ile His Phe Gly Val Leu
            435                 440                 445

Gln Arg Leu Pro Asn Gly Leu Thr Val Gln Gly Arg Val Ser Ala Glu
        450                 455                 460

Arg Glu Arg Tyr His Gly Lys Leu Leu Arg Leu Val Asn Pro Asp Asp
465                 470                 475                 480

Val Tyr Arg Thr Asp Lys Thr Leu Thr Leu Gln Thr Ser Ile Trp His
                    485                 490                 495

Lys Asp Ile His Trp Leu Gly Leu Thr Pro Lys Leu Thr Tyr Arg Tyr
                500                 505                 510

Ser Lys Asn Asn Ser Asn Leu Pro Ala Leu Tyr Ser His Asn Lys Gln
            515                 520                 525

Asn Phe Tyr Leu Glu Leu Gly Arg Ser Phe
530                 535
```

(2) INFORMATION FOR SEQ ID NO:19:

(i) SEQUENCE CHARACTERISTICS:
        (A) LENGTH: 1076 amino acids
        (B) TYPE: amino acid
        (C) STRANDEDNESS: single
        (D) TOPOLOGY: linear (xi) SEQUENCE DESCRIPTION: SEQ ID NO:19:

```
Met Asn Gln Ser Lys Gln Asn Asn Lys Ser Lys Lys Ser Lys Gln Val
1                   5                   10                  15
```

```
Leu Lys Leu Ser Ala Leu Ser Leu Gly Leu Leu Asn Ile Thr Gln Val
         20                  25                  30

Ala Leu Ala Asn Thr Thr Ala Asp Lys Ala Glu Ala Thr Asp Lys Thr
         35                  40                  45

Asn Leu Val Val Val Leu Asp Glu Thr Val Val Thr Ala Lys Lys Asn
 50                  55                  60

Ala Pro Val Ser Arg Lys Ala Asn Glu Val Thr Gly Leu Gly Lys Val
 65                  70                  75                  80

Val Lys Thr Ala Glu Thr Ile Asn Lys Glu Gln Val Leu Asn Ile Arg
                 85                  90                  95

Asp Leu Thr Arg Tyr Asp Pro Gly Ile Ala Val Glu Gln Gly Arg
                100                 105                 110

Gly Ala Ser Ser Gly Tyr Ser Ile Arg Gly Met Asp Lys Asn Arg Val
                115                 120                 125

Ala Val Leu Val Asp Gly Ile Asn Gln Ala Gln His Tyr Gln Gly Pro
130                 135                 140

Val Ala Gly Lys Asn Tyr Ala Ala Gly Ala Ile Asn Glu Ile Glu
145                 150                 155                 160

Tyr Glu Asn Val Arg Ser Val Glu Ile Ser Lys Gly Ala Asn Ser Ser
                165                 170                 175

Glu Tyr Gly Ser Gly Ala Leu Ser Gly Ser Val Ala Phe Val Thr Lys
                180                 185                 190

Thr Ala Asp Asp Ile Ile Lys Asp Gly Lys Asp Trp Gly Val Gln Thr
                195                 200                 205

Lys Thr Ala Tyr Ala Ser Lys Asn Asn Ala Trp Val Asn Ser Val Ala
210                 215                 220

Ala Ala Gly Lys Ala Gly Ser Phe Ser Gly Leu Ile Ile Tyr Thr Asp
225                 230                 235                 240

Arg Arg Gly Gln Glu Tyr Lys Ala His Asp Asp Ala Tyr Gln Gly Ser
                245                 250                 255

Gln Ser Phe Asp Arg Ala Val Ala Thr Thr Asp Pro Asn Asn Arg Thr
                260                 265                 270

Phe Leu Ile Ala Asn Glu Cys Ala Asn Gly Asn Tyr Glu Ala Cys Ala
                275                 280                 285

Ala Gly Gly Gln Thr Lys Leu Gln Ala Lys Pro Thr Asn Val Arg Asp
290                 295                 300

Lys Val Asn Val Lys Asp Tyr Thr Gly Pro Asn Arg Leu Ile Pro Asn
305                 310                 315                 320

Pro Leu Thr Gln Asp Ser Lys Ser Leu Leu Leu Arg Pro Gly Tyr Gln
                325                 330                 335

Leu Asn Asp Lys His Tyr Val Gly Val Tyr Glu Ile Thr Lys Gln
                340                 345                 350

Asn Tyr Ala Met Gln Asp Lys Thr Val Pro Ala Tyr Leu Ala Val His
                355                 360                 365

Asp Ile Glu Lys Ser Arg Leu Ser Asn His Ala Gln Ala Asn Gly Tyr
                370                 375                 380

Tyr Gln Gly Asn Asn Leu Gly Glu Arg Ile Arg Asp Thr Ile Gly Pro
385                 390                 395                 400

Asp Ser Gly Tyr Gly Ile Asn Tyr Ala His Gly Val Phe Tyr Asp Glu
                405                 410                 415

Lys His Gln Lys Asp Arg Leu Gly Leu Glu Tyr Val Tyr Asp Ser Lys
                420                 425                 430

Gly Glu Asn Lys Trp Phe Asp Asp Val Arg Val Ser Tyr Asp Lys Gln
                435                 440                 445
```

```
Asp Ile Thr Leu Arg Ser Gln Leu Thr Asn Thr His Cys Ser Thr Tyr
450                 455                 460

Pro His Ile Asp Lys Asn Cys Thr Pro Asp Val Asn Lys Pro Phe Ser
465                 470                 475                 480

Val Lys Glu Val Asp Asn Asn Ala Tyr Lys Glu Gln His Asn Leu Ile
                485                 490                 495

Lys Ala Val Phe Asn Lys Lys Met Ala Leu Gly Ser Thr His His His
                500                 505                 510

Ile Asn Leu Gln Val Gly Tyr Asp Lys Phe Asn Ser Ser Leu Ser Arg
        515                 520                 525

Val Glu Tyr Arg Leu Ala Thr His Gln Ser Tyr Gln Lys Leu Asp Tyr
    530                 535                 540

Thr Pro Pro Ser Asn Pro Leu Pro Asp Lys Phe Lys Pro Ile Leu Gly
545                 550                 555                 560

Ser Asn Asn Lys Pro Ile Cys Leu Asp Ala Tyr Gly Tyr Gly His Asp
                565                 570                 575

His Pro Gln Ala Cys Asn Ala Lys Asn Ser Thr Tyr Gln Asn Phe Ala
            580                 585                 590

Ile Lys Lys Gly Ile Glu Gln Tyr Asn Gln Lys Thr Asn Thr Asp Lys
        595                 600                 605

Ile Asp Tyr Gln Ala Ile Ile Asp Gln Tyr Asp Lys Gln Asn Pro Asn
610                 615                 620

Ser Thr Leu Lys Pro Phe Glu Lys Ile Lys Gln Ser Leu Gly Gln Glu
625                 630                 635                 640

Lys Tyr Asn Lys Ile Asp Glu Leu Gly Phe Lys Ala Tyr Lys Asp Leu
                645                 650                 655

Arg Asn Glu Trp Ala Gly Trp Thr Asn Asp Asn Ser Gln Gln Asn Ala
            660                 665                 670

Asn Lys Gly Thr Asp Asn Ile Tyr Gln Pro Asn Gln Ala Thr Val Val
        675                 680                 685

Lys Asp Asp Lys Cys Lys Tyr Ser Glu Thr Asn Ser Tyr Ala Asp Cys
690                 695                 700

Ser Thr Thr Pro Arg His Ile Ser Gly Asp Asn Tyr Phe Ile Ala Leu
705                 710                 715                 720

Lys Asp Asn Met Thr Ile Asn Lys Tyr Val Asp Leu Gly Leu Gly Ala
                725                 730                 735

Arg Tyr Asp Arg Ile Lys His Lys Ser Asp Val Pro Leu Val Asp Asn
            740                 745                 750

Ser Ala Ser Asn Gln Leu Ser Trp Asn Phe Gly Val Val Lys Pro
        755                 760                 765

Thr Asn Trp Leu Asp Ile Ala Tyr Arg Ser Ser Gln Gly Phe Arg Met
770                 775                 780

Pro Ser Phe Ser Glu Met Tyr Gly Glu Arg Phe Gly Val Thr Ile Gly
785                 790                 795                 800

Lys Gly Thr Gln His Gly Cys Lys Gly Leu Tyr Tyr Ile Cys Gln Gln
                805                 810                 815

Thr Val His Gln Thr Lys Leu Lys Pro Glu Lys Ser Phe Asn Gln Glu
            820                 825                 830

Ile Gly Ala Thr Leu His Asn His Leu Gly Ser Leu Glu Val Ser Tyr
        835                 840                 845

Phe Lys Asn Arg Tyr Thr Asp Leu Ile Val Gly Lys Ser Glu Glu Ile
850                 855                 860

Arg Thr Leu Thr Gln Gly Asp Asn Ala Gly Lys Gln Arg Gly Lys Gly
```

```
                865                 870                 875                 880
Asp Leu Gly Phe His Asn Gly Gln Asp Ala Asp Leu Thr Gly Ile Asn
                    885                 890                 895
Ile Leu Gly Arg Leu Asp Leu Asn Ala Ala Asn Ser Arg Leu Pro Tyr
                900                 905                 910
Gly Leu Tyr Ser Thr Leu Ala Tyr Asn Lys Val Asp Val Lys Gly Lys
                915                 920                 925
Thr Leu Asn Pro Thr Leu Ala Gly Thr Asn Ile Leu Phe Asp Ala Ile
    930                 935                 940
Gln Pro Ser Arg Tyr Val Val Gly Leu Gly Tyr Asp Ala Pro Ser Gln
945                 950                 955                 960
Lys Trp Gly Ala Asn Ala Ile Phe Thr His Ser Asp Ala Lys Asn Pro
                965                 970                 975
Ser Glu Leu Leu Ala Asp Lys Asn Leu Gly Asn Gly Asn Ile Gln Thr
                980                 985                 990
Lys Gln Ala Thr Lys Ala Lys Ser Thr Pro Trp Gln Thr Leu Asp Leu
                995                 1000                1005
Ser Gly Tyr Val Asn Ile Lys Asp Asn Phe Thr Leu Arg Ala Gly Val
                1010                1015                1020
Tyr Asn Val Phe Asn Thr Tyr Tyr Thr Thr Trp Glu Ala Leu Arg Gln
1025                1030                1035                1040
Thr Ala Lys Gly Ala Val Asn Gln His Thr Gly Leu Ser Gln Asp Lys
                    1045                1050                1055
His Tyr Gly Arg Tyr Ala Ala Pro Gly Arg Asn Tyr Gln Leu Ala Leu
                    1060                1065                1070
Glu Met Lys Phe
            1075

(2) INFORMATION FOR SEQ ID NO:20:

(i) SEQUENCE CHARACTERISTICS:
         (A) LENGTH: 753 amino acids
         (B) TYPE: amino acid
         (C) STRANDEDNESS: single
         (D) TOPOLOGY: linear (xi) SEQUENCE DESCRIPTION: SEQ ID NO:20:

Gln Tyr Thr Arg Lys Gly Glu Asn Lys Ala His Ser Asp Leu Asn Gly
1                   5                   10                  15
Ile Asn Gln Ser Leu Tyr Arg Leu Gly Ala Trp Gln Gln Lys Tyr Asp
                20                  25                  30
Leu Arg Lys Pro Asn Glu Leu Phe Ala Gly Thr Ser Tyr Ile Thr Glu
            35                  40                  45
Ser Cys Leu Ala Ser Asp Asp Pro Lys Ser Cys Val Gln Tyr Pro Tyr
    50                  55                  60
Val Tyr Thr Lys Ala Arg Pro Asp Gly Ile Gly Asn Arg Asn Phe Ser
65                  70                  75                  80
Glu Leu Ser Asp Ala Glu Lys Ala Gln Tyr Leu Ala Ser Thr His Pro
                85                  90                  95
His Glu Val Val Ser Ala Lys Asp Tyr Thr Gly Ile Tyr Arg Leu Leu
                100                 105                 110
Pro Asp Pro Met Asp Tyr Arg Ser Asp Ser Tyr Leu Ala Arg Leu Asn
                115                 120                 125
Ile Lys Ile Thr Pro Asn Leu Val Xaa Lys Leu Leu Leu Glu Asp Thr
            130                 135                 140
Lys Gln Thr Tyr Asn Ile Arg Asp Met Arg His Cys Ser Tyr His Gly
```

```
                        145                 150                 155                 160
Ala Arg Leu Gly Asn Asp Gly Lys Pro Ala Asn Gly Gly Ser Ile Val
                        165                 170                 175
Leu Cys Asp Asp Tyr Gln Glu Tyr Leu Asn Ala Asn Asp Ala Ser Gln
                180                 185                 190
Ala Leu Phe Arg Pro Gly Ala Asn Asp Ala Pro Ile Pro Lys Leu Ala
                195                 200                 205
Tyr Ala Arg Ser Ser Val Phe Asn Gln Glu His Gly Lys Thr Arg Tyr
            210                 215                 220
Gly Leu Ser Phe Glu Phe Lys Pro Asp Thr Pro Trp Phe Lys Gln Ala
225                 230                 235                 240
Lys Leu Asn Leu His Gln Gln Asn Ile Gln Ile Asn His Asp Ile
                    245                 250                 255
Lys Lys Ser Cys Ser Gln Tyr Pro Lys Val Asp Ser Asn Cys Gly Ile
                260                 265                 270
Ser Glu Ile Gly His Tyr Glu Tyr Gln Xaa Asn Tyr Arg Tyr Lys Glu
            275                 280                 285
Gly Arg Ala Ser Leu Thr Gly Lys Leu Asp Phe Asn Phe Asp Leu Leu
        290                 295                 300
Gly Gln His Asp Leu Thr Val Leu Ala Gly Thr Asp Lys Val Lys Ser
305                 310                 315                 320
Gln Phe Arg Ala Asn Asn Pro Arg Arg Thr Ile Ile Asp Thr Thr Gln
                325                 330                 335
Gly Asp Ala Ile Ile Asp Glu Ser Thr Leu Thr Ala Gln Glu Gln Ala
                340                 345                 350
Lys Phe Lys Gln Ser Gly Ala Ala Trp Ile Val Lys Asn Arg Leu Gly
            355                 360                 365
Arg Leu Glu Glu Lys Asp Ala Cys Gly Asn Ala Asn Glu Cys Glu Arg
        370                 375                 380
Ala Pro Ile His Gly Ser Asn Gln Tyr Val Gly Ile Asn Asn Leu Tyr
385                 390                 395                 400
Thr Pro Asn Asp Tyr Val Asp Xaa Ser Phe Gly Gly Arg Leu Asp Lys
                405                 410                 415
Gln Arg Ile His Ser Thr Asp Ser Asn Ile Ile Ser Lys Thr Tyr Thr
                420                 425                 430
Asn Lys Ser Tyr Asn Phe Gly Ala Ala Val His Leu Thr Pro Asp Phe
            435                 440                 445
Ser Leu Leu Tyr Lys Thr Ala Lys Gly Phe Arg Thr Pro Ser Phe Tyr
        450                 455                 460
Glu Leu Tyr Asn Tyr Asn Ser Thr Ala Ala Gln His Lys Asn Asp Pro
465                 470                 475                 480
Asp Val Ser Phe Pro Lys Arg Ala Val Asp Val Lys Pro Glu Thr Ser
                485                 490                 495
Asn Thr Asn Glu Tyr Gly Phe Arg Tyr Gln His Pro Trp Gly Asp Val
                500                 505                 510
Glu Met Ser Met Phe Lys Ser Arg Tyr Lys Asp Met Leu Asp Lys Ala
            515                 520                 525
Ile Pro Asn Leu Thr Lys Ala Gln Gln Glu Tyr Cys Arg Ala His Leu
        530                 535                 540
Asp Ser Asn Glu Cys Val Gly Asn Pro Pro Thr Pro Lys Thr Ser Asp
545                 550                 555                 560
Glu Val Phe Ala Asn Leu Tyr Asn Ala Thr Ile Lys Gly Val Ser Val
                565                 570                 575
```

-continued

```
Lys Gly Lys Leu Asp Leu His Ala Met Thr Ser Lys Leu Pro Asp Gly
            580                 585                 590
Leu Glu Met Thr Leu Gly Tyr Gly His Thr Lys Leu Gly Lys Phe Xaa
            595                 600                 605
Tyr Ile Ala Pro Lys Asp Ala Asp Gly Trp Tyr Gln Ala Arg Pro Ala
610                 615                 620
Phe Trp Asp Ala Ile Thr Pro Ala Arg Tyr Val Val Gly Leu Asn Tyr
625                 630                 635                 640
Asp His Pro Ser Gln Val Trp Gly Ile Gly Ala Thr Leu Thr His Ser
            645                 650                 655
Lys Gln Lys Asp Glu Asn Glu Leu Ser Ala Leu Arg Ile Arg Asn Gly
            660                 665                 670
Lys Arg Glu Thr Gln Thr Leu Thr His Thr Ile Pro Lys Ala Tyr Thr
            675                 680                 685
Leu Leu Asp Met Thr Gly Tyr Tyr Ser Pro Thr Glu Ser Ile Thr Ala
            690                 695                 700
Arg Leu Gly Ile Asn Asn Val Leu Asn Thr Arg Tyr Thr Thr Trp Glu
705                 710                 715                 720
Ala Ala Arg Gln Leu Pro Ser Glu Ala Ala Ser Ser Thr Gln Ser Thr
            725                 730                 735
Arg Tyr Ile Ala Pro Gly Arg Ser Tyr Phe Ala Ser Leu Glu Met Lys
            740                 745                 750
Phe
```

(2) INFORMATION FOR SEQ ID NO:21:

(i) SEQUENCE CHARACTERISTICS:
        (A) LENGTH: 585 amino acids
        (B) TYPE: amino acid
        (C) STRANDEDNESS: single
        (D) TOPOLOGY: linear (xi) SEQUENCE DESCRIPTION: SEQ ID NO:21:

```
Gln Tyr Thr Arg Lys Gly Glu Asn Lys Ala His Ser Asp Leu Asn Gly
1               5                   10                  15
Ile Asn Gln Ser Leu Tyr Arg Leu Gly Ala Trp Gln Gln Lys Tyr Asp
            20                  25                  30
Leu Arg Lys Pro Asn Glu Leu Phe Ala Gly Thr Ser Tyr Ile Thr Glu
            35                  40                  45
Ser Cys Leu Ala Ser Asp Asp Pro Lys Ser Cys Val Gln Tyr Pro Tyr
            50                  55                  60
Val Tyr Thr Lys Ala Arg Pro Asp Gly Ile Gly Asn Arg Asn Phe Ser
65                  70                  75                  80
Glu Leu Ser Asp Ala Glu Lys Ala Gln Tyr Leu Ala Ser Thr His Pro
            85                  90                  95
His Glu Val Val Ser Ala Lys Asp Tyr Thr Gly Thr Tyr Arg Leu Leu
            100                 105                 110
Pro Asp Pro Met Asp Tyr Arg Ser Asp Ser Tyr Leu Ala Arg Leu Asn
            115                 120                 125
Ile Lys Ile Thr Pro Asn Leu Val Ser Lys Leu Leu Leu Glu Asp Thr
            130                 135                 140
Lys Gln Thr Tyr Asn Ile Arg Asp Met Arg His Cys Ser Tyr His Gly
145                 150                 155                 160
Ala Arg Leu Gly Asn Asp Gly Lys Pro Ala Asn Gly Gly Ser Ile Val
            165                 170                 175
Leu Cys Asp Asp Tyr Gln Glu Tyr Leu Asn Ala Asn Asp Ala Ser Gln
```

```
            180             185             190
Ala Ser Phe Arg Pro Gly Ala Asn Asp Ala Pro Ile Pro Lys Leu Ala
            195             200             205
Tyr Ala Arg Ser Ser Val Phe Asn Gln Glu His Gly Lys Thr Arg Tyr
210             215             220
Gly Leu Gly Phe Glu Phe Lys Pro Asp Thr Pro Trp Phe Lys Gln Ala
225             230             235             240
Lys Leu Asn Leu His Gln Gln Asn Ile Gln Ile Asn Thr Asp Ser
            245             250             255
Asn Ile Ile Ser Lys Thr Tyr Thr Asn Lys Ser Tyr Asn Phe Gly Ala
            260             265             270
Ala Val His Xaa Thr Pro Asp Phe Ser Leu Leu Tyr Lys Thr Ala Lys
            275             280             285
Gly Phe Arg Thr Pro Ser Phe Tyr Glu Leu Tyr Asn Tyr Asn Ser Thr
290             295             300
Ala Ala Gln His Lys Asn Asp Pro Asp Val Ser Phe Pro Lys Arg Ala
305             310             315             320
Val Asp Val Lys Pro Glu Thr Ser Asn Thr Asn Glu Tyr Gly Phe Arg
            325             330             335
Tyr Gln His Pro Trp Gly Asp Ile Glu Met Ser Met Phe Lys Ser Arg
            340             345             350
Tyr Lys Asp Met Leu Asp Lys Ala Ile Pro Asn Leu Thr Lys Ala Gln
            355             360             365
Gln Glu Tyr Cys Lys Ala His Leu Asp Ser Asn Glu Cys Val Gly Asn
            370             375             380
Pro Pro Thr Pro Lys Thr Ser Asp Glu Val Phe Ala Asn Leu Tyr Asn
385             390             395             400
Ala Thr Ile Lys Gly Val Ser Val Lys Gly Lys Leu Asp Leu His Ala
            405             410             415
Met Thr Ser Lys Leu Pro Asp Gly Leu Glu Met Thr Leu Gly Tyr Gly
            420             425             430
His Thr Lys Leu Gly Lys Phe Xaa Tyr Ile Ala Pro Lys Asp Ala Asp
            435             440             445
Gly Trp Tyr Gln Ala Arg Pro Ala Phe Trp Asp Ala Ile Thr Pro Ala
450             455             460
Arg Tyr Val Val Gly Leu Asn Tyr Asp His Pro Ser Gln Val Trp Gly
465             470             475             480
Ile Gly Thr Thr Leu Thr His Ser Lys Gln Lys Asp Glu Asn Glu Leu
            485             490             495
Ser Ala Leu Arg Ile Arg Asn Gly Lys Arg Glu Ile Gln Thr Leu Thr
            500             505             510
His Thr Ile Pro Lys Ala Tyr Thr Leu Leu Asp Met Thr Gly Tyr Tyr
            515             520             525
Ser Pro Thr Glu Ser Ile Thr Ala Arg Leu Gly Ile Asn Asn Val Leu
            530             535             540
Asn Thr Arg Tyr Thr Thr Trp Glu Ala Ala Arg Gln Leu Pro Ser Glu
545             550             555             560
Ala Ala Ser Ser Thr Gln Ser Thr Arg Tyr Ile Ala Pro Gly Arg Ser
            565             570             575
Tyr Phe Ala Ser Leu Glu Met Lys Phe
            580             585
```

(2) INFORMATION FOR SEQ ID NO:22:

(i) SEQUENCE CHARACTERISTICS:
      (A) LENGTH: 15 amino acids
      (B) TYPE: amino acid
      (C) STRANDEDNESS: single
      (D) TOPOLOGY: linear (xi) SEQUENCE DESCRIPTION: SEQ ID NO:22:

Met Val Gln Tyr Thr Tyr Arg Lys Gly Lys Glu Asn Lys Ala His
1               5                   10                  15

(2) INFORMATION FOR SEQ ID NO:23:

(i) SEQUENCE CHARACTERISTICS:
      (A) LENGTH: 944 amino acids
      (B) TYPE: amino acid
      (C) STRANDEDNESS: single
      (D) TOPOLOGY: linear (xi) SEQUENCE DESCRIPTION: SEQ ID NO:23:

Met Asn Lys Lys His Gly Phe Gln Leu Thr Leu Thr Ala Leu Ala Val
1               5                   10                  15

Ala Ala Ala Phe Pro Ser Tyr Ala Ala Asn Pro Glu Thr Ala Ala Pro
            20                  25                  30

Asp Ala Ala Gln Thr Gln Ser Leu Lys Glu Val Thr Val Arg Ala Ala
            35                  40                  45

Lys Val Gly Arg Arg Ser Lys Glu Ala Val Thr Gly Leu Gly Lys Ile
    50                  55                  60

Ala Lys Thr Ser Glu Thr Leu Asn Lys Glu Gln Val Leu Gly Ile Arg
65                  70                  75                  80

Asp Leu Thr Arg Tyr Asp Pro Gly Val Ala Val Glu Gln Gly Asn
                85                  90                  95

Gly Ala Ser Gly Gly Tyr Ser Ile Arg Gly Val Asp Lys Asn Arg Val
                100                 105                 110

Ala Val Ser Val Asp Gly Val Ala Gln Ile Gln Ala Phe Thr Val Gln
            115                 120                 125

Gly Ser Leu Ser Gly Tyr Gly Gly Arg Gly Ser Gly Ala Ile Asn
            130                 135                 140

Glu Ile Glu Tyr Glu Asn Ile Ser Thr Val Glu Ile Asp Lys Gly Ala
145                 150                 155                 160

Gly Ser Ser Asp His Gly Ser Gly Ala Leu Gly Gly Ala Val Ala Phe
                165                 170                 175

Arg Thr Lys Glu Ala Ala Asp Leu Ile Ser Asp Gly Lys Ser Trp Gly
                180                 185                 190

Ile Gln Ala Lys Thr Ala Tyr Gly Ser Lys Asn Arg Gln Phe Met Lys
        195                 200                 205

Ser Leu Gly Ala Gly Phe Ser Lys Asp Gly Trp Glu Gly Leu Leu Ile
        210                 215                 220

Arg Thr Glu Arg Gln Gly Arg Glu Thr His Pro His Gly Asp Ile Ala
225                 230                 235                 240

Asp Gly Val Ala Tyr Gly Ile Asn Arg Leu Asp Ala Phe Arg Gln Thr
                245                 250                 255

Tyr Gly Ile Lys Lys Pro Ser Glu Gly Gly Glu Tyr Phe Leu Ala Glu
                260                 265                 270

Gly Glu Ser Glu Leu Lys Pro Val Ala Lys Val Ala Gly Asn Gly Asn
            275                 280                 285

Tyr Leu Asn Asn Gln Leu Asn Arg Trp Val Lys Glu Arg Ile Glu Gln
            290                 295                 300

Asn Gln Pro Leu Ser Ala Glu Glu Ala Met Val Arg Glu Ala Gln

-continued

```
305                 310                 315                 320
Ala Arg His Glu Asn Leu Ser Ala Gln Ala Tyr Thr Gly Gly Arg
                325                 330                 335
Ile Leu Pro Asp Pro Met Asp Tyr Arg Ser Gly Ser Trp Leu Ala Lys
                340                 345                 350
Leu Gly Tyr Arg Phe Gly Gly Arg His Tyr Val Gly Val Phe Glu
                355                 360                 365
Asp Thr Lys Gln Arg Tyr Asp Ile Arg Asp Met Thr Glu Lys Gln Tyr
                370                 375                 380
Tyr Gly Thr Asp Glu Ala Lys Lys Phe Arg Asp Lys Ser Gly Val Tyr
385                 390                 395                 400
Asp Gly Asp Asp Phe Arg Asp Gly Leu Tyr Phe Val Pro Asn Ile Glu
                405                 410                 415
Glu Trp Lys Gly Asp Gln Lys Leu Ile Arg Gly Ile Gly Leu Lys Tyr
                420                 425                 430
Ser Arg Thr Lys Phe Ile Asp Glu His His Arg Arg Arg Met Gly
                435                 440                 445
Leu Leu Tyr Arg Tyr Glu Asn Glu Lys Tyr Ser Asp Asn Trp Ala Asp
                450                 455                 460
Lys Ala Val Leu Ser Phe Asp Lys Gln Gly Val Ala Thr Asp Asn Asn
465                 470                 475                 480
Thr Leu Lys Leu Asn Cys Ala Val Tyr Pro Ala Val Asp Lys Ser Cys
                485                 490                 495
Arg Ala Ser Ala Asp Lys Pro Tyr Ser Tyr Asp Ser Ser Asp Arg Phe
                500                 505                 510
His Tyr Arg Glu Gln His Asn Val Leu Asn Ala Ser Phe Glu Lys Ser
                515                 520                 525
Leu Lys Asn Lys Trp Thr Lys His His Leu Thr Leu Gly Phe Gly Tyr
                530                 535                 540
Asp Ala Ser Asn Ala Ile Ser Arg Pro Glu Gln Leu Ser His Asn Ala
545                 550                 555                 560
Ala Arg Ile Ser Glu Tyr Ser Asp Tyr Thr Asp Lys Gly Asp Lys Tyr
                565                 570                 575
Leu Leu Gly Lys Pro Glu Val Val Glu Gly Ser Val Cys Gly Tyr Ile
                580                 585                 590
Glu Thr Leu Arg Ser Arg Lys Cys Val Pro Arg Lys Ile Asn Gly Ser
                595                 600                 605
Asn Ile His Ile Ser Leu Asn Asp Arg Phe Ser Ile Gly Lys Tyr Phe
                610                 615                 620
Asp Phe Ser Leu Gly Gly Arg Tyr Asp Arg Lys Asn Phe Thr Thr Ser
625                 630                 635                 640
Glu Glu Leu Val Arg Ser Gly Arg Tyr Val Asp Arg Ser Trp Asn Ser
                645                 650                 655
Gly Ile Val Phe Lys Pro Asn Arg His Phe Ser Leu Ser Tyr Arg Ala
                660                 665                 670
Ser Ser Gly Phe Arg Thr Pro Ser Phe Gln Glu Leu Phe Gly Ile Asp
                675                 680                 685
Ile Tyr His Asp Tyr Pro Lys Gly Trp Gln Arg Pro Ala Leu Lys Ser
                690                 695                 700
Glu Lys Ala Ala Asn Arg Glu Ile Gly Leu Gln Trp Lys Gly Asp Phe
705                 710                 715                 720
Gly Phe Leu Glu Ile Ser Ser Phe Arg Asn Arg Tyr Thr Asp Met Ile
                725                 730                 735
```

```
Ala Val Ala Asp His Lys Thr Lys Leu Pro Asn Gln Ala Gly Gln Leu
            740                 745                 750

Thr Glu Ile Asp Ile Arg Asp Tyr Tyr Asn Ala Gln Asn Met Ser Leu
            755                 760                 765

Gln Gly Val Asn Ile Leu Gly Lys Ile Asp Trp Asn Gly Val Tyr Gly
770             775                 780

Lys Leu Pro Glu Gly Leu Tyr Thr Thr Leu Ala Tyr Asn Arg Ile Lys
785                 790                 795                 800

Pro Lys Ser Val Ser Asn Arg Pro Gly Leu Ser Leu Arg Ser Tyr Ala
                805                 810                 815

Leu Asp Ala Val Gln Pro Ser Arg Tyr Val Leu Gly Phe Gly Tyr Asp
                820                 825                 830

Gln Pro Glu Gly Lys Trp Gly Ala Asn Ile Met Leu Thr Tyr Ser Lys
                835                 840                 845

Gly Lys Asn Pro Asp Glu Leu Ala Tyr Leu Ala Gly Asp Gln Lys Arg
850                 855                 860

Tyr Ser Thr Lys Arg Ala Ser Ser Trp Ser Thr Ala Asp Val Ser
865             870                 875                 880

Ala Tyr Leu Asn Leu Lys Lys Arg Leu Thr Leu Arg Ala Ala Ile Tyr
                885                 890                 895

Asn Ile Gly Asn Tyr Arg Tyr Val Thr Trp Glu Ser Leu Arg Gln Thr
                900                 905                 910

Ala Glu Ser Thr Ala Asn Arg His Gly Gly Asp Ser Asn Tyr Gly Arg
            915                 920                 925

Tyr Ala Ala Pro Gly Arg Asn Phe Ser Leu Ala Leu Glu Met Lys Phe
930                 935                 940

(2) INFORMATION FOR SEQ ID NO:24:

(i) SEQUENCE CHARACTERISTICS:
        (A) LENGTH: 944 amino acids
        (B) TYPE: amino acid
        (C) STRANDEDNESS: single
        (D) TOPOLOGY: linear (xi) SEQUENCE DESCRIPTION: SEQ ID NO:24:

Met Asn Lys Lys His Gly Phe Pro Leu Thr Leu Thr Ala Leu Ala Ile
1               5                   10                  15

Ala Thr Ala Phe Pro Ala Tyr Ala Ala Gln Ala Gly Ala Ala Ala Leu
            20                  25                  30

Asp Ala Ala Gln Ser Gln Ser Leu Lys Glu Val Thr Val Arg Ala Ala
            35                  40                  45

Lys Val Gly Arg Arg Ser Lys Pro Glu Ala Thr Gly Leu Gly Lys Ile
50                  55                  60

Ala Lys Thr Ser Glu Thr Leu Asn Lys Glu Gln Val Leu Gly Ile Arg
65              70                  75                  80

Asp Leu Thr Arg Tyr Asp Pro Gly Val Ala Val Glu Gln Gly Asn
                85                  90                  95

Gly Ala Ser Gly Gly Tyr Ser Ile Arg Gly Val Asp Lys Asn Arg Val
                100                 105                 110

Ala Val Ser Val Asp Gly Val Ala Gln Ile Gln Ala Phe Thr Val Gln
            115                 120                 125

Gly Ser Leu Ser Gly Tyr Gly Arg Gly Gly Ser Gly Ala Ile Asn
            130                 135                 140

Glu Ile Glu Tyr Glu Asn Ile Ser Thr Val Glu Ile Asp Lys Gly Ala
145                 150                 155                 160
```

-continued

```
Gly Ser Ser Asp His Gly Ser Gly Ala Leu Gly Gly Ala Val Ala Phe
                165                 170                 175
Arg Thr Lys Glu Ala Ala Asp Leu Ile Ser Asp Gly Lys Ser Trp Gly
            180                 185                 190
Ile Gln Ala Lys Thr Ala Tyr Gly Ser Lys Asn Arg Gln Phe Met Lys
        195                 200                 205
Ser Leu Gly Ala Gly Phe Ser Lys Asp Gly Trp Glu Gly Leu Leu Ile
    210                 215                 220
Arg Thr Glu Arg Gln Gly Arg Glu Thr Arg Pro His Gly Asp Ile Ala
225                 230                 235                 240
Asp Gly Val Glu Tyr Gly Ile Asp Arg Leu Asp Ala Phe Arg Gln Thr
                245                 250                 255
Tyr Asp Ile Lys Arg Lys Thr Thr Glu Pro Phe Phe Leu Val Glu Gly
            260                 265                 270
Glu Asn Thr Leu Lys Pro Val Ala Lys Leu Ala Gly Tyr Gly Ile Tyr
        275                 280                 285
Leu Asn Arg Gln Leu Asn Arg Trp Val Lys Glu Arg Ile Glu Gln Asn
    290                 295                 300
Gln Pro Leu Ser Ala Glu Glu Ala Gln Val Arg Glu Ala Gln Ala
305                 310                 315                 320
Arg His Glu Asn Leu Ser Ala Gln Ala Tyr Thr Gly Gly Arg Ile
                325                 330                 335
Leu Pro Asp Pro Met Asp Tyr Arg Ser Gly Ser Trp Leu Ala Lys Leu
            340                 345                 350
Gly Tyr Arg Phe Gly Gly Arg His Tyr Val Gly Gly Val Phe Glu Asp
        355                 360                 365
Thr Lys Gln Arg Tyr Asp Ile Arg Asp Met Thr Glu Lys Gln Tyr Tyr
    370                 375                 380
Gly Thr Asp Glu Ala Glu Lys Phe Arg Asp Lys Ser Gly Val Tyr Asp
385                 390                 395                 400
Gly Asp Asp Phe Arg Asp Gly Leu Tyr Phe Val Pro Asn Ile Glu Glu
                405                 410                 415
Trp Lys Gly Asp Lys Asn Leu Val Lys Gly Ile Gly Leu Lys Tyr Ser
            420                 425                 430
Arg Thr Lys Phe Ile Asp Glu His His Arg Arg Arg Met Gly Leu
        435                 440                 445
Leu Tyr Arg Tyr Glu Asn Glu Lys Tyr Ser Asp Asn Trp Ala Asp Lys
    450                 455                 460
Ala Val Leu Ser Phe Asp Lys Gln Gly Val Ala Thr Asp Asn Asn Thr
465                 470                 475                 480
Leu Lys Leu Asn Cys Ala Val Tyr Pro Ala Val Asp Lys Ser Cys Arg
                485                 490                 495
Ala Ser Ala Asp Lys Pro Tyr Ser Tyr Asp Ser Ser Asp Arg Phe His
            500                 505                 510
Tyr Arg Glu Gln His Asn Val Leu Asn Ala Ser Phe Glu Lys Ser Leu
        515                 520                 525
Lys Asn Lys Trp Thr Lys His His Leu Thr Leu Gly Phe Gly Tyr Asp
    530                 535                 540
Ala Ser Lys Ala Val Ser Arg Pro Glu Gln Leu Ser His Asn Ala Ala
545                 550                 555                 560
Arg Ile Ser Glu Ser Thr Gly Phe Asp Glu Lys Asn Gln Asp Lys Tyr
                565                 570                 575
Arg Leu Gly Lys Pro Glu Val Val Glu Gly Ser Val Cys Gly Tyr Ile
            580                 585                 590
```

```
Glu Thr Leu Arg Ser Arg Lys Cys Val Pro Arg Lys Ile Asn Gly Ser
            595                 600                 605

Asn Ile His Ile Ser Leu Asn Asp Arg Phe Ser Ile Gly Lys Tyr Phe
            610                 615                 620

Asp Phe Ser Leu Gly Gly Arg Tyr Asp Arg Lys Asn Phe Thr Thr Ser
625                 630                 635                 640

Glu Glu Leu Val Arg Ser Gly Arg Tyr Ala Asp Arg Ser Trp Asn Ser
            645                 650                 655

Gly Ile Val Phe Lys Pro Asn Arg His Phe Ser Val Ser Tyr Arg Ala
            660                 665                 670

Ser Ser Gly Phe Arg Thr Pro Ser Phe Gln Glu Leu Phe Gly Ile Asp
            675                 680                 685

Ile Tyr His Asp Tyr Pro Lys Gly Trp Gln Arg Pro Ala Leu Lys Ser
            690                 695                 700

Glu Lys Ala Ala Asn Arg Glu Ile Gly Leu Gln Trp Lys Gly Asp Phe
705                 710                 715                 720

Gly Phe Leu Glu Ile Ser Ser Phe Arg Asn Arg Tyr Thr Asp Met Ile
            725                 730                 735

Ala Val Ala Asp Gln Lys Thr Lys Leu Pro Asp Ser Ala Gly Arg Leu
            740                 745                 750

Thr Glu Ile Asp Ile Arg Asp Tyr Tyr Asn Ala Gln Asn Met Ser Leu
            755                 760                 765

Gln Gly Ile Asn Ile Leu Gly Lys Ile Asp Trp Asn Gly Val Tyr Gly
            770                 775                 780

Lys Leu Pro Glu Gly Leu Tyr Thr Thr Leu Ala Tyr Asn Arg Ile Lys
785                 790                 795                 800

Pro Lys Ser Val Ser Asn Arg Pro Asp Leu Ser Leu Arg Ser Tyr Ala
            805                 810                 815

Leu Asp Ala Val Gln Pro Ser Arg Tyr Val Leu Gly Phe Gly Tyr Asp
            820                 825                 830

Gln Pro Glu Gly Lys Trp Gly Ala Asn Ile Met Leu Thr Tyr Ser Lys
            835                 840                 845

Gly Lys Asn Pro Asp Glu Leu Ala Tyr Leu Ala Gly Asp Gln Lys Arg
            850                 855                 860

Tyr Ser Ala Gly Arg Val Thr Ser Ser Trp Lys Thr Ala Asp Val Ser
865                 870                 875                 880

Ala Tyr Leu Asn Leu Lys Lys Arg Leu Thr Leu Arg Ala Ala Ile Tyr
            885                 890                 895

Asn Ile Gly Asn Tyr Arg Tyr Val Thr Trp Glu Ser Leu Arg Gln Thr
            900                 905                 910

Ala Glu Ser Thr Ala Asn Arg His Gly Gly Asp Ser Asn Tyr Gly Arg
            915                 920                 925

Tyr Ala Ala Pro Gly Arg Asn Phe Ser Leu Ala Leu Glu Met Lys Phe
930                 935                 940

(2) INFORMATION FOR SEQ ID NO:25:

(i) SEQUENCE CHARACTERISTICS:
        (A) LENGTH: 702 amino acids
        (B) TYPE: amino acid
        (C) STRANDEDNESS: single
        (D) TOPOLOGY: linear (xi) SEQUENCE DESCRIPTION: SEQ ID NO:25:

Met Lys His Ile Pro Leu Thr Thr Leu Cys Val Ala Ile Ser Ala Val
1               5                   10                  15
```

```
Leu Leu Thr Ala Cys Gly Gly Ser Gly Ser Asn Pro Ala Pro
         20              25              30

Thr Pro Ile Pro Asn Ala Ser Gly Ser Gly Asn Thr Gly Asn Thr Gly
         35              40              45

Asn Ala Gly Gly Thr Asp Asn Thr Ala Asn Ala Gly Asn Thr Gly Gly
 50              55              60

Thr Asn Ser Gly Thr Gly Ser Ala Asn Thr Pro Glu Pro Lys Tyr Gln
 65              70              75              80

Asp Val Pro Thr Glu Lys Asn Glu Lys Asp Lys Val Ser Ser Ile Gln
             85              90              95

Glu Pro Ala Met Gly Tyr Gly Met Ala Leu Ser Lys Ile Asn Leu His
            100             105             110

Asn Arg Gln Asp Thr Pro Leu Asp Glu Lys Asn Ile Ile Thr Leu Asp
            115             120             125

Gly Lys Lys Gln Val Ala Glu Gly Lys Lys Ser Pro Leu Pro Phe Ser
            130             135             140

Leu Asp Val Glu Asn Lys Leu Leu Asp Gly Tyr Ile Ala Lys Met Asn
145             150             155             160

Val Ala Asp Lys Asn Ala Ile Gly Asp Arg Ile Lys Lys Gly Asn Lys
            165             170             175

Glu Ile Ser Asp Glu Leu Ala Lys Gln Ile Lys Glu Ala Val Arg
            180             185             190

Lys Ser His Glu Phe Gln Gln Val Leu Ser Ser Leu Glu Asn Lys Ile
            195             200             205

Phe His Ser Asn Asp Gly Thr Thr Lys Ala Thr Thr Arg Asp Leu Lys
            210             215             220

Tyr Val Asp Tyr Gly Tyr Tyr Leu Ala Asn Asp Gly Asn Tyr Leu Thr
225             230             235             240

Val Lys Thr Asp Lys Leu Trp Asn Leu Gly Pro Val Gly Gly Val Phe
            245             250             255

Tyr Asn Gly Thr Thr Thr Ala Lys Glu Leu Pro Thr Gln Asp Ala Val
            260             265             270

Lys Tyr Lys Gly His Trp Asp Phe Met Thr Asp Val Ala Asn Arg Arg
            275             280             285

Asn Arg Phe Ser Glu Val Lys Glu Asn Ser Gln Ala Gly Trp Tyr Tyr
            290             295             300

Gly Ala Ser Ser Lys Asp Glu Tyr Asn Arg Leu Leu Thr Lys Glu Asp
305             310             315             320

Ser Ala Pro Asp Gly His Ser Gly Glu Tyr Gly His Ser Ser Glu Phe
            325             330             335

Thr Val Asn Phe Lys Glu Lys Lys Leu Thr Gly Lys Leu Phe Ser Asn
            340             345             350

Leu Gln Asp Arg His Lys Gly Asn Val Thr Lys Thr Glu Arg Tyr Asp
            355             360             365

Ile Asp Ala Asn Ile His Gly Asn Arg Phe Arg Gly Ser Ala Thr Ala
            370             375             380

Ser Asn Lys Asn Asp Thr Ser Lys His Pro Phe Thr Ser Asp Ala Asn
385             390             395             400

Asn Arg Leu Glu Gly Gly Phe Tyr Gly Pro Lys Gly Glu Glu Leu Ala
                405             410             415

Gly Lys Phe Leu Thr Asn Asp Asn Lys Leu Phe Gly Val Phe Gly Ala
            420             425             430

Lys Arg Glu Ser Lys Ala Glu Glu Lys Thr Glu Ala Ile Leu Asp Ala
```

```
                  435                 440                 445
Tyr Ala Leu Gly Thr Phe Asn Thr Ser Asn Ala Thr Thr Phe Thr Pro
    450                 455                 460
Phe Thr Glu Lys Gln Leu Asp Asn Phe Gly Asn Ala Lys Lys Leu Val
465                 470                 475                 480
Leu Gly Ser Thr Val Ile Asp Leu Val Pro Thr Asp Ala Thr Lys Asn
                485                 490                 495
Glu Phe Thr Lys Asp Lys Pro Glu Ser Ala Thr Asn Glu Ala Gly Glu
                500                 505                 510
Thr Leu Met Val Asn Asp Glu Val Ser Val Lys Thr Tyr Gly Lys Asn
            515                 520                 525
Phe Glu Tyr Leu Lys Phe Gly Glu Leu Ser Ile Gly Gly Ser His Ser
530                 535                 540
Val Phe Leu Gln Gly Glu Arg Thr Ala Thr Thr Gly Glu Lys Ala Val
545                 550                 555                 560
Pro Thr Thr Gly Thr Ala Lys Tyr Leu Gly Asn Trp Val Gly Tyr Ile
                565                 570                 575
Thr Gly Lys Asp Thr Gly Thr Gly Thr Gly Lys Ser Phe Thr Asp Ala
                580                 585                 590
Gln Asp Val Ala Asp Phe Asp Ile Asp Phe Gly Asn Lys Ser Val Ser
            595                 600                 605
Gly Lys Leu Ile Thr Lys Gly Arg Gln Asp Pro Val Phe Ser Ile Thr
610                 615                 620
Gly Gln Ile Ala Gly Asn Gly Trp Thr Gly Thr Ala Ser Thr Thr Lys
625                 630                 635                 640
Ala Asp Ala Gly Gly Tyr Lys Ile Asp Ser Ser Ser Thr Gly Lys Ser
                645                 650                 655
Ile Ala Ile Lys Asp Ala Asn Val Thr Gly Gly Phe Tyr Gly Pro Asn
                660                 665                 670
Ala Asn Glu Met Gly Gly Ser Phe Thr His Asn Ala Asp Asp Ser Lys
            675                 680                 685
Ala Ser Val Val Phe Gly Thr Lys Arg Gln Gln Glu Val Lys
            690                 695                 700

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:26:

Leu Glu Met Lys Phe
1               5

(2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:27:

Leu Glu Gly Gly Phe Tyr
1               5

(2) INFORMATION FOR SEQ ID NO:28:
```

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:28:

Gln Tyr Thr Arg Lys Gly Glu Asn Lys Ala
1               5                   10

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:29:

CAATATACCG TAAAGGTGAA AATAAAGC                                              28

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:30:

CAATATACCG TAAAGGTGAA AATAAAGC                                              28

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:31:

CAATATACCG TAAAGGTGAA AACAAAGC                                              28

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:32:

CAATATACCG TAAAGGCGAA AATAAAGC                                              28

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:33:

CAATATACCG CAAAGGCGAA AACAAAGC                                              28

(2) INFORMATION FOR SEQ ID NO:34:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (xi) SEQUENCE DESCRIPTION: SEQ ID NO:34:

CAATATACCG CAAAGGCGAA AATAAAGC                                              28

(2) INFORMATION FOR SEQ ID NO:35:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO:35:

CAATATACCG CAAAGGTGAA AATAAAGC                                              28

(2) INFORMATION FOR SEQ ID NO:36:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO:36:

CAATATACCG CAAAGGTGAA AACAAAGC                                              28

(2) INFORMATION FOR SEQ ID NO:37:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:37:

CTTGAAATGA AGTTTTAA                                                         18

(2) INFORMATION FOR SEQ ID NO:38:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:38:

GAACTTTACT TCAAAATT                                                         18

(2) INFORMATION FOR SEQ ID NO:39:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:39:

Asp Gly Leu Gly
1

(2) INFORMATION FOR SEQ ID NO:40:

(i) SEQUENCE CHARACTERISTICS:

(A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:40:

Met Ser Lys Ser Ile Thr
1               5

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:41:

GGAATTCCAT ATGTCAAAAT CTATCACAAA                                    30

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:42:

Leu Asp Ala Ile Thr Val Thr Ala Ala
1               5

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:43:

TTTAGATGCC ATCACGGTAA CCGCCGCCCC                                    30

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:44:

AAATCTACGG TAGTGCCATT GGCGGCGGGG                                    30

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:45:

Gly Lys Leu Asp Leu His Ala Met Thr Ser
1               5                   10

(2) INFORMATION FOR SEQ ID NO:46:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:46:

GGCAAACTGG ATTTGCATGC CATGACATCA                                                    30

(2) INFORMATION FOR SEQ ID NO:47:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:47:

Ser Leu Glu Met Lys Phe
1               5

(2) INFORMATION FOR SEQ ID NO:48:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:48:

AGTCTTGAAA TGAAGTTTTA A                                                             21

(2) INFORMATION FOR SEQ ID NO:49:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:49:

TCAGAACTTT ACTTCAAAAT TGCCCTAGGG C                                                  31

(2) INFORMATION FOR SEQ ID NO:50:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:50:

Met Thr Thr His Arg Leu
1               5

(2) INFORMATION FOR SEQ ID NO:51:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:51:

GGAATTCCAT ATGACCACGC ACCGCTTAAA                                                    30

(2) INFORMATION FOR SEQ ID NO:52:

(i) SEQUENCE CHARACTERISTICS:
    (A) LENGTH: 9 amino acids
    (B) TYPE: amino acid
    (C) STRANDEDNESS: single
    (D) TOPOLOGY: linear (xi) SEQUENCE DESCRIPTION: SEQ ID NO:52:

Met Ser Thr Val Lys Thr Pro His Ile
1               5

(2) INFORMATION FOR SEQ ID NO:53:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (xi) SEQUENCE DESCRIPTION: SEQ ID NO:53:

GGAATTCCAT ATGAGTACTG TCAAAACCCC CCACA                35

(2) INFORMATION FOR SEQ ID NO:54:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:54:

Ile Pro Asn Thr Gly His Asp Asn Thr Asn
1               5                   10

(2) INFORMATION FOR SEQ ID NO:55:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:55:

AATACCGAAC ACAGGTCATG ACAACACCAA T                    31

(2) INFORMATION FOR SEQ ID NO:56:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:

TTATGGCTTG TGTCCAGTAC TGTTGTGGTT A                    31

(2) INFORMATION FOR SEQ ID NO:57:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:57:

Asn Glu Pro Thr His Glu Lys Thr Phe Ala
1               5                   10

(2) INFORMATION FOR SEQ ID NO:58:

```
        (i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:58:

AATGAGCCTA CTCATGAAAA AACCTTTGCC                                              30

(2) INFORMATION FOR SEQ ID NO:59:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:59:

Gly Ala Val Phe Gly Ala Val Lys Asp Lys
1               5                   10

(2) INFORMATION FOR SEQ ID NO:60:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:60:

GGGCTGTCTT TGGGGCTGTT AAAGATAAAT AA                                           32

(2) INFORMATION FOR SEQ ID NO:61:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:61:

CCCGACAGAA ACCCCGACAA TTTCTATTTA TTCCTAGGGC                                   40

(2) INFORMATION FOR SEQ ID NO:62:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:62:

Met Cys Arg Ser Asp Asp Ile Ser Val Asn
1               5                   10

(2) INFORMATION FOR SEQ ID NO:63:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:63:

GGAATTCCAT ATGTGCCGCT CTGATGACAT CAGCGTCAAT                                   40

(2) INFORMATION FOR SEQ ID NO:64:
```

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:64:

Phe Leu Lys Gln Val
1               5

(2) INFORMATION FOR SEQ ID NO:65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:65:

TTTTTAAAGC AGGTG                                                        15

(2) INFORMATION FOR SEQ ID NO:66:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:66:

AAAAATTTCG TC                                                           12

(2) INFORMATION FOR SEQ ID NO:67:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:67:

Met Val Gln Tyr Thr Arg Lys Gly Glu Asn Lys Ala His
1               5                   10

What we claim is:

1. A purified and isolated nucleic acid molecule encoding at least one lactoferrin binding protein of Moraxella and having a restriction map as shown in FIG. 3 for *M. catarrhalis* strain 4223 or a restriction map as shown in FIG. 5 for *M. catarrhalis* strain Q8.

2. A purified and isolated nucleic acid molecule which encodes a lactoferrin receptor protein and having a DNA sequence selected from the group consisting of:

(a) a DNA sequence as set forth in SEQ ID Nos. 1, 2, 3, 4, 5, 6, 7, 8, 9, and 10 or the fully complementary DNA sequence thereto;

(b) a DNA sequence encoding an amino acid sequence as set forth in SEQ ID Nos. 11, 12, 13, 14, 15, 16, 17, and 18 or the fully complementary DNA sequence thereto; and (c) a DNA sequence which encodes a lactoferrin receptor protein of a strain of Morexella and which hybridizes under stringent conditions to any one of the DNA sequences defined in (a) or (b).

3. A vector adapted for transformation of a host comprising the nucleic acid molecule of claim 2.

4. The vector of claim 3 encoding a lactoferrin receptor protein and having the characteristics of a plasmid selected from the group consisting of pLD3 as seen in FIG. 10, pLDW3 as seen in FIG. 10, pLD1-8 (ATCC 97,997) as seen in FIG. 12 and pLDW1 (ATCC 97998) as seen in FIG. 12.

5. The vector of claim 3 further comprising expression means operatively coupled to the nucleic acid molecule for expression of said lactoferrin receptor protein of a strain of Moraxella by the host containing the vector.

6. The vector of claim 5 having the characteristics of plasmid pRD1A as seen in FIG. 10, pRD1B as seen in FIG. 10, pQW1A as seen in FIG. 10, PQW1B as seen in FIG. 10, pRD2A as seen in FIG. 12, pRD2B as seen in FIG. 12, pQW2A as seen in FIG. 12, pQW2B as seen in FIG. 12, pLRD3 as seen in FIG. 13 and pLQW3 as seen in FIG. 13.

7. A transformed host containing an expression vector as claimed in claimed 5.

* * * * *